US011192890B2

(12) United States Patent
Patterson et al.

(10) Patent No.: US 11,192,890 B2
(45) Date of Patent: Dec. 7, 2021

(54) FGFR KINASE INHIBITORS AND PHARMACEUTICAL USES

(71) Applicants: AUCKLAND UNISERVICES LIMITED, Auckland (NZ); GUANGZHOU INSTITUTE OF BIOMEDICINE AND HEALTH, Guangdong (CN)

(72) Inventors: Adam Vorn Patterson, Auckland (NZ); Jeffrey Bruce Smaill, Auckland (NZ); Amir Ashoorzadeh, Auckland (NZ); Christopher Paul Guise, Auckland (NZ); Christopher John Squire, Auckland (NZ); Swarnalatha Akuratiya Gamage, Auckland (NZ); Maria Rosaria Abbattista, Auckland (NZ); Matthew Roy Bull, Auckland (NZ); Angus Cheverton Grey, Auckland (NZ); Xueqiang Li, Guangdong (CN); Ke Ding, Guangdong (CN); Xiaomei Ren, Guangdong (CN); Shuang Jiang, Guangdong (CN); Zhengchao Tu, Guangdong (CN)

(73) Assignees: AUCKLAND UNISERVICES LIMITED, Auckland (NZ); GUANGZHOU INSTITUTE OF BIOMEDICINE AND HEALTH, Guangdong (CN)

( * ) Notice: Subject to any disclaimer, the term of this patent is extended or adjusted under 35 U.S.C. 154(b) by 12 days.

(21) Appl. No.: 16/490,717

(22) PCT Filed: Mar. 2, 2018

(86) PCT No.: PCT/NZ2018/050022
§ 371 (c)(1),
(2) Date: Sep. 3, 2019

(87) PCT Pub. No.: WO2018/160076
PCT Pub. Date: Sep. 7, 2018

(65) Prior Publication Data
US 2020/0017491 A1  Jan. 16, 2020

(30) Foreign Application Priority Data
Mar. 3, 2017 (NZ) .................................. 729651

(51) Int. Cl.
*C07D 471/04* (2006.01)
*A61P 35/00* (2006.01)
*C07D 487/04* (2006.01)

(52) U.S. Cl.
CPC ............ *C07D 471/04* (2013.01); *A61P 35/00* (2018.01); *C07D 487/04* (2013.01)

(58) Field of Classification Search
CPC .......................... C07D 487/04; C07D 471/04
See application file for complete search history.

(56) References Cited

U.S. PATENT DOCUMENTS

2015/0126508 A1   5/2015  Li et al.
2018/0148454 A1*  5/2018  Li ........................ C07D 475/00

FOREIGN PATENT DOCUMENTS

| CN | 104418860 B | | 9/2016 |
|---|---|---|---|
| WO | WO 2010/104406 A1 | | 9/2010 |
| WO | WO 2014/182829 A1 | | 11/2014 |
| WO | WO 2015/006492 A1 | | 1/2015 |
| WO | WO 2015120049 | * | 8/2015 |
| WO | WO 2016/115412 A1 | | 7/2016 |
| WO | WO 2016192609 | * | 8/2016 |

OTHER PUBLICATIONS

Machine translation of CN 104418860, 2015. (Year: 2015).*
Teven. Genes and Diseases, 2014, 1, 199-213 (Year: 2014).*
Extended European Search Report, European Patent Application No. 18761052.2, dated Jul. 15, 2020, 7 pages.
Xu, S. et al., "Design, Synthesis, and Biological Evaluation of 2-Oxo-3,4-dihydropyrimido[4,5-d]pyrimidinyl Derivatives as New Irreversible Epidermal Growth Factor Receptor Inhibitors with Improved Pharmacokinetic Properties," *Journal of Medicinal Chemistry*, vol. 56, No. 21, Oct. 14, 2013, pp. 8803-8813.
Li, X. et al., "2-Oxo-3, 4-dihydropyrimido [4, 5-d] pyrimidinyl derivatives as new irreversible pan fibroblast growth factor receptor (FGFR) inhibitors," European Journal of Medicinal Chemistry, Jul. 28, 2017, pp. 531-543, vol. 135.
PCT International Search Report and Written Opinion, PCT Application No. PCT/NZ2018/050022, dated May 1, 2018, 12 pages.

\* cited by examiner

*Primary Examiner* — Noble E Jarrell
(74) *Attorney, Agent, or Firm* — Fenwick & West LLP

(57) ABSTRACT

Fibroblast Growth Factor Receptor kinase inhibitors and prodrugs thereof of Formula (I) and their use for the treatment of hyper-proliferative diseases such as retinopathy, psoriasis, rheumatoid arthritis, osteoarthritis, septic arthritis, tumour metastasis, periodontal disease, corral ulceration, proteinuria, coronary thrombosis from atherosclerotic plaque, aneurismal aorta, dystrophobic epidermolysis bullosa, degenerative cartilage loss following traumatic joint injury, osteopenias mediated by MMP activity, tempero mandibular joint disease, and demyelating disease of the nervous system.

22 Claims, 16 Drawing Sheets

Specification includes a Sequence Listing.

Figure 3
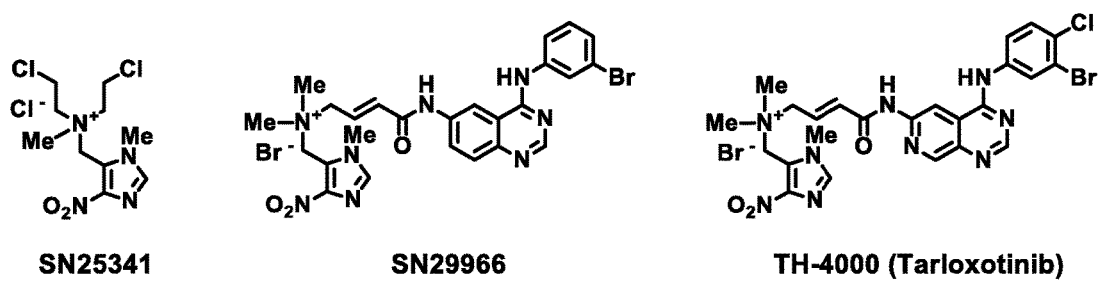
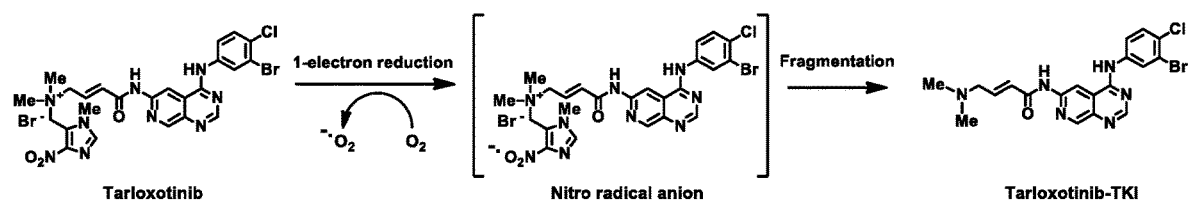
Figure 4

FIIN-1 NMQ    PD173074 NMQ (I)

FGFR KINASE INHIBITORS AND PHARMACEUTICAL USES

TECHNICAL FIELD

The invention relates to a novel class of Fibroblast Growth Factor Receptor kinase inhibitors and prodrugs thereof, and their use for the treatment of hyper-proliferative diseases such as cancer.

BACKGROUND OF THE INVENTION

The Fibroblast Growth Factor Receptor Family

Fibroblast growth factor receptors (FGFR) belong to a receptor tyrosine kinases superfamily which consists of four highly conserved functional members (FGFR1-4) [Touat et al., Clin. Cancer Res. 2015, 2684-2694]. After being activated by fibroblast growth factors (FGFs), the FGFR family regulates many key biological processes, such as embryonic development, cell proliferation, differentiation, migration, apoptosis, angiogenesis and metabolism [Beenken et al., Nat. Rev. Drug Discov. 2009, 235-53]. FGFR aberrations (i.e., amplification, gene fusion or mutation) are identified in a variety of human cancers [Helsten et al., Clin. Cancer Res. 2016, 259-267]. For instance, FGFR1 amplification is commonly observed in approximately 20% of squamous non-small cell lung cancer [Tiseo et al., Cancer Treat. Rev. 2015, 527-539], 10-15% of breast cancer and 5% of ovarian cancer. FGFR2 is also amplified in about 10% of gastric cancer and 4% of triple-negative breast cancer, and an FGFR2 mutation is detected in about 12-14% of endometrial cancer. Activating mutations of FGFR3 are observed in 38-66% of non-invasive urothelial carcinoma and its amplification and translocation are frequently found in bladder cancer [Hallinan et al, Cancer Treat. Rev. 2016, 51-62]. In addition, approximately 50% of hepatocellular carcinomas exhibit overexpression of FGFR4 [Gauglhofer et al., Carcinogenesis 2014, 2331-2338]. Abnormal activation of the FGFR family has been associated with survival and migration of cancer cells, tumour angiogenesis and poor prognosis, and substantial studies demonstrate that deregulated FGFR signalling is a key driver in the development of resistance to chemotherapy [Pardo et al., J. Biol. Chem. 2002, 12040-12046] and acquired resistance to targeted therapies [Manchado et al., Nature 2016, 647-651; Yadav et al., J. Biol. Chem. 2012, 28087-28098]. Thus, there is an urgent need to develop potent selective inhibitors of the FGFR family for the treatment of FGFR-dependent cancers.

Small Molecule FGFR Inhibitors

Early attempts to identify a selective FGFR inhibitor led to the discovery of PD173074 as a prototypic biology tool compound [Hamby et al., J. Med. Chem. 1997, 2296-2303]. Since then, several selective or non-selective small molecule FGFR inhibitors have been advanced into different stages of clinical investigation [Dieci et al., Cancer Discov. 2013, 264-79]. While non-selective FGFR inhibitors show efficacy in patients with deregulated FGFR signalling, severe side effects are also observed [Launay-Vacher et al., Anticancer Drugs 2009, 81-82] due to inhibition against a number of off-target kinases such as VEGFR, KDR and PDGFR (e.g., BIBF-1120 [Roth et al., J. Med. Chem. 2009, 4466-4480], TKI-258 [André et al., Clin. Cancer Res. 2013, 3693-3702], AZD-2171 [Wedge et al., Cancer Res. 2005, 4389-4400] (FIG. 1)).

Several reversible FGFR inhibitors with an improved selectivity profile relative to other receptor tyrosine kinases and therefore a safety profile anticipated to be more favourable, have also been developed into clinical investigation (e.g., BGJ-398 [Guagnano et al., J. Med. Chem. 2011, 7066-83], AZD-4547 [Gavine et al., Cancer Res. 2012, 2045-2056], JNJ-42756493 [Tabernero et al., J. Clin. Oncol. 2015, 3401-8], CH-5183284 [Ebiike et al., J. Med. Chem. 2016, 10586-10600] (FIG. 1)). Preliminary results indicate that clinical benefits are observed in patients with tumours harbouring FGFR alterations [Touat et al., Clin. Cancer Res. 2015, 2684-2694] although response rates and duration of response are modest and examples of FGFR-amplified disease, such as FGFR1-amplified squamous cell carcinoma of the lung, appear to be particularly refractory to treatment [Weeden et al., Cell Death Discovery, 2015, 15049].

There is an increasing interest in developing irreversible kinase inhibitors for the treatment of various cancers due to their superior efficacy, improved functional selectivity and ability to overcome clinical resistance [Barf et al., J. Med. Chem. 2012, 6243-6262]. The regulatory approval of ibrutinib [Byrd et al., N. Engl. J. Med. 2013, 32], afatinib [Nelson et al., Onco. Targets. Ther. 2013, 135-143] and osimertinib [Greig, Drugs, 2016, 263-73] as irreversible kinase inhibitors for the treatment of chronic lymphocytic leukemia, EGFR-mutant positive non-small cell lung cancer and EGFR-T790M-mutant-positive non-small cell lung cancer, respectively has validated this approach significantly.

The first reported selective irreversible FGFR inhibitor, FIIN-1 (FIG. 2), was designed from an available FGFR1/PD173074 co-crystal structure. FIIN-1 is highly active for FGFR and exhibits potent anti-proliferative activity against various FGFR-dependent tumour cells [Zhou et al., Chem. Biol. 2010, 285-295]. Structural analysis of FIIN-1 revealed that it possessed some key structural elements which form crucial interactions with the FGFR protein: (1) a heterocyclic moiety (so-called "head region") forming a hydrogen bond network with residues in the kinase hinge region; (2) a 2,6-dichloro-3,5-dimethoxyphenyl group occupying the hydrophobic pocket behind the gatekeeper residue; and (3) a side chain with an acrylamide moiety targeting an unpaired cysteine (Cys486) conserved on the p-loop of the FGFR1-4 proteins. Two further covalent FGFR inhibitor examples based on this approach, termed FIIN-2 and FIIN-3 have been reported (FIG. 2). They displayed strong anti-proliferative effects against cells with gatekeeper mutants of FGFR1 or FGFR2 which confer resistance to BGJ398 and AZD4547 [Tan et al., Proc. Natl. Acad. Sci. U.S.A 2014, 1-9]. Recent reports indicate two further irreversible FGFR inhibitors TAS-120 [Hallinan et al., Cancer Treat. Rev. 2016, 51-62] and PRN1317 [Piha-Paul et al., ASCO. 2016, Abstract No. 2602; Brameld et al., J Med Chem. 2017, 60(15), 6516-6527; Venetsanakos et al., Mol. Cancer Ther. 2017, 16, 2668-2676] are being evaluated in phase I clinical trials, with the latter agent being derived from an earlier lead candidate, PRN1109 [Phan et al., Eu. J. Cancer, 2014, 50(6), 157] (FIG. 2).

Toxicity of Selective FGFR Inhibitors in Clinical Trial

The FGFR family plays a critical role in normal physiology, including phosphate and vitamin D homeostasis [Beenken et al., Nat. Rev. Drug Discov. 2009, 235-53]. Indeed, studies indicate that small molecule FGFR inhibitors have severe dose-limiting side-effects, including hyperphosphatemia-mediated tissue calcification owing to blockade of autocrine FGF23 ligand release from bone with loss of FGF23 signalling in kidney [Brown et al., Toxicol. Pathol. 2005; 33:449-55; Dieci et al., Cancer Discov. 2013, 264-79]. Other toxicities observed include stomatitis, alopecia, decreased appetite, nausea, fatigue, retinal pigmented epithelial detachment and nail changes. The recommended Phase II scheduling of both AZD4547 and BGJ398 include mandatory week-long treatment breaks [Smyth et al., J. Clin. Oncol. 2015, Suppl. Abs. 2508; Javie et al., J. Clin. Oncol. 2016, Suppl. 4S, abs. 335] to allow increases in plasma phosphate levels to return to baseline before resumption of dosing. Such treatment breaks would be expected to be detrimental to inhibiting the growth of FGFR-dependent cancers.

On-mechanism toxicities due to FGFR1/2/3 inhibition in normal tissues results in a poor therapeutic 'window' to silence this pathway in human cancers. The applicants consider that this phenomenon will be exacerbated for irreversible FGFR1-4 inhibitors resulting in a subsequent reduction in the achievable drug exposure of these agents, relative to their reversible comparators.

Tumour Targeting of Kinase Inhibitors Through Use of Hypoxia-Activated Prodrugs

Hypoxia is a prevailing feature of human tumours associated with resistance to radiotherapy [Hill et al., Semin. Radiat. Oncol. 2015, 260-72], chemotherapy [Bertout et al., Nature Reviews Cancer 2008, 967-75; Dhani et al., Semin. Nucl. Med. 2015, 110-2] and immunotherapy [Hatfield et al., Sci. Transl. Med. 2015, 277ra30]. Correlation of hypoxia with a worse overall prognosis is firmly established [Vaupel et al., Cancer Metastasis Rev. 2007, 225-39]. Novel therapeutic strategies that alleviate or exploit this micro-environmental abnormality of cancers are urgently sought, including small molecule hypoxia-activated prodrugs (HAP) [Guise et al., Chin. J. Cancer 2014, 80-6; Phillips, Cancer Chemother. Pharmacol. 2016, 441-57].

The nitroarylmethyl quaternary (NMQ) ammonium salts represent a particular class of hypoxia-activated fragmenting prodrugs. The NMQ "triggers" are frangible units that mask the basicity of aliphatic tertiary nitrogen containing "effector" molecules while simultaneously limiting the resulting cationic prodrug entity from transiting across plasma membranes to exert a biological effect. This dual mode of deactivation renders the prodrugs less active against intracellular targets, minimising toxicities particularly due to on-target activity of the effector molecule. Reported examples of NMQ prodrugs include SN25341 [Tercel et al., J. Med. Chem. 2001, 3511-3522], SN29966 [Lu et al., Tetrahedon 2013, 9130-8] and TH-4000 (tarloxotinib bromide) [Smaill et al., WO 2010/104406 A1; Smaill et al., WO 2011/028135 A1; Silva et al., Mol. Cancer Ther. 2015, A67; Jackson et al., Mol. Cancer Ther. 2015, A66] (FIG. 3).

The latter example, TH-4000, is a hypoxia-activated irreversible EGFR inhibitor that has been investigated in phase II clinical trials. Appending the NMQ trigger to the irreversible EGFR inhibitor (tarloxotinib-TKI) masks its activity. This restricts on-mechanism toxicity in normal tissues (diarrhoea and skin rash) permitting significantly greater doses to be administered. Under conditions of limiting oxygen (hypoxia) the prodrug undergoes one-electron (1e−) reduction by human enzymes and then fragments to release the irreversible EGFR inhibitor (FIG. 4). Hypoxia is present in the majority of solid cancers thereby focusing the delivery of the kinase inhibitor to tumours.

The invention is therefore based on a novel series of FGFR kinase inhibitors with optimised cellular potency for inhibition of the FGFR family. Preferred examples have been identified as irreversible inhibitors of FGFR1-3. Hypoxia-activated prodrugs of these inhibitors have been prepared and utilised to provide improved tumour-selectivity of FGFR kinase inhibition, relative to that derived from systemic administration of the FGFR inhibitors in their non-prodrug form. This approach is expected to provide an increased dose-intensity of FGFR inhibitor in the tumour and therefore improved anticancer activity due to superior FGFR target inhibition in the tumour.

The applicants have found that the compounds of the invention not only exhibit greater potency as inhibitors of FGFR kinases in vitro than previously known compounds, but were also found to be irreversible inhibitors of FGFR-3 as well as FGFR-1 and FGFR-2. This surprising finding strongly indicates greater effectiveness as therapeutic agents for a range of hyper-proliferative diseases, particularly cancer. Further, the applicants found that prodrugs of the compounds are effective for improving the toxicity profile of the compounds of the invention.

It is therefore an object of the invention to provide novel FGFR kinase inhibitors and prodrugs thereof for use in the treatment of hyper-proliferative diseases such as cancer, or to at least provide useful alternatives to other therapeutic agents for treating such diseases.

SUMMARY OF THE INVENTION

In a first aspect of the invention there is provided a compound of Formula (I):

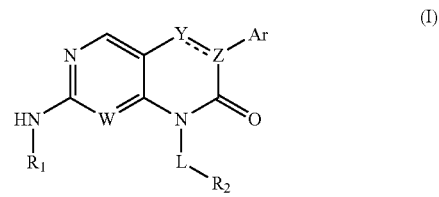

wherein:
W is N or CH;
Y is N, CH or $CH_2$;
Z is N or C;
Ar is an aryl group optionally substituted with halogen, alkyl or alkoxy;
===== denotes either a single bond or a double bond;
$R_1$ is hydrogen, or is selected from the group comprising C1-C6 alkyl, C3-C6 cycloalkyl, heterocyclyl, aryl, and heteroaryl each of which is optionally substituted with hydroxy, alkyl, alkenyl, alkynyl, alkoxy, acetyl, thiol, alkylthio, arylthio, aralkylthio, halogen, carboxylic acid, carboxylate alkyl ester, carboxamide, alkylcarboxamide, dialkylcarboxamide, alkylsulfonyl, alkylsulfoxide, haloalkyl, haloalkoxy, amino, alkylamino, dialkylamino, morpholinyl, thiomorpholinyl, piperazinyl, N-alkylpiperazinyl, N-acetylpiperazinyl, N-alkylsulfonylpiperazinyl, pyrrolidinyl, piperidinyl, imidazolyl, or nitro;
L is a radical of selected from the group comprising Formulae (A)-(J):

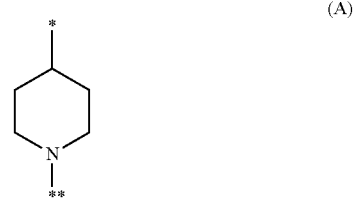

-continued (B)
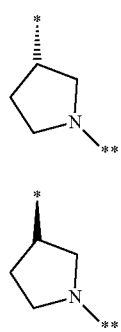

(C)
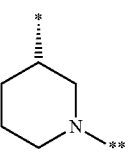

(D)
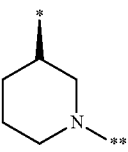

(E)
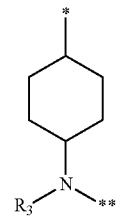

(F)
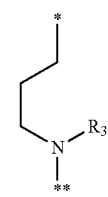

(G)
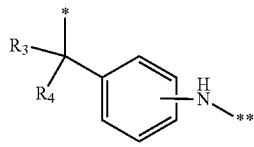

(H)
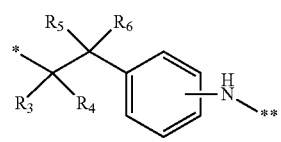

(J)

wherein:
is a point of attachment to the heterocyclic nitrogen atom of Formula (I);
* is a point of attachment to $R_2$; and
$R_3$, $R_4$, $R_5$ and $R_6$ are independently selected from hydrogen and C1-C6 alkyl;

$R_2$ is a radical of Formula (K) or (L):

(K)
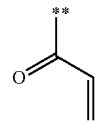

(L)
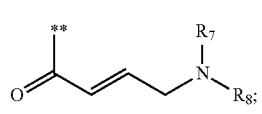

wherein:
$R_7$ and $R_8$ are independently C1-C6 alkyl or may together form a heterocyclic ring; and
* is a point of attachment to L;

with the provisos:
(i) $R_3$ and $R_4$ are not both hydrogen when $R_2$ is a radical of Formula (K), L is a radical of Formula (H), Y is $CH_2$ and Z is N; and
(ii) $R_3$, $R_4$, $R_5$ and $R_6$ are not all hydrogen when $R_2$ is a radical of Formula (K), L is a radical of Formula (J) where the amino group is para-substituted, Y is CH and Z is C;

or a prodrug thereof, a pharmaceutically acceptable salt thereof, or a solvate thereof.

In some embodiments of the invention, $R_1$ is C1-C6 alkyl or is a radical selected from the group comprising Formulae (M)-(FF):

(M)

(N)
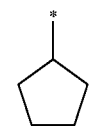

(O)
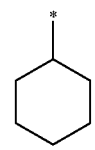

(P)
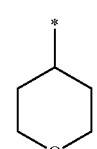

(Q)
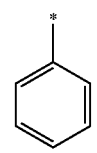

(R) 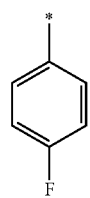
(S) 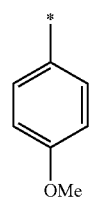
(T) 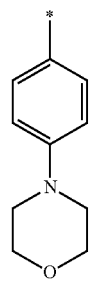
(U) 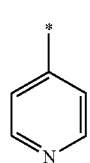
(W) 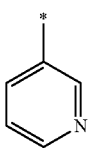
(Y) 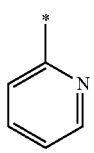
(Z) 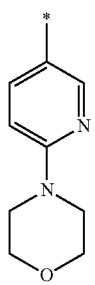
(AA) 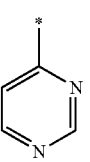
(BB) 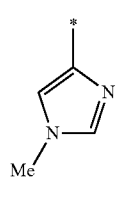
(CC) 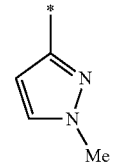
(DD) 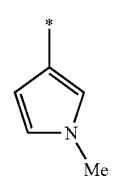
(EE) 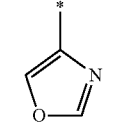
(FF) 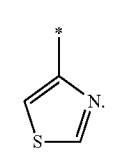
In some embodiments of the invention, Ar is a radical selected from the group comprising Formulae (GG)-(LLL):
(GG) 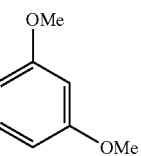
(HH) 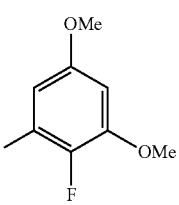
(JJ) 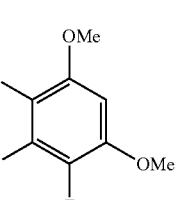

-continued
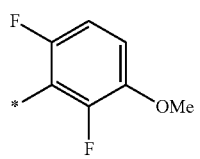 (KK)
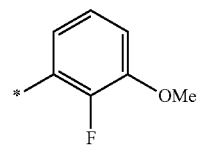 (LL)
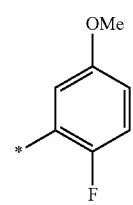 (MM)
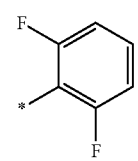 (NN)
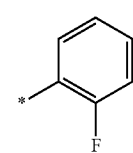 (OO)
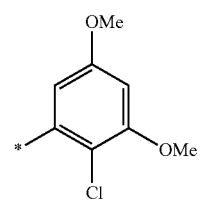 (PP)
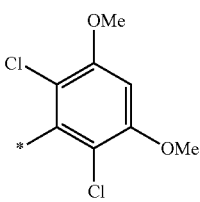 (QQ)
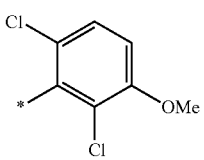 (RR)
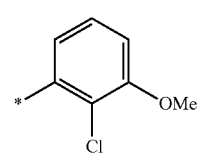 (SS)
-continued
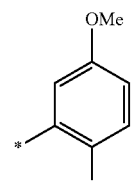 (TT)
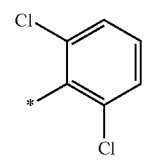 (UU)
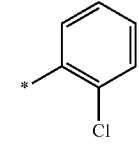 (VV)
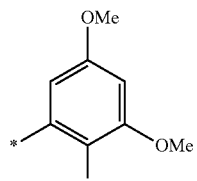 (WW)
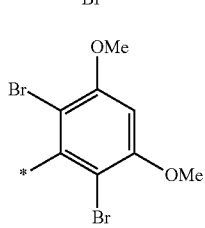 (YY)
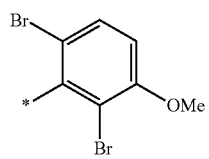 (ZZ)
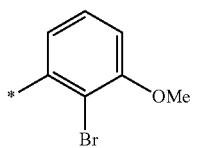 (AAA)
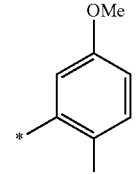 (BBB)
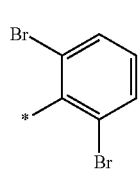 (CCC)

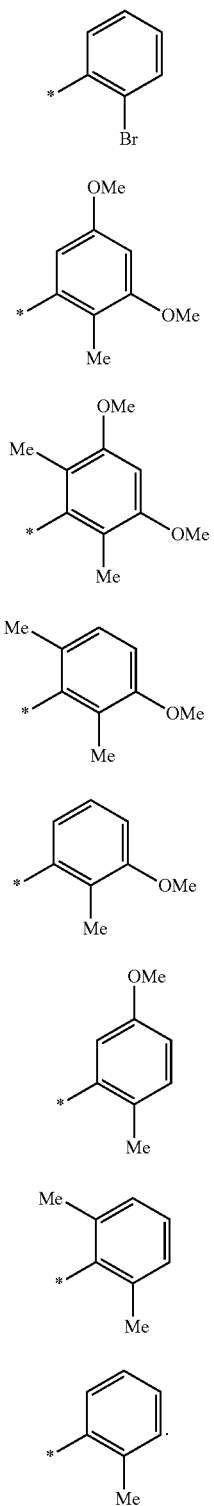

In some embodiments of the invention, the compounds have a formula selected from the group comprising Formulae (II) to (VII):

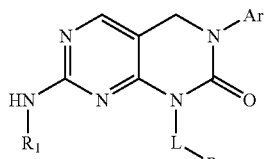

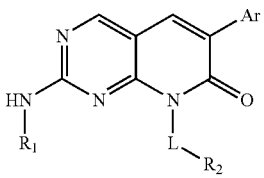

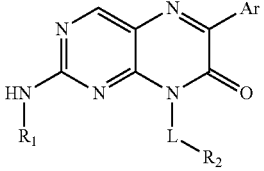

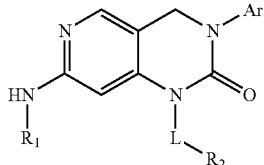

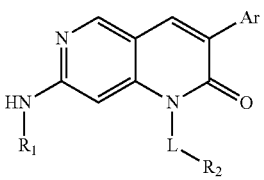

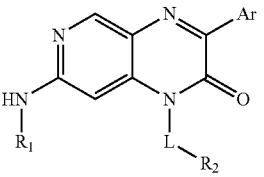

wherein Ar, $R_1$ and $R_2$ are as defined above.

Preferred embodiments of the invention include those where $R_1$ is alkylamino. Preferably, the alkylamino is $-(CH_2)_n NR_{10}R_{11}$ where n is an integer from 1-6, $R_{10}$ is H or alkyl, and $R_{11}$ is H or alkyl, or $R_{10}$ and $R_{11}$ taken together form a non-aromatic heterocyclic ring.

In some embodiments of the invention, L is a radical of Formula (B), (C) or (H) as defined above. Preferably, L is a radical of Formula (B) as defined above.

In some embodiments of the invention, $R_3$, $R_4$, $R_5$ and $R_6$ are each independently hydrogen or methyl. For example, $R_3$, $R_4$, $R_5$ and $R_6$ may all be hydrogen.

In some embodiments of the invention, $R_2$ is a radical of Formula (K). Preferably, $R_7$ and $R_8$ together form a heterocyclic ring, or $R_7$ and $R_8$ may both be methyl. The heterocyclic ring may preferably be a pyrrolidinyl, piperidinyl, piperazinyl, N-alkylpiperazinyl or morpholinyl ring.

In some embodiments of the invention, the compound is a prodrug of a compound of Formula (I). The prodrug is preferably a compound where $R_2$ is a radical of Formula (MMM):

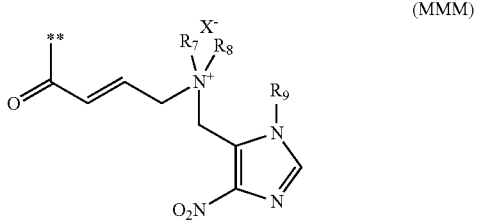
(MMM)

wherein $R_7$ and $R_8$ are as defined above, and $R_9$ is hydrogen or C1-C6 alkyl.

In some embodiments of the invention, $X^-$ is fluoride, chloride, bromide, iodide, acetate, trifluoroacetate, methanesulfonate or tosylate. Preferably, $X^-$ is bromide.

Some preferred compounds of the invention include the following:
(a) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (100);
(b) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (101);
(c) (R,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (102);
(d) (S,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (103);
(e) (S,E)-3-(2,6-dichloro-3,5-dimethoxyphenyl)-1-(1-(4-(dimethylamino)but-2-enoyl)pyrrolidin-3-yl)-7-(isopropylamino)-3,4-dihydropyrimido[4,5-d]pyrimidin-2(1H)-one (104);
(f) (S,E)-7-(cyclohexylamino)-3-(2,6-dichloro-3,5-dimethoxyphenyl)-1-(1-(4-(dimethylamino)but-2-enoyl)pyrrolidin-3-yl)-3,4-dihydropyrimido[4,5-d]pyrimidin-2(1H)-one (105);
(g) (S,E)-3-(2,6-dichloro-3,5-dimethoxyphenyl)-1-(1-(4-(dimethylamino)but-2-enoyl)pyrrolidin-3-yl)-7-(phenylamino)-3,4-dihydropyrimido[4,5-d]pyrimidin-2(1H)-one (106);
(h) (E)-3-(2,6-dichloro-3,5-dimethoxyphenyl)-1-(1-(4-(dimethylamino)but-2-enoyl)piperidin-4-yl)-7-(methylamino)-3,4-dihydropyrimido[4,5-d]pyrimidin-2(1H)-one (107);
(i) (E)-3-(2,6-dichloro-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (108);
(j) (E)-3-(2,6-dichloro-3,5-dimethoxyphenyl)-1-(1-(4-(dimethylamino)but-2-enoyl)piperidin-4-yl)-7-((tetrahydrofuran-3-yl)amino)-3,4-dihydropyrimido[4,5-d]pyrimidin-2(1H)-one (109);
(k) (E)-7-(cyclohexylamino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (110);
(l) (E)-3-(2,6-dichloro-3,5-dimethoxyphenyl)-1-(1-(4-(dimethylamino)but-2-enoyl)piperidin-4-yl)-7-((tetrahydro-2H-pyran-4-yl)amino)-3,4-dihydropyrimido[4,5-d]pyrimidin-2(1H)-one (111);
(m) (E)-3-(2,6-dichloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (112);
(n) (E)-3-(2,6-dichloro-3,5-dimethoxyphenyl)-1-(1-(4-(dimethylamino)but-2-enoyl)piperidin-4-yl)-7-((3-methoxyphenyl)amino)-3,4-dihydropyrimido[4,5-d]pyrimidin-2(1H)-one (113);
(o) (E)-3-(2,6-dichloro-3,5-dimethoxyphenyl)-1-(1-(4-(dimethylamino)but-2-enoyl)piperidin-4-yl)-7-(m-tolylamino)-3,4-dihydropyrimido[4,5-d]pyrimidin-2(1H)-one (114);
(p) (E)-3-(2,6-dichloro-3,5-dimethoxyphenyl)-1-(1-(4-(dimethylamino)but-2-enoyl)piperidin-4-yl)-7-((3-fluorophenyl)amino)-3,4-dihydropyrimido[4,5-d]pyrimidin-2(1H)-one (115);
(q) (E)-3-(2,6-dichloro-3,5-dimethoxyphenyl)-7-((3,5-difluorophenyl)amino)-1-(1-(4-(dimethylamino)but-2-enoyl)piperidin-4-yl)-3,4-dihydropyrimido[4,5-d]pyrimidin-2(1H)-one (116);
(r) (E)-3-(2,6-dichloro-3,5-dimethoxyphenyl)-7-((3,4-difluorophenyl)amino)-1-(1-(4-(dimethylamino)but-2-enoyl)piperidin-4-yl)-3,4-dihydropyrimido[4,5-d]pyrimidin-2(1H)-one (117);
(s) (E)-3-(2,6-dichloro-3,5-dimethoxyphenyl)-1-(1-(4-(dimethylamino)but-2-enoyl)piperidin-4-yl)-7-((4-fluoro-3-methoxyphenyl)amino)-3,4-dihydropyrimido[4,5-d]pyrimidin-2(1H)-one (118);
(t) (E)-7-((3-chloro-4-fluorophenyl)amino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (119);
(u) (E)-3-(2,6-dichloro-3,5-dimethoxyphenyl)-1-(1-(4-(dimethylamino)but-2-enoyl)piperidin-4-yl)-7-((4-fluorophenyl)amino)-3,4-dihydropyrimido[4,5-d]pyrimidin-2(1H)-one (120);
(v) (E)-3-(2,6-dichloro-3,5-dimethoxyphenyl)-1-(1-(4-(dimethylamino)but-2-enoyl)piperidin-4-yl)-7-((2-methoxyphenyl)amino)-3,4-dihydropyrimido[4,5-d]pyrimidin-2(1H)-one (121);
(w) (E)-3-(2,6-dichloro-3,5-dimethoxyphenyl)-1-(1-(4-(dimethylamino)but-2-enoyl)piperidin-4-yl)-7-((4-methoxyphenyl)amino)-3,4-dihydropyrimido[4,5-d]pyrimidin-2(1H)-one (122);
(x) (E)-3-(2,6-dichloro-3,5-dimethoxyphenyl)-7-(methylamino)-1-(1-(4-morpholinobut-2-enoyl)piperidin-4-yl)-3,4-dihydropyrimido[4,5-d]pyrimidin-2(1H)-one (123);
(y) (E)-3-(2,6-dichloro-3,5-dimethoxyphenyl)-7-(methylamino)-1-(1-(4-(piperidin-1-yl)but-2-enoyl)piperidin-4-yl)-3,4-dihydropyrimido[4,5-d]pyrimidin-2(1H)-one (124);
(z) (E)-N-(3-(3-(2,6-dichloro-3,5-dimethoxyphenyl)-7-(methylamino)-2-oxo-3,4-dihydropyrimido[4,5-d]pyrimidin-1(2H)-yl)propyl)-4-(dimethylamino)but-2-enamide (125);
(aa) (E)-N-(4-(3-(2,6-dichloro-3,5-dimethoxyphenyl)-7-(methylamino)-2-oxo-3,4-dihydropyrimido[4,5-d]pyrimidin-1(2H)-yl)cyclohexyl)-4-(dimethylamino)but-2-enamide (126);
(bb) (E)-N-(3-((3-(2,6-dichloro-3,5-dimethoxyphenyl)-7-(methylamino)-2-oxo-3,4-dihydropyrimido[4,5-d]pyrimidin-1(2H)-yl)methyl)phenyl)-4-(dimethylamino)but-2-enamide (127);
(cc) (E)-3-(2-chloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (128);

(dd) (E)-3-(2,6-dichloro-3,5-dimethoxyphenyl)-1-(1-(4-(dimethylamino)but-2-enoyl)piperidin-4-yl)-7-((4-morpholinophenyl)amino)-3,4-dihydropyrimido[4,5-d]pyrimidin-2(1H)-one (129);

(ee) (E)-3-(2-chloro-3,5-dimethoxyphenyl)-1-(1-(4-(dimethylamino)but-2-enoyl) piperidin-4-yl)-7-((4-morpholinophenyl)amino)-3,4-dihydropyrimido[4,5-d]pyrimidin-2(1H)-one (130);

(ff) (E)-3-(3,5-dimethoxyphenyl)-1-(1-(4-(dimethylamino)but-2-enoyl)piperidin-4-yl)-7-((4-morpholinophenyl)amino)-3,4-dihydropyrimido[4,5-d]pyrimidin-2(1H)-one (131);

(gg) (E)-6-(2,6-dichloro-3,5-dimethoxyphenyl)-8-(1-(4-(dimethylamino)but-2-enoyl)piperidin-4-yl)-2-(methylamino)pyrido[2,3-d]pyrimidin-7(8H)-one (132);

(hh) (E)-6-(2,6-dichloro-3,5-dimethoxyphenyl)-8-(1-(4-(dimethylamino)but-2-enoyl)piperidin-4-yl)-2-(isopropylamino)pyrido[2,3-d]pyrimidin-7(8H)-one (133);

(ii) (E)-6-(2,6-dichloro-3,5-dimethoxyphenyl)-8-(1-(4-(dimethylamino)but-2-enoyl)piperidin-4-yl)-2-((tetrahydrofuran-3-yl)amino)pyrido[2,3-d]pyrimidin-7(8H)-one (134);

(jj) (E)-6-(2,6-dichloro-3,5-dimethoxyphenyl)-8-(1-(4-(dimethylamino)but-2-enoyl)piperidin-4-yl)-2-((tetrahydro-2H-pyran-4-yl)amino)pyrido[2,3-d]pyrimidin-7(8H)-one (135);

(kk) (E)-2-(cyclohexylamino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (136);

(ll) (E)-6-(2,6-dichloro-3,5-dimethoxyphenyl)-8-(1-(4-(dimethylamino)but-2-enoyl)piperidin-4-yl)-2-(((tetrahydro-2H-pyran-4-l)methyl)amino)pyrido[2,3-d]pyrimidin-7(8H)-one (137);

(mm) (E)-6-(2,6-dichloro-3,5-dimethoxyphenyl)-8-(1-(4-(dimethylamino)but-2-enoyl)piperidin-4-yl)-2-(phenylamino)pyrido[2,3-d]pyrimidin-7(8H)-one (138);

(nn) (E)-6-(2,6-dichloro-3,5-dimethoxyphenyl)-8-(1-(4-(dimethylamino)but-2-enoyl)piperidin-4-yl)-2-((4-fluorophenyl)amino)pyrido[2,3-d]pyrimidin-7(8H)-one (139);

(oo) (E)-6-(2,6-dichloro-3,5-dimethoxyphenyl)-8-(1-(4-(dimethylamino)but-2-enoyl)piperidin-4-yl)-2-((3-methoxyphenyl)amino)pyrido[2,3-d]pyrimidin-7(8H)-one (140);

(pp) (E)-6-(2,6-dichloro-3,5-dimethoxyphenyl)-8-(1-(4-(dimethylamino)but-2-enoyl)piperidin-4-yl)-2-((4-fluoro-3-methoxyphenyl)amino)pyrido[2,3-d]pyrimidin-7(8H)-one (141);

(qq) (E)-2-((3-chloro-4-fluorophenyl)amino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (142);

(rr) (E)-N-(3-((6-(2,6-dichloro-3,5-dimethoxyphenyl)-2-(methylamino)-7-oxopyrido[2,3-d]pyrimidin-8(7H)-yl)methyl)phenyl)-4-(dimethylamino)but-2-enamide (143);

(ss) (E)-N-(3-((6-(2,6-dichloro-3,5-dimethoxyphenyl)-2-(ethylamino)-7-oxopyrido[2,3-d]pyrimidin-8(7H)-yl)methyl)phenyl)-4-(dimethylamino)but-2-enamide (144);

(tt) (E)-N-(3-((6-(2,6-dichloro-3,5-dimethoxyphenyl)-2-(isopropylamino)-7-oxopyrido[2,3-d]pyrimidin-8(7H)-yl)methyl)phenyl)-4-(dimethylamino)but-2-enamide (145);

(uu) (E)-N-(3-(1-(6-(2,6-dichloro-3,5-dimethoxyphenyl)-2-(methylamino)-7-oxopyrido[2,3-d]pyrimidin-8(7H)-yl)ethyl)phenyl)-4-(dimethylamino)but-2-enamide (146);

(vv) (E)-3-(2,6-dichloro-3,5-dimethoxyphenyl)-1-(1-(4-(dimethylamino)but-2-enoyl)piperidin-4-yl)-7-(isopropylamino)pyrido[3,4-b]pyrazin-2(1H)-one (147);

(ww) (E)-3-(2,6-dichloro-3,5-dimethoxyphenyl)-1-(1-(4-(dimethylamino)but-2-enoyl)piperidin-4-yl)-7-(methylamino)-1,6-naphthyridin-2(1H)-one (148);

(xx) (E)-3-(2,6-dichloro-3,5-dimethoxyphenyl)-1-(1-(4-(dimethylamino)but-2-enoyl)piperidin-4-yl)-7-(isopropylamino)-1,6-naphthyridin-2(1H)-one (149);

(yy) (S,E)-3-(3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (150);

(zz) (E)-3-(2,6-dibromo-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (151);

(aaa) (E)-6-(2,6-dibromo-3,5-dimethoxyphenyl)-8-(1-(4-(dimethylamino)but-2-enoyl)piperidin-4-yl)-2-(phenylamino)pyrido[2,3-d]pyrimidin-7(8H)-one (152);

(bbb) (E)-6-(2,6-dibromo-3,5-dimethoxyphenyl)-8-(1-(4-(dimethylamino)but-2-enoyl)piperidin-4-yl)-2-(isopropylamino)pyrido[2,3-d]pyrimidin-7(8H)-one (153);

(ccc) (E)-3-(2,6-dibromo-3,5-dimethoxyphenyl)-1-(1-(4-(dimethylamino)but-2-enoyl)piperidin-4-yl)-7-(isopropylamino)pyrido[3,4-b]pyrazin-2(1H)-one (154);

(ddd) (E)-3-(2,6-dibromo-3,5-dimethoxyphenyl)-1-(1-(4-(dimethylamino)but-2-enoyl)piperidin-4-yl)-7-(isopropylamino)-1,6-naphthyridin-2(1H)-one (155);

(eee) 1-(1-acryloylpiperidin-4-yl)-3-(2,6-dichloro-3,5-dimethoxyphenyl)-7-(methylamino)-3,4-dihydropyrimido[4,5-d]pyrimidin-2(1H)-one (156);

(fff) (E)-3-(2,6-dichloro-3,5-dimethoxyphenyl)-1-(1-(4-(dimethylamino)but-2-enoyl)piperidin-4-yl)-7-(pyridin-2-ylamino)-3,4-dihydropyrimido[4,5-d]pyrimidin-2(1H)-one (157);

(ggg) (E)-3-(2,6-dichloro-3,5-dimethoxyphenyl)-1-(1-(4-(dimethylamino)but-2-enoyl)piperidin-4-yl)-7-(pyridin-3-ylamino)-3,4-dihydropyrimido[4,5-d]pyrimidin-2(1H)-one (158);

(hhh) (E)-3-(2,6-dichloro-3,5-dimethoxyphenyl)-1-(1-(4-(dimethylamino)but-2-enoyl)piperidin-4-yl)-7-(pyridin-4-ylamino)-3,4-dihydropyrimido[4,5-d]pyrimidin-2(1H)-one (159);

(iii) (E)-3-(2,6-dichloro-3,5-dimethoxyphenyl)-1-(1-(4-(dimethylamino)but-2-enoyl)piperidin-4-yl)-7-((1-methyl-1H-pyrazol-3-yl)amino)-3,4-dihydropyrimido[4,5-d]pyrimidin-2(1H)-one (160);

(jjj) (E)-3-(2,6-dichloro-3,5-dimethoxyphenyl)-1-(1-(4-(dimethylamino)but-2-enoyl)piperidin-4-yl)-7-((5-morpholinopyridin-2-yl)amino)-3,4-dihydropyrimido[4,5-d]pyrimidin-2(1H)-one (161);

(kkk) (E)-3-(2,6-dichloro-3,5-dimethoxyphenyl)-1-(1-(4-(dimethylamino)but-2-enoyl)piperidin-4-yl)-7-(pyrimidin-4-ylamino)-3,4-dihydropyrimido[4,5-d]pyrimidin-2(1H)-one (162);

(lll) (S,E)-4-(3-(3-(2,6-dichloro-3,5-dimethoxyphenyl)-7-(methylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (200);

(mmm) (S,E)-4-(3-(3-(2,6-dichloro-3,5-dimethoxyphenyl)-7-(isopropylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (201);

(nnn) (E)-4-(4-(3-(2,6-dichloro-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (202);

(ooo) (E)-4-(4-(3-(2,6-dichloro-3,5-dimethoxyphenyl)-2-oxo-7-((tetrahydro-2H-pyran-4-yl)amino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (203);

(ppp) (E)-4-(4-(3-(2,6-dichloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (204);

(qqq) (E)-4-(4-(3-(2,6-dichloro-3,5-dimethoxyphenyl)-7-((4-fluorophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (205);

(rrr) (E)-4-(4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (206);

(sss) (E)-4-(4-(3-(2,6-dibromo-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (207);

(ttt) (E)-4-(4-(6-(2,6-dichloro-3,5-dimethoxyphenyl)-2-(methylamino)-7-oxopyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (208);

(uuu) (E)-4-(4-(6-(2,6-dichloro-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (209);

(vvv) (E)-4-(4-(6-(2,6-dibromo-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (210);

(www) (E)-4-(4-(6-(2,6-dichloro-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (211);

(xxx) (E)-4-(4-(6-(2,6-dibromo-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (212);

(yyy) (E)-4-((3-((6-(2,6-dichloro-3,5-dimethoxyphenyl)-2-(isopropylamino)-7-oxopyrido[2,3-d]pyrimidin-8(7H)-yl)methyl)phenyl)amino)-N,N-dimethyl-N-((1-methyl-4-nitro-1H-imidazol-5-yl)methyl)-4-oxobut-2-en-1-aminium bromide (213);

(zzz) (E)-4-((4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)cyclohexyl)amino)-N,N-dimethyl-N-((1-methyl-4-nitro-1H-imidazol-5-yl)methyl)-4-oxobut-2-en-1-aminium bromide (214);

(aaaa) (E)-4-(4-(3-(2,6-dichloro-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (215);

(bbbb) (E)-4-(4-(3-(2,6-dibromo-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (216);

(cccc) (E)-4-(4-(3-(2-chloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (217);

(dddd) (E)-4-(4-(3-(2,6-dichloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (218);

(eeee) (E)-4-(4-(3-(2-chloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (219);

(ffff) (E)-4-(4-(3-(3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (220);

(gggg) (E)-4-(4-(3-(2,6-dichloro-3,5-dimethoxyphenyl)-2-oxo-7-(pyridin-2-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (221);

(hhhh) (E)-4-(4-(3-(2,6-dichloro-3,5-dimethoxyphenyl)-2-oxo-7-(pyridin-3-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (222);

(iiii) (E)-4-(4-(3-(2,6-dichloro-3,5-dimethoxyphenyl)-2-oxo-7-(pyridin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (223);

(jjjj) (E)-4-(4-(3-(2,6-dichloro-3,5-dimethoxyphenyl)-7-((1-methyl-1H-pyrazol-3-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (224);

(kkkk) (E)-4-(4-(3-(2,6-dichloro-3,5-dimethoxyphenyl)-7-((5-morpholinopyridin-2-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (225);

(llll) (E)-4-(4-(3-(2,6-dichloro-3,5-dimethoxyphenyl)-2-oxo-7-(pyrimidin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (226); and (mmmm) (E)-3-(2,6-dichloro-3,5-dimethoxyphenyl)-1-(1-(4-(dimethylamino)but-2-enoyl)piperidin-4-yl)-7-(phenylamino)-1,6-naphthyridin-2(1H)-one (232).

In another aspect of the invention there is provided a pharmaceutical composition comprising a compound of Formula (I), together with a pharmaceutically acceptable carrier.

In a further aspect of the invention there is provided a method of treating of a hyper-proliferative disease associated with inhibition of a fibroblast growth factor receptor (FGFR) kinase comprising administering to a human or other animal a therapeutically effective amount of a compound of Formula (I).

In another aspect of the invention there is provided the use of a compound of Formula (I) in the manufacture of a medicament for treating of a hyper-proliferative disease associated with inhibition of a fibroblast growth factor receptor (FGFR) kinase.

In another aspect of the invention there is provided a pharmaceutical composition comprising a compound of Formula (I) for use in the treatment of a hyper-proliferative disease associated with inhibition of a fibroblast growth factor receptor (FGFR) kinase.

In the abovementioned aspects of the invention, the FGFR kinase may be FGFR-1, FGFR-2, FGFR-3 or FGFR-4, or any other FGFR kinase. In preferred embodiments of the invention, the hyper-proliferative disease is cancer. Examples of cancer include, but are not limited to, lung cancer, breast cancer, ovarian cancer, endometrial cancer, urothelial cancer, bladder cancer, gastric cancer, head and neck cancer, multiple myeloma, prostate cancer, leukaemia, brain cancer, eye cancer, liver cancer, and skin cancer.

In the abovementioned aspects of the invention, the compound of Formula (I) may be any compound of Formulae (II) to (VIII). Specific examples of such compounds are listed above. It will be appreciated that the compounds of the invention are not limited to those compounds listed and may be any compound of Formula (I) as defined above.

BRIEF DESCRIPTION OF THE FIGURES

FIG. 3 shows some examples of known NMQ prodrugs.

FIG. 4 shows the mechanism of action of the NMQ prodrug TH-4000 (tarloxotinib).

DETAILED DESCRIPTION

Definitions

Figure 1:
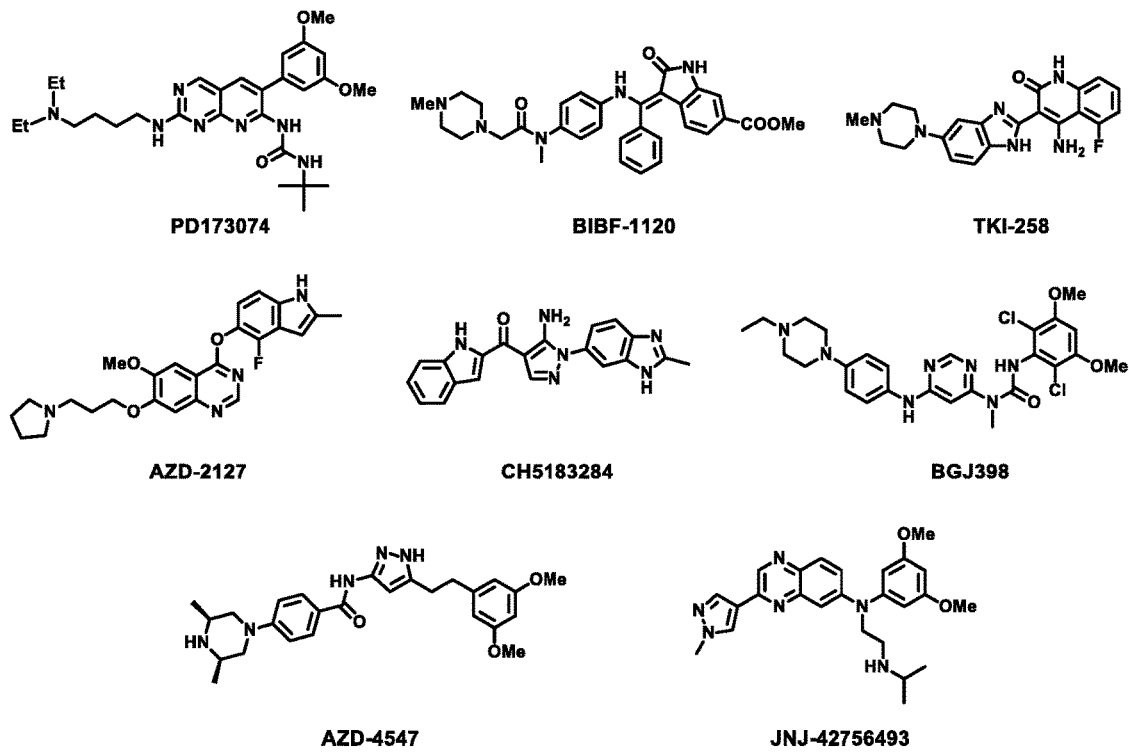
FIG. 1 shows some examples of known reversible FGFR inhibitors.
Figure 2:
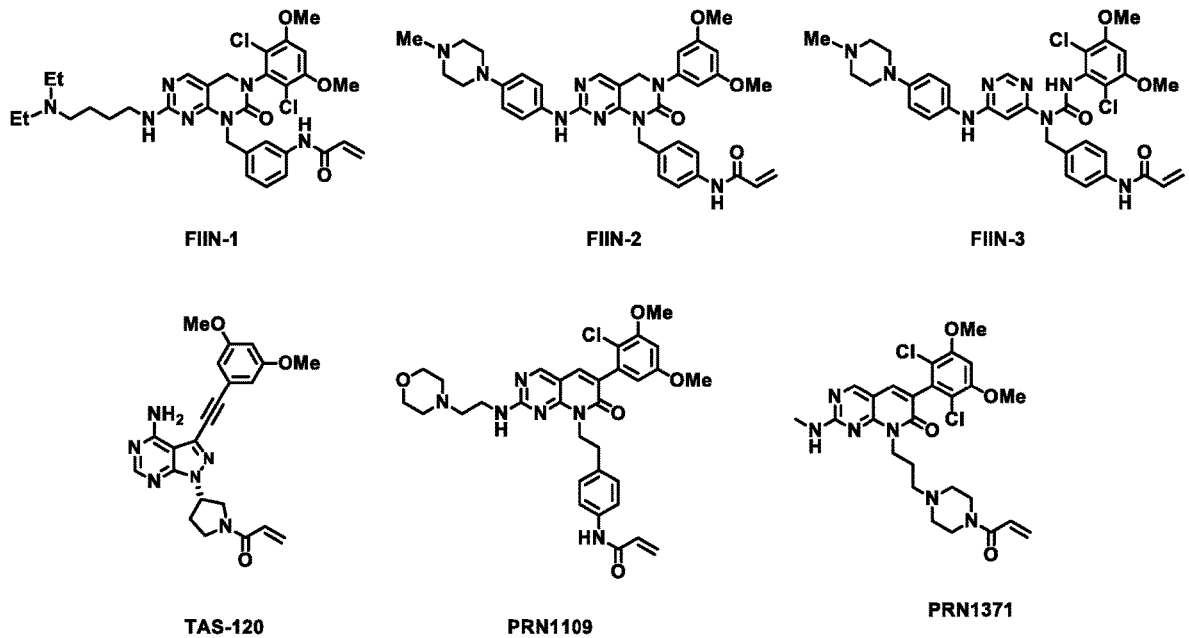
FIG. 2 shows the known irreversible FGFR inhibitors FIIN-1, FIIN-2, FIIN-3, TAS-120, PRN1109 and PRN1371.

The term "alkyl" means any saturated hydrocarbon radical and is intended to include both straight-chain and branched-chain alkyl groups. Examples of alkyl groups include, but are not limited to, methyl, ethyl, n-propyl, iso-propyl, n-butyl, iso-butyl, sec-butyl, t-butyl, n-pentyl, 1,1-dimethylpropyl, 1,2-dimethylpropyl, 2,2-dimethylpropyl, 1-ethylpropyl, 2-ethylpropyl, n-hexyl, and 1-methyl-2-ethylpropyl. The term "C1-C6 alkyl" means any alkyl radical having up to 6 carbon atoms.

The term "alkenyl" means any hydrocarbon radical having at least one double bond, and is intended to include both straight- and branched-chain alkenyl groups. Examples of alkenyl groups include, but are not limited to, ethenyl, n-propenyl, iso-propenyl, n-butenyl, iso-butenyl, sec-butenyl, t-butenyl, n-pentenyl, 1,1-dimethylpropenyl, 1,2-dimethylpropenyl, 2,2-dimethylpropenyl, 1-ethylpropenyl, 2-ethylpropenyl, n-hexenyl, and 1-methyl-2-ethylpropenyl.

The term "alkynyl" means any hydrocarbon radical having at least one triple bond, and is intended to include both straight- and branched-chain alkynyl groups. Examples of alkynyl groups include, but are not limited to, ethynyl, n-propynyl, iso-propynyl, n-butynyl, iso-butynyl, sec-butynyl, t-butynyl, n-pentynyl, 1,1-dimethylpropynyl, 1,2-dimethylpropynyl, 2,2-dimethylpropynyl, 1-ethylpropynyl, 2-ethylpropynyl, n-hexynyl, and 1-methyl-2-ethylpropynyl.

The term "alkylene" means a diradical corresponding to an alkyl group. Examples of alkylene groups include, but are not limited to, methylene and ethylene.

The term "cycloalkyl" means a saturated or partially saturated non-aromatic carbocyclic group, having preferably from 3 to 8 ring carbon atoms. Examples of cycloalkyl groups include, but are not limited to, cyclopropyl, cyclobutyl, cyclopentyl, cyclohexyl, cycloheptyl, and cyclooctyl.

The term "heterocyclyl" means a cycloalkyl group where one or more of the ring carbon atoms is replaced with one or more heteroatoms, e.g. nitrogen, oxygen or sulfur. Examples of heterocyclyl groups include, but are not limited to, pyrrolidinyl, pyrrolinyl, pyrazolidinyl, aziridinyl, thiiranyl, 1,2-dithietanyl, morpholinyl, furanyl, pyranyl, thiophenyl, isoxazolyl, furazanyl, tetrahydrofuranyl, thietanyl, piperidinyl, azetidinyl, oxiranyl, epoxide, and thiacyclohexyl.

The term "alkoxy" means an alkyl group singular bonded to an oxygen atom. Examples of alkoxy groups include, but are not limited to, methoxy, ethoxy, propoxy, n-butoxy, iso-butoxy, sec-butoxy, and t-butoxy.

The term "aryl" means an aromatic radical. Examples include monocyclic groups as well as fused groups such as bicyclic groups and tricyclic groups. Examples include, but are not limited to, phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopenta-cyclooctenyl, and benzocyclooctenyl.

The term "heteroaryl" means a heterocyclic aromatic (heteroaromatic) radical. Examples include monocyclic groups as well as fused groups such as bicyclic groups and tricyclic groups. Examples include, but are not limited to, pyridyl, pyrrolyl, pyridazinyl, pyrimidinyl, pyrazinyl, triazolyl, tetrazolyl, benzotriazolyl, pyrazolyl, imidazolyl, benzimidazolyl, indolyl, isoindolyl, indolizinyl, purinyl, indazolyl, furyl, pyranyl, benzofuryl, isobenzofuryl, thienyl, thiazolyl, isothiazolyl, benzothiazolyl, oxazolyl, and isoxazolyl.

The term "aralkyl" means an aryl group which is attached to an alkylene moiety, where aryl and alkylene are as defined above. Examples include benzyl group.

The term "prodrug" as used herein refers to a drug substance that is inactive or weakly active in the intended pharmacological actions and is converted into the pharmacologically active or more active agent by metabolic or physico-chemical transformation.

The term "pharmaceutical composition" as used herein refers to a mixture of one or more of the compounds of Formula (I), or pharmaceutically acceptable salts, or hydrates thereof, with other chemical components, such as physiologically acceptable carriers and excipients. The purpose of a pharmaceutical composition is to facilitate administration of a compound to an organism.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carrier may also be saline, gum acacia, gelatin, starch paste, talc, keratin, colloidal silica, urea, and the like. In addition, auxiliary, stabilizing, thickening, lubricating and colouring agents may be used. Other examples of suitable pharmaceutical carriers are described in "Remington's Pharmaceutical Sciences" by E.W. Martin, herein incorporated by reference.

The term "effective amount" means an amount of a compound that, when administered to a subject for treating a disease, is sufficient to effect such treatment for the disease. The "effective amount" will vary depending on the disease to be treated, the compound to be administered, the severity of the disease treated, the age and relative health of the subject, the route and form of administration, whether the treatment is monotherapy or combination therapy, the judgement of the attending clinician, and other factors.

The term "pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "pharmaceutically acceptable salt" as used herein refers to any salt of a compound provided herein which retains its biological properties and which is not toxic or otherwise undesirable for pharmaceutical use and is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of Formula (I).

COMPOUNDS OF THE INVENTION

The compounds of the invention are defined according to Formula (I) above. The applicants have found that the compounds of the invention not only exhibit greater potency as inhibitors of FGFR kinases in vitro than previously known compounds, but were also found to be irreversible inhibitors of FGFR-3 as well as FGFR-1 and FGFR-2. This surprising finding strongly indicates greater effectiveness as therapeutic agents for a range of hyper-proliferative diseases, particularly cancer. Further, the applicants found that prodrugs of the compounds are effective for improving the toxicity profile of the compounds of the invention.

The prodrugs may be any suitable prodrug capable of delivering the active inhibitor. Preferred prodrugs of the invention are quaternary nitrogen salt prodrugs defined generally by the Formula (I) where $R_2$ is a radical of Formula (MMM):

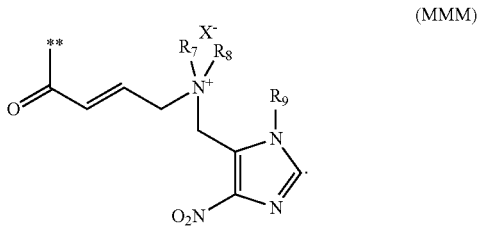

(MMM)

The preparation of prodrugs of this type is described in the Examples as well as in WO 2011/028135.

Therapeutic Applications of Compounds of the Invention

The compounds of the invention have application in any therapeutic approach in which inhibition of the activity of a kinase is desirable. The invention therefore relates to methods for treating and preventing diseases, for example, hyper-proliferative, inflammatory and angiogenesis disorders and osteoporosis in mammals by administering a compound of this invention or a pharmaceutical composition comprising one or more compounds of this invention.

The invention particularly relates to a method of treating or preventing cancer and other hyper-proliferative disorders by administering a compound of the invention or a pharmaceutical composition comprising one or more compounds of the invention, whether alone as a monotherapy or in combination with a second anti-proliferative agent.

Optional anti-proliferative agents which can also be administered include, but are not limited to, compounds listed on the cancer chemotherapy drug regimens in the 14th Edition of the Merck Index (2006), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Additional anti-proliferative agents include other molecular targeted agents which modulate parallel pathways such as MEK 1/2 inhibitors, AKT inhibitors and mTOR inhibitors, monoclonal antibodies, oxaliplatin, gemcitabine, gefinitib, taxotere, ara A, ara C, herceptin, BCNU, CCNU, DTIC, and actinomycin D. Still further anti-proliferative agents include, but are not limited to, those compounds acknowledged to be used in the treatment of neoplastic diseases in *Goodman and Gilman's The Pharmacological Basis of Therapeutics* (Eleventh Edition), editor Molinoff et al., publ. by McGraw-Hill, pages 1225-1287 (2006), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, tenipdside, testosterone propionate, thiotepa, trimethylmelamine, uridine, and vinorelbine.

Cancer and hyperproliferative disorders as used herein include, but are not limited to, solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to, invasive ductal carcinoma, invasive lobular carcinoma, ductal carcinoma in situ, and lobular carcinoma in situ. Examples of cancers of the respiratory tract include, but are not limited to, small-cell and non-small-cell lung carcinoma, as well as bronchial adenoma and pleuropulmonary blastoma. Examples of brain cancers include, but are not limited to, brain stem and hypophthalmic glioma, cerebellar and cerebral astrocytoma, medulloblastoma, ependymoma, as well as neuroectodermal and pineal tumour.

Tumours of the male reproductive organs include, but are not limited to, prostate and testicular cancer. Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, esophageal, gall bladder, gastric, pancreatic, rectal, small-intestine, and salivary gland cancers. Tumours of the urinary tract include, but are not limited to, bladder, penile, kidney, renal pelvis, ureter, and urethral cancers. Eye cancers include, but are not limited to, intraocular melanoma and retinoblastoma. Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer. Head-and-neck cancers include, but are not limited to, laryngeal cancer, hypopharyngeal cancer, nasopharyngeal cancer, oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to, sarcoma of the soft tissue, osteosarcoma, malignant fibrous histiocytoma, lymphosarcoma, and rhabdomyosarcoma. Leukemias include, but are not limited to, acute myeloid leukemia, acute lymphoblastic leukemia, chronic lymphocytic leukemia, chronic myelogenous leukemia, and hairy cell leukemia.

These disorders have been well characterised in man, but also exist with a similar etiology in other warm-blooded animals, and can be treated by pharmaceutical compositions of the present invention.

Conditions within a human or other warm-blooded animal which can be treated by administering a compound of this invention include tumour growth, retinopathy, including diabetic retinopathy, ischemic retinal-vein occlusion, retinopathy of prematurity and age related macular degeneration; psoriasis, or bullous disorder associated with subepidermal blister formation, including bullous pemphigoid, erythema multiforme, or dermatitis herpetiformis, rheumatoid arthritis, osteoarthritis, septic arthritis, tumour metastasis, periodontal disease, cornal ulceration, proteinuria, coronary thrombosis from atherosclerotic plaque, aneurismal aorta, dystrophobic epidermolysis bullosa, degenerative cartilage loss following traumatic joint injury, osteopenias mediated by MMP activity, tempero mandibular joint disease or demyelating disease of the nervous system.

It will be appreciated by those skilled in the art that a particular method of therapy will employ a selected route of administration which will in turn depend on a variety of factors, all of which are considered routinely when administering therapeutics. It will be further appreciated by one skilled in the art that the optimal course of treatment, i.e., the mode of treatment and the daily number of doses of a compound of this invention given for a defined number of days, can be ascertained by those skilled in the art using conventional treatment tests.

Therapeutic dosages will likely be in the range of 1 mg to 3000 mg per day. The specific dose level selected for any particular patient will depend upon a variety of factors, including the activity of the specific compound employed, the age, body weight, general health, sex, diet, time of administration, route of administration, and rate of excretion, drug combination and the severity of the condition undergoing therapy.

Pharmaceutical Compositions of Compounds of the Invention

The invention also includes pharmaceutical compositions comprising a compound of this invention and a pharmaceutically acceptable carrier.

The compounds may be administered orally, topically, parenterally, by inhalation or spray or rectally in dosage unit formulations. The term 'administration by injection' includes intravenous, intramuscular, subcutaneous and parenteral injections, as well as use of infusion techniques. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavouring agents, colouring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally occurring phosphatide, for example, lecithin, or condensation products or an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavouring and colouring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavouring and colouring agents.

The compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

Synthesis of Compounds

A general method of synthesis of preferred examples of Formula II of the invention is outlined in Scheme 1. Commercially available ethyl 4-chloro-2-(methylthio)-pyrimidine-5-carboxylate (300) was reacted with Boc-protected amines to yield adducts of Formula VIIa, which were reduced to alcohols of Formula VIII by treatment with lithium aluminium hydride. Oxidation of the alcohols (VIII) by $MnO_2$ afforded aldehydes of Formula IX. Next, the aniline intermediates of Formula X were readily prepared by reductive amination of the aldehydes (IX) with 3,5-dimethoxyaniline. Cyclisation of the anilines (X) using triphosgene produced the heterocyclic intermediates of Formula XI. Chlorination with $SO_2Cl_2$ yielded compounds of Formula XII, which were oxidised with m-CPBA to give the key methylsulfonyl intermediates of Formula XIII. Nucleophilic substitution of methylsufonyl intermediates (XIII) with different amines, followed by Boc-deprotection employing trifluoroacetic acid, afforded compounds of Formula XIV, which were coupled with trans-4-dimethylaminocrotonic acid hydrochloride to afford tertiary amine compounds of Formula IIa. Quaternisation of these by reaction with the appropriate 4-nitroimidazole precursor then gave quaternary ammonium salts of Formula IIb.

Scheme 1:

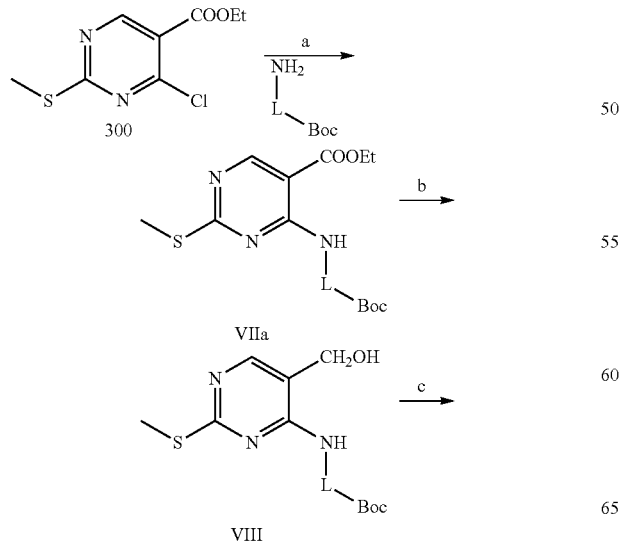

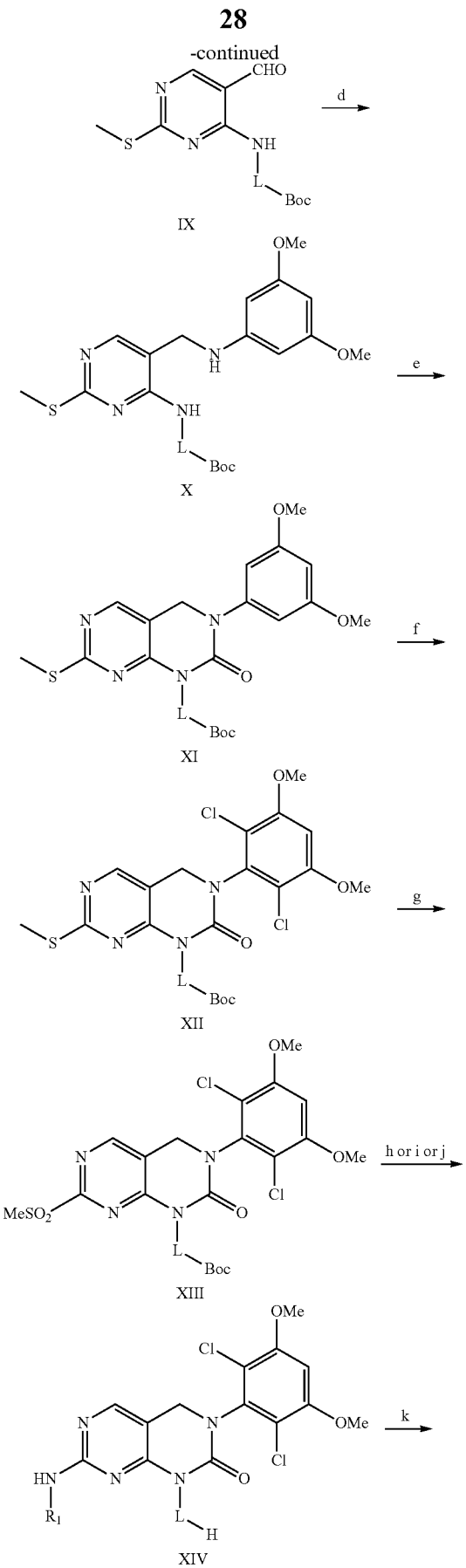

Scheme 2:

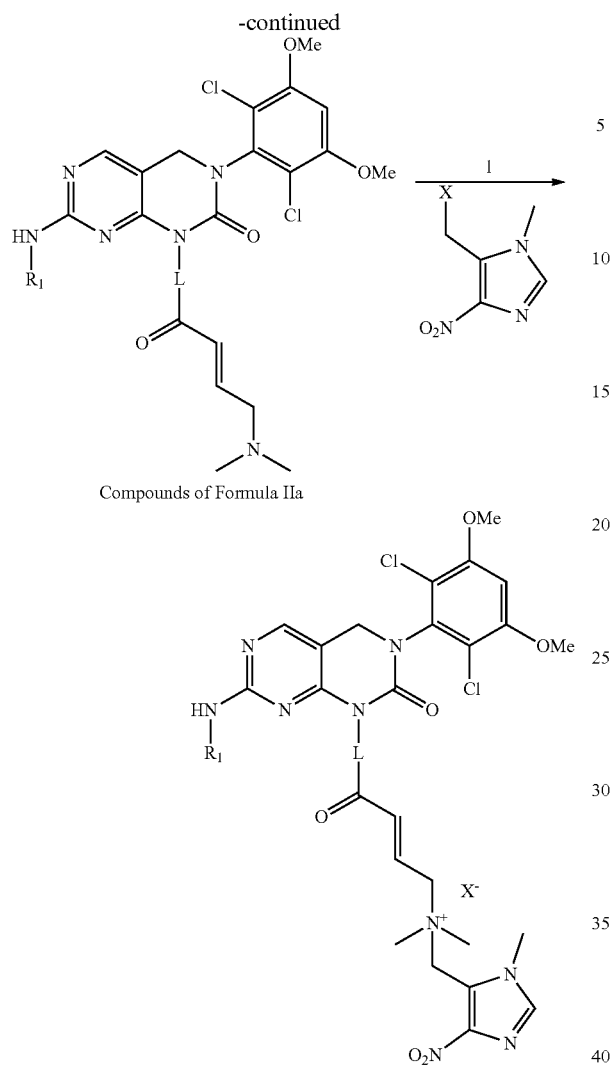

Compounds of Formula IIa

Compounds of Formula IIb

Reagents and conditions: (a) K₂CO₃, DMF, 60° C.; (b) LiAlH₄, THF, -40° C. to 0° C.; (c) MnO₂, CH₂Cl₂, rt, overnight; (d) 3,5-Dimethoxyaniline, CH₃COOH, NaBH₄, CH₃OH, 0° C. to rt; (e) triphosgene, ethyl di-isopropylamine, CH₂Cl₂, 0° C. to rt; (f) (1) SO₂Cl₂, CH₃CN, 0° C.; (2) DIPEA, Di-tert-butyl dicarbonate, CH₂Cl₂; (g) 3-chloroperbenzoic acid, CH₂Cl₂, rt; (h) (1) R₁NH₂, TFA, 1,4-dioxane, 110° C.; (2) TFA, CH₂Cl₂, rt; (i) (1) R₁NH₂, 1,4-dioxane, 110° C.; (2) TFA, CH₂Cl₂, rt; (j) (1) R₁NH₂, KOᵗBu, DMSO, rt; (2) TFA, CH₂Cl₂, rt; (k) HATU, DIPEA, trans-4-Dimethylaminocrotonic acid hydrochloride, CH₃CN, rt; (l) DMA, rt.

A general method of synthesis of preferred examples of Formula III of the invention is outlined in Scheme 2. Aldehydes (IX) prepared as described in Scheme 1 were condensed with methyl 2-(3,5-dimethoxyphenyl)acetate to give compounds of Formula XV. Chlorination with SO₂Cl₂ yielded compounds of Formula XVI, which were oxidised with m-CPBA to give the key methylsulfonyl intermediates of Formula XVII. Nucleophilic substitution of methylsufonyl intermediates (XVII) with different amines, followed by Boc-deprotection employing trifluoroacetic acid, afforded compounds of Formula XVIII, which were coupled with trans-4-dimethylaminocrotonic acid hydrochloride to afford tertiary amine compounds of Formula IIIa. Quaternisation of these by reaction with the appropriate 4-nitroimidazole precursor then gave quaternary ammonium salts of Formula IIIb.

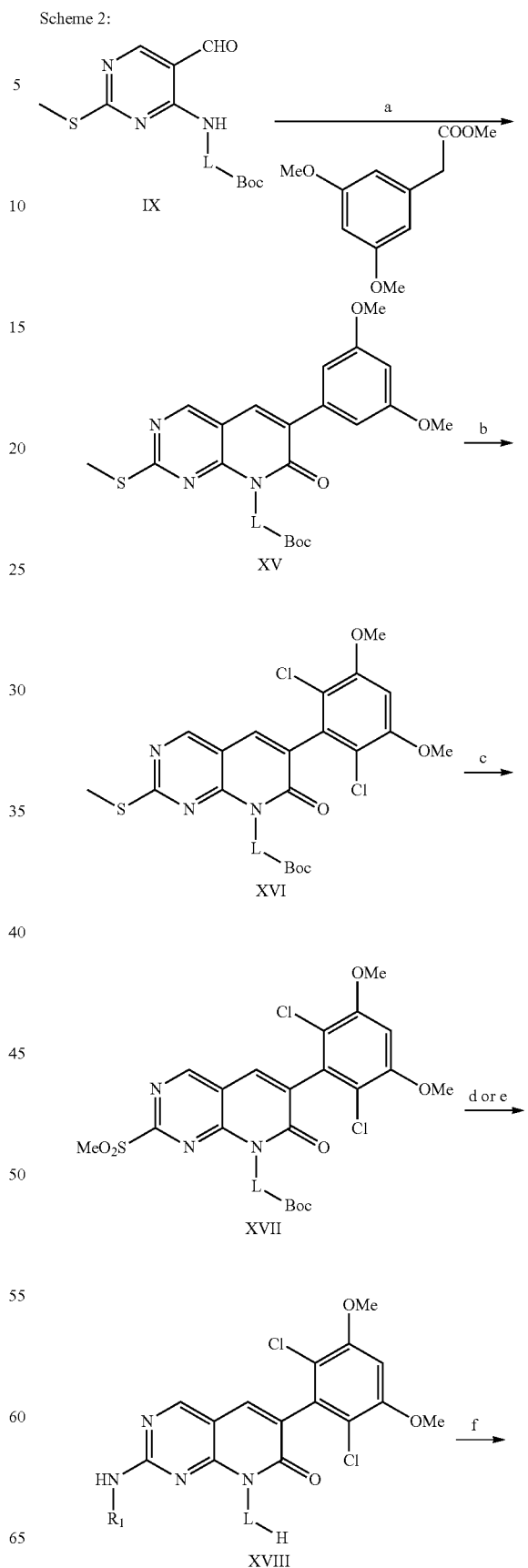

-continued

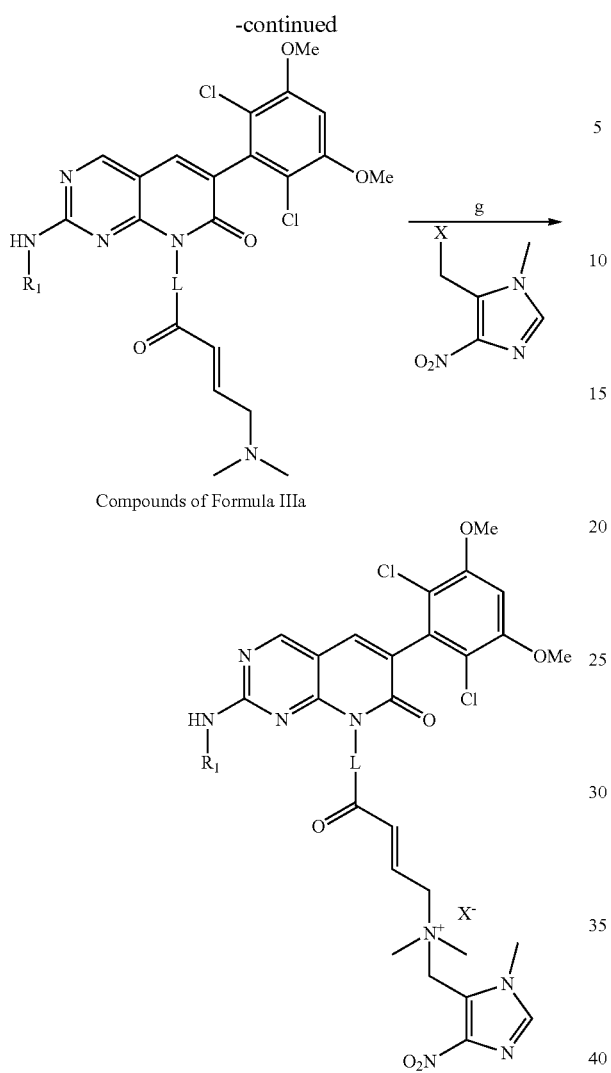

Compounds of Formula IIIa

Compounds of Formula IIIb

Reagents and conditions: (a) K₂CO₃, DMF, 110° C.; (b) (1) SO₂Cl₂, CH₃CN, 0° C.; (2) DIPEA, Di-tert-butyl dicarbonate, CH₂Cl₂; (c) 3-chloroperbenzoic acid, CH₂Cl₂, rt; (d) (1) R₁NH₂, 1,4-dioxane, 100° C.; (2) TFA, CH₂Cl₂, rt; (e) (1) R₁NH₂, KO$^t$Bu, DMSO, rt; (2) TFA, CH₂Cl₂, rt; (f) HATU, DIPEA, trans-4-Dimethylaminocrotonic acid hydrochloride, CH₃CN, rt; (g) DMA, rt.

A general method of synthesis of preferred examples of Formula VI of the invention is outlined in Scheme 3. Commercially available ethyl 4,6-dichloronicotinate (323) was reacted with Boc-protected amines to yield adducts of Formula XIX, which were reduced to alcohols of Formula XX by treatment with lithium borohydride or lithium aluminium hydride. Oxidation of the alcohols (XX) by MnO₂ afforded aldehydes of Formula XXI. Aldehydes (XXI) were condensed with methyl 2-(3,5-dimethoxyphenyl)acetate under basic conditions to give compounds of Formula XXII. Chlorination with SO₂Cl₂ yielded compounds of Formula XXIII. Nucleophilic substitution of chloropyridyl intermediates (XXIII) with different amines employing either thermal or palladium catalysis gave intermediates of Formula XXIV. Boc-deprotection employing trifluoroacetic acid, afforded compounds of Formula XXV, which were coupled with trans-4-dimethylaminocrotonic acid hydrochloride to afford tertiary amine compounds of Formula VIa. Quaternisation of these by reaction with the appropriate 4-nitro-imidazole precursor then gave quaternary ammonium salts of Formula VIb.

Scheme 3:

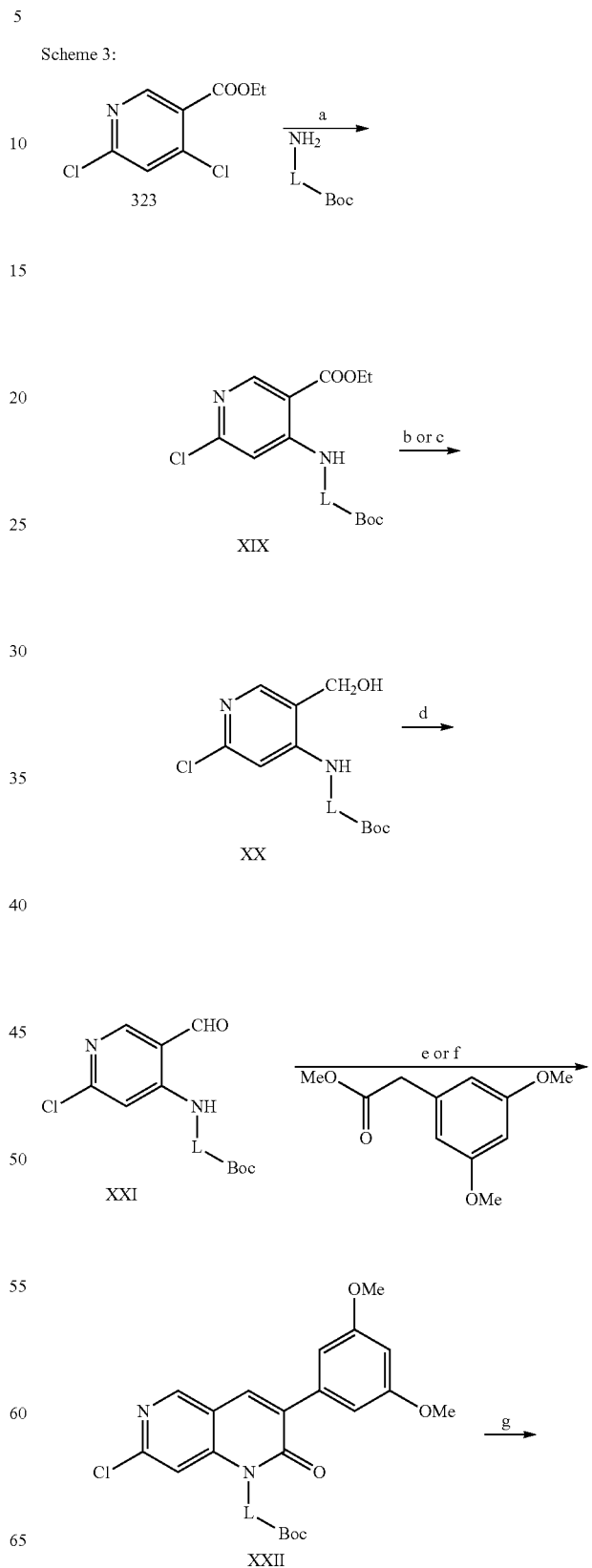

-continued

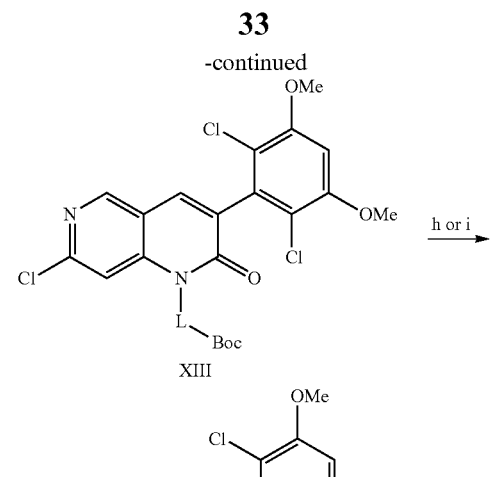

XIII

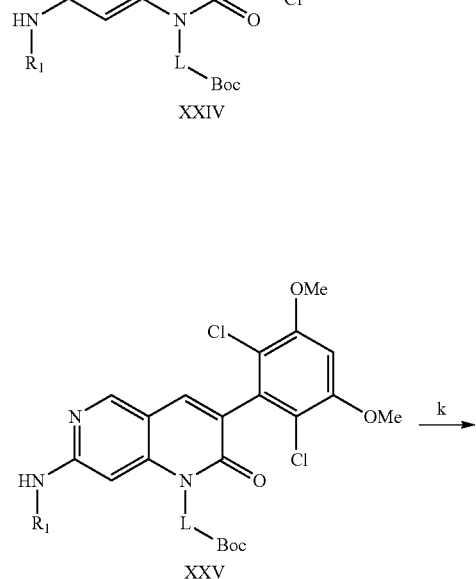

XXIV

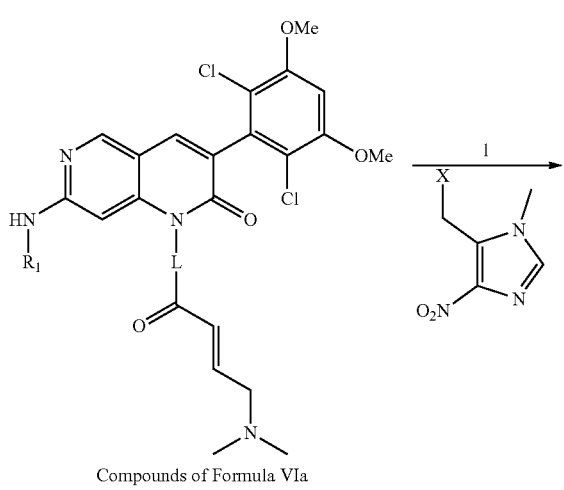

XXV

Compounds of Formula VIa

-continued

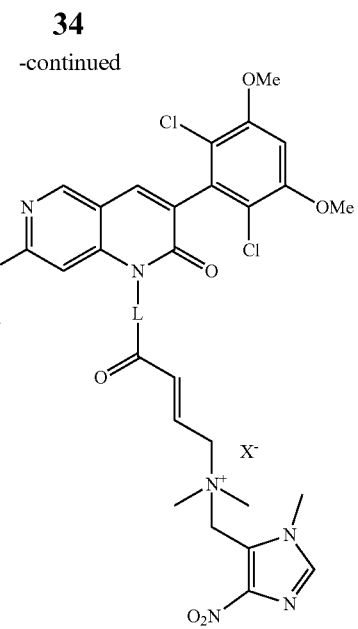

Compounds of Formula VIb

Reagents and conditions: (a) DIPEA, CH₃CN, 70° C.; (b) LiBH₄, THF/MeOH, 55° C.; (c) LiAlH₄, THF, -70° C. to 0° C.; (d) MnO₂, CH₂Cl₂, rt, overnight; (e) K₂CO₃, DMF, 100° C.; (f) Cs₂CO₃, DMF, 100° C.; (g) (1) SO₂Cl₂, CH₃CN, -10° C.; (2) DIPEA, Di-tert-butyl dicarbonate, CH₂Cl₂; (h) R₁NH₂, 1,4-dioxane, 110° C.; (i) R₁NH₂, 1,4-dioxane, XPhos, Cs₂CO₃, Pd₂(dba)₃, 120° C.; (j) TFA, CH₂Cl₂, rt; (k) HATU, DIPEA, trans-4-Dimethylaminocrotonic acid hydrochloride, CH₃CN, rt; (l) DMA, rt.

A general method of synthesis of preferred examples of Formula II of the invention is outlined in Scheme 4. Commercially available ethyl 4-chloro-2-(methylthio)-pyrimidine-5-carboxylate (300) was reacted with nitrophenylmethanamines to yield adducts of Formula XXVI, which were reduced to alcohols of Formula XXVII by treatment with lithium aluminium hydride. Oxidation of the alcohols (XXVII) by MnO₂ afforded aldehydes of Formula XXVIII. Next, the aniline intermediates of Formula XXIX were readily prepared by reductive amination of the aldehydes (XXVIII) with 3,5-dimethoxyaniline. Cyclisation of the anilines (XXIX) using triphosgene produced the heterocyclic intermediates of Formula XXX. Chlorination with SO₂Cl₂ yielded compounds of Formula XXXI, which were oxidised with m-CPBA to give the key methylsulfonyl intermediates of Formula XXXII. Nucleophilic substitution of methylsufonyl intermediates (XXXII) with different amines afforded compounds of Formula XXXIII, which were reduced employing sodium borohydride to give amines XXXIV. These were coupled with trans-4-dimethylaminocrotonic acid hydrochloride to afford tertiary amine compounds of Formula IIc. Quaternisation of these by reaction with the appropriate 4-nitroimidazole precursor then gave quaternary ammonium salts of Formula IId.

Scheme 4:

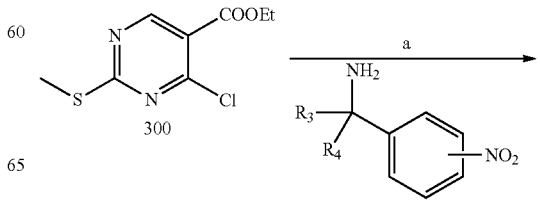

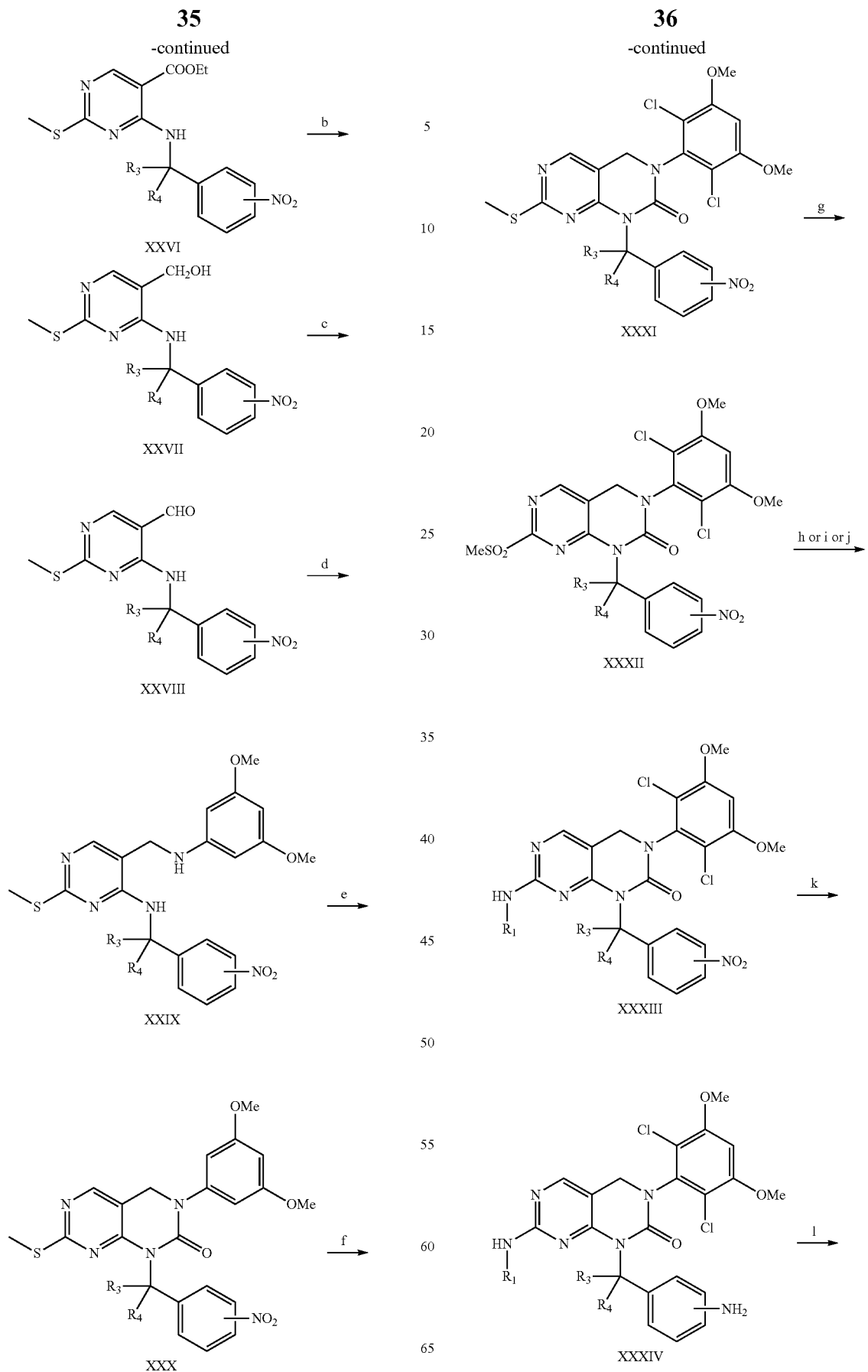

Scheme 5:

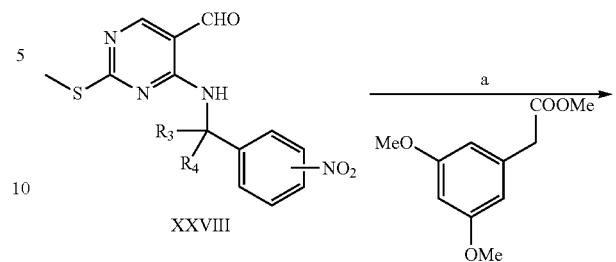

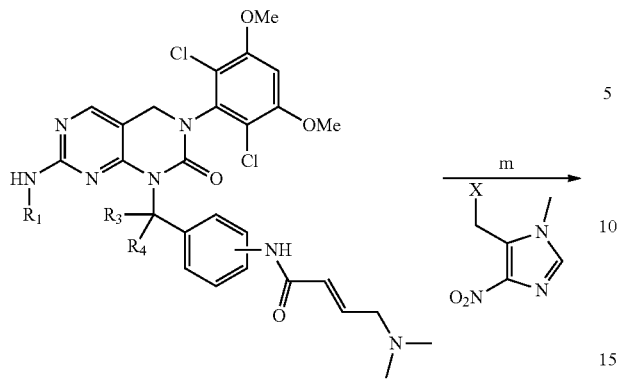

Compounds of Formula IIc

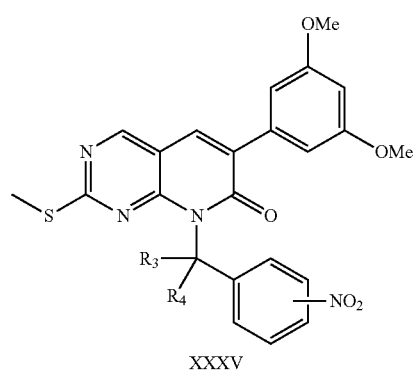

XXXV

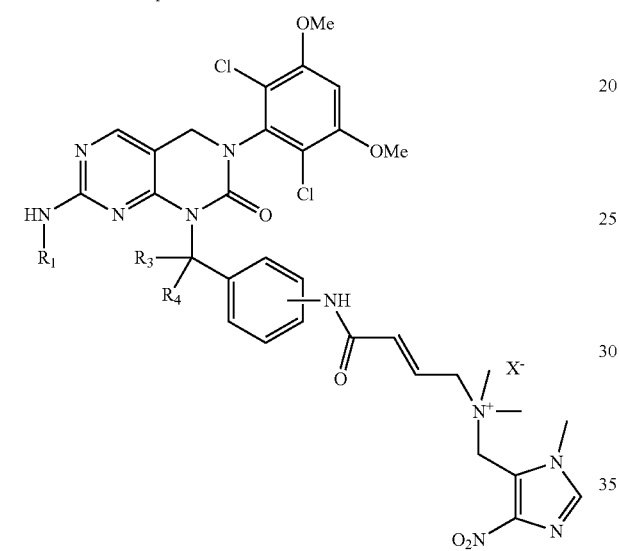

Compounds of Formula IId

Reagents and conditions: (a) K$_2$CO$_3$, DMF, 60° C.; (b) LiAlH$_4$, THF, -50° C. to 0° C.; (c) MnO$_2$, CH$_2$Cl$_2$, rt, overnight; (d) 3,5-Dimethoxyaniline, CH$_3$COOH, NaBH$_4$, CH$_3$OH, 0° C. to rt; (e) triphosgene, ethyl di-isopropylamine, CH$_2$Cl$_2$, 0° C. to rt; (f) (1) SO$_2$Cl$_2$, CH$_3$CN, 0° C.; (g) 3-chloroperbenzoic acid, CH$_2$Cl$_2$, rt; (h) R$_1$NH$_2$, TFA, 1,4-dioxane, 110° C.; (i) R$_1$NH$_2$, 1,4-dioxane, 110° C.; (j) R$_1$NH$_2$, KO$^t$Bu, DMSO, rt; (k) NaBH$_4$, NiCl$_2$·6H$_2$O, CH$_3$OH/THF. (l) HATU, DIPEA, trans-4-Dimethylaminocrotonic acid hydrochloride, CH$_3$CN, rt; (m) DMA, rt.

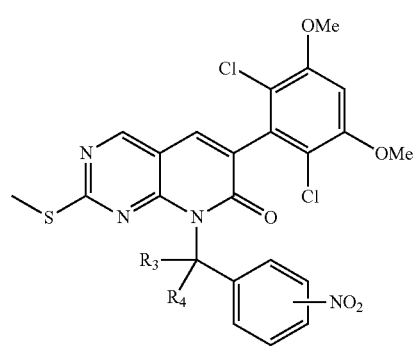

XXXVI

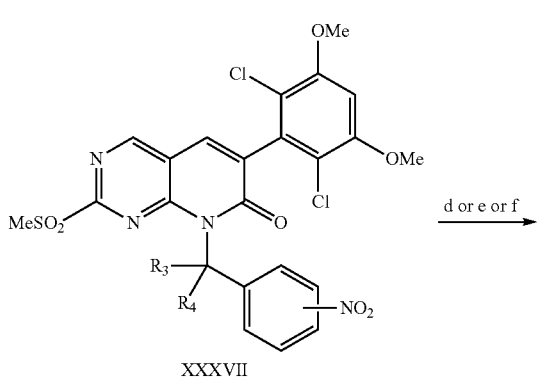

XXXVII

A general method of synthesis of preferred examples of Formula III of the invention is outlined in Scheme 5. Aldehydes (XXVIII) prepared as described in Scheme 4 were condensed with methyl 2-(3,5-dimethoxyphenyl)acetate to give compounds of Formula XXXV. Chlorination with SO$_2$Cl$_2$ yielded compounds of Formula XXXVI, which were oxidised with m-CPBA to give the key methylsulfonyl intermediates of Formula XXXVII. Nucleophilic substitution of methylsufonyl intermediates (XXXVII) with different amines then gives intermediates of Formula XXXVIII. Reduction with sodium borohydride then gives compounds of Formula XXXIX, which were coupled with trans-4-dimethylaminocrotonic acid hydrochloride to afford tertiary amine compounds of Formula Inc. Quaternisation of these by reaction with the appropriate 4-nitroimidazole precursor then gave quaternary ammonium salts of Formula IIId.

-continued

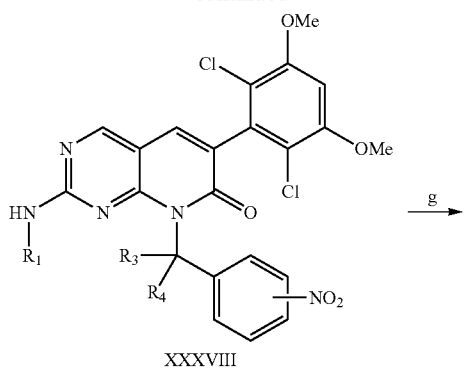

XXXVIII

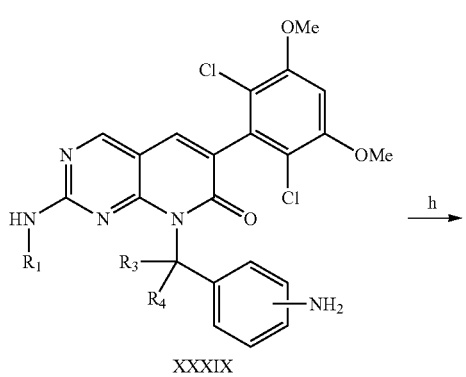

XXXIX

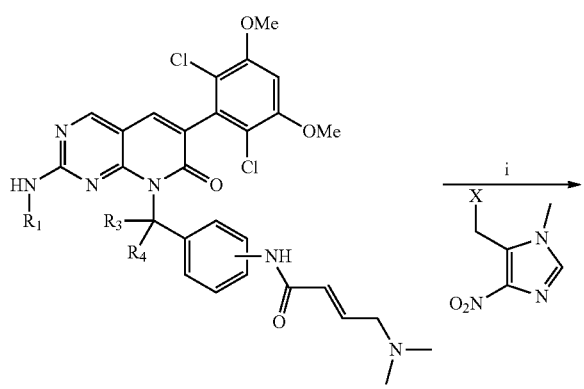

Compounds of Formula IIIc

-continued

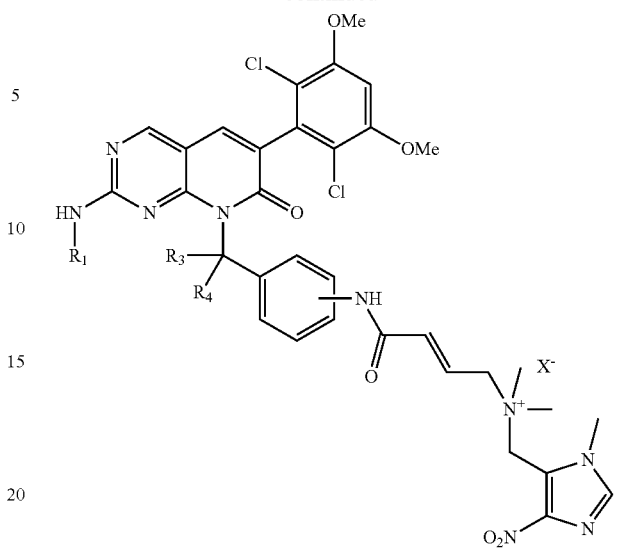

Compounds of Formula IIId

Reagents and conditions: (a) K₂CO₃, DMF, 110° C.; (b) SO₂Cl₂, CH₃CN, 0° C.; (c) 3-chloroperbenzoic acid, CH₂Cl₂, rt; (d) R₁NH₂, TFA, 1,4-dioxane, 110° C.; (e) R₁NH₂, 1,4-dioxane, 110° C.; (f) R₁NH₂, KO'Bu, DMSO, rt; (g) NaBH₄, NiCl₂·6H₂O, CH₃OH/THF; (h) HATU, DIPEA, trans-4-Dimethylaminocrotonic acid hydrochloride, CH₃CN, rt; (i) DMA, rt.

A general method of synthesis of preferred examples of Formula VI of the invention is outlined in Scheme 6. Commercially available ethyl 4,6-dichloronicotinate (323) was reacted with nitrophenylmethanamines to yield adducts of Formula XL, which were reduced to alcohols of Formula XLI by treatment with lithium aluminium hydride. Oxidation of the alcohols (XLI) by MnO₂ afforded aldehydes of Formula XLII. Aldehydes (XLII) were condensed with methyl 2-(3,5-dimethoxyphenyl)acetate under basic conditions to give compounds of Formula XLIII. Chlorination with SO₂Cl₂ yielded compounds of Formula XLIV. Nucleophilic substitution of chloropyridyl intermediates (XLIV) with different amines employing either thermal or palladium catalysis gave intermediates of Formula XLV. Reduction with sodium borohydride then afforded compounds of Formula XLVI, which were coupled with trans-4-dimethylaminocrotonic acid hydrochloride to afford tertiary amine compounds of Formula VIc. Quaternisation of these by reaction with the appropriate 4-nitroimidazole precursor then gave quaternary ammonium salts of Formula VId.

Scheme 6:

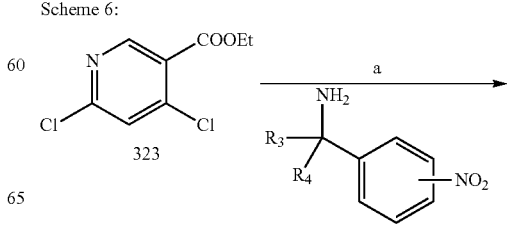

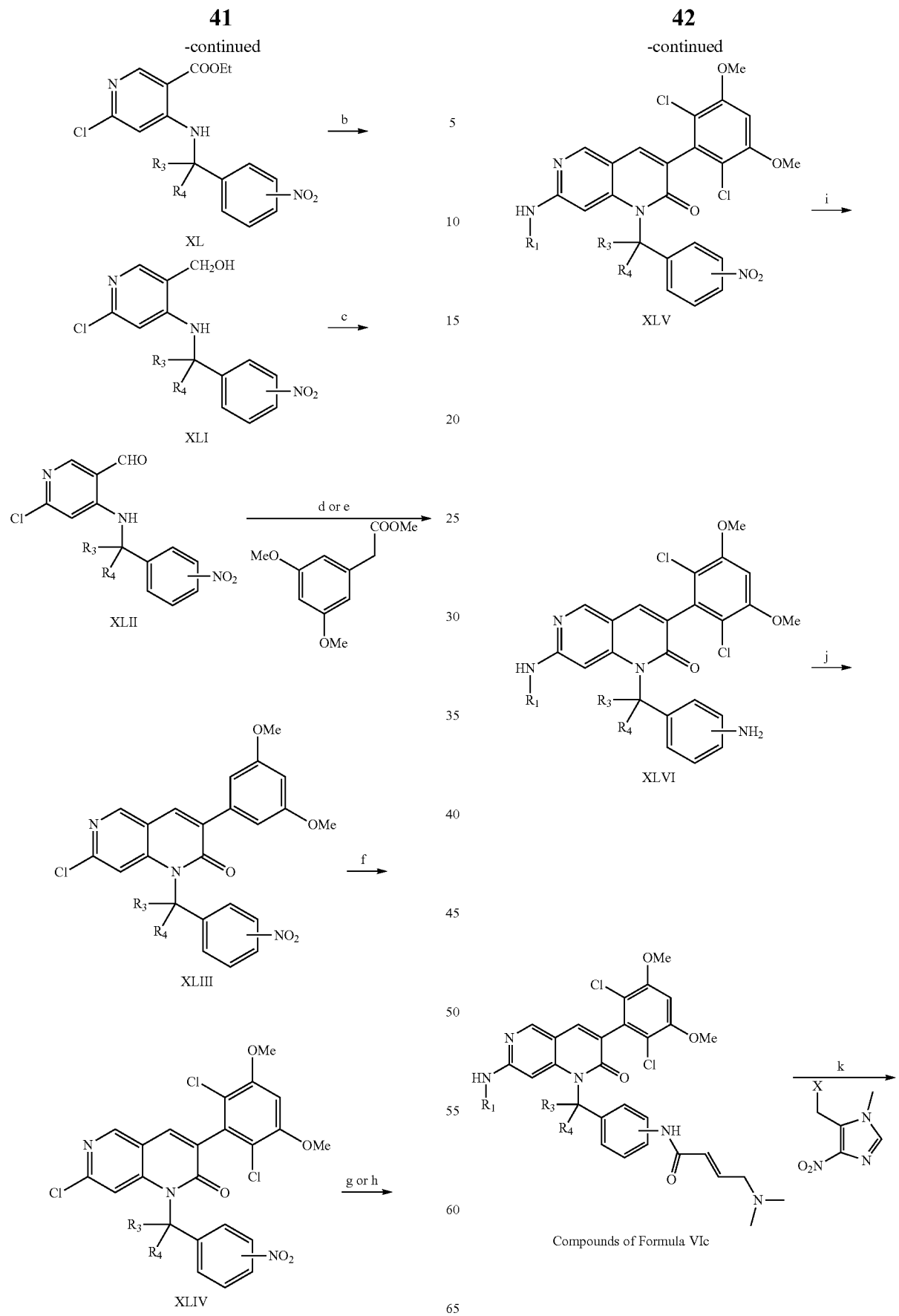

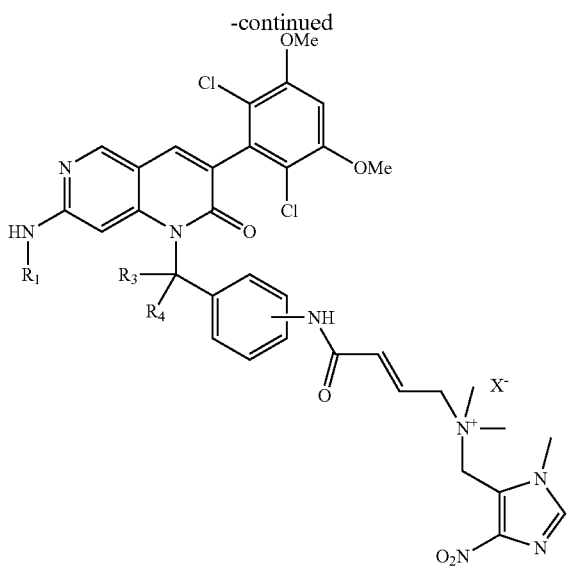

Compounds of Formula VId
Reagents and conditions: (a) DIPEA, CH₃CN, 70° C.; (b) LiAlH₄, THF, -50° C. to 0° C.;
(c) MnO₂, CH₂Cl₂, rt, overnight; (d) K₂CO₃, DMF, 100° C.; (e) Cs₂CO₃, DMF, 100° C.;
(f) SO₂Cl₂, CH₃CN, -10° C.; (g) R₁NH₂, 1,4-dioxane, 110° C.; (h) R₁NH₂, 1,4-dioxane, XPhos, Cs₂CO₃, Pd₂(dba)₃, 120° C.; (i) NaBH₄, NiCl₂•6H₂O, CH₃OH/THF;
(j) HATU, DIPEA, trans-4-Dimethylaminocrotonic acid hydrochloride, CH₃CN, rt;
(k) DMA, rt.

EXAMPLE COMPOUNDS OF THE INVENTION (a) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (100);
(b) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (101);
(c) (R,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (102);
(d) (S,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (103);
(e) (S,E)-3-(2,6-dichloro-3,5-dimethoxyphenyl)-1-(1-(4-(dimethylamino)but-2-enoyl)pyrrolidin-3-yl)-7-(isopropylamino)-3,4-dihydropyrimido[4,5-d]pyrimidin-2(1H)-one (104);
(f) (S,E)-7-(cyclohexylamino)-3-(2,6-dichloro-3,5-dimethoxyphenyl)-1-(1-(4-(dimethylamino)but-2-enoyl)pyrrolidin-3-yl)-3,4-dihydropyrimido[4,5-d]pyrimidin-2(1H)-one (105);
(g) (S,E)-3-(2,6-dichloro-3,5-dimethoxyphenyl)-1-(1-(4-(dimethylamino)but-2-enoyl)pyrrolidin-3-yl)-7-(phenylamino)-3,4-dihydropyrimido[4,5-d]pyrimidin-2(1H)-one (106);
(h) (E)-3-(2,6-dichloro-3,5-dimethoxyphenyl)-1-(1-(4-(dimethylamino)but-2-enoyl)piperidin-4-yl)-7-(methylamino)-3,4-dihydropyrimido[4,5-d]pyrimidin-2(1H)-one (107);
(i) (E)-3-(2,6-dichloro-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (108);
(j) (E)-3-(2,6-dichloro-3,5-dimethoxyphenyl)-1-(1-(4-(dimethylamino)but-2-enoyl)piperidin-4-yl)-7-((tetrahydrofuran-3-yl)amino)-3,4-dihydropyrimido[4,5-d]pyrimidin-2(1H)-one (109);
(k) (E)-7-(cyclohexylamino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (110);
(l) (E)-3-(2,6-dichloro-3,5-dimethoxyphenyl)-1-(1-(4-(dimethylamino)but-2-enoyl)piperidin-4-yl)-7-((tetrahydro-2H-pyran-4-yl)amino)-3,4-dihydropyrimido[4,5-d]pyrimidin-2(1H)-one (111);
(m) (E)-3-(2,6-dichloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (112);
(n) (E)-3-(2,6-dichloro-3,5-dimethoxyphenyl)-1-(1-(4-(dimethylamino)but-2-enoyl)piperidin-4-yl)-7-((3-methoxyphenyl)amino)-3,4-dihydropyrimido[4,5-d]pyrimidin-2(1H)-one (113);
(o) (E)-3-(2,6-dichloro-3,5-dimethoxyphenyl)-1-(1-(4-(dimethylamino)but-2-enoyl)piperidin-4-yl)-7-(m-tolylamino)-3,4-dihydropyrimido[4,5-d]pyrimidin-2(1H)-one (114);
(p) (E)-3-(2,6-dichloro-3,5-dimethoxyphenyl)-1-(1-(4-(dimethylamino)but-2-enoyl)piperidin-4-yl)-7-((3-fluorophenyl)amino)-3,4-dihydropyrimido[4,5-d]pyrimidin-2(1H)-one (115);
(q) (E)-3-(2,6-dichloro-3,5-dimethoxyphenyl)-7-((3,5-difluorophenyl)amino)-1-(1-(4-(dimethylamino)but-2-enoyl)piperidin-4-yl)-3,4-dihydropyrimido[4,5-d]pyrimidin-2(1H)-one (116);
(r) (E)-3-(2,6-dichloro-3,5-dimethoxyphenyl)-7-((3,4-difluorophenyl)amino)-1-(1-(4-(dimethylamino)but-2-enoyl)piperidin-4-yl)-3,4-dihydropyrimido[4,5-d]pyrimidin-2(1H)-one (117);
(s) (E)-3-(2,6-dichloro-3,5-dimethoxyphenyl)-1-(1-(4-(dimethylamino)but-2-enoyl)piperidin-4-yl)-7-((4-fluoro-3-methoxyphenyl)amino)-3,4-dihydropyrimido[4,5-d]pyrimidin-2(1H)-one (118);
(t) (E)-7-((3-chloro-4-fluorophenyl)amino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (119);
(u) (E)-3-(2,6-dichloro-3,5-dimethoxyphenyl)-1-(1-(4-(dimethylamino)but-2-enoyl)piperidin-4-yl)-7-((4-fluorophenyl)amino)-3,4-dihydropyrimido[4,5-d]pyrimidin-2(1H)-one (120);
(v) (E)-3-(2,6-dichloro-3,5-dimethoxyphenyl)-1-(1-(4-(dimethylamino)but-2-enoyl)piperidin-4-yl)-7-((2-methoxyphenyl)amino)-3,4-dihydropyrimido[4,5-d]pyrimidin-2(1H)-one (121);
(w) (E)-3-(2,6-dichloro-3,5-dimethoxyphenyl)-1-(1-(4-(dimethylamino)but-2-enoyl)piperidin-4-yl)-7-((4-methoxyphenyl)amino)-3,4-dihydropyrimido[4,5-d]pyrimidin-2(1H)-one (122);
(x) (E)-3-(2,6-dichloro-3,5-dimethoxyphenyl)-7-(methylamino)-1-(1-(4-morpholinobut-2-enoyl)piperidin-4-yl)-3,4-dihydropyrimido[4,5-d]pyrimidin-2(1H)-one (123);
(y) (E)-3-(2,6-dichloro-3,5-dimethoxyphenyl)-7-(methylamino)-1-(1-(4-(piperidin-1-yl)but-2-enoyl)piperidin-4-yl)-3,4-dihydropyrimido[4,5-d]pyrimidin-2(1H)-one (124);
(z) (E)-N-(3-(3-(2,6-dichloro-3,5-dimethoxyphenyl)-7-(methylamino)-2-oxo-3,4-dihydropyrimido[4,5-d]pyrimidin-1(2H)-yl)propyl)-4-(dimethylamino)but-2-enamide (125);

(aa) (E)-N-(4-(3-(2,6-dichloro-3,5-dimethoxyphenyl)-7-(methylamino)-2-oxo-3,4-dihydropyrimido[4,5-d]pyrimidin-1(2H)-yl)cyclohexyl)-4-(dimethylamino)but-2-enamide (126);

(bb) (E)-N-(3-((3-(2,6-dichloro-3,5-dimethoxyphenyl)-7-(methylamino)-2-oxo-3,4-dihydropyrimido[4,5-d]pyrimidin-1(2H)-yl)methyl)phenyl)-4-(dimethylamino)but-2-enamide (127);

(cc) (E)-3-(2-chloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (128);

(dd) (E)-3-(2,6-dichloro-3,5-dimethoxyphenyl)-1-(1-(4-(dimethylamino)but-2-enoyl)piperidin-4-yl)-7-((4-morpholinophenyl)amino)-3,4-dihydropyrimido[4,5-d]pyrimidin-2(1H)-one (129);

(ee) (E)-3-(2-chloro-3,5-dimethoxyphenyl)-1-(1-(4-(dimethylamino)but-2-enoyl) piperidin-4-yl)-7-((4-morpholinophenyl)amino)-3,4-dihydropyrimido[4,5-d]pyrimidin-2(1H)-one (130);

(ff) (E)-3-(3,5-dimethoxyphenyl)-1-(1-(4-(dimethylamino)but-2-enoyl)piperidin-4-yl)-7-((4-morpholinophenyl)amino)-3,4-dihydropyrimido[4,5-d]pyrimidin-2(1H)-one (131);

(gg) (E)-6-(2,6-dichloro-3,5-dimethoxyphenyl)-8-(1-(4-(dimethylamino)but-2-enoyl)piperidin-4-yl)-2-(methylamino)pyrido[2,3-d]pyrimidin-7(8H)-one (132);

(hh) (E)-6-(2,6-dichloro-3,5-dimethoxyphenyl)-8-(1-(4-(dimethylamino)but-2-enoyl)piperidin-4-yl)-2-(isopropylamino)pyrido[2,3-d]pyrimidin-7(8H)-one (133);

(ii) (E)-6-(2,6-dichloro-3,5-dimethoxyphenyl)-8-(1-(4-(dimethylamino)but-2-enoyl)piperidin-4-yl)-2-((tetrahydrofuran-3-yl)amino)pyrido[2,3-d]pyrimidin-7(8H)-one (134);

(jj) (E)-6-(2,6-dichloro-3,5-dimethoxyphenyl)-8-(1-(4-(dimethylamino)but-2-enoyl)piperidin-4-yl)-2-((tetrahydro-2H-pyran-4-yl)amino)pyrido[2,3-d]pyrimidin-7(8H)-one (135);

(kk) (E)-2-(cyclohexylamino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (136);

(ll) (E)-6-(2,6-dichloro-3,5-dimethoxyphenyl)-8-(1-(4-(dimethylamino)but-2-enoyl)piperidin-4-yl)-2-(((tetrahydro-2H-pyran-4-l)methyl)amino)pyrido[2,3-d]pyrimidin-7(8H)-one (137);

(mm) (E)-6-(2,6-dichloro-3,5-dimethoxyphenyl)-8-(1-(4-(dimethylamino)but-2-enoyl)piperidin-4-yl)-2-(phenylamino)pyrido[2,3-d]pyrimidin-7(8H)-one (138);

(nn) (E)-6-(2,6-dichloro-3,5-dimethoxyphenyl)-8-(1-(4-(dimethylamino)but-2-enoyl)piperidin-4-yl)-2-((4-fluorophenyl)amino)pyrido[2,3-d]pyrimidin-7(8H)-one (139);

(oo) (E)-6-(2,6-dichloro-3,5-dimethoxyphenyl)-8-(1-(4-(dimethylamino)but-2-enoyl)piperidin-4-yl)-2-((3-methoxyphenyl)amino)pyrido[2,3-d]pyrimidin-7(8H)-one (140);

(pp) (E)-6-(2,6-dichloro-3,5-dimethoxyphenyl)-8-(1-(4-(dimethylamino)but-2-enoyl)piperidin-4-yl)-2-((4-fluoro-3-methoxyphenyl)amino)pyrido[2,3-d]pyrimidin-7(8H)-one (141);

(qq) (E)-2-((3-chloro-4-fluorophenyl)amino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (142);

(rr) (E)-N-(3-((6-(2,6-dichloro-3,5-dimethoxyphenyl)-2-(methylamino)-7-oxopyrido[2,3-d]pyrimidin-8(7H)-yl)methyl)phenyl)-4-(dimethylamino)but-2-enamide (143);

(ss) (E)-N-(3-((6-(2,6-dichloro-3,5-dimethoxyphenyl)-2-(ethylamino)-7-oxopyrido[2,3-d]pyrimidin-8(7H)-yl)methyl)phenyl)-4-(dimethylamino)but-2-enamide (144);

(tt) (E)-N-(3-((6-(2,6-dichloro-3,5-dimethoxyphenyl)-2-(isopropylamino)-7-oxopyrido[2,3-d]pyrimidin-8(7H)-yl)methyl)phenyl)-4-(dimethylamino)but-2-enamide (145);

(uu) (E)-N-(3-(1-(6-(2,6-dichloro-3,5-dimethoxyphenyl)-2-(methylamino)-7-oxopyrido[2,3-d]pyrimidin-8(7H)-yl)ethyl)phenyl)-4-(dimethylamino)but-2-enamide (146);

(vv) (E)-3-(2,6-dichloro-3,5-dimethoxyphenyl)-1-(1-(4-(dimethylamino)but-2-enoyl)piperidin-4-yl)-7-(isopropylamino)pyrido[3,4-b]pyrazin-2(1H)-one (147);

(ww) (E)-3-(2,6-dichloro-3,5-dimethoxyphenyl)-1-(1-(4-(dimethylamino)but-2-enoyl)piperidin-4-yl)-7-(methylamino)-1,6-naphthyridin-2(1H)-one (148);

(xx) (E)-3-(2,6-dichloro-3,5-dimethoxyphenyl)-1-(1-(4-(dimethylamino)but-2-enoyl)piperidin-4-yl)-7-(isopropylamino)-1,6-naphthyridin-2(1H)-one (149);

(yy) (S,E)-3-(3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (150);

(zz) (E)-3-(2,6-dibromo-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (151);

(aaa) (E)-6-(2,6-dibromo-3,5-dimethoxyphenyl)-8-(1-(4-(dimethylamino)but-2-enoyl)piperidin-4-yl)-2-(phenylamino)pyrido[2,3-d]pyrimidin-7(8H)-one (152);

(bbb) (E)-6-(2,6-dibromo-3,5-dimethoxyphenyl)-8-(1-(4-(dimethylamino)but-2-enoyl)piperidin-4-yl)-2-(isopropylamino)pyrido[2,3-d]pyrimidin-7(8H)-one (153);

(ccc) (E)-3-(2,6-dibromo-3,5-dimethoxyphenyl)-1-(1-(4-(dimethylamino)but-2-enoyl)piperidin-4-yl)-7-(isopropylamino)pyrido[3,4-b]pyrazin-2(1H)-one (154);

(ddd) (E)-3-(2,6-dibromo-3,5-dimethoxyphenyl)-1-(1-(4-(dimethylamino)but-2-enoyl)piperidin-4-yl)-7-(isopropylamino)-1,6-naphthyridin-2(1H)-one (155);

(eee) 1-(1-acryloylpiperidin-4-yl)-3-(2,6-dichloro-3,5-dimethoxyphenyl)-7-(methylamino)-3,4-dihydropyrimido[4,5-d]pyrimidin-2(1H)-one (156);

(fff) (E)-3-(2,6-dichloro-3,5-dimethoxyphenyl)-1-(1-(4-(dimethylamino)but-2-enoyl)piperidin-4-yl)-7-(pyridin-2-ylamino)-3,4-dihydropyrimido[4,5-d]pyrimidin-2(1H)-one (157);

(ggg) (E)-3-(2,6-dichloro-3,5-dimethoxyphenyl)-1-(1-(4-(dimethylamino)but-2-enoyl)piperidin-4-yl)-7-(pyridin-3-ylamino)-3,4-dihydropyrimido[4,5-d]pyrimidin-2(1H)-one (158);

(hhh) (E)-3-(2,6-dichloro-3,5-dimethoxyphenyl)-1-(1-(4-(dimethylamino)but-2-enoyl)piperidin-4-yl)-7-(pyridin-4-ylamino)-3,4-dihydropyrimido[4,5-d]pyrimidin-2(1H)-one (159);

(iii) (E)-3-(2,6-dichloro-3,5-dimethoxyphenyl)-1-(1-(4-(dimethylamino)but-2-enoyl)piperidin-4-yl)-7-((1-methyl-1H-pyrazol-3-yl)amino)-3,4-dihydropyrimido[4,5-d]pyrimidin-2(1H)-one (160);

(jjj) (E)-3-(2,6-dichloro-3,5-dimethoxyphenyl)-1-(1-(4-(dimethylamino)but-2-enoyl)piperidin-4-yl)-7-((5-morpholinopyridin-2-yl)amino)-3,4-dihydropyrimido[4,5-d]pyrimidin-2(1H)-one (161);

(kkk) (E)-3-(2,6-dichloro-3,5-dimethoxyphenyl)-1-(1-(4-(dimethylamino)but-2-enoyl)piperidin-4-yl)-7-(pyrimidin-4-ylamino)-3,4-dihydropyrimido[4,5-d]pyrimidin-2(1H)-one (162);

(lll) (S,E)-4-(3-(3-(2,6-dichloro-3,5-dimethoxyphenyl)-7-(methylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (200);

(mmm) (S,E)-4-(3-(3-(2,6-dichloro-3,5-dimethoxyphenyl)-7-(isopropylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (201);

(nnn) (E)-4-(4-(3-(2,6-dichloro-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (202);

(ooo) (E)-4-(4-(3-(2,6-dichloro-3,5-dimethoxyphenyl)-2-oxo-7-((tetrahydro-2H-pyran-4-yl)amino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (203);

(ppp) (E)-4-(4-(3-(2,6-dichloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (204);

(qqq) (E)-4-(4-(3-(2,6-dichloro-3,5-dimethoxyphenyl)-7-((4-fluorophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (205);

(rrr) (E)-4-(4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (206);

(sss) (E)-4-(4-(3-(2,6-dibromo-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (207);

(ttt) (E)-4-(4-(6-(2,6-dichloro-3,5-dimethoxyphenyl)-2-(methylamino)-7-oxopyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (208);

(uuu) (E)-4-(4-(6-(2,6-dichloro-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (209);

(vvv) (E)-4-(4-(6-(2,6-dibromo-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (210);

(www) (E)-4-(4-(6-(2,6-dichloro-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (211);

(xxx) (E)-4-(4-(6-(2,6-dibromo-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (212);

(yyy) (E)-4-((3-((6-(2,6-dichloro-3,5-dimethoxyphenyl)-2-(isopropylamino)-7-oxopyrido[2,3-d]pyrimidin-8(7H)-yl)methyl)phenyl)amino)-N,N-dimethyl-N-((1-methyl-4-nitro-1H-imidazol-5-yl)methyl)-4-oxobut-2-en-1-aminium bromide (213);

(zzz) (E)-4-((4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)cyclohexyl)amino)-N,N-dimethyl-N-((1-methyl-4-nitro-1H-imidazol-5-yl)methyl)-4-oxobut-2-en-1-aminium bromide (214);

(aaaa) (E)-4-(4-(3-(2,6-dichloro-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (215);

(bbbb) (E)-4-(4-(3-(2,6-dibromo-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (216);

(cccc) (E)-4-(4-(3-(2-chloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (217);

(dddd) (E)-4-(4-(3-(2,6-dichloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (218);

(eeee) (E)-4-(4-(3-(2-chloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (219);

(ffff) (E)-4-(4-(3-(3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (220);

(gggg) (E)-4-(4-(3-(2,6-dichloro-3,5-dimethoxyphenyl)-2-oxo-7-(pyridin-2-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (221);

(hhhh) (E)-4-(4-(3-(2,6-dichloro-3,5-dimethoxyphenyl)-2-oxo-7-(pyridin-3-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (222);

(iiii) (E)-4-(4-(3-(2,6-dichloro-3,5-dimethoxyphenyl)-2-oxo-7-(pyridin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (223);

(jjjj) (E)-4-(4-(3-(2,6-dichloro-3,5-dimethoxyphenyl)-7-((1-methyl-1H-pyrazol-3-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (224);

(kkkk) (E)-4-(4-(3-(2,6-dichloro-3,5-dimethoxyphenyl)-7-((5-morpholinopyridin-2-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (225);

(llll) (E)-4-(4-(3-(2,6-dichloro-3,5-dimethoxyphenyl)-2-oxo-7-(pyrimidin-4-ylamino)-3,4-dihydropyrimido[4,5-d]pyrimidin-1(2H)-yl)piperidin-1-yl)-N,N-dimethyl-N-

((1-methyl-4-nitro-1H-imidazol-5-yl)methyl)-4-oxobut-2-en-1-aminium bromide (226); and
(mmmm) (E)-3-(2,6-dichloro-3,5-dimethoxyphenyl)-1-(1-(4-(dimethylamino)but-2-enoyl)piperidin-4-yl)-7-(phenylamino)-1,6-naphthyridin-2(1H)-one (232).
Chemical Structures of Some Example Compounds of the Invention
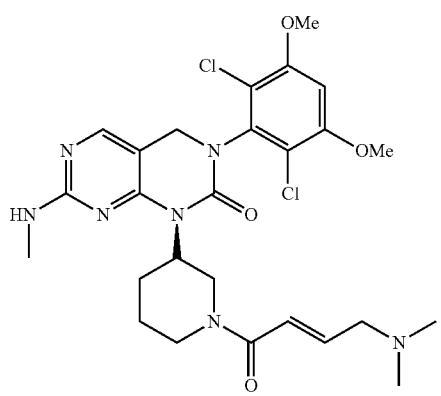
100
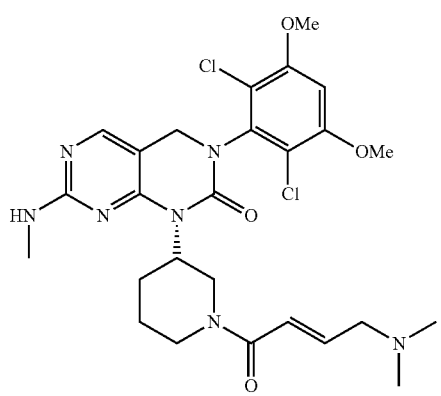
101
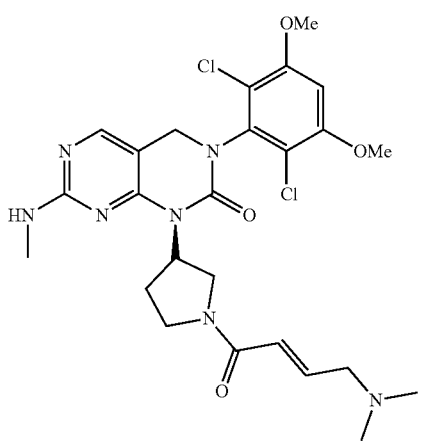
102
-continued
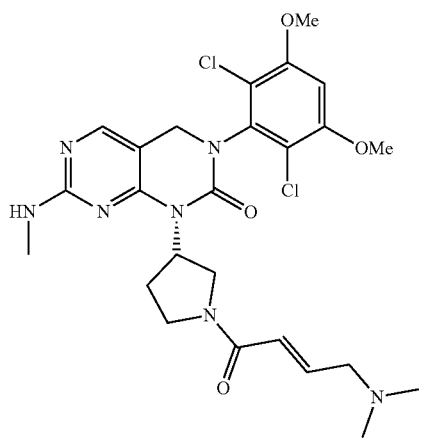
103
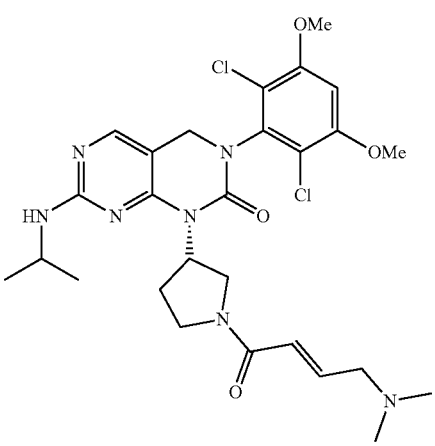
104
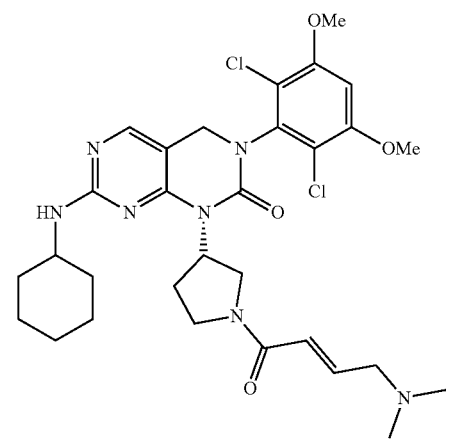
105

-continued
106
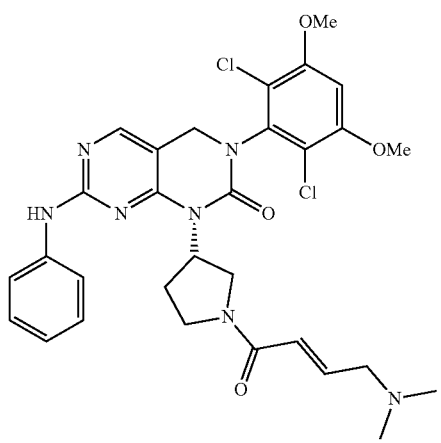
107
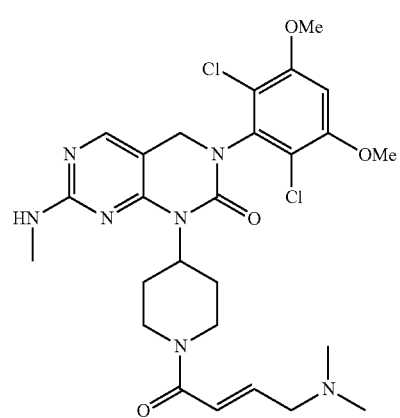
108
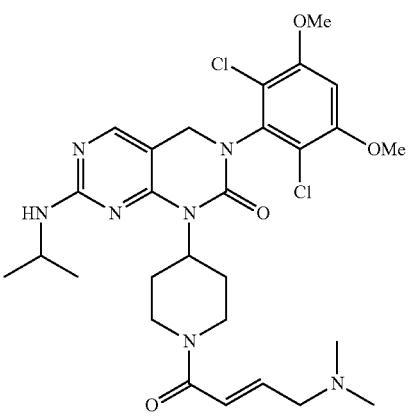
-continued
109
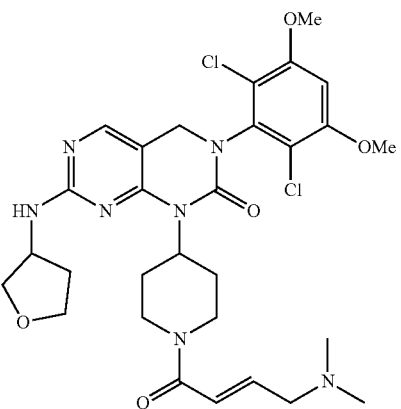
110
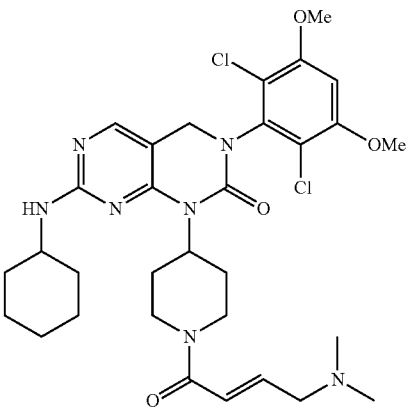
111
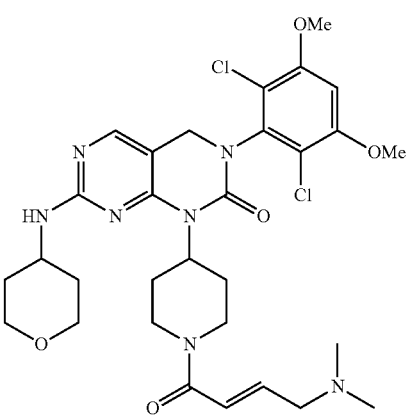
112
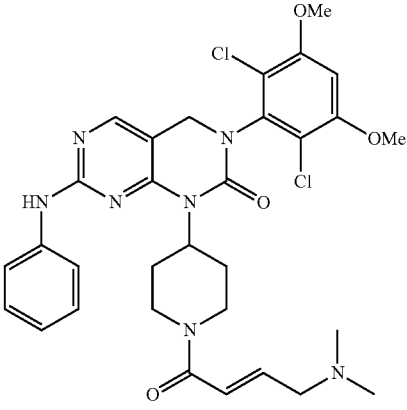

113 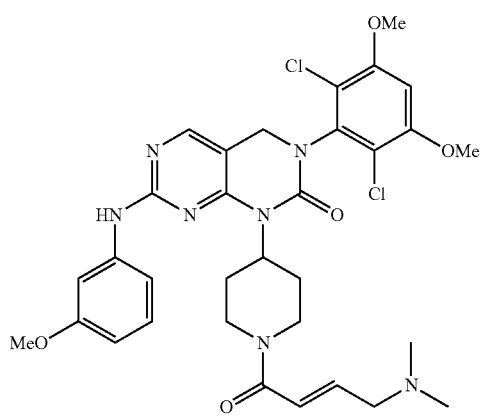
114 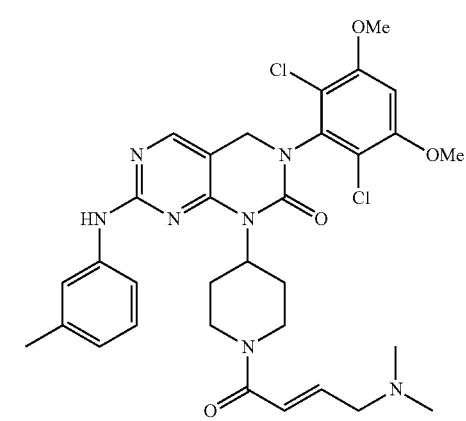
115 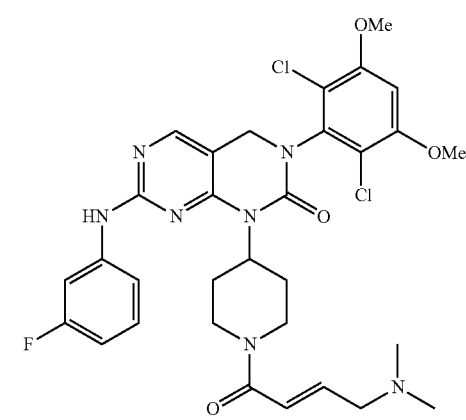
116 
117 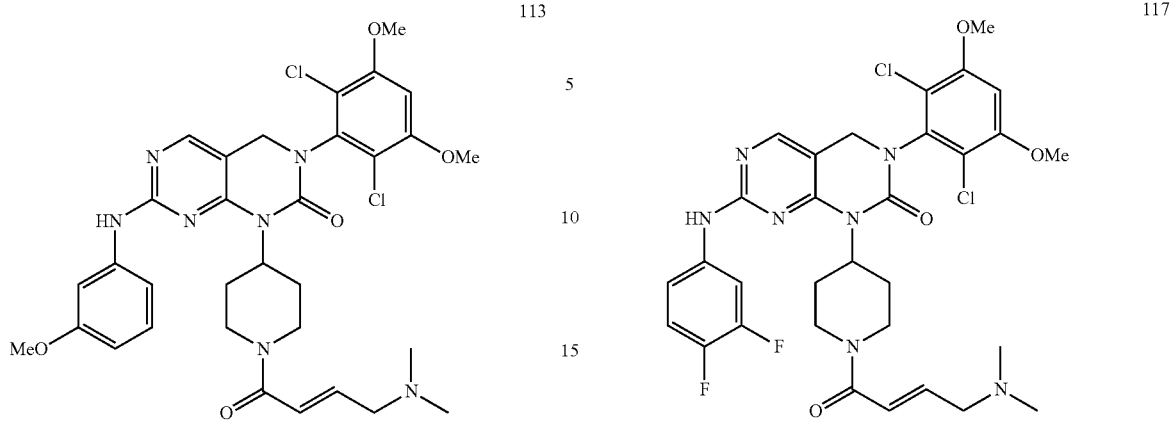
118 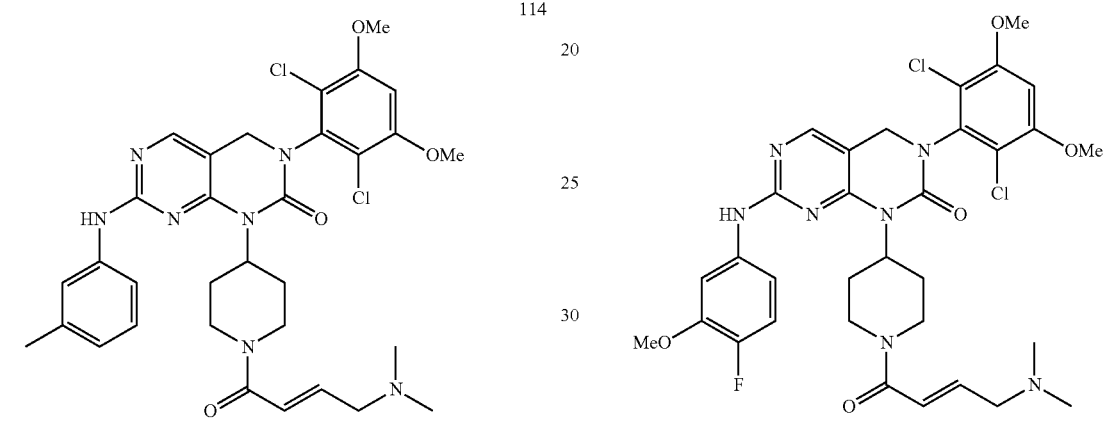
119 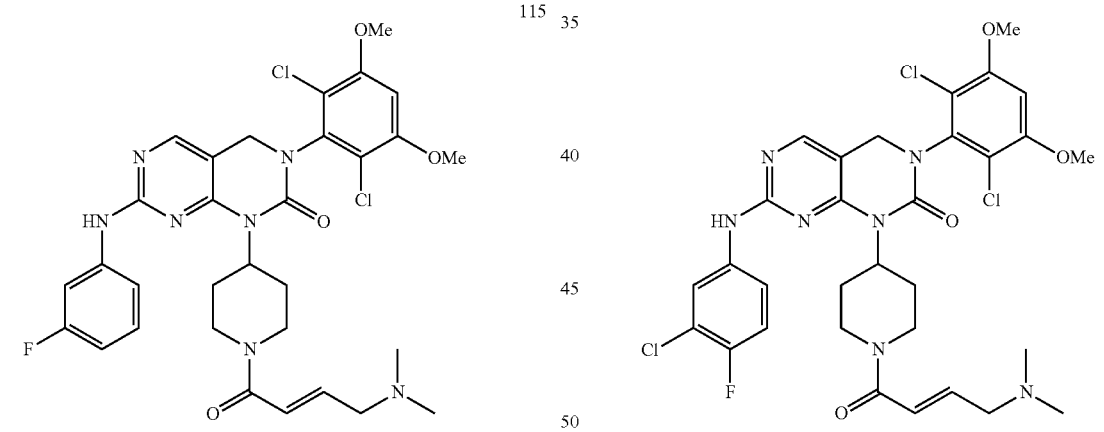
120 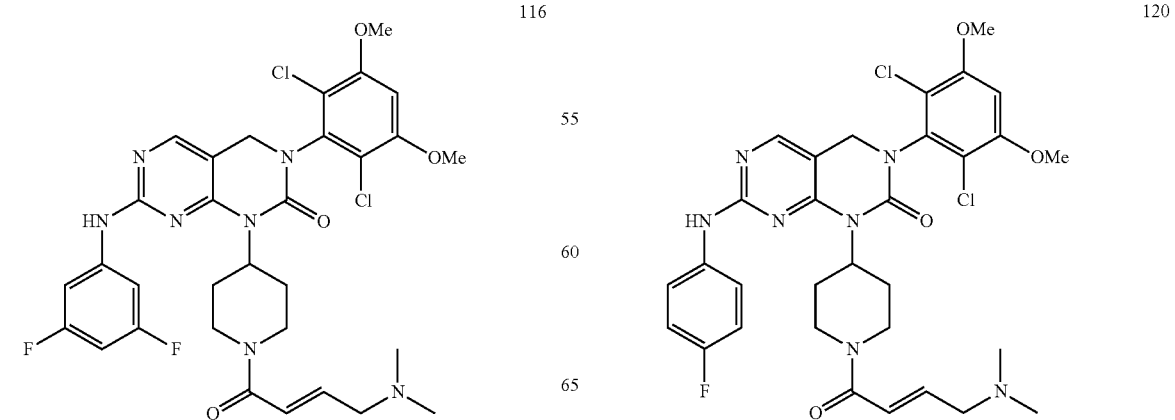

-continued
121
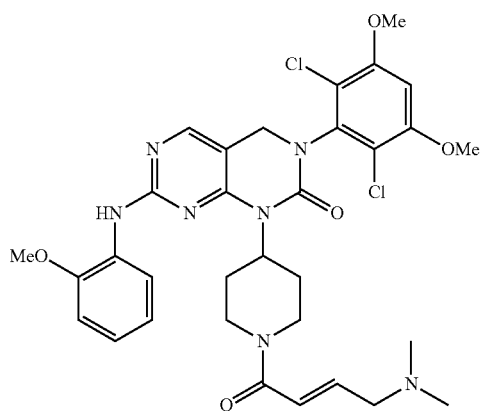
122
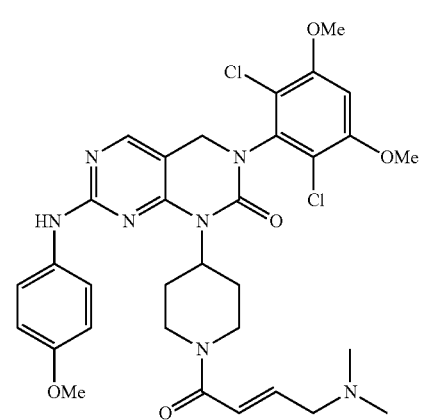
123
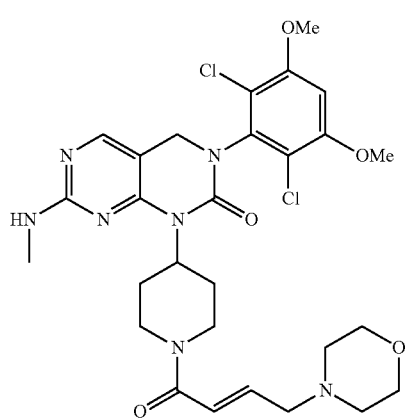
124
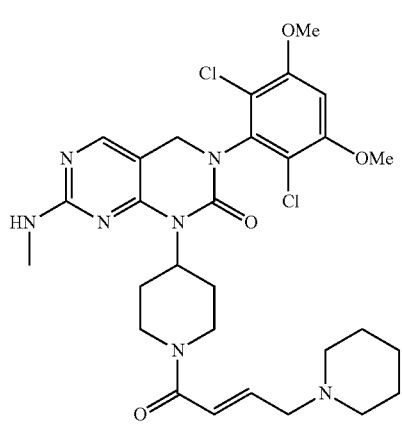
-continued
125
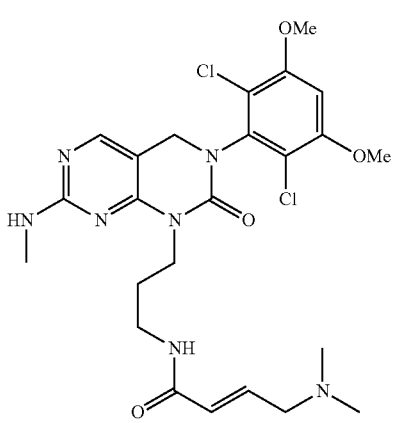
126
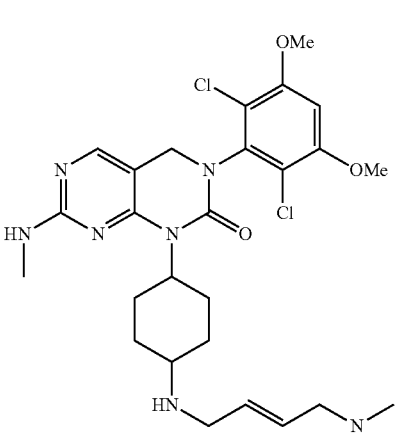
127
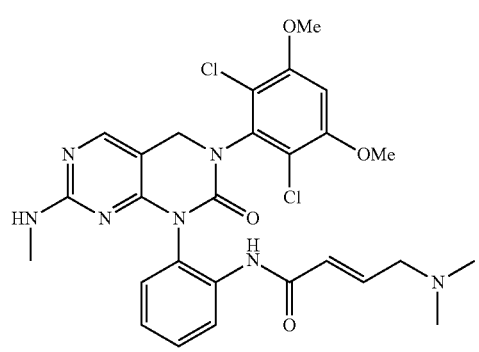
128
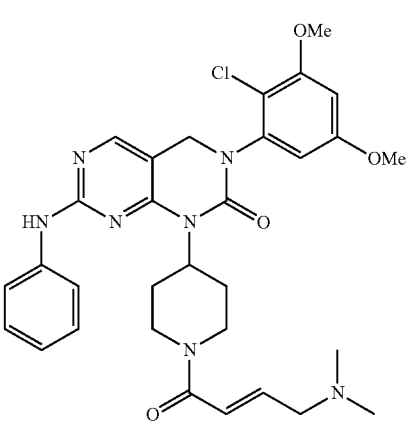

129
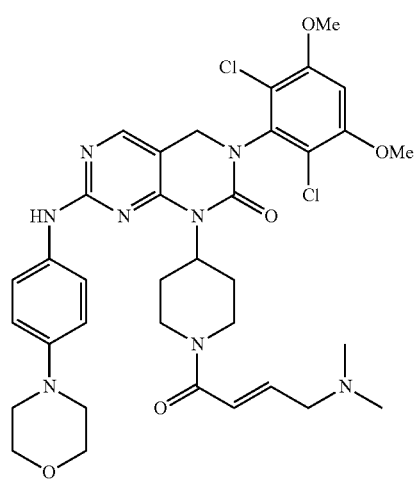
130
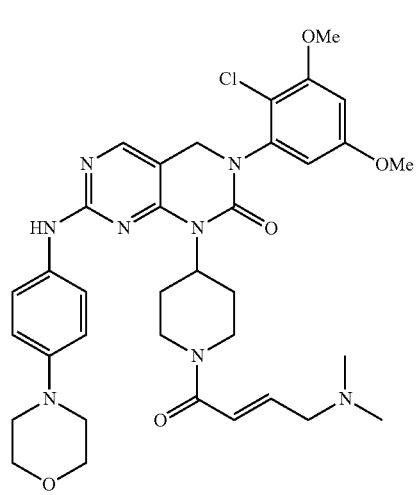
131
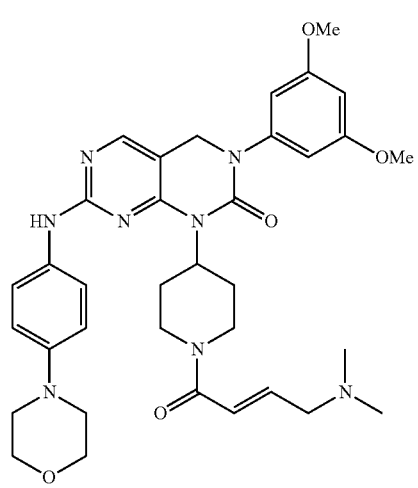
132
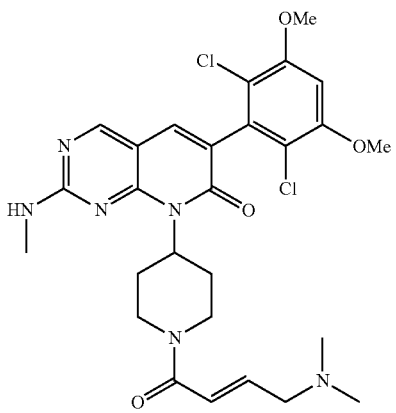
133
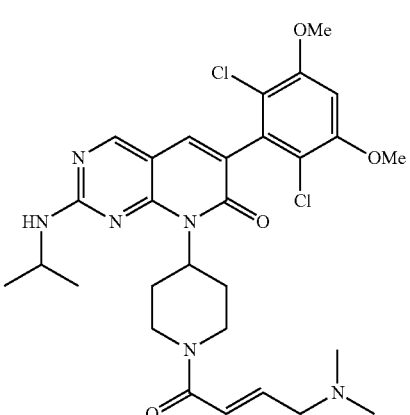
134
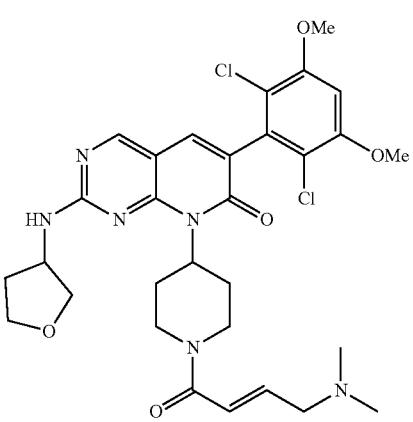
135
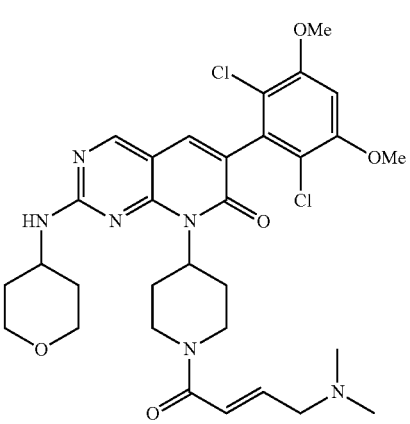

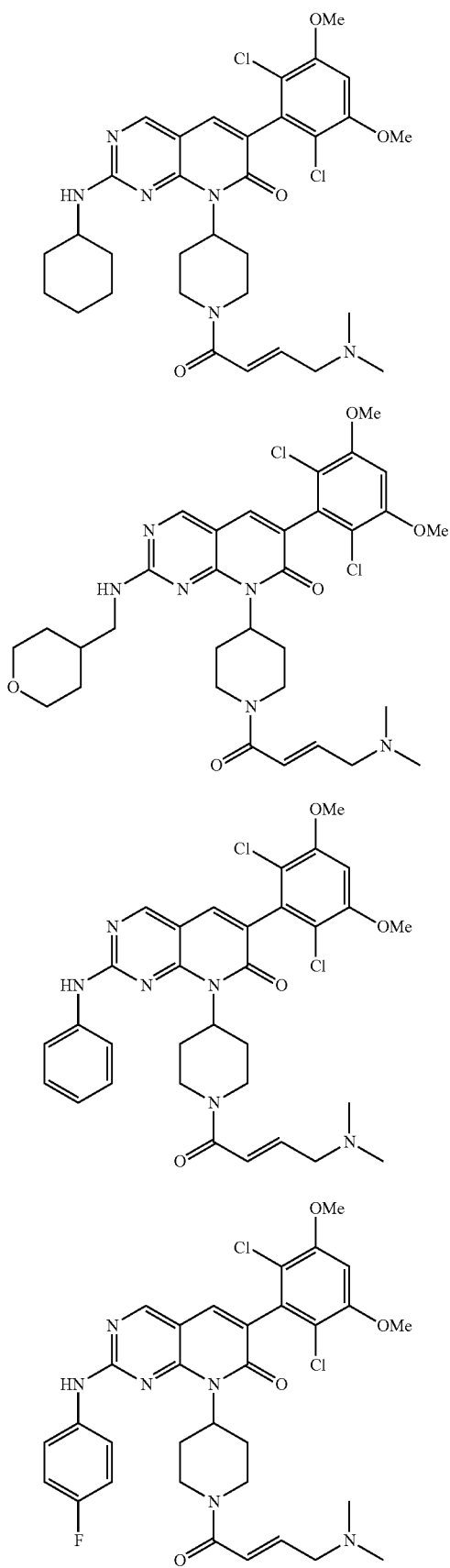
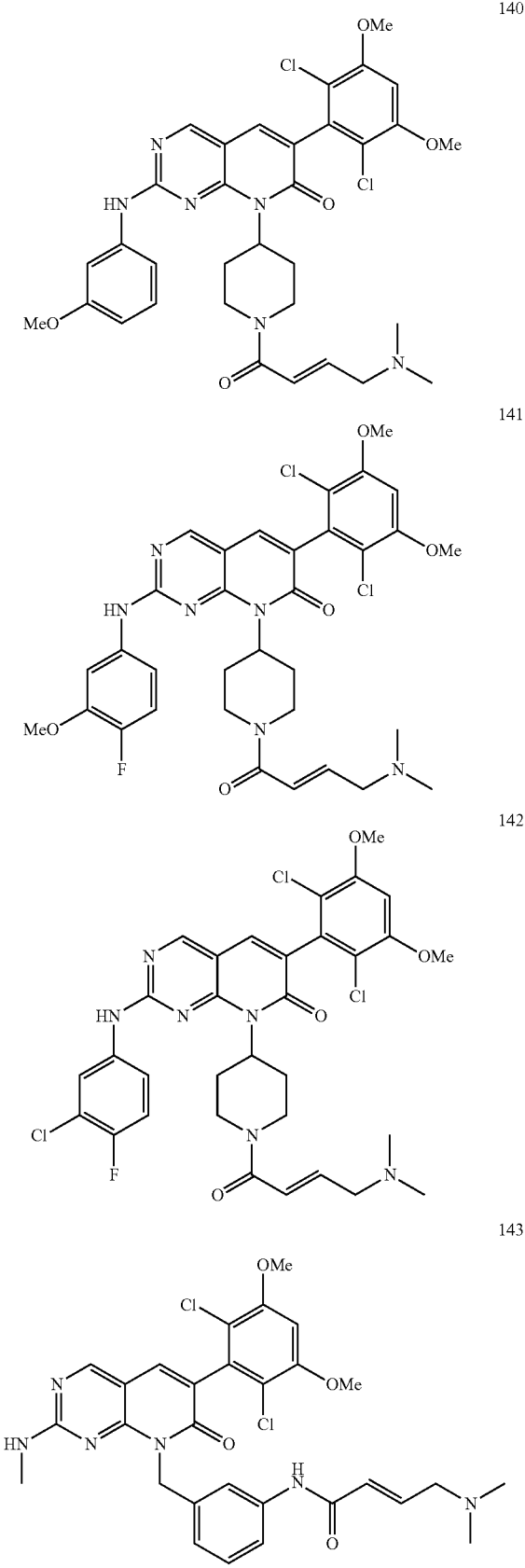

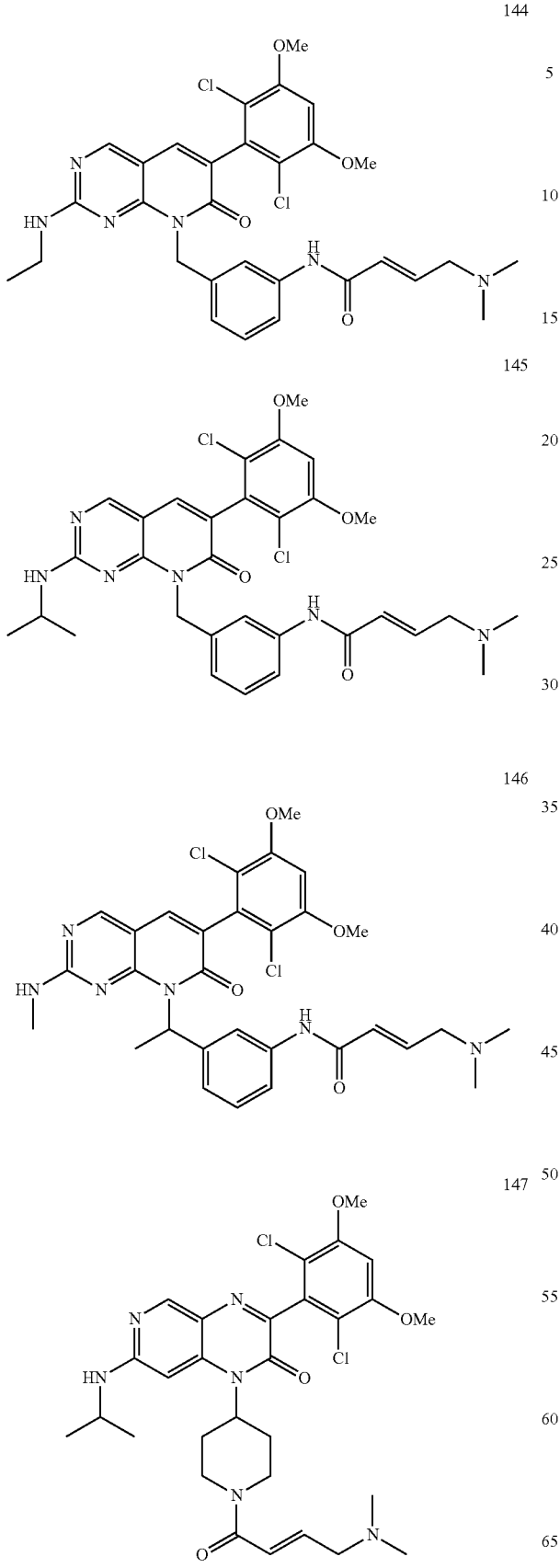
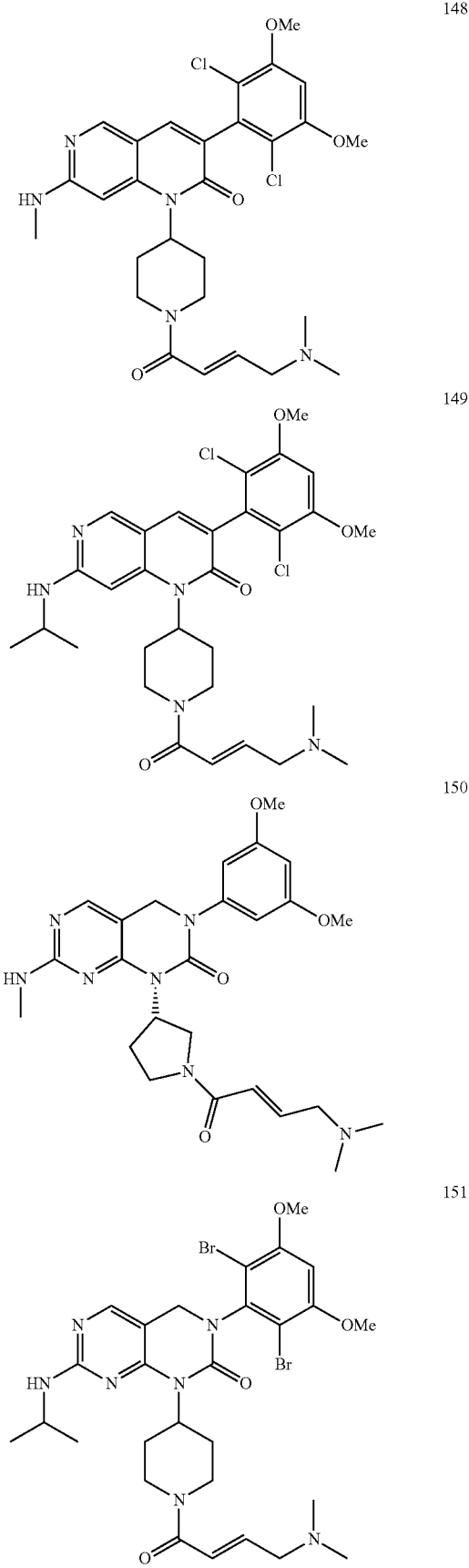

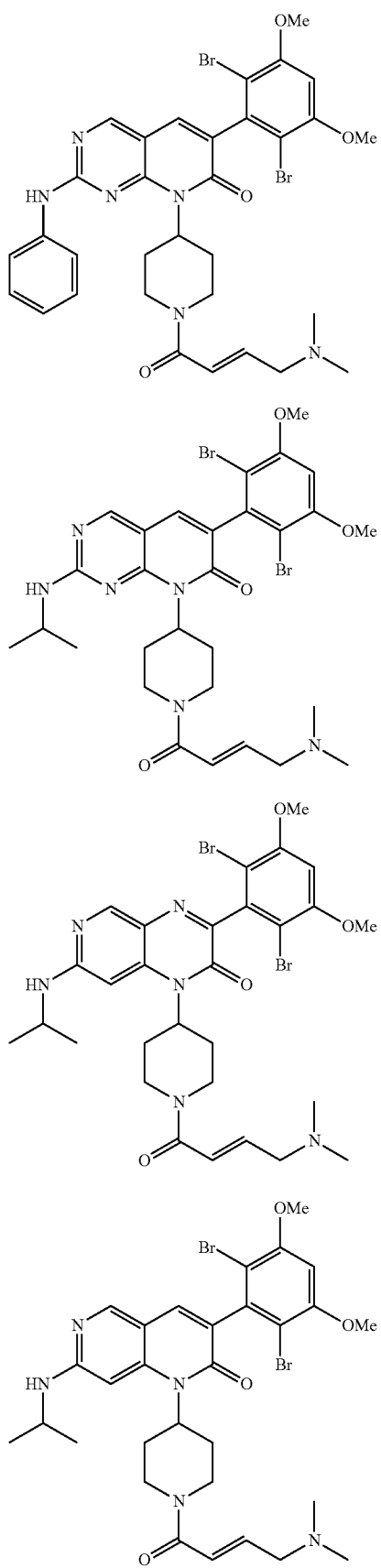
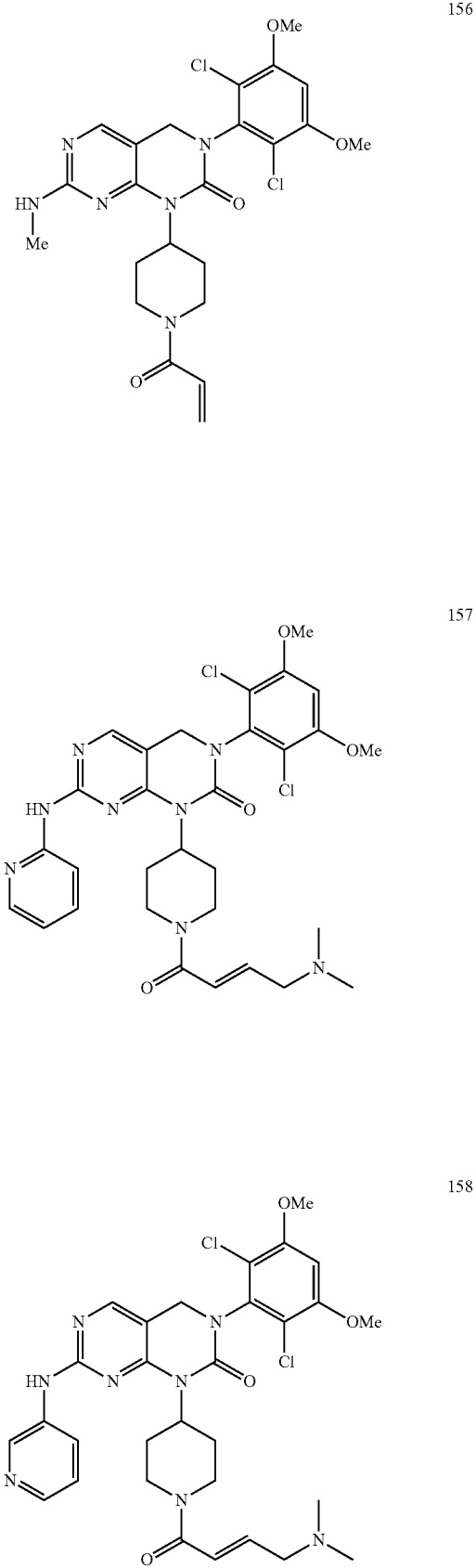

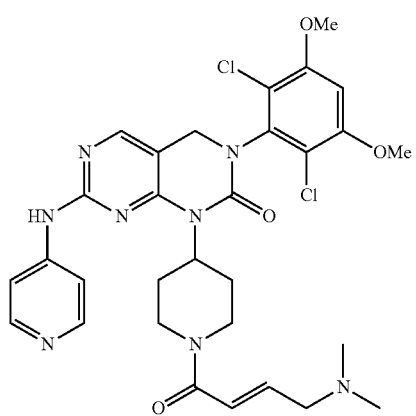
159
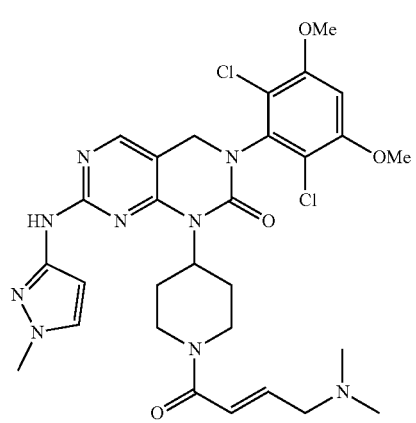
160
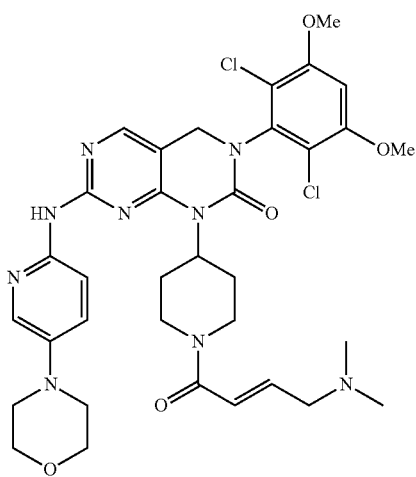
161
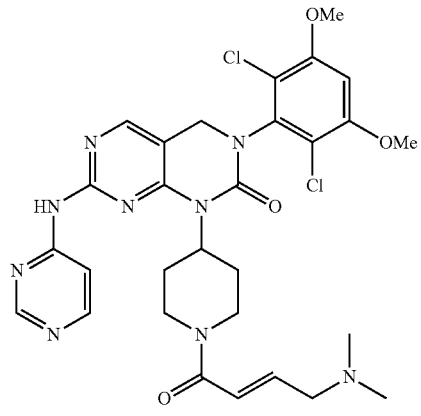
162
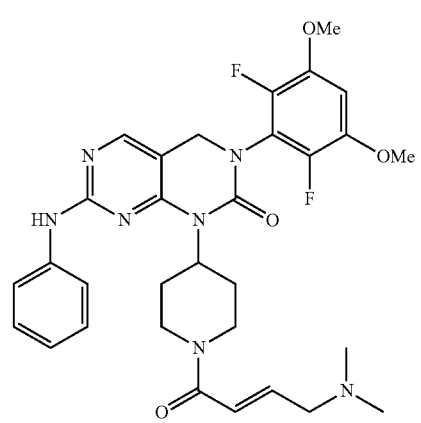
163
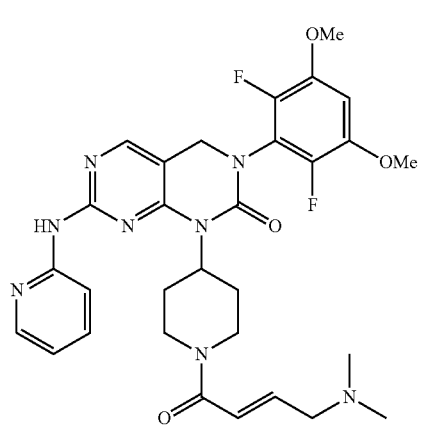
164
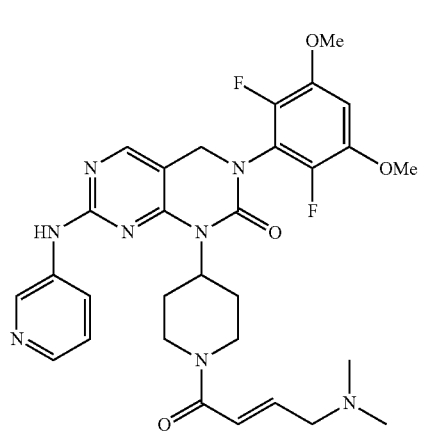
165

166 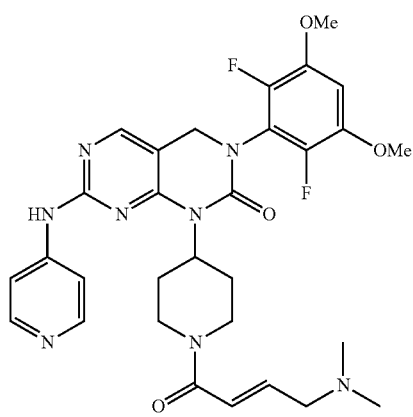
167 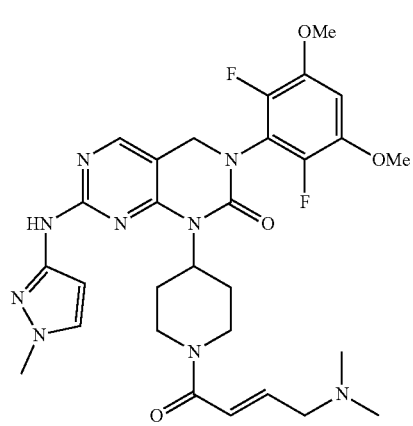
168 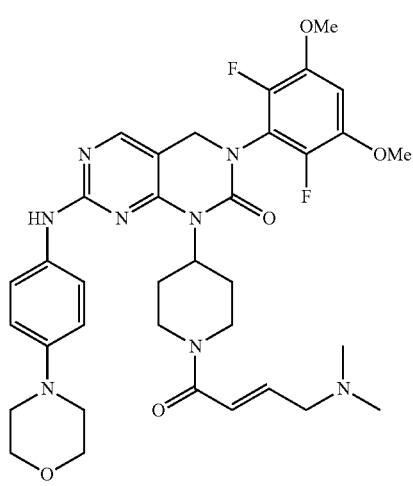
169 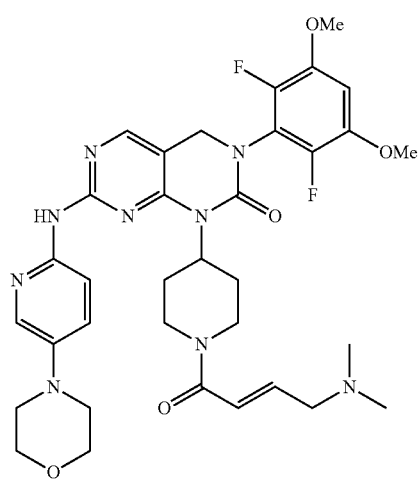
170 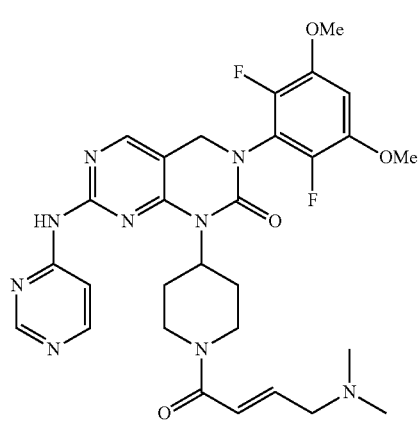
171 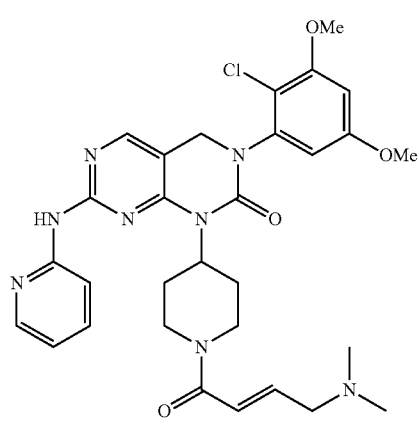

172 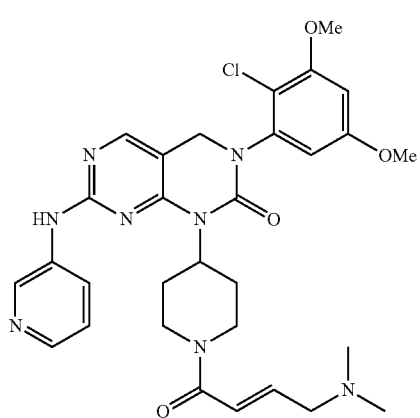
173 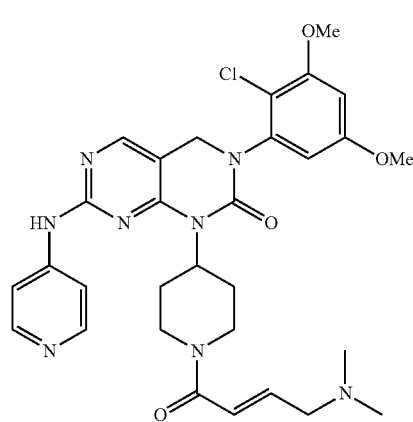
174 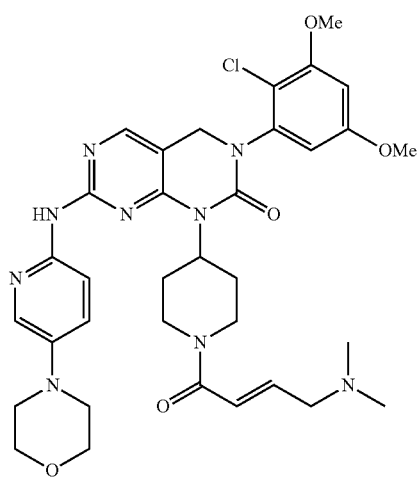
175 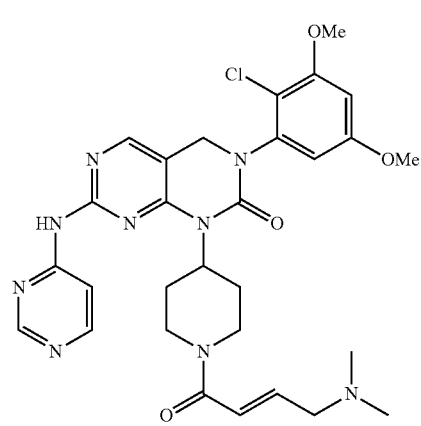
176 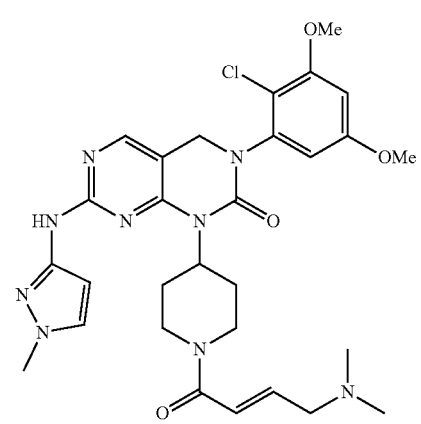
177 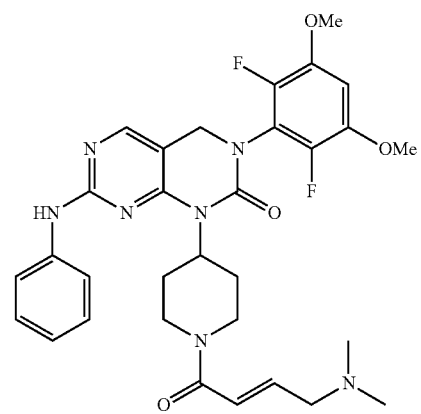
178 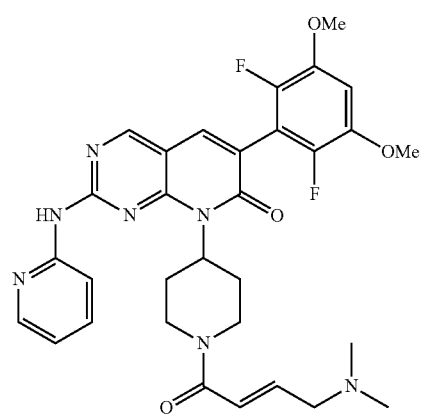

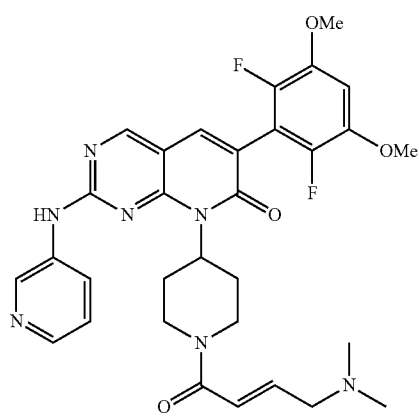
179
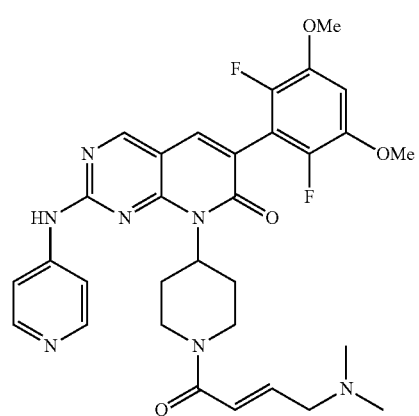
180
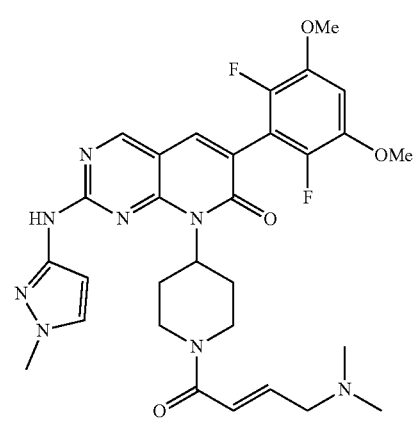
181
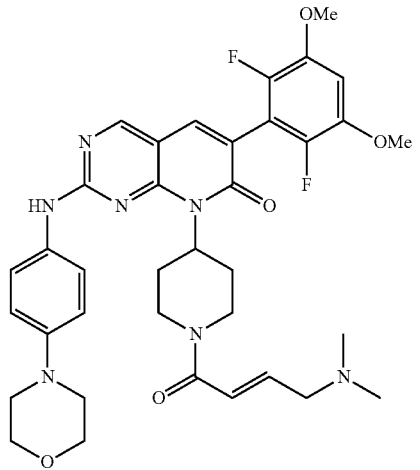
182
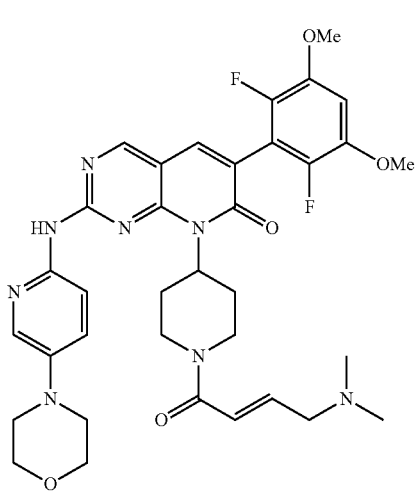
183
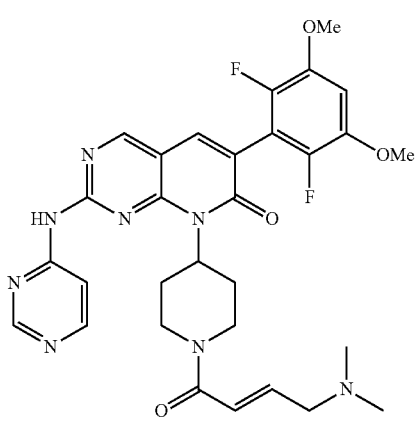
184

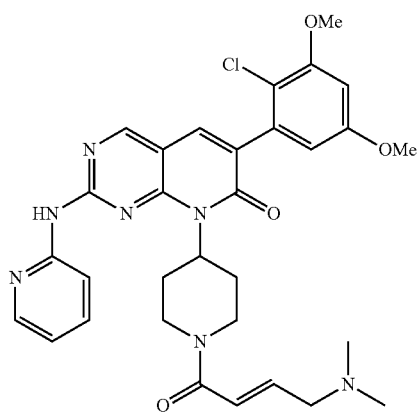
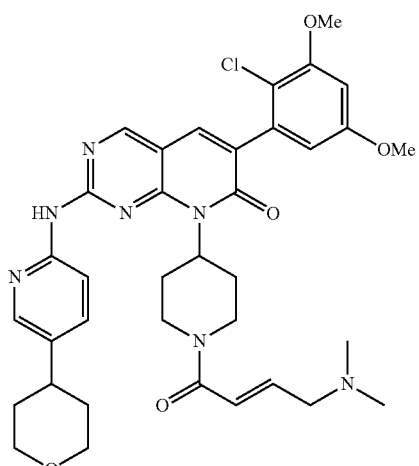

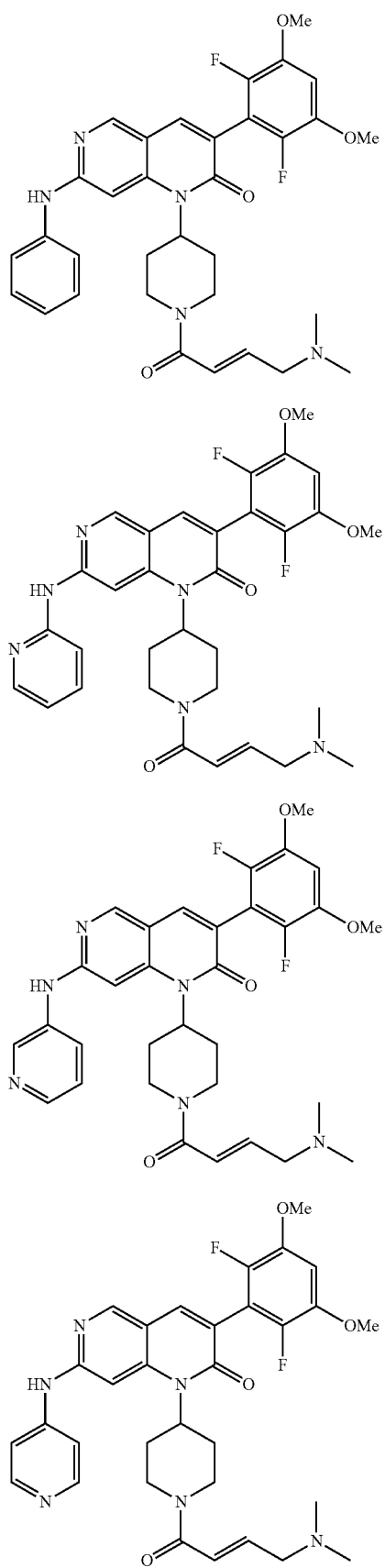
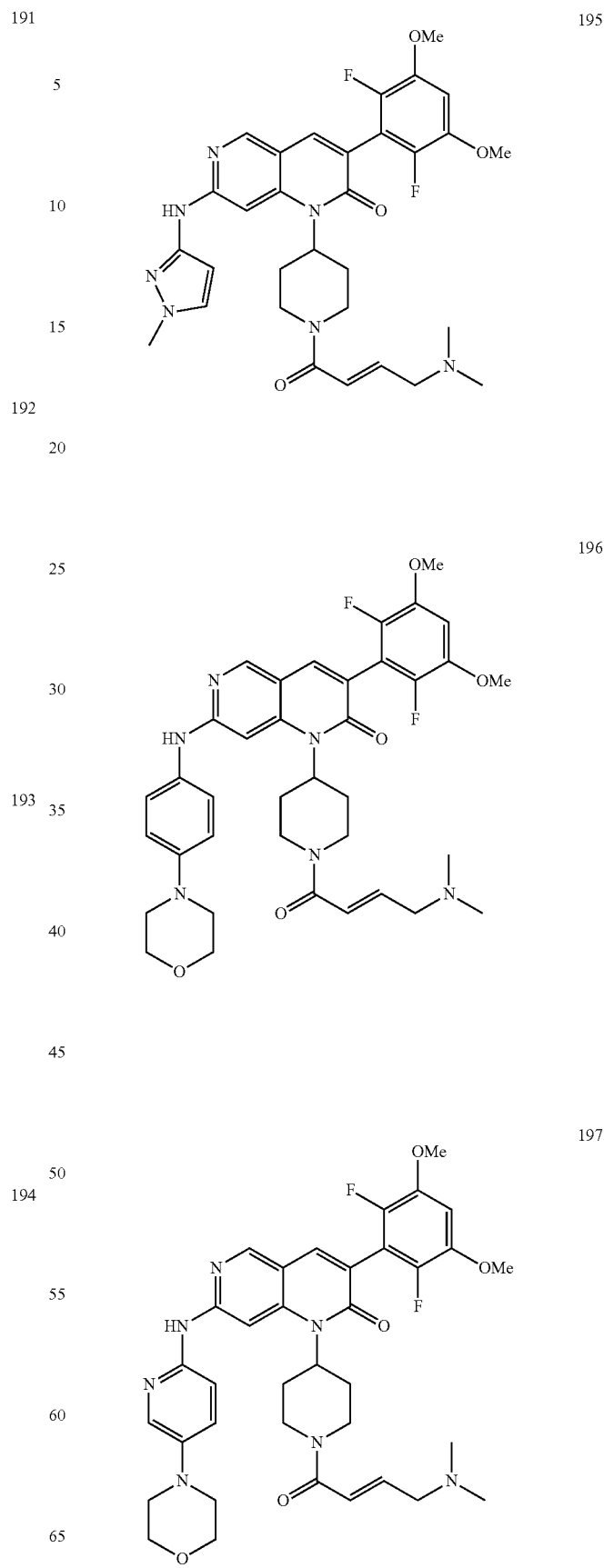

77
-continued
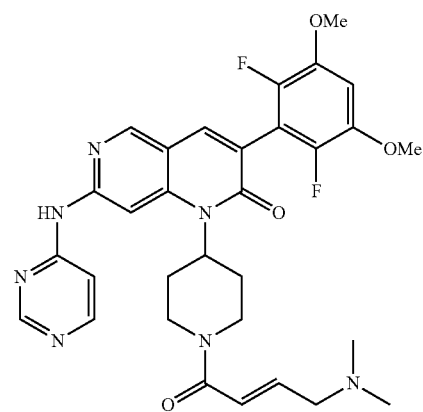
198
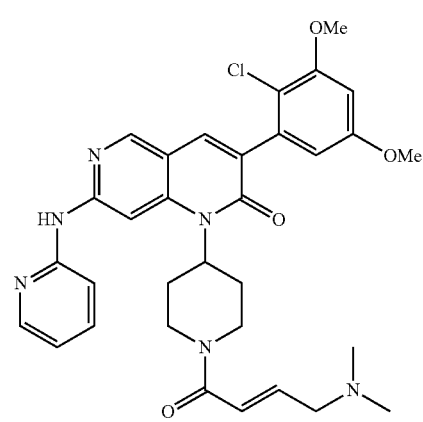
199
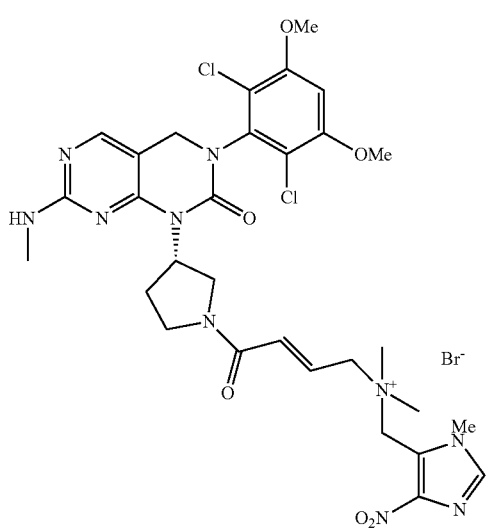
200
78
-continued
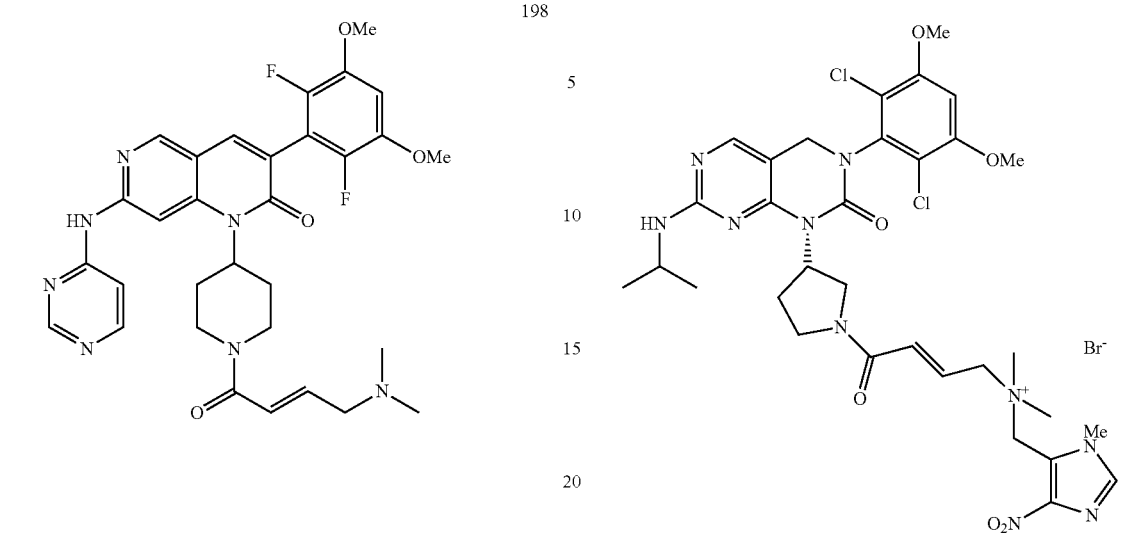
201
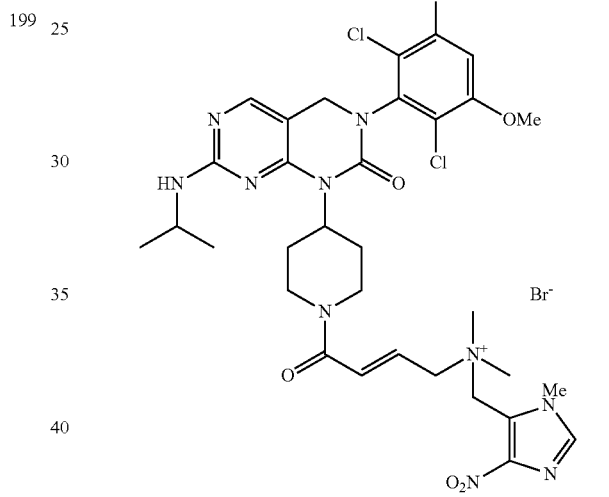
202
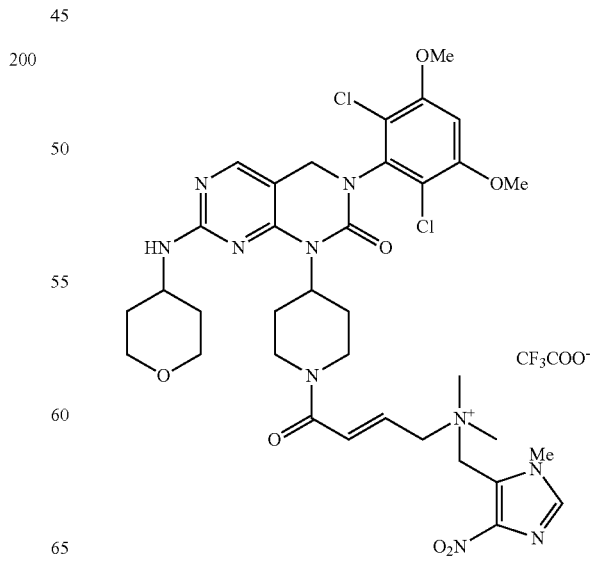
203

204
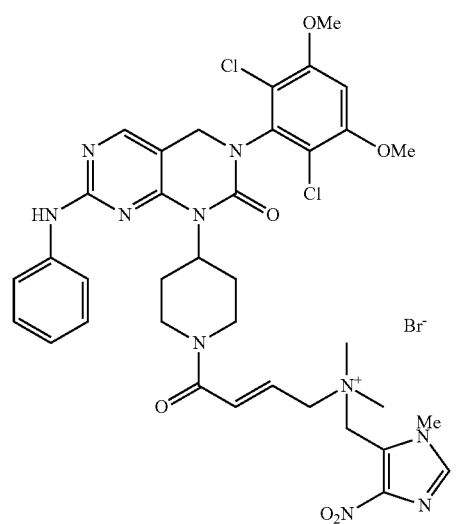
205
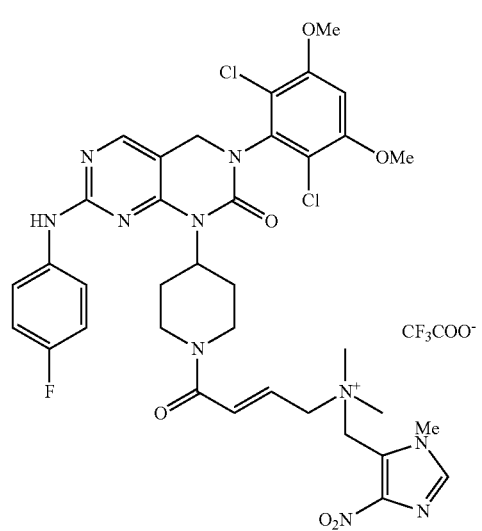
206
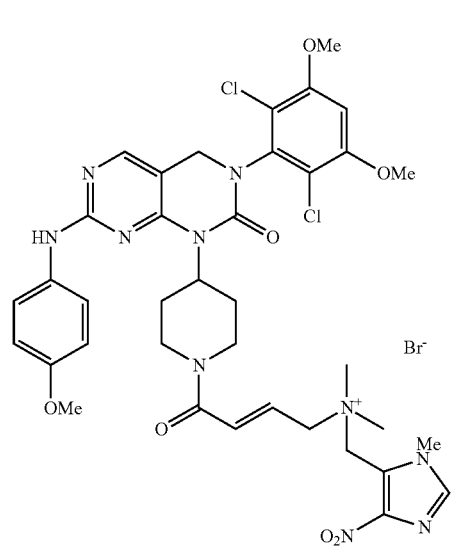
207
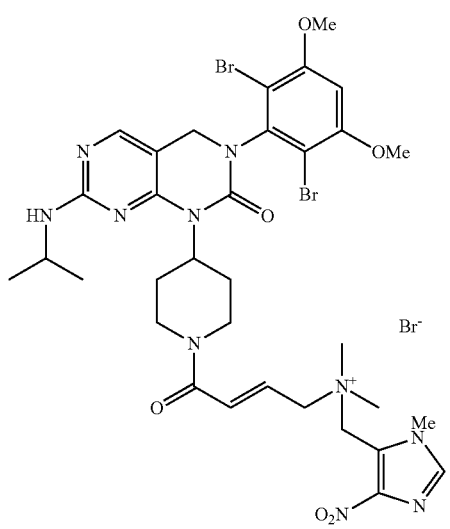
208
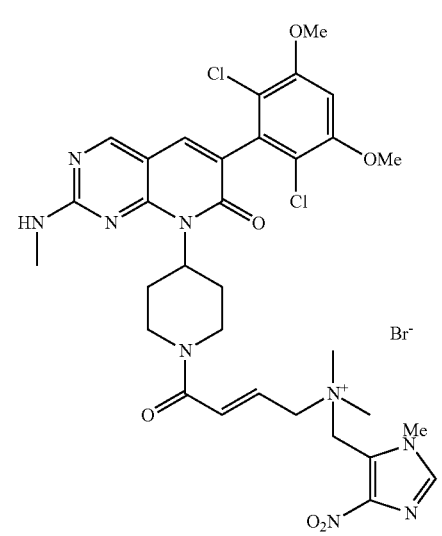
209
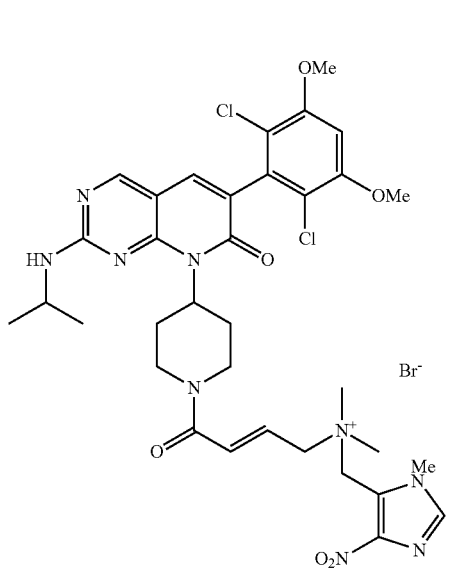

210
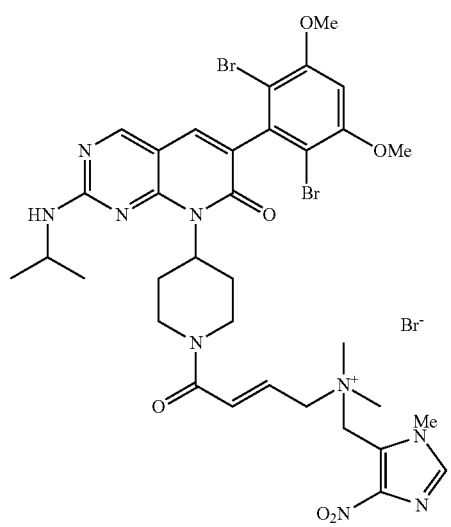
211
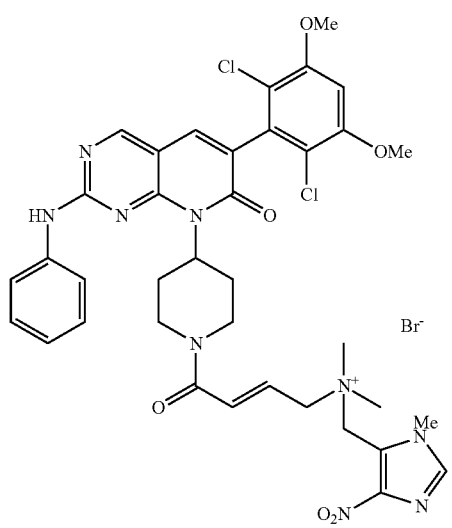
212
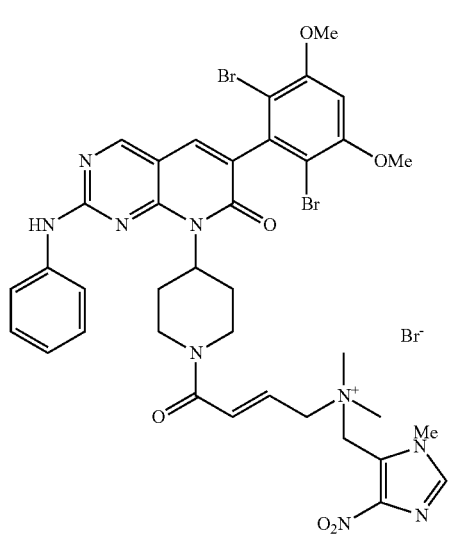
213
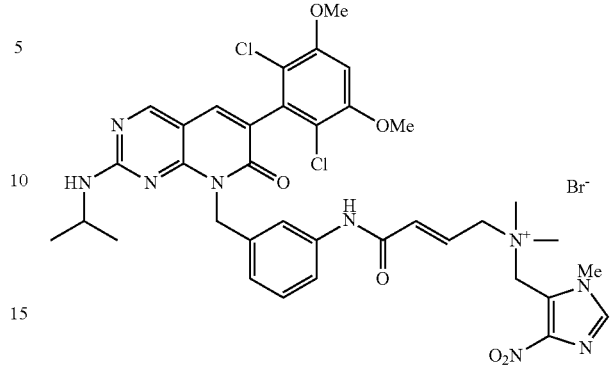
214
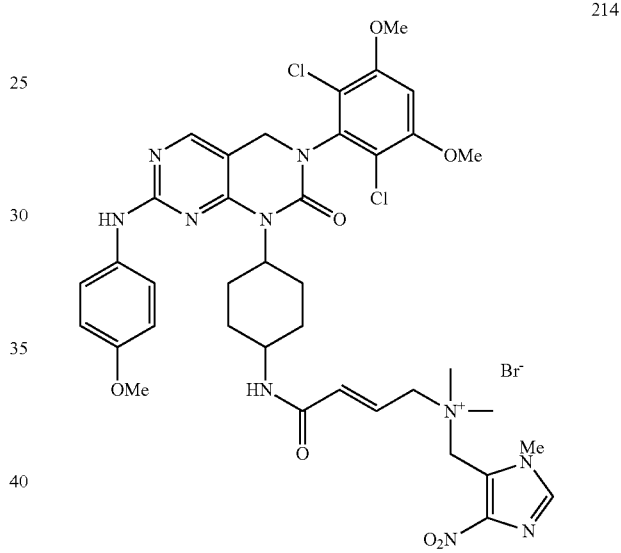
215
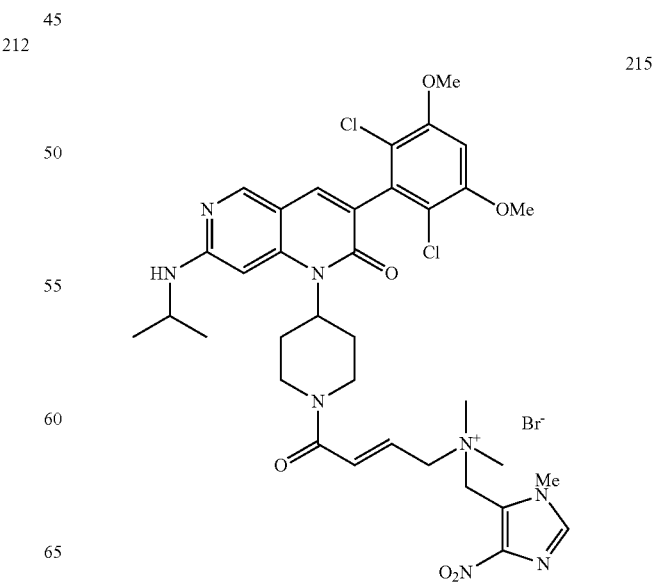

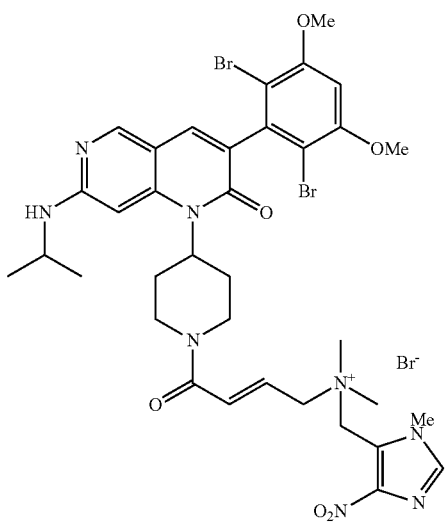
216
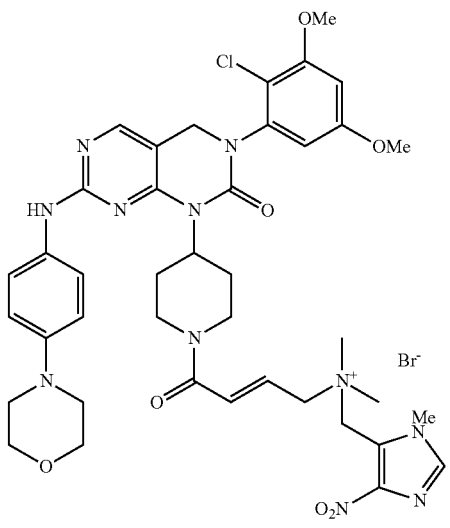
219
217
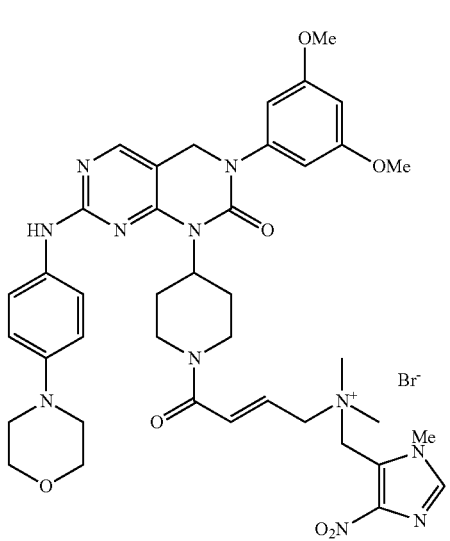
220
218
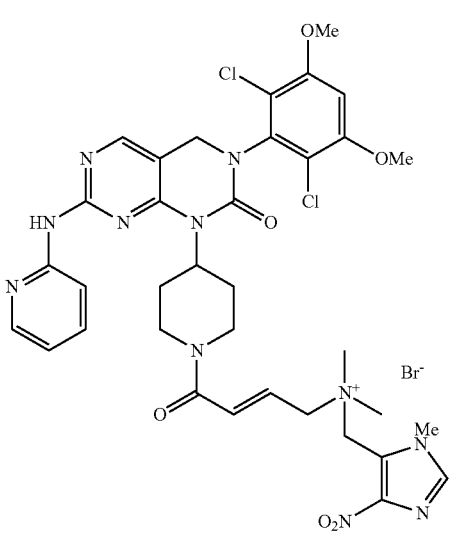
221

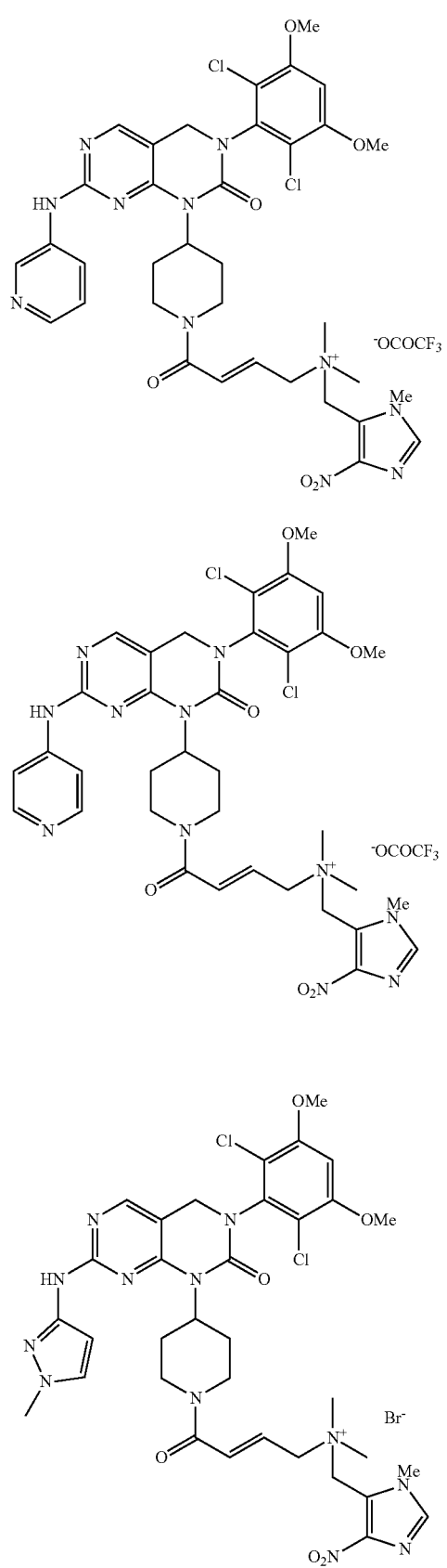
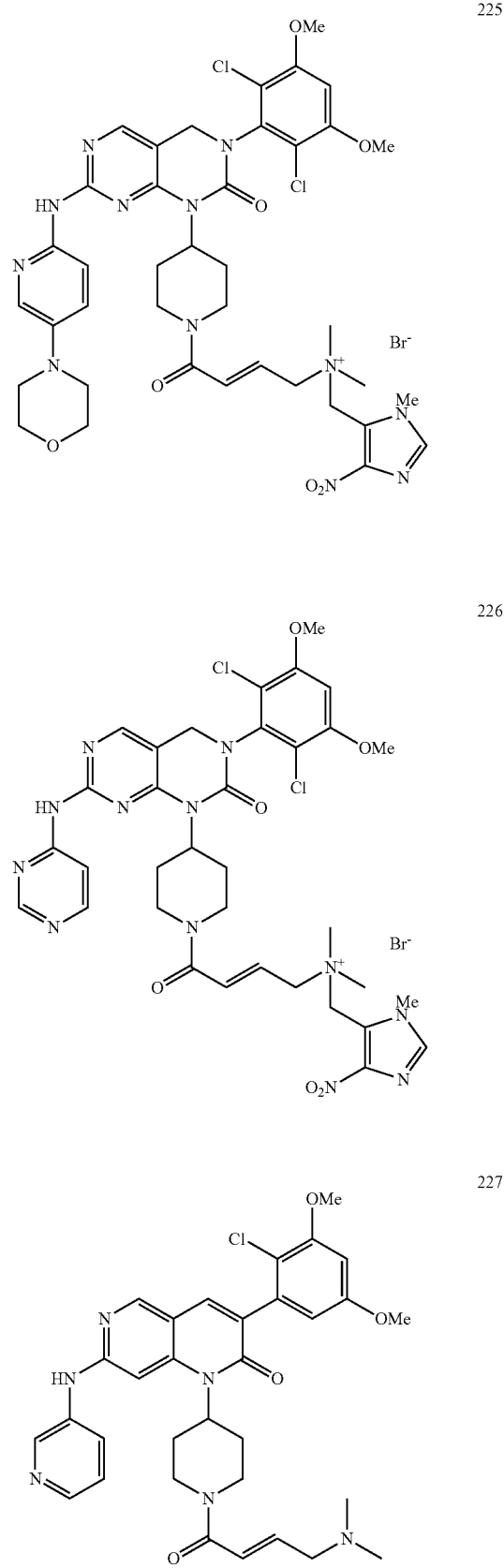

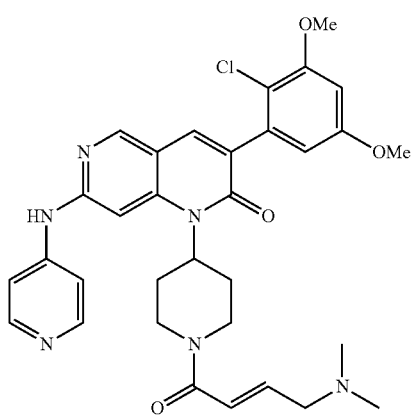
228
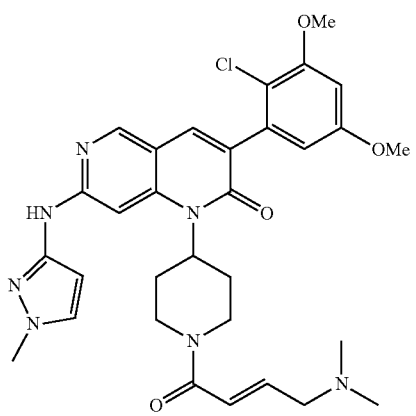
231
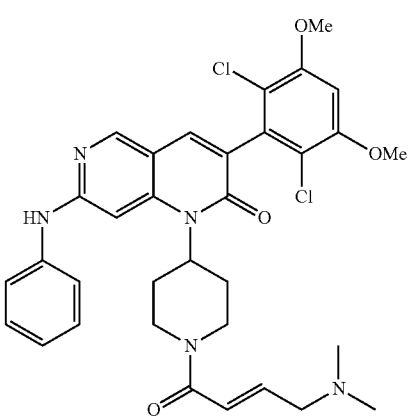
232
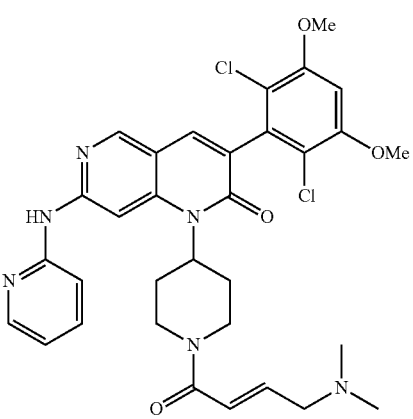
233
229
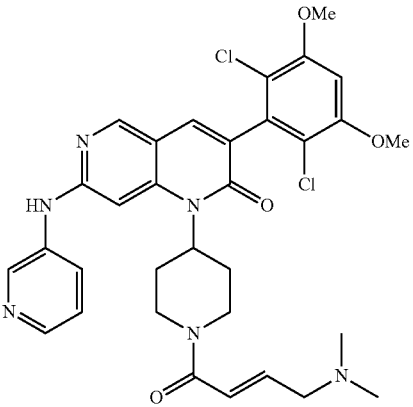
234
230

235
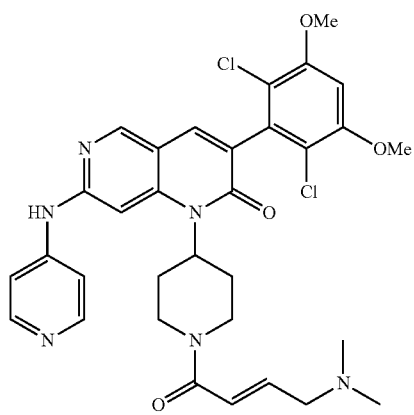
236
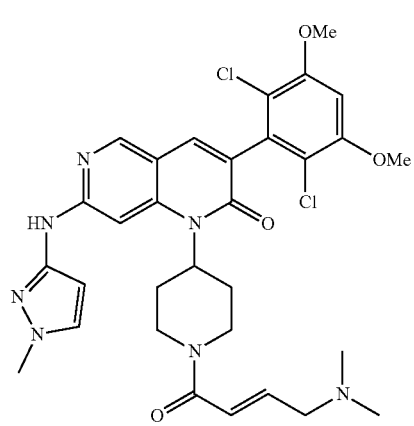
237
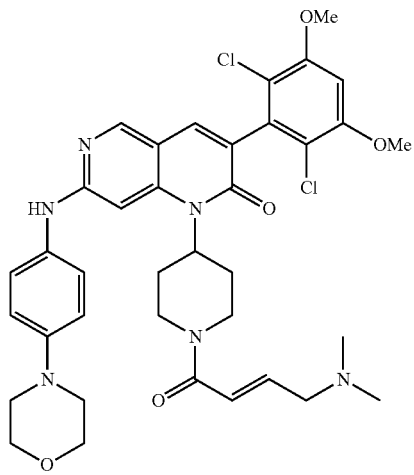
238
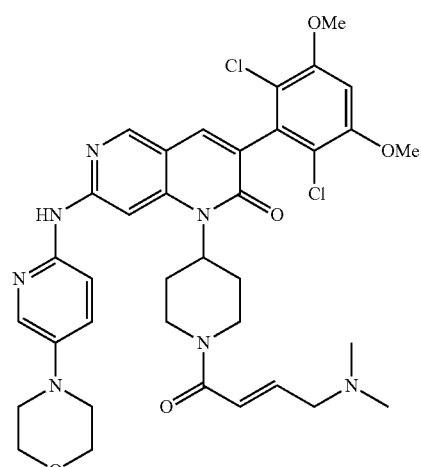
239
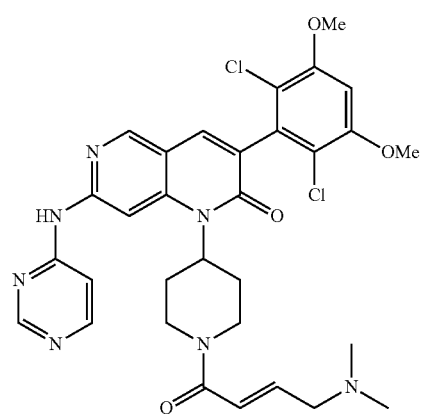
240
241
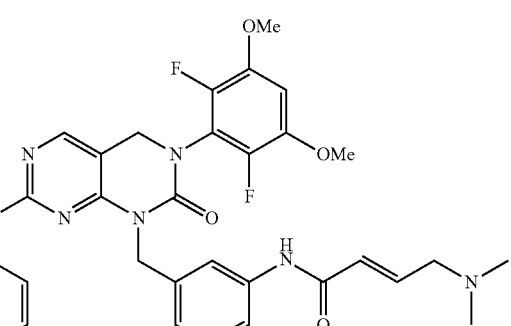

242 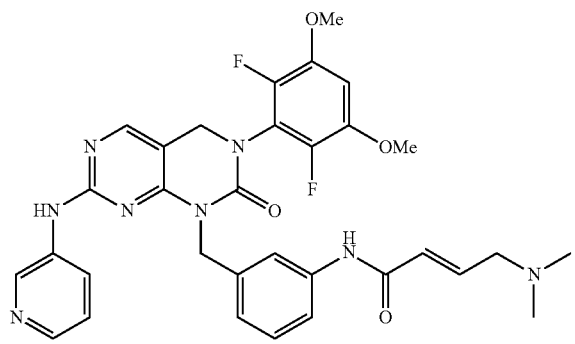
243 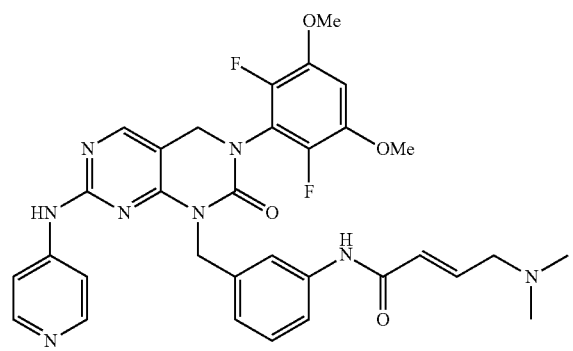
244 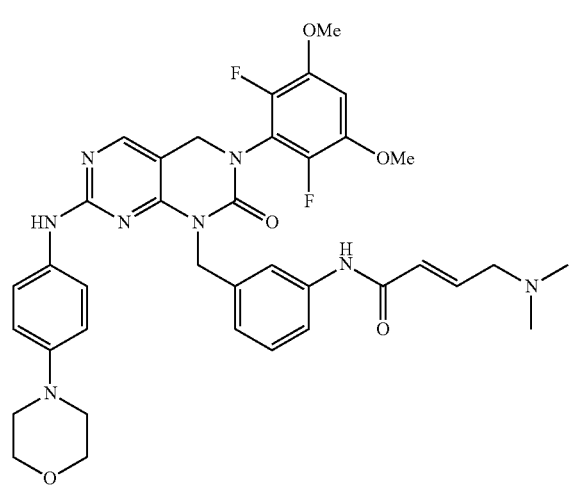
245 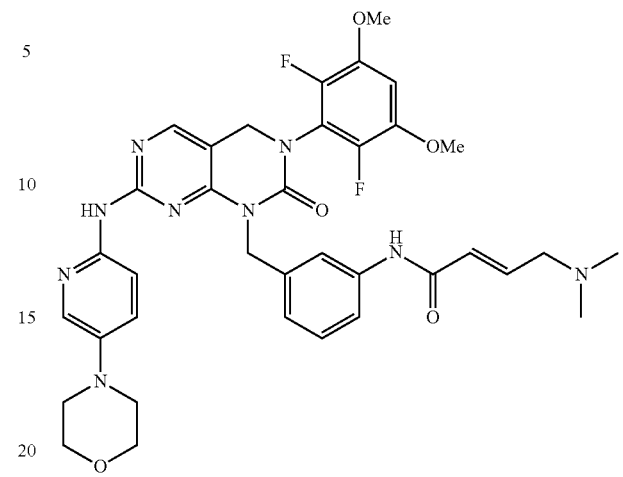
246 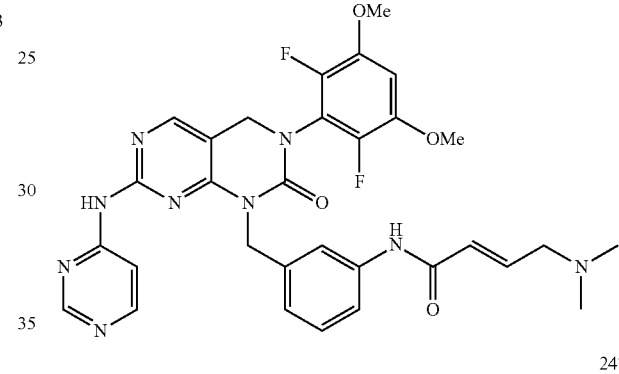
247 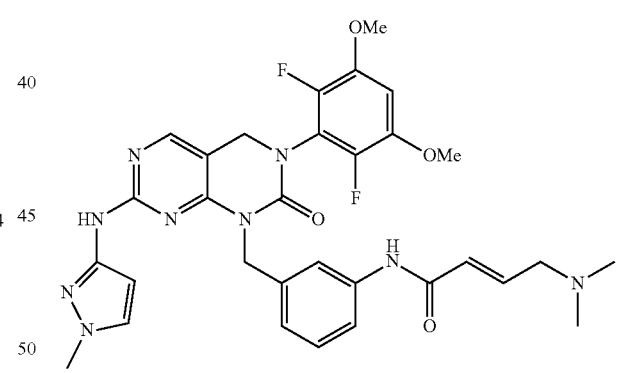
248 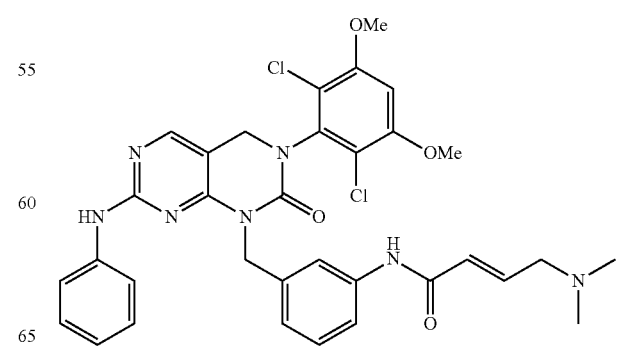

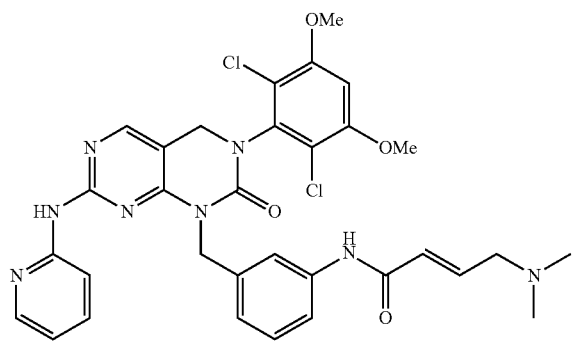
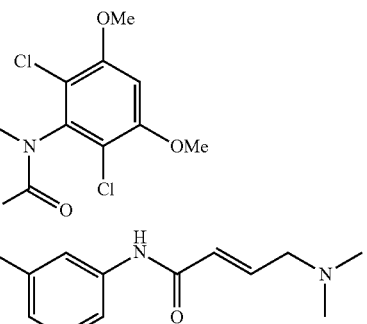
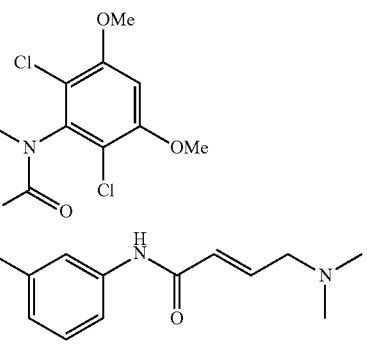
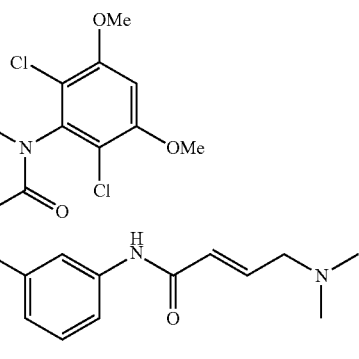
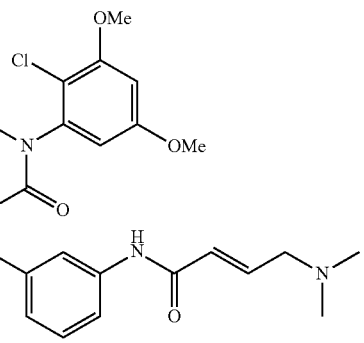

-continued
257
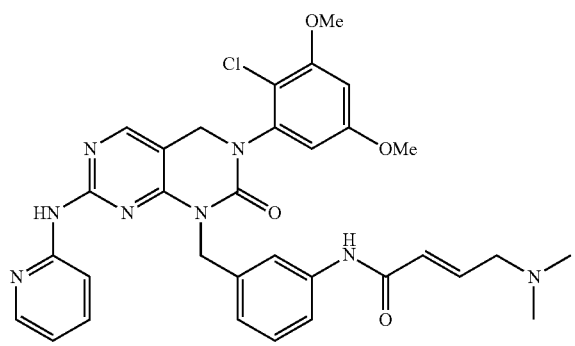
258
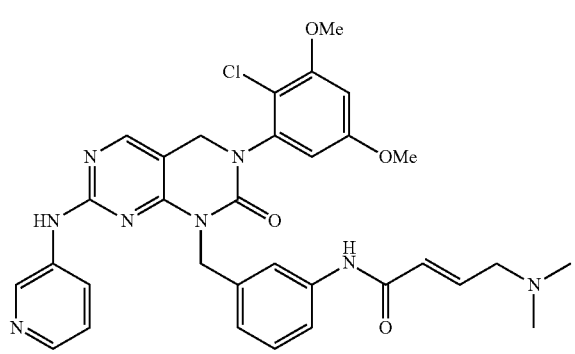
259
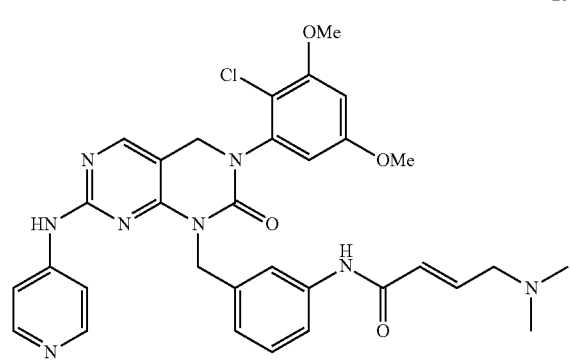
260
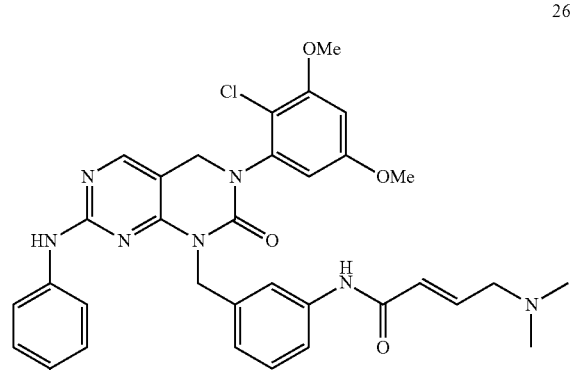
-continued
261
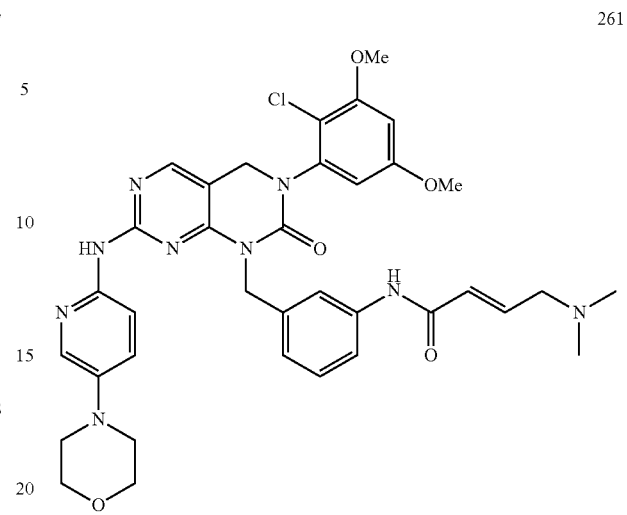
262
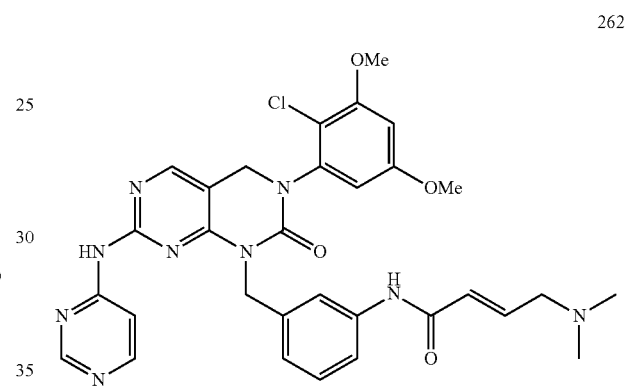
263
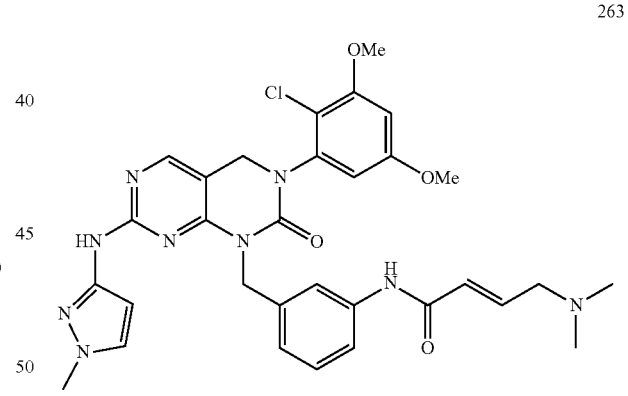
264
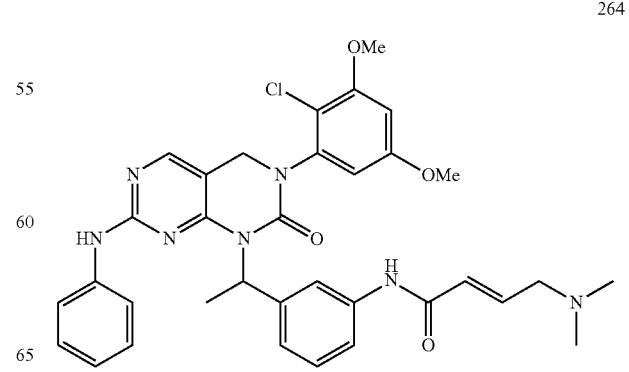

265
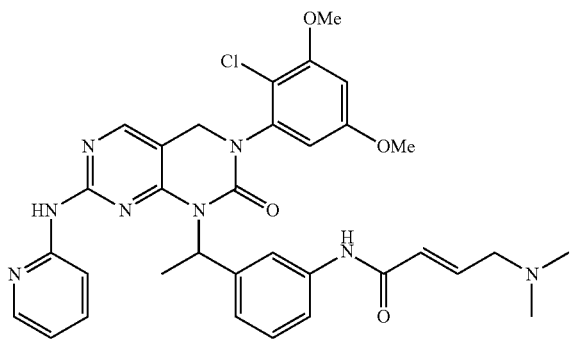
266
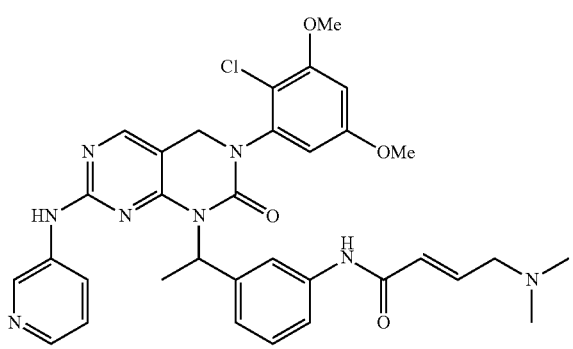
267
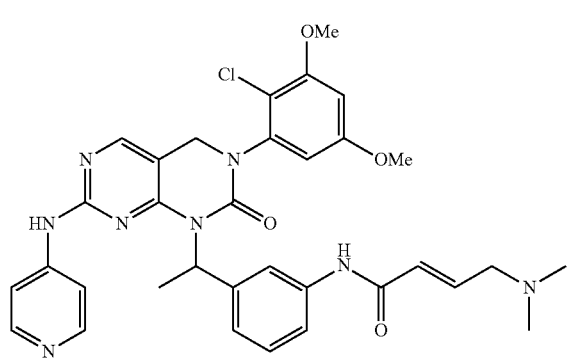
268
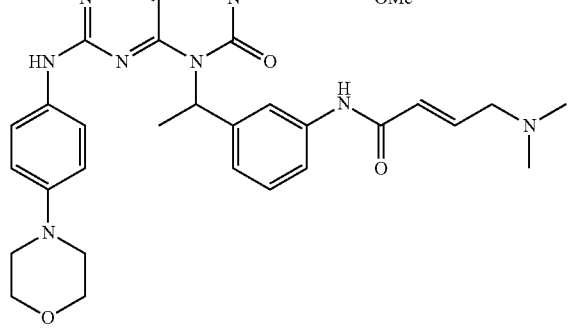
269
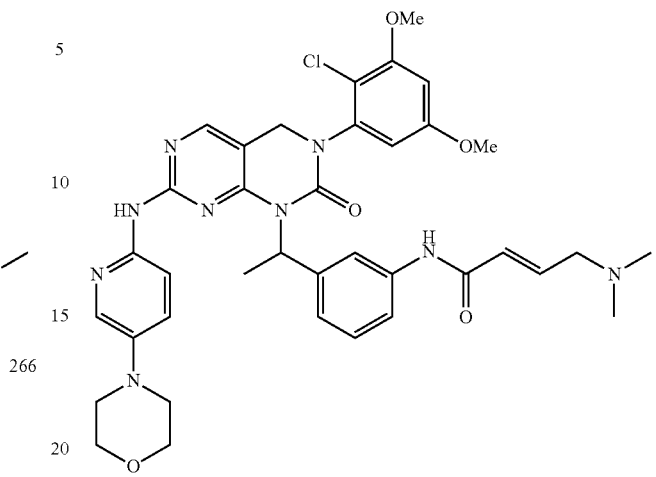
270
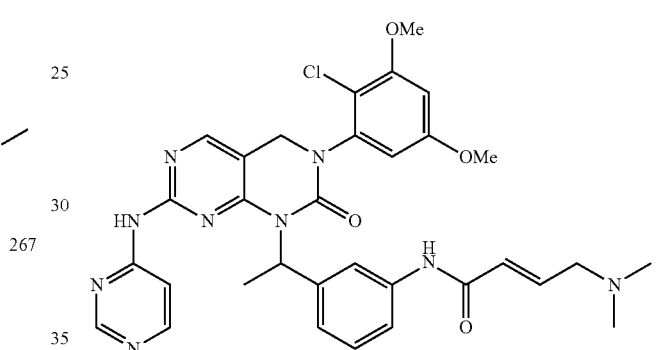
271
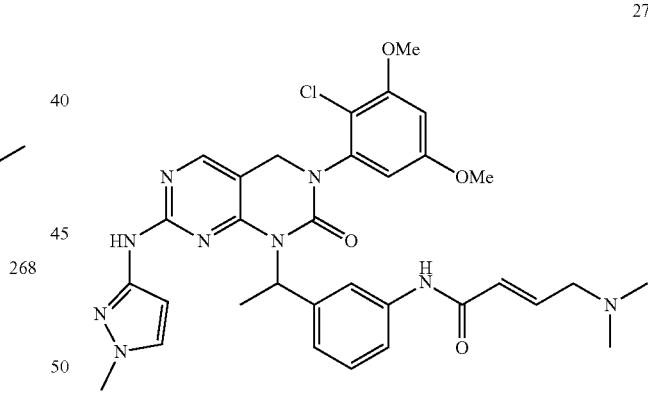
272
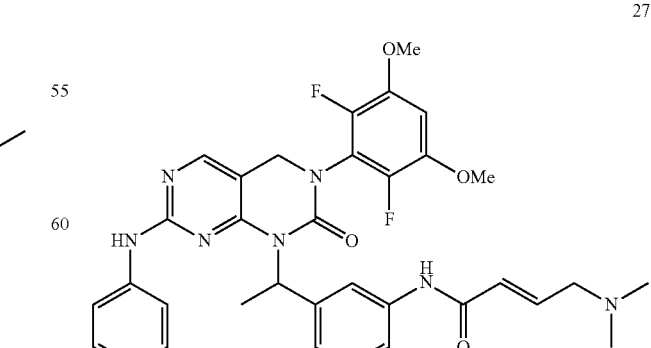

273
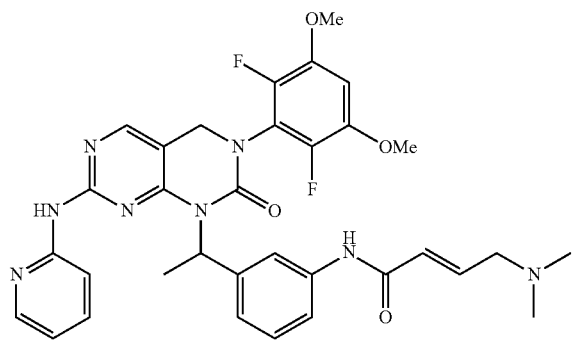
274
275
276
277
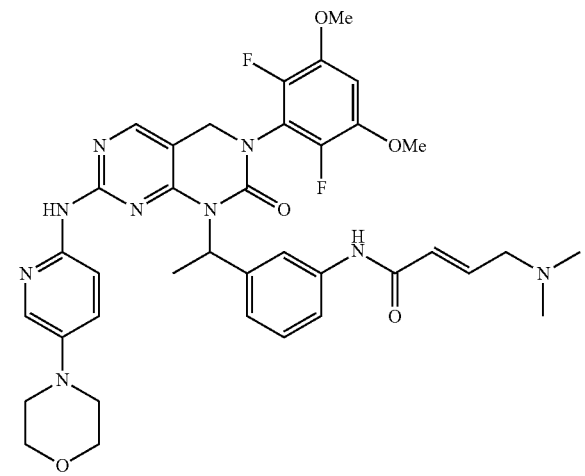
278
279
280
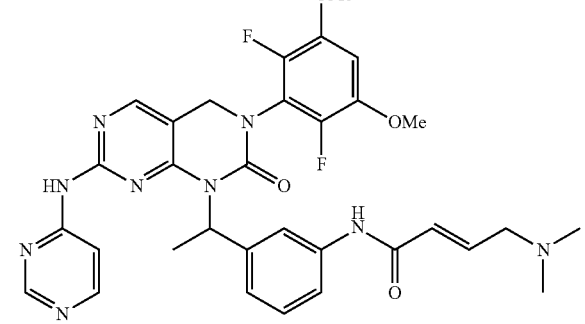
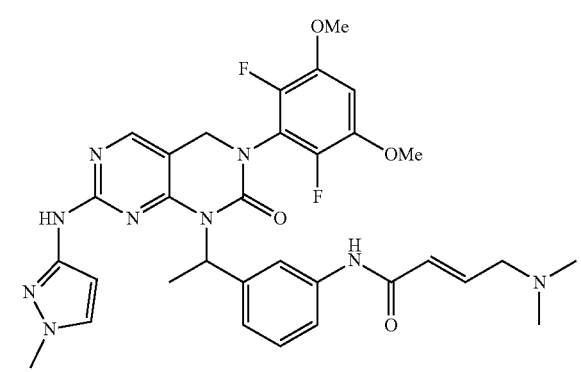
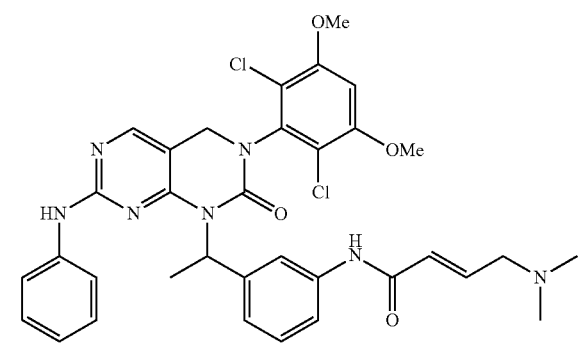

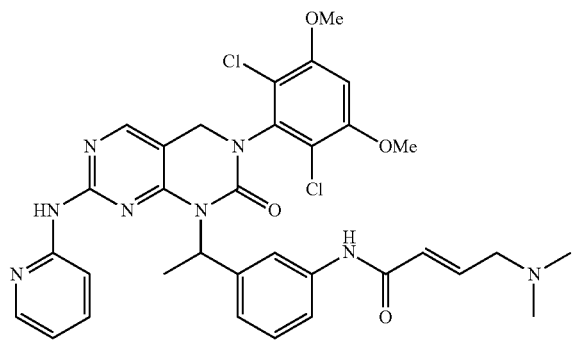
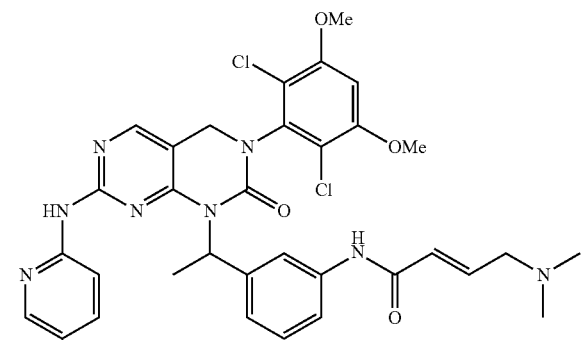

289
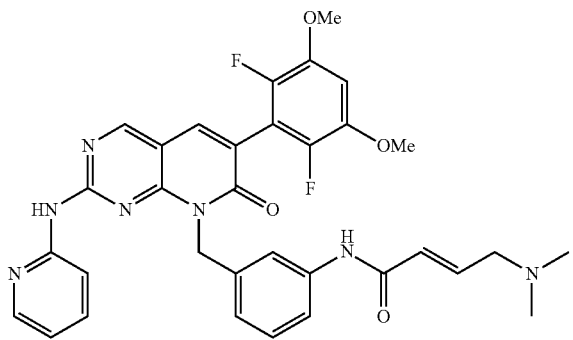
290
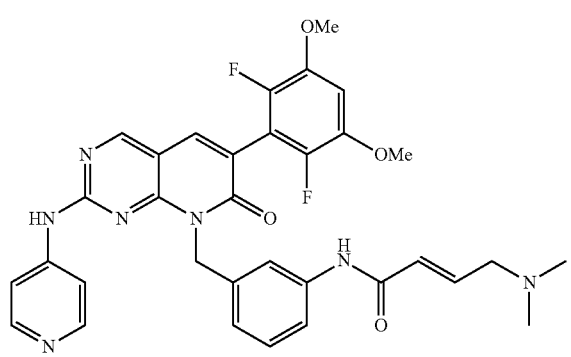
291
292
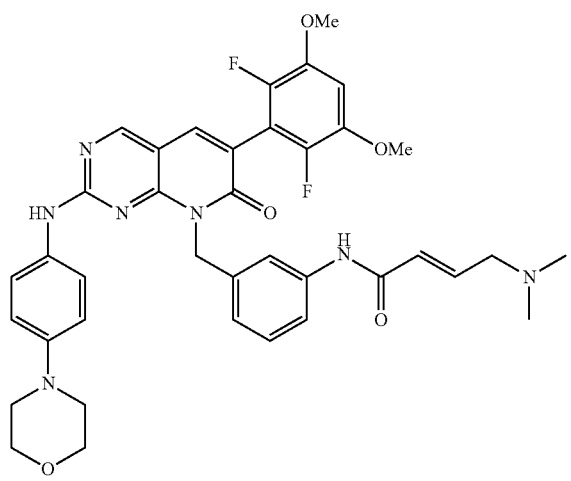
293
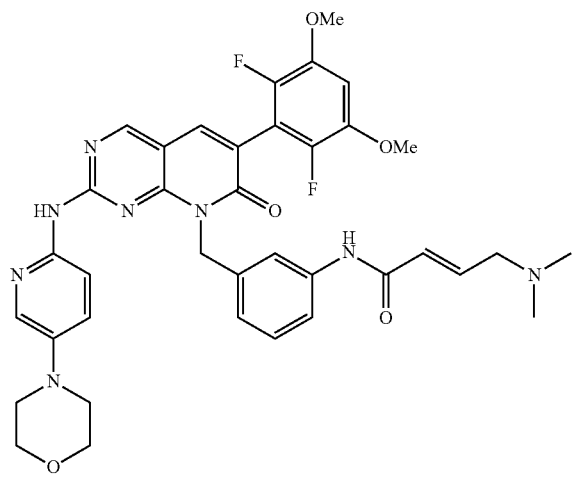
294
295
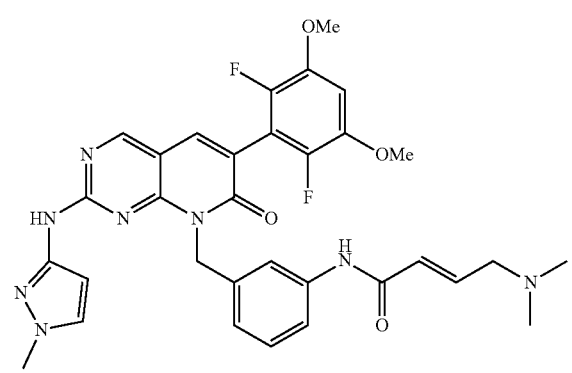
298
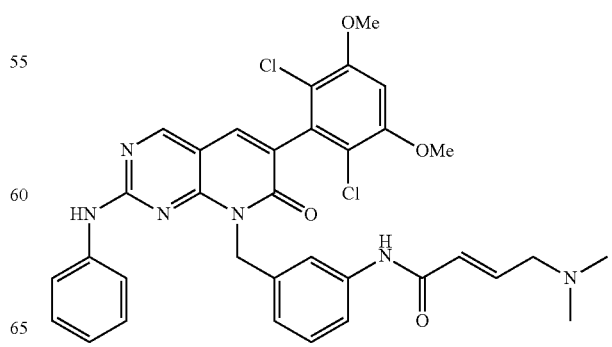

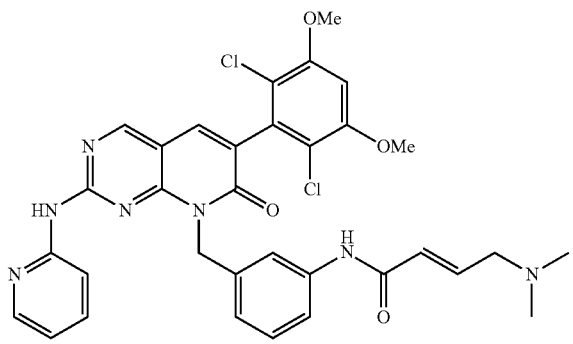
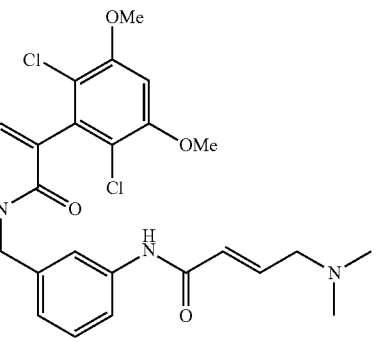
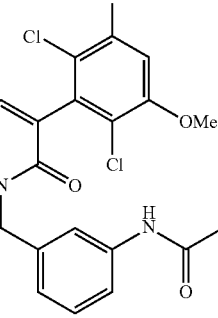
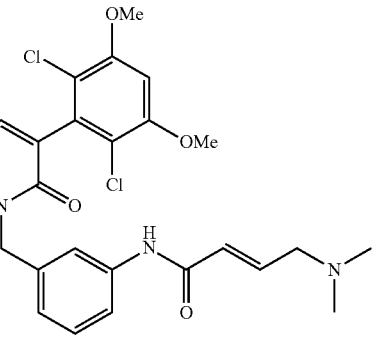
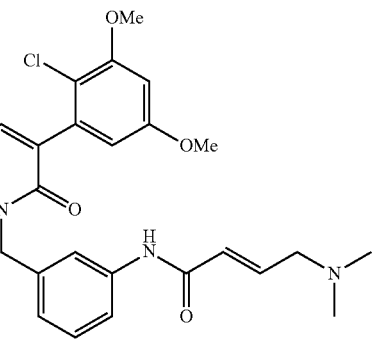

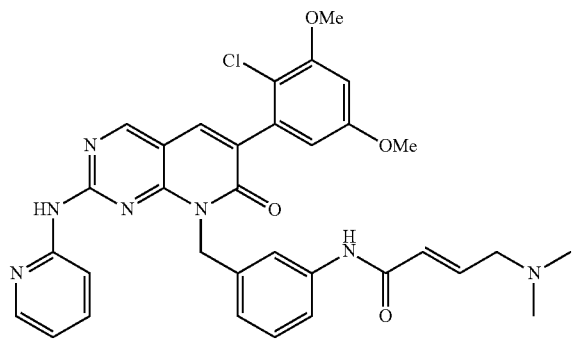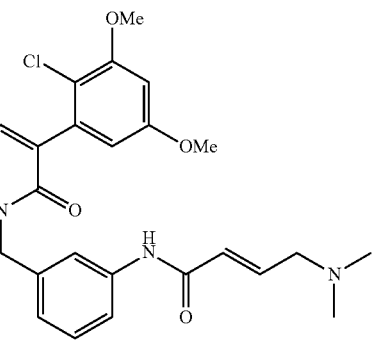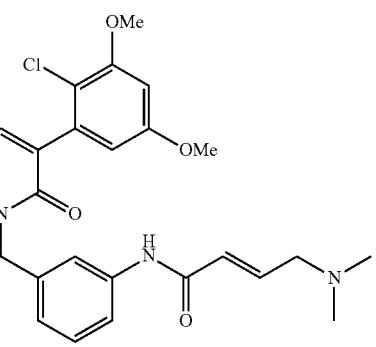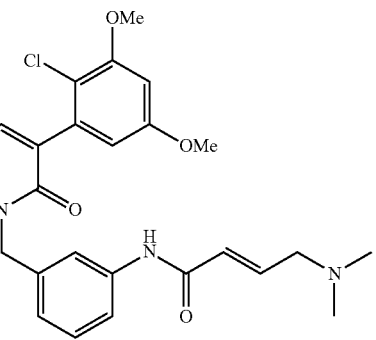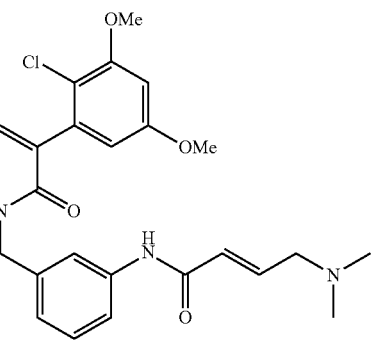

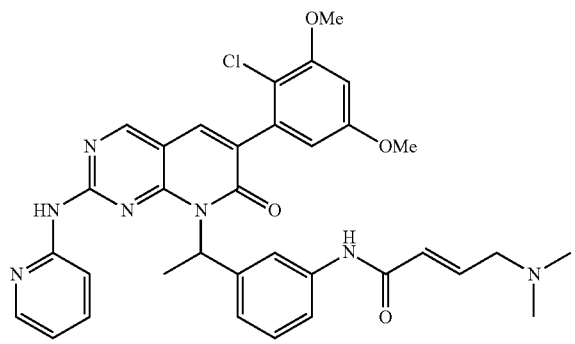
339
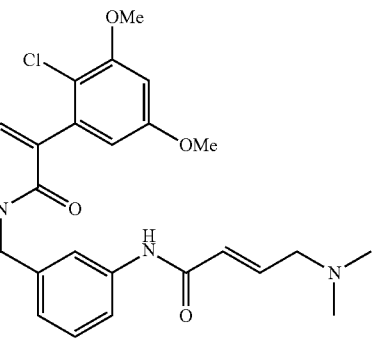
343
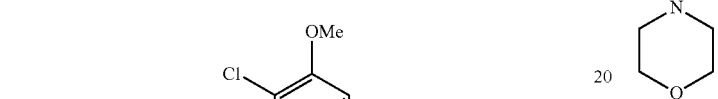
340
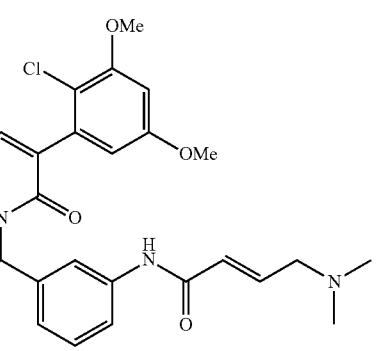
344
341
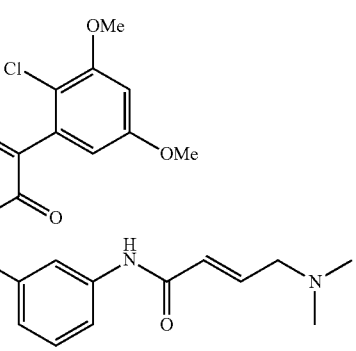
345
342
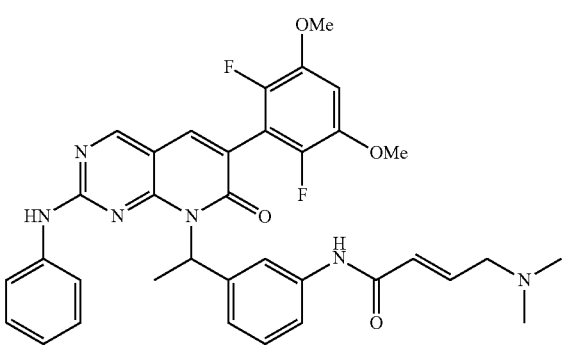
346

347
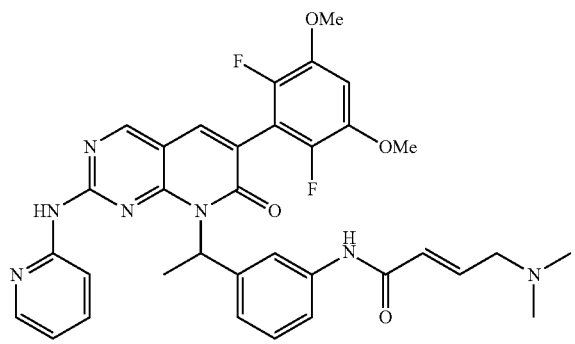
348
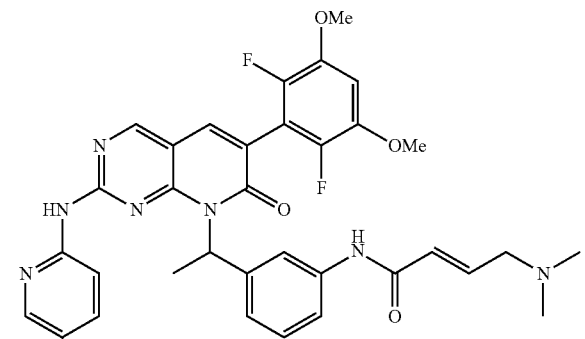
351
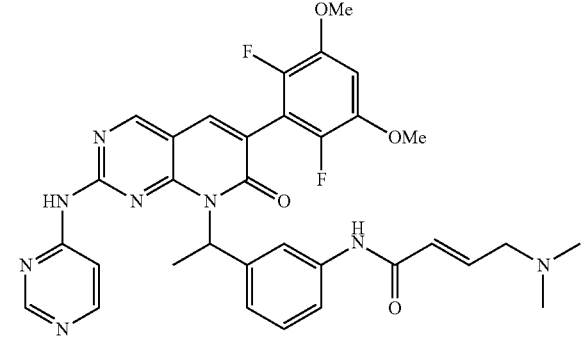
352
353
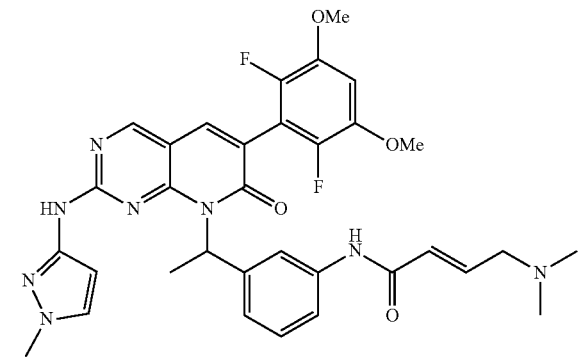
354
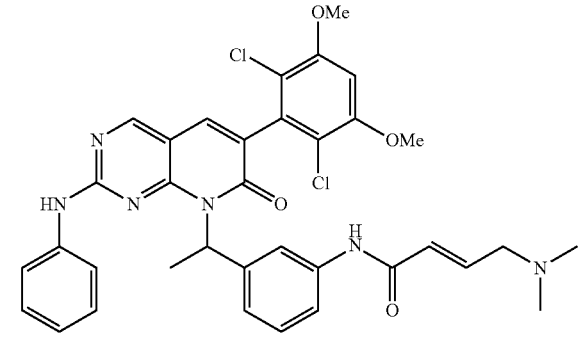

355
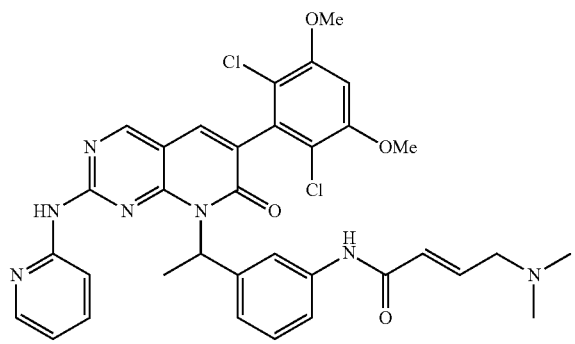
356
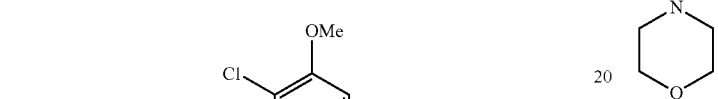
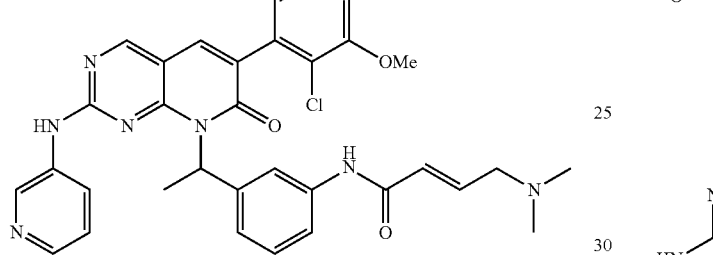
357
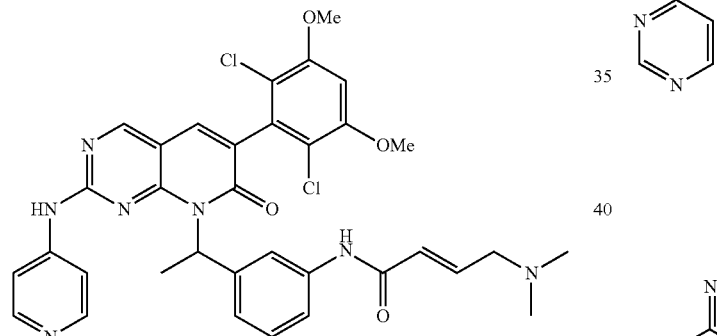
358
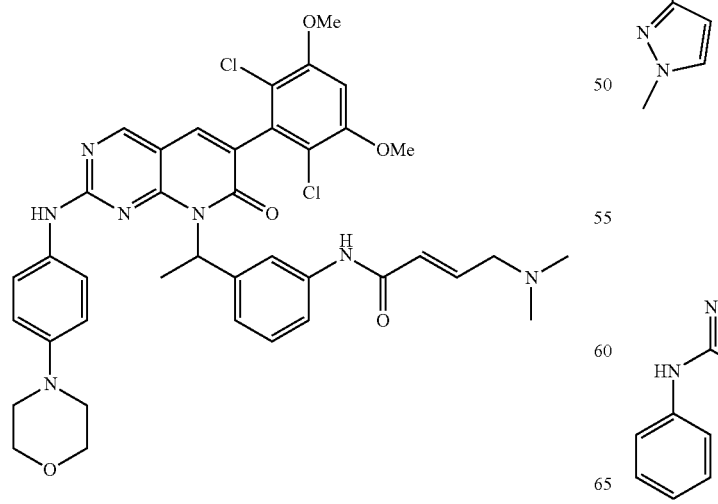
359
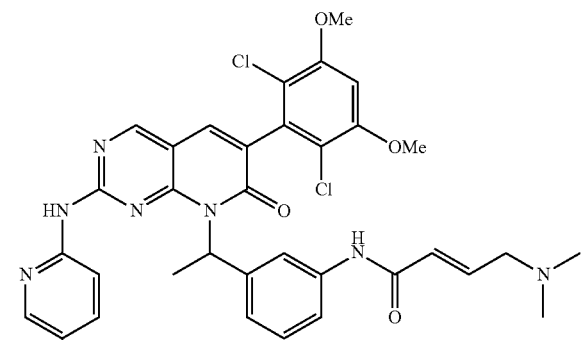
360
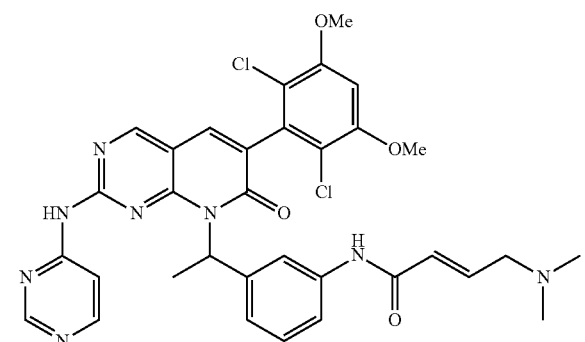
361
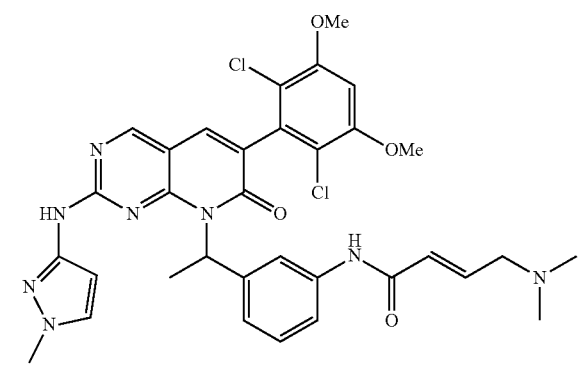
362
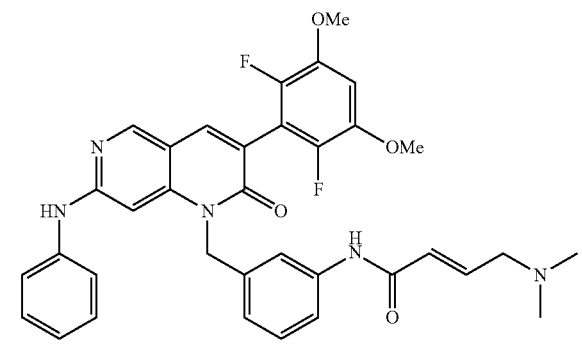

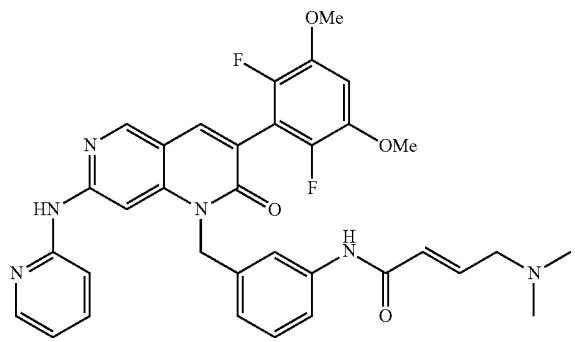
363
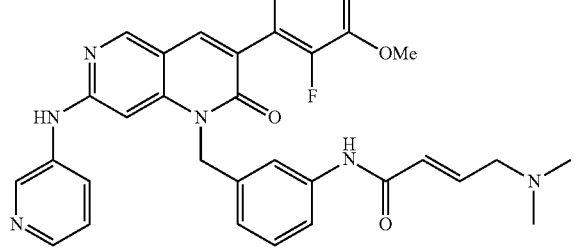
364
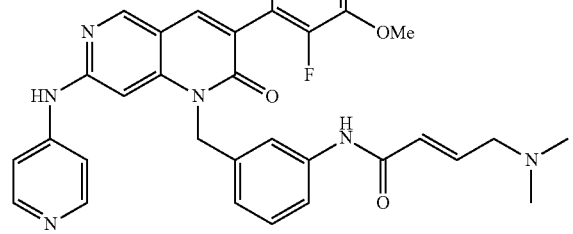
365
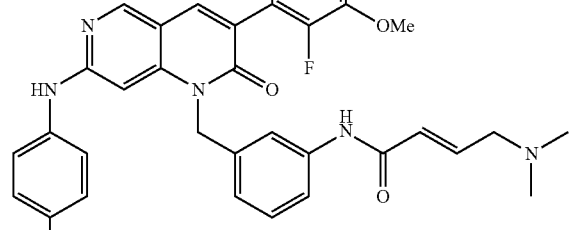
366
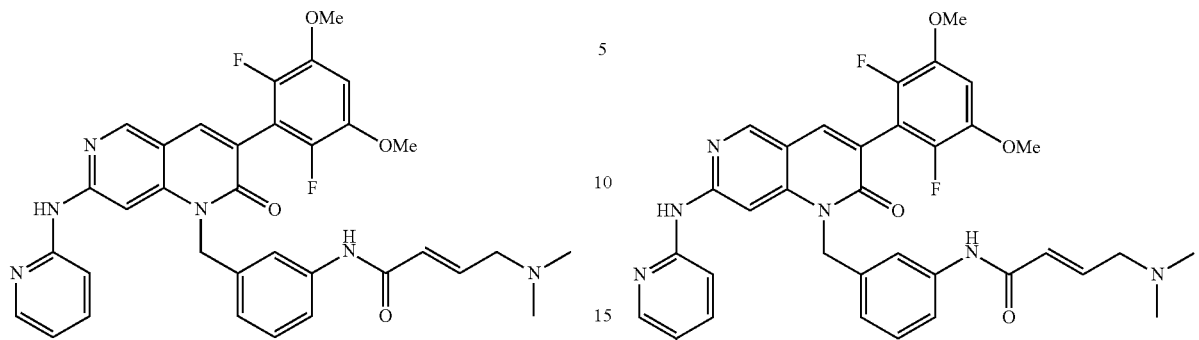
367
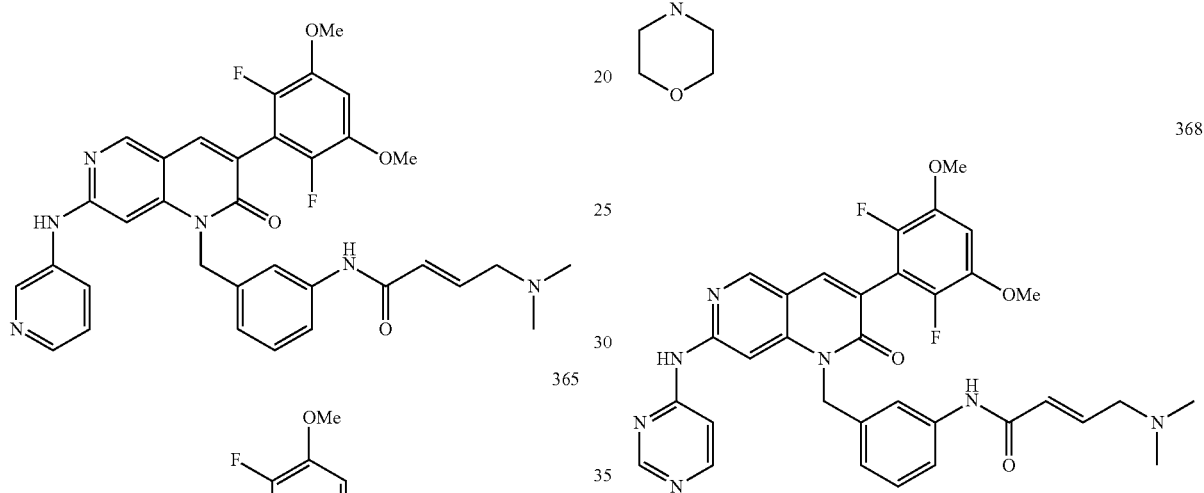
368
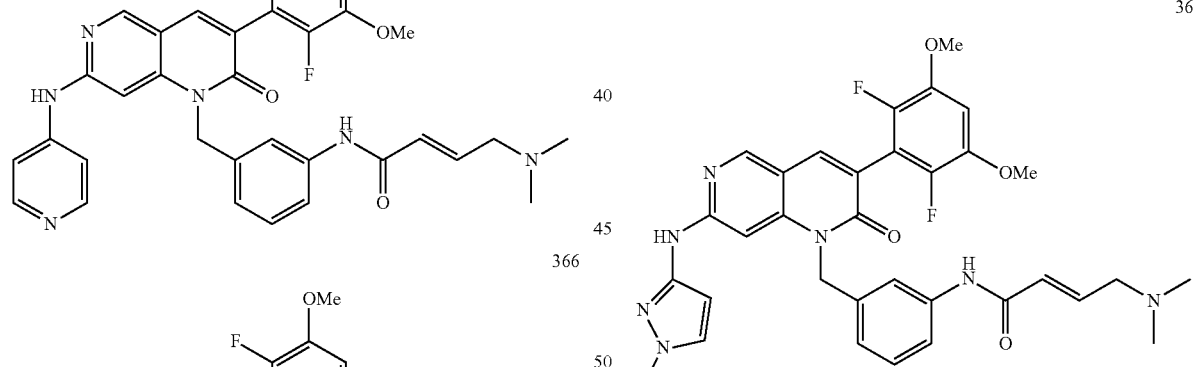
369
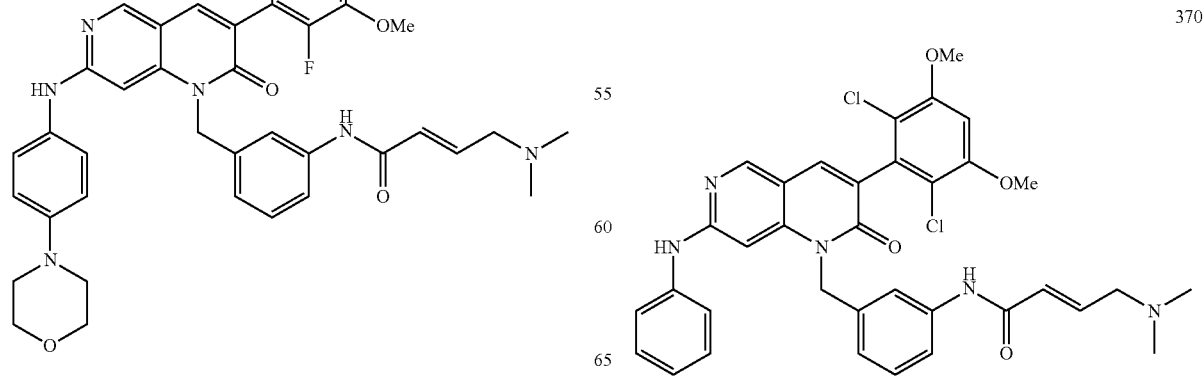
370

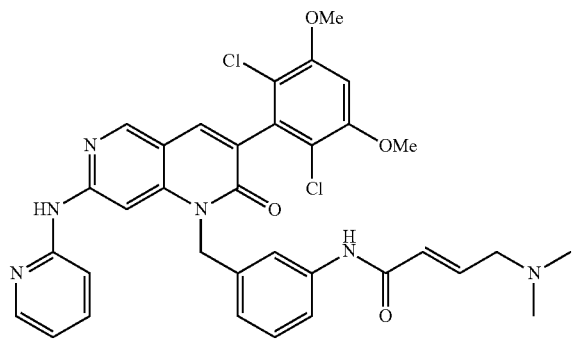
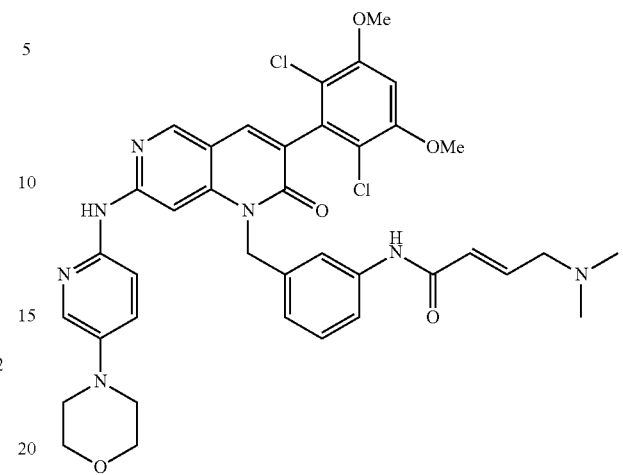

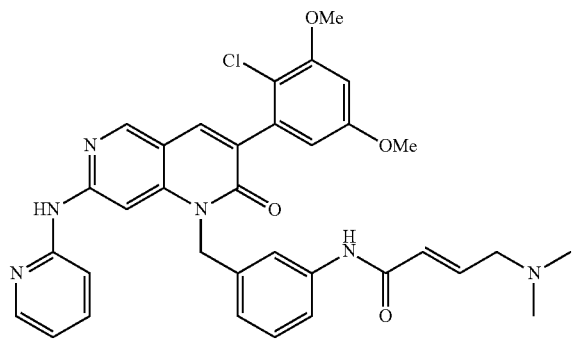
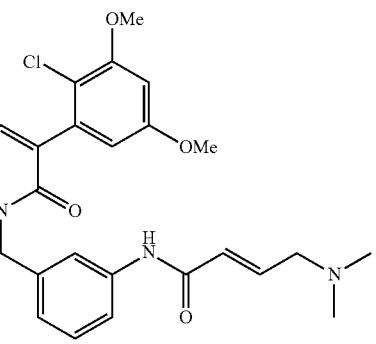
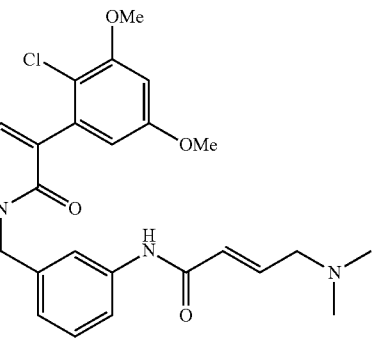
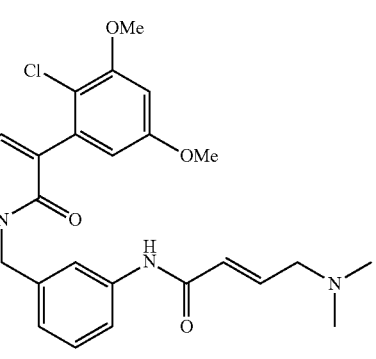
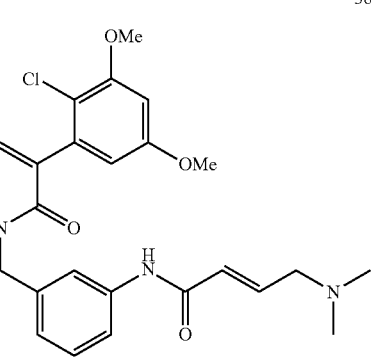

387
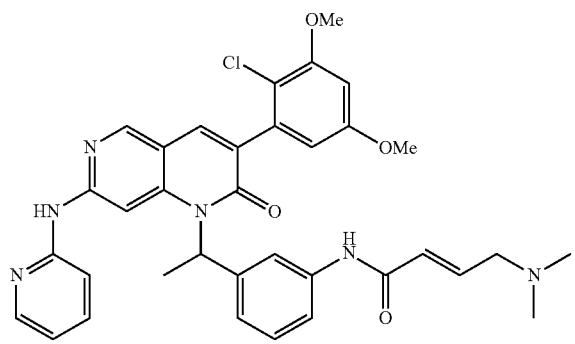
388
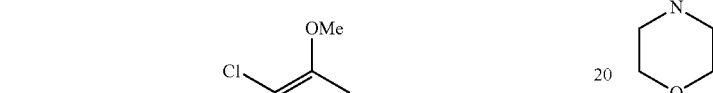
389
390
391
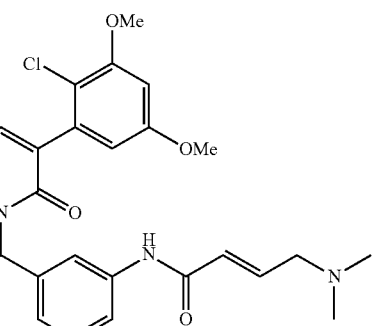
392
393
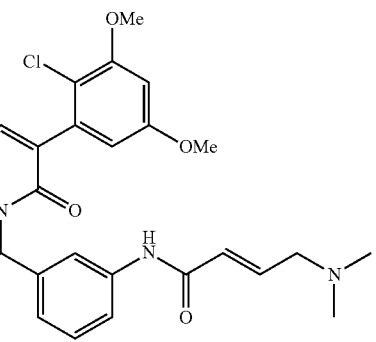
394
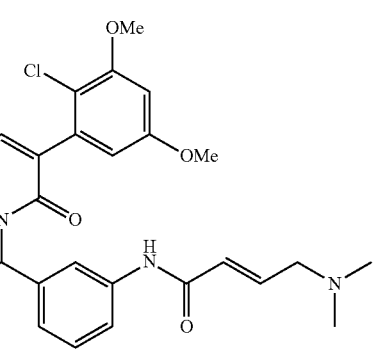
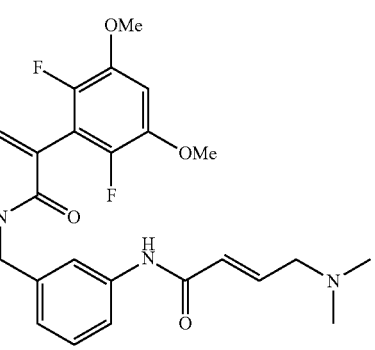

395
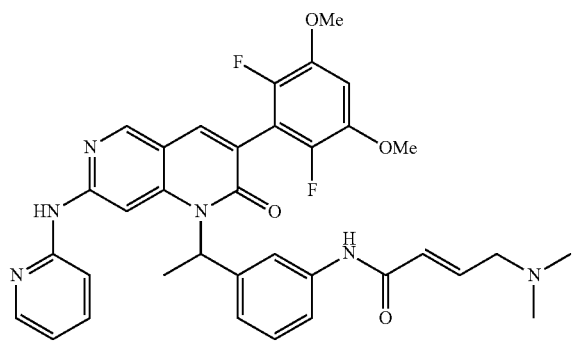
396
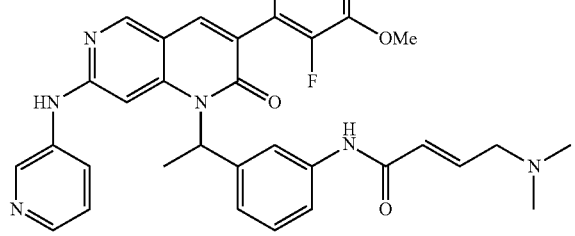
397
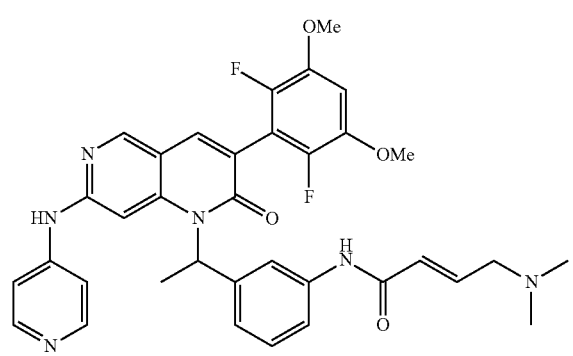
398
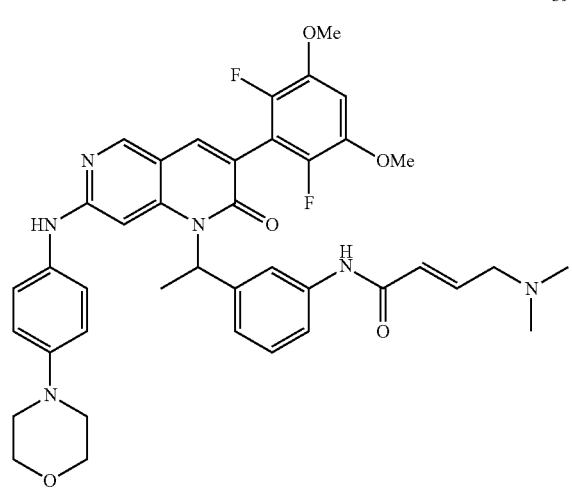
399
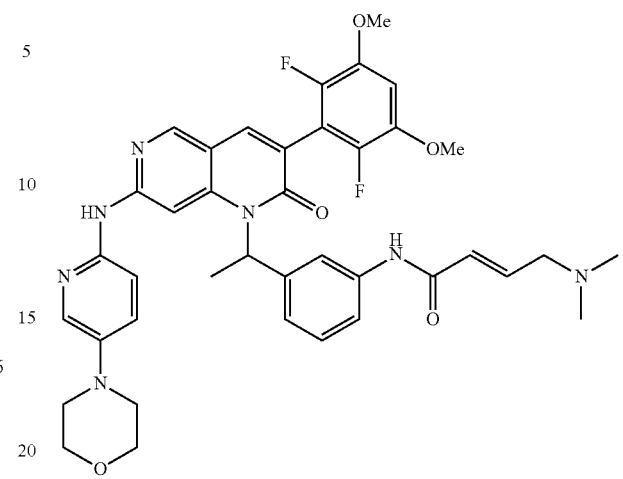
400
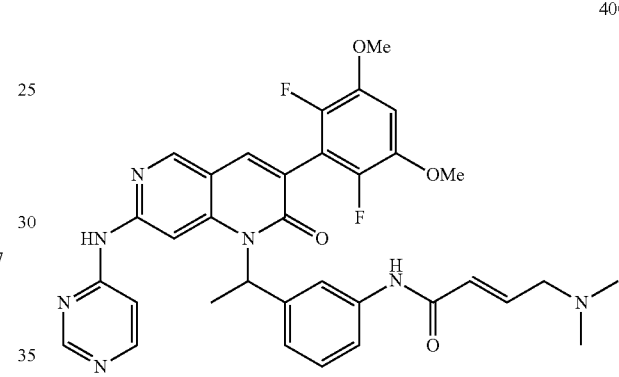
401
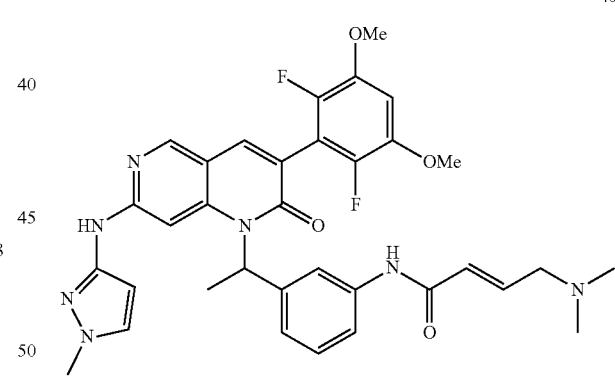
402
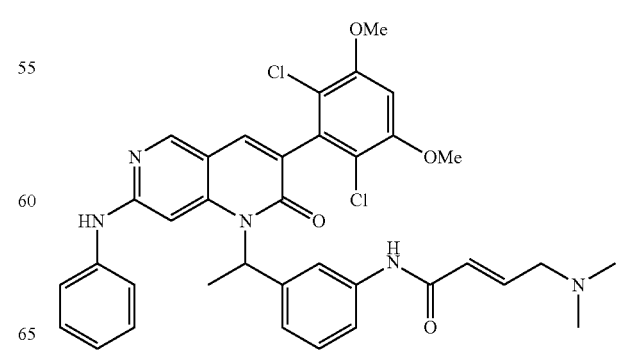

403
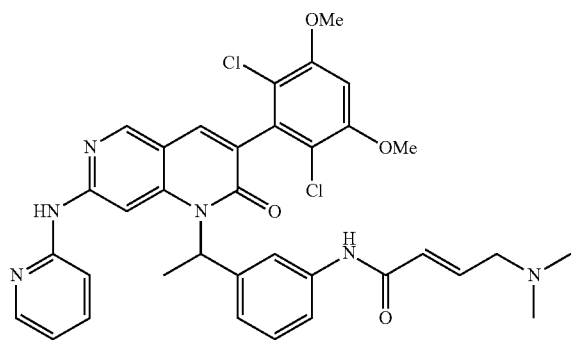
404
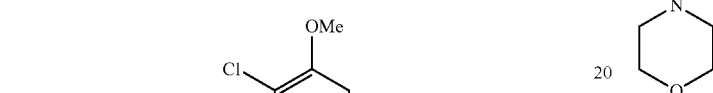
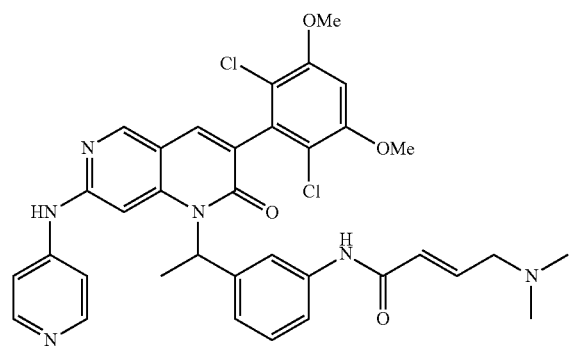
405
406
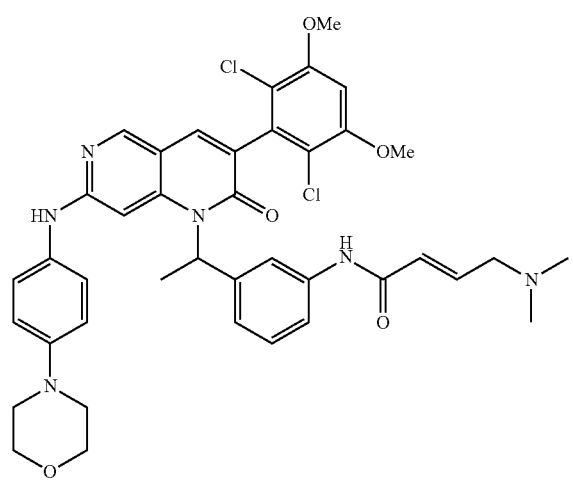
407
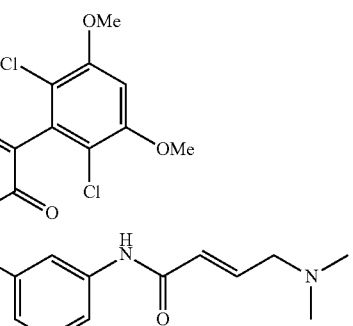
408
409
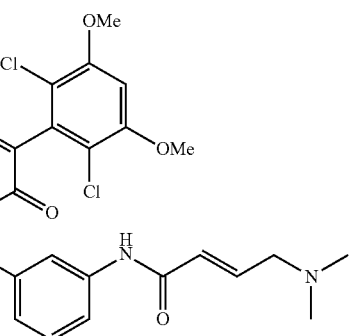

410
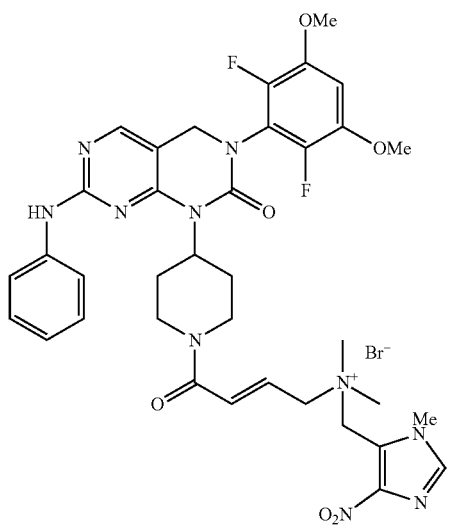
411
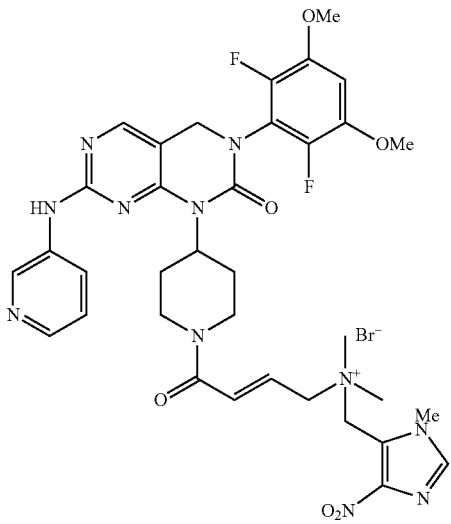
412
413
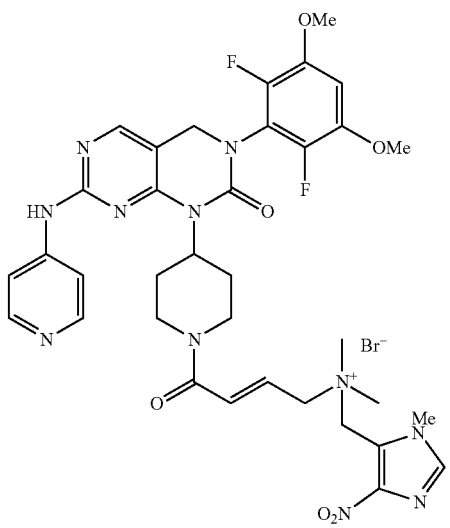
414
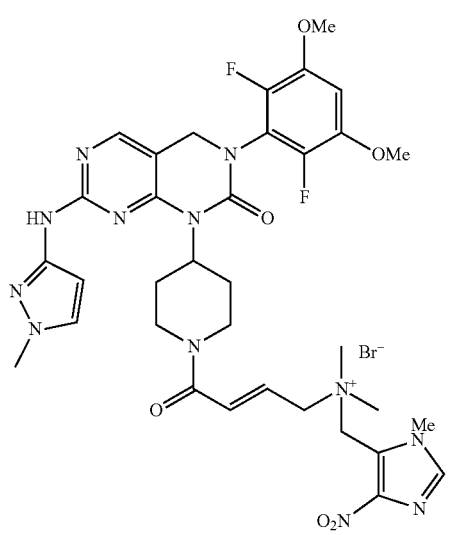
415
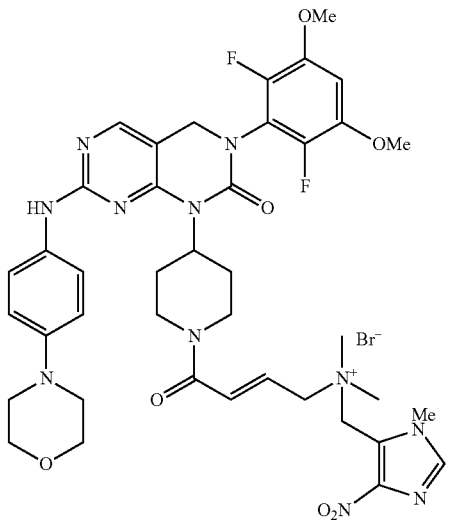

416 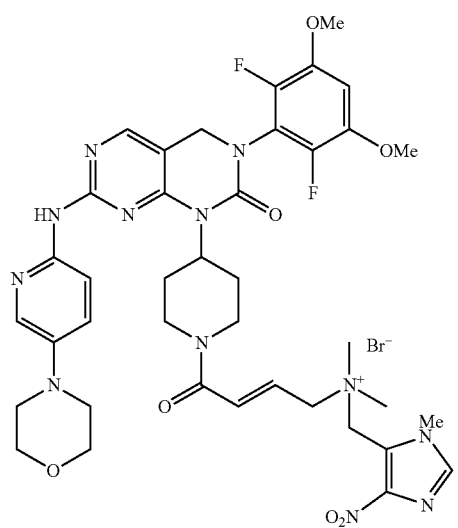
417 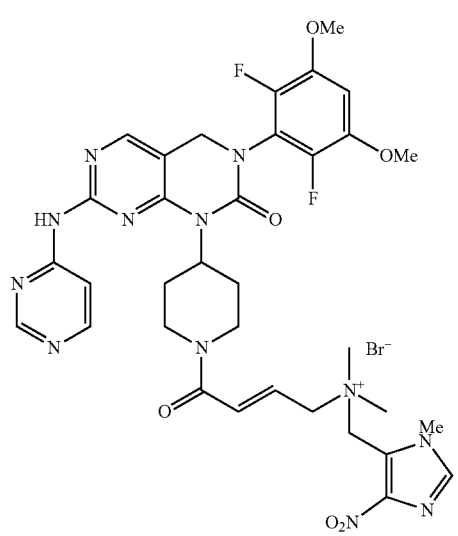
418 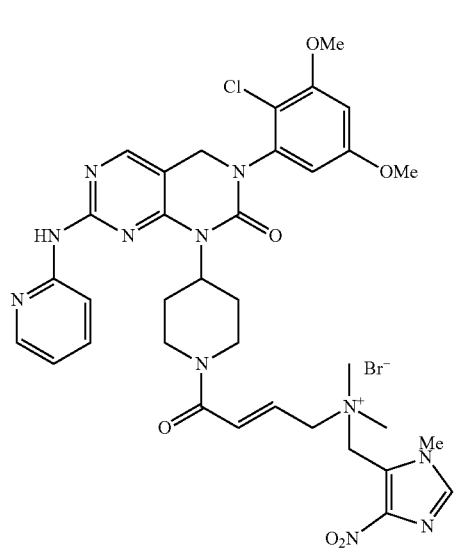
419 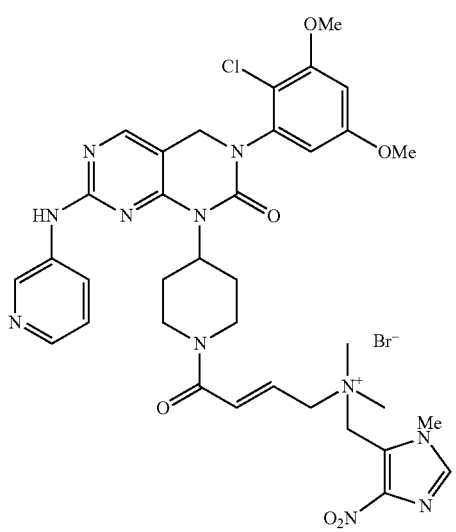
420 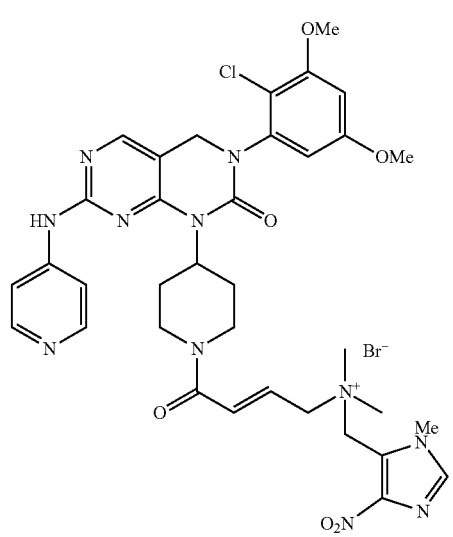
421 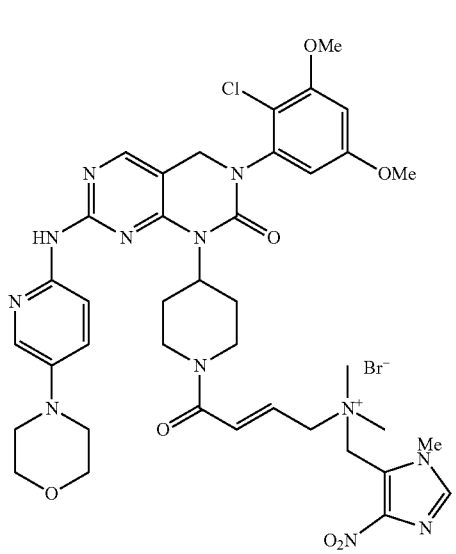

422
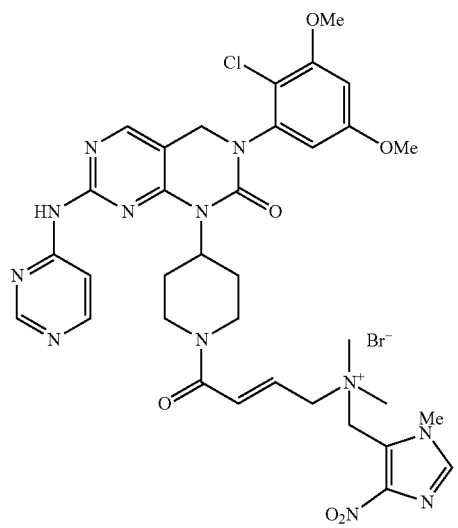
423
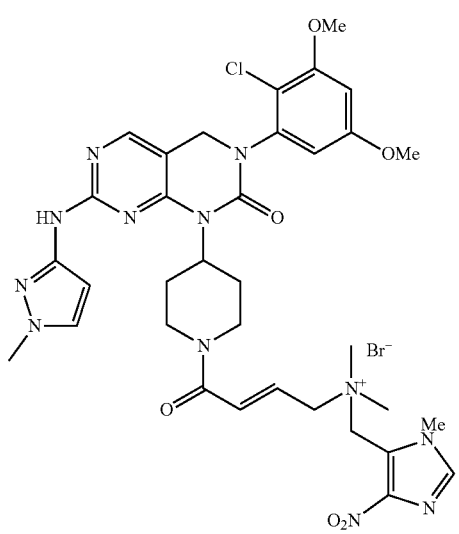
424
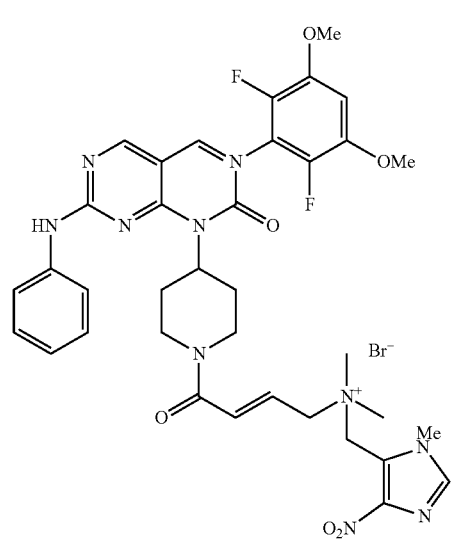
425
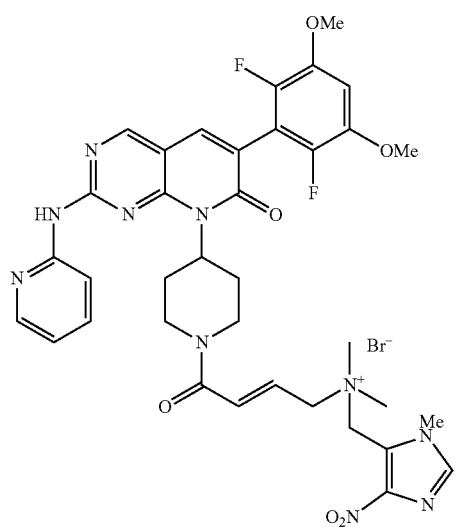
426
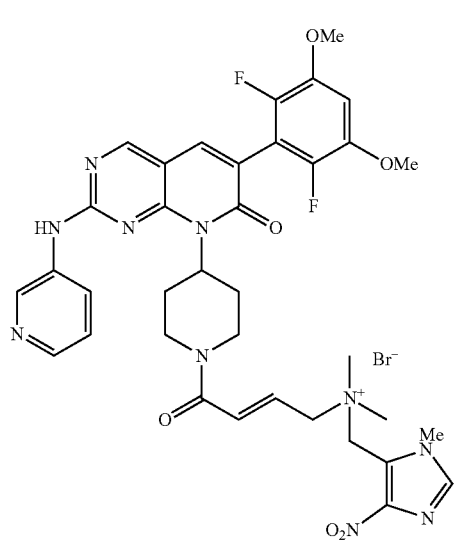
427
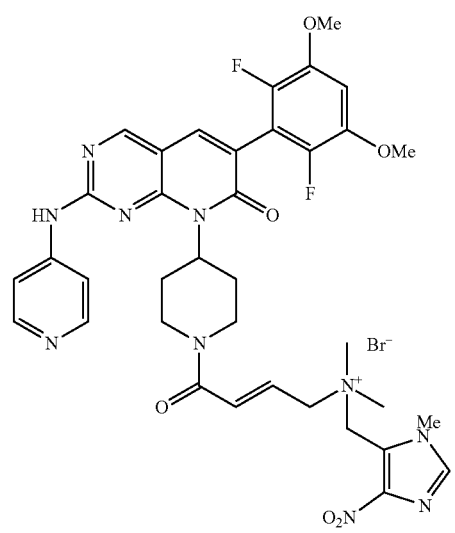

133
428
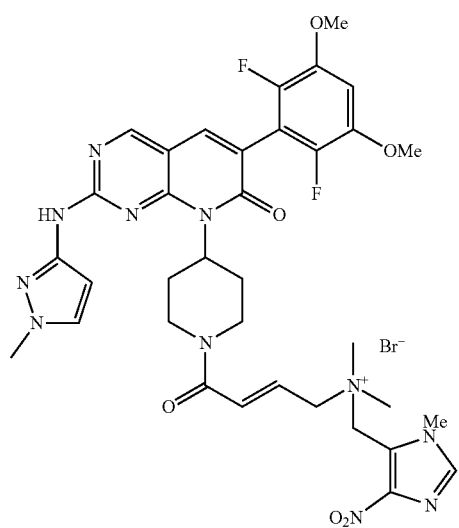
429
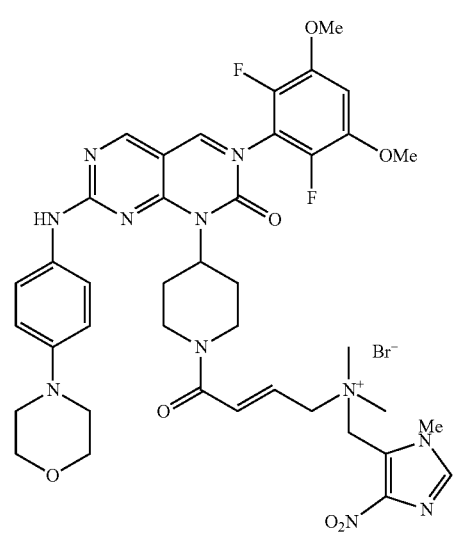
430
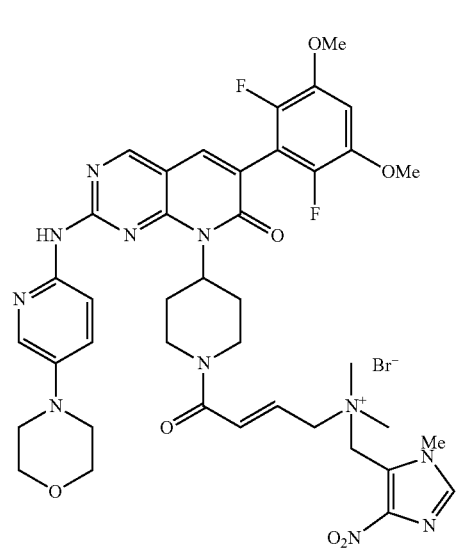
134
431
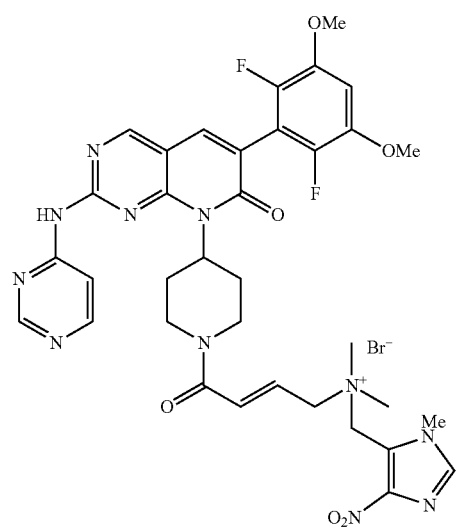
432
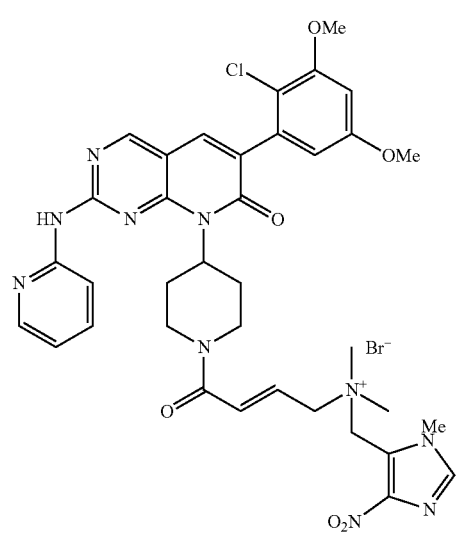
433
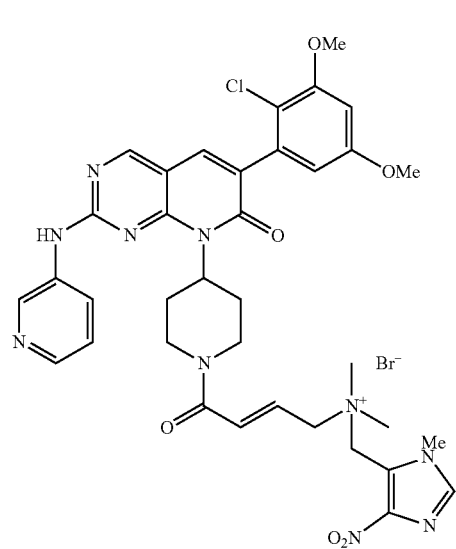

434
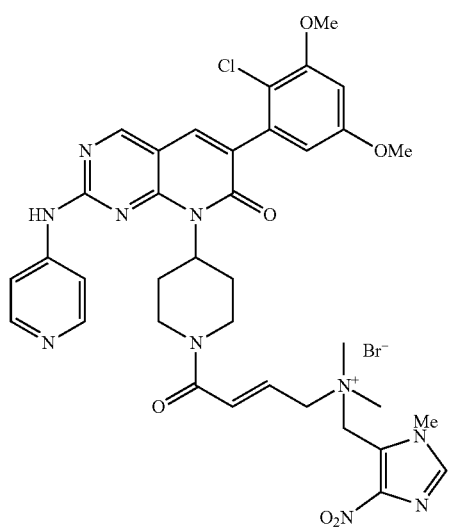
435
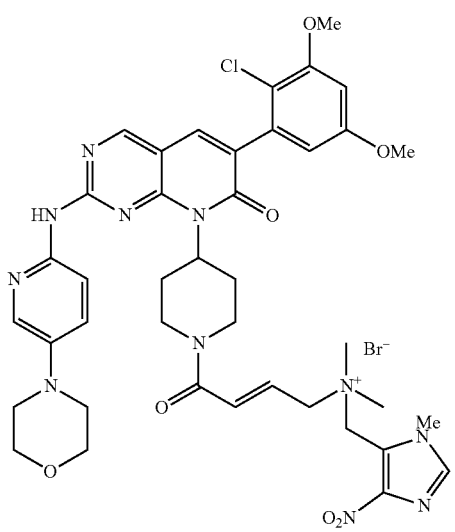
436
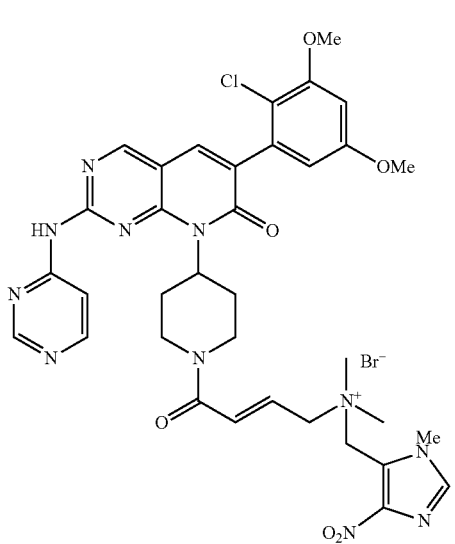
437
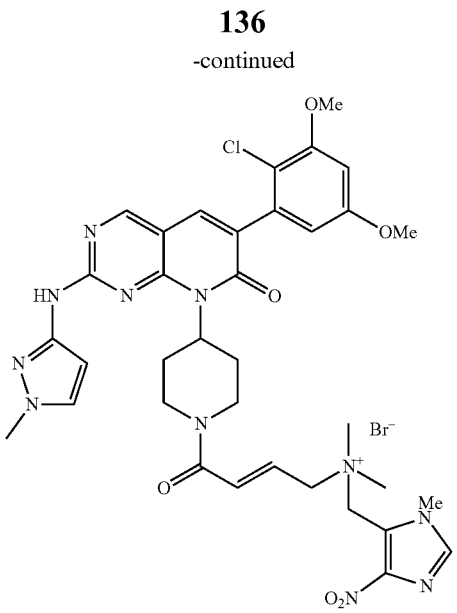
438
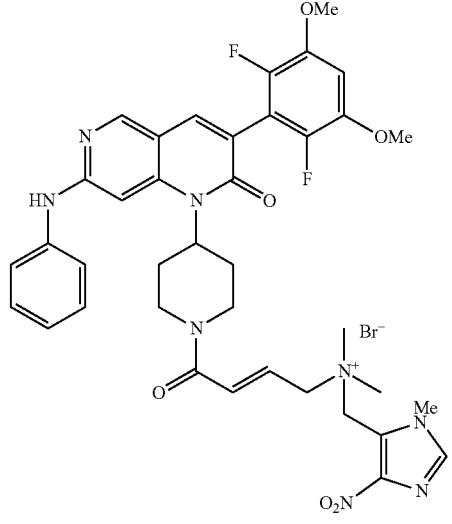
439
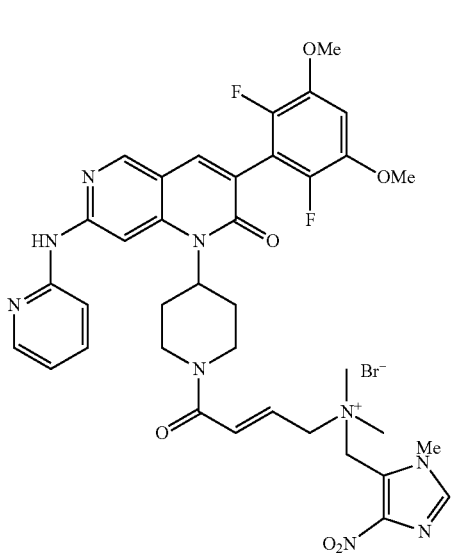

440 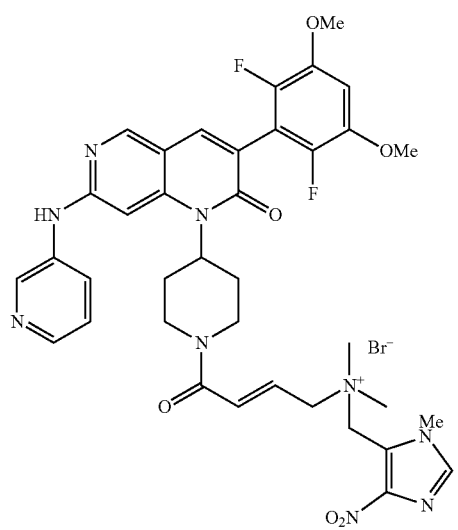
441 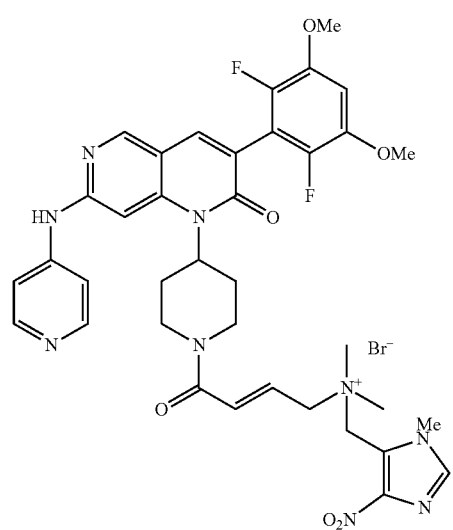
442 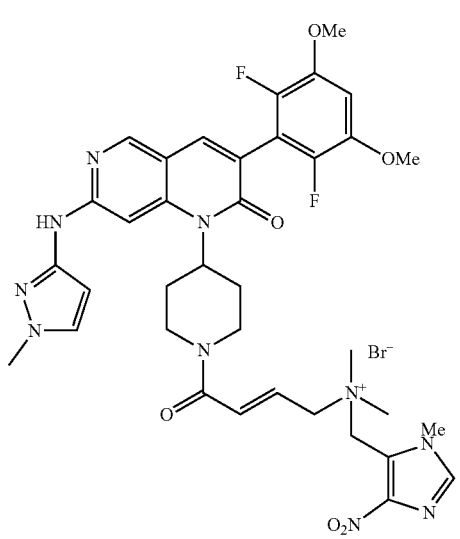
443 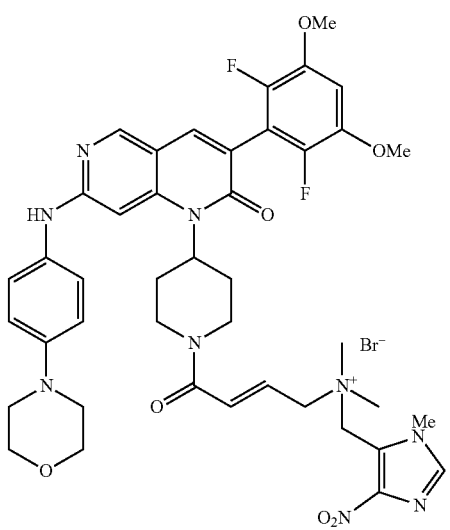
444 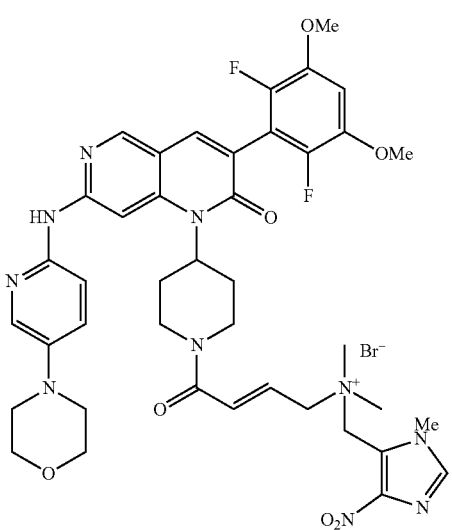
445 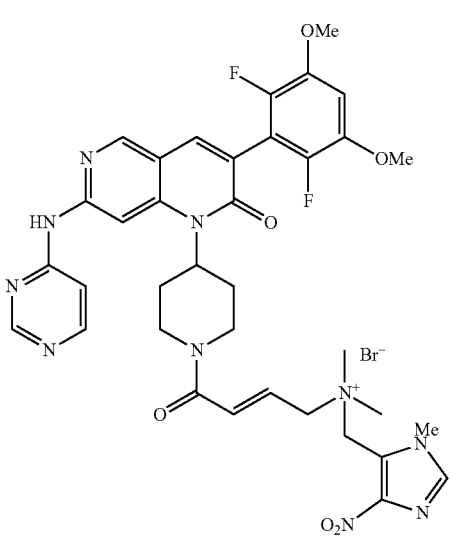

446 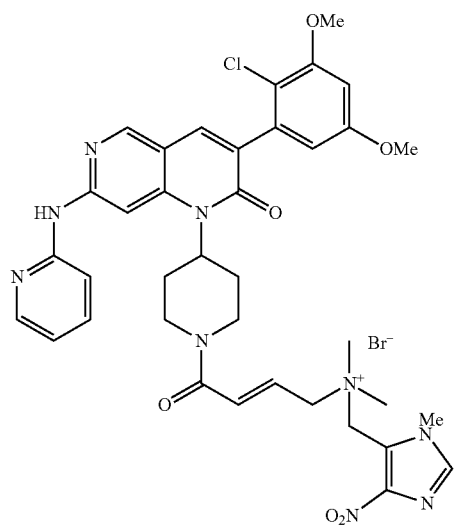
447 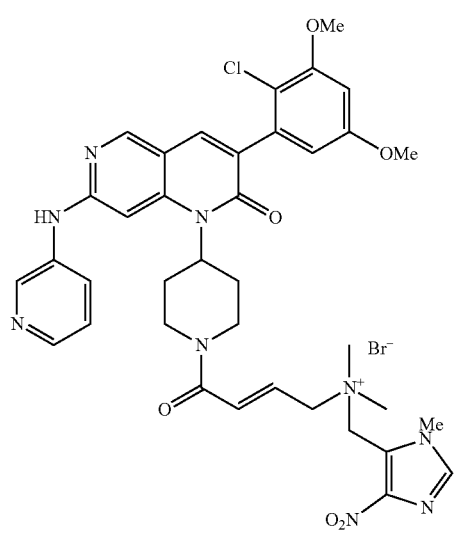
448 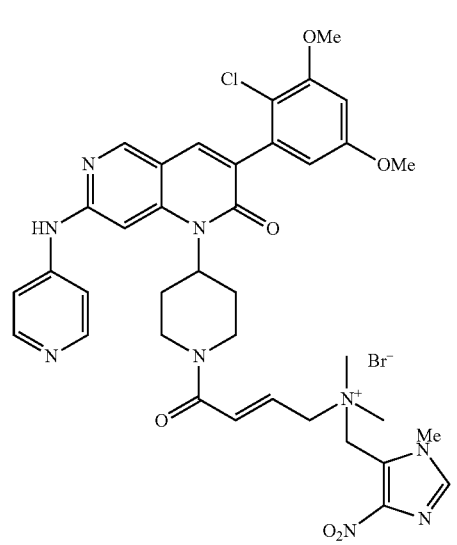
449 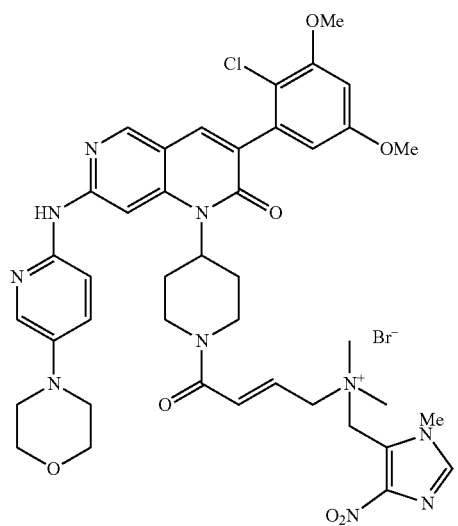
450 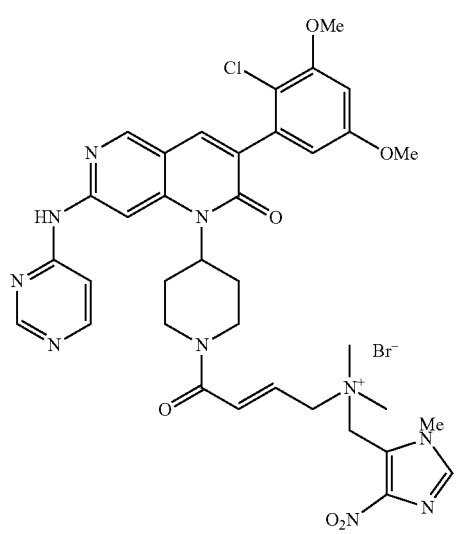
451 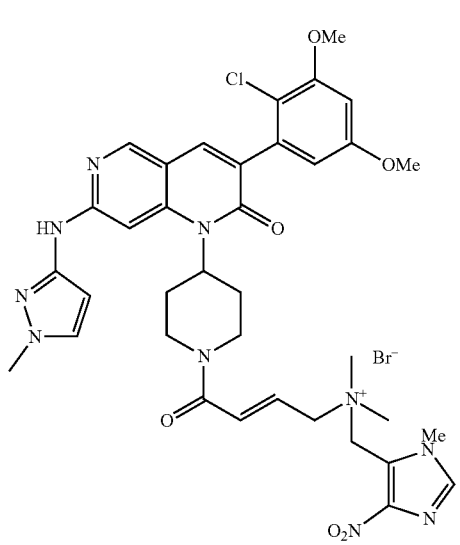

452 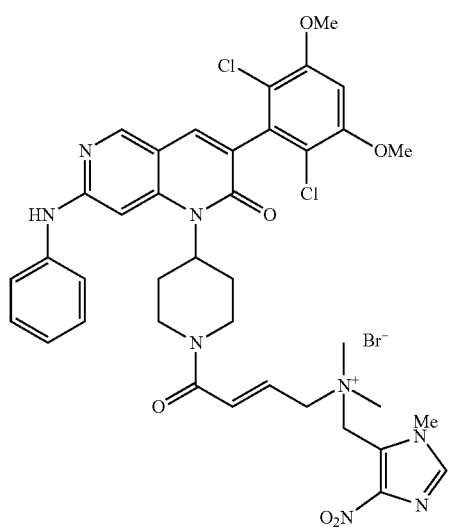
453 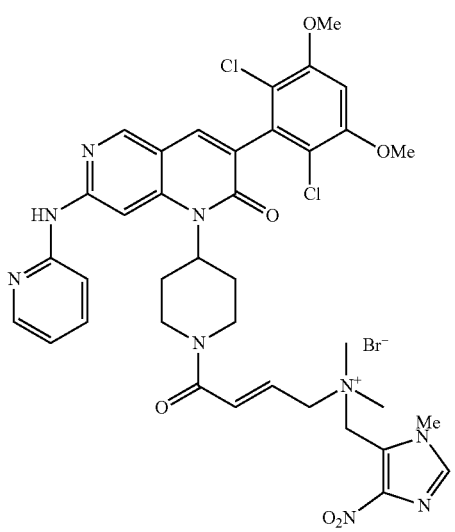
454 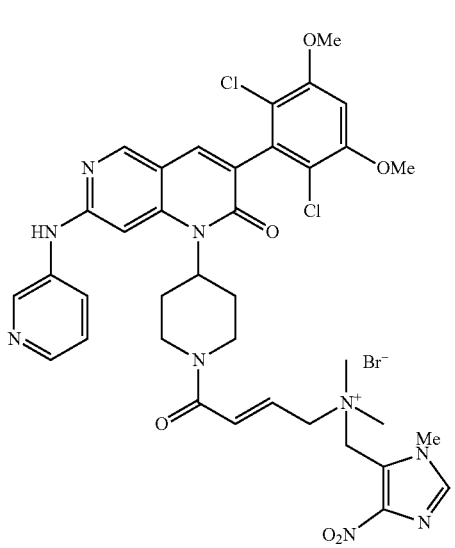
455 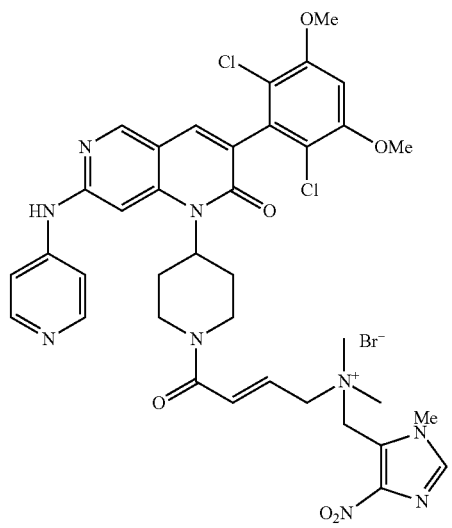
456 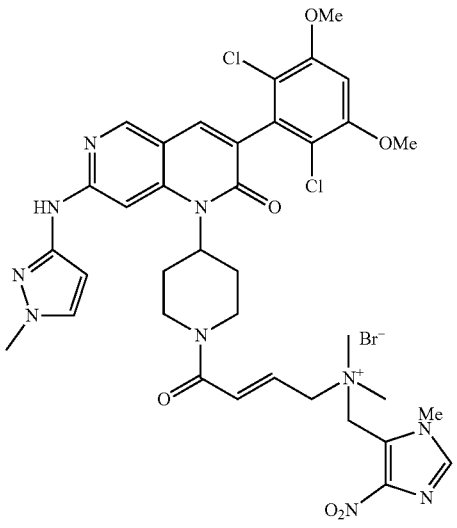
457 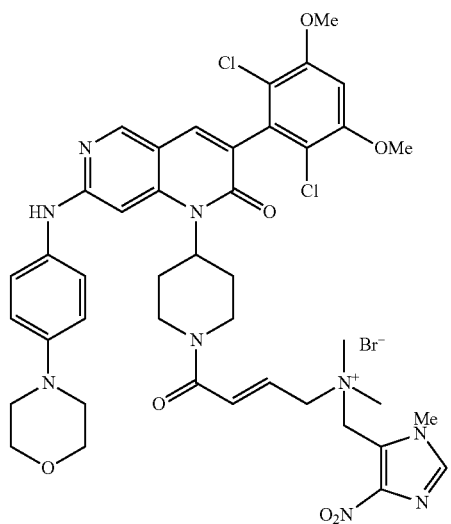

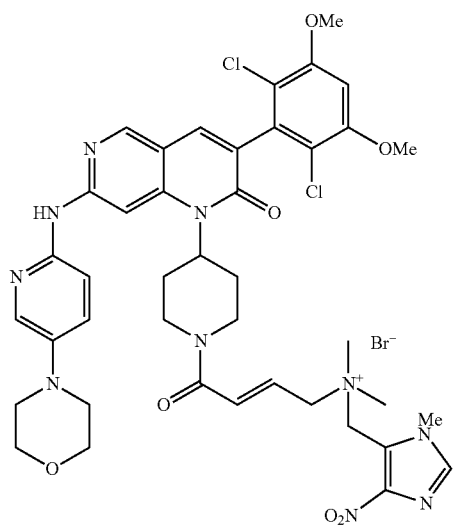
458
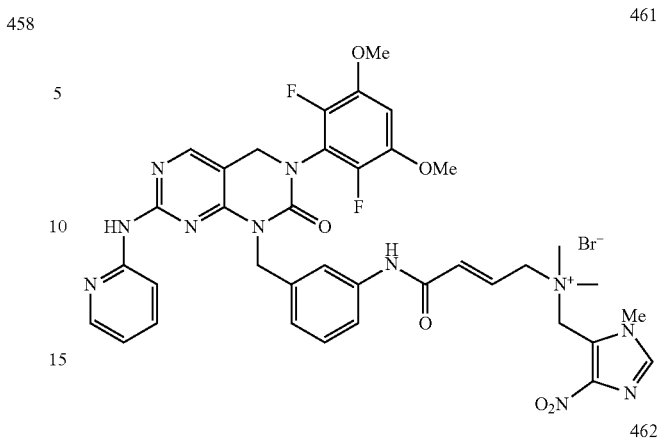
461
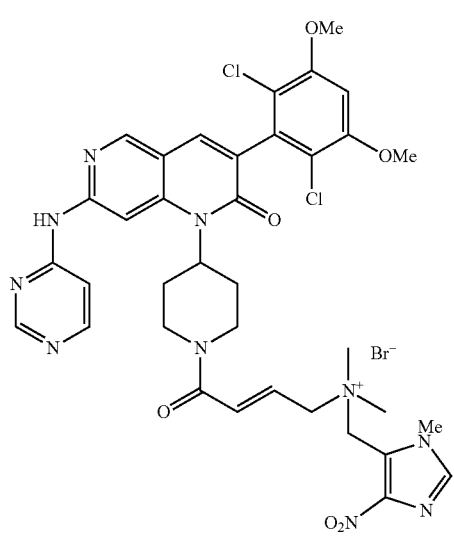
459
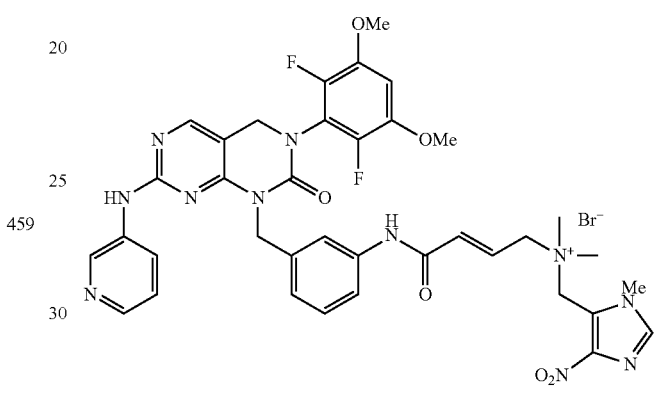
462
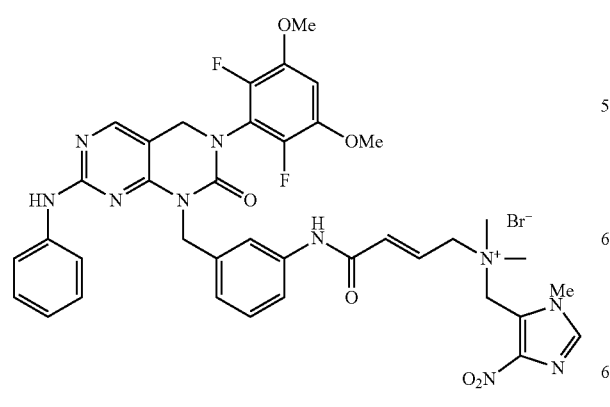
460
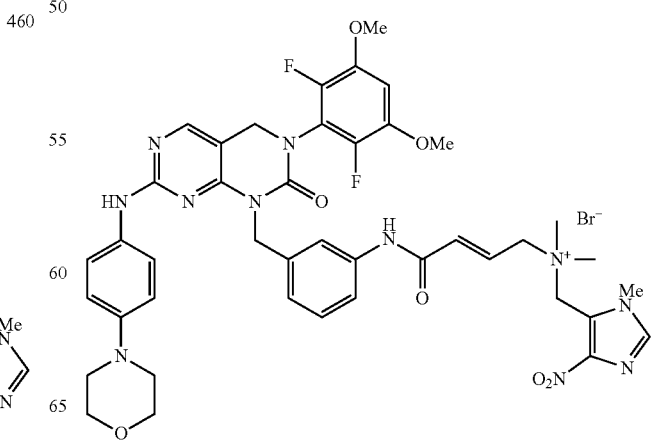
463
464

465
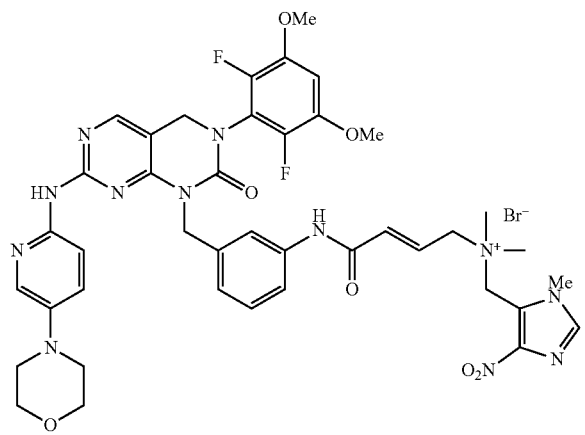
466
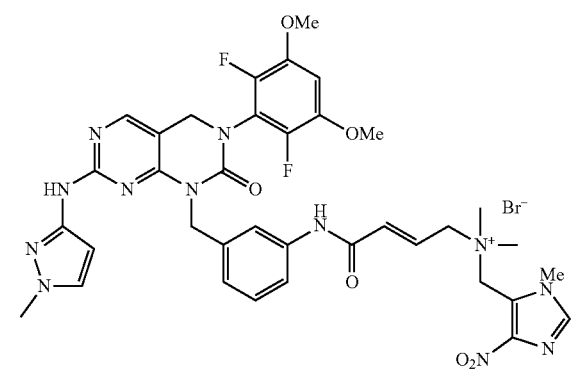
467
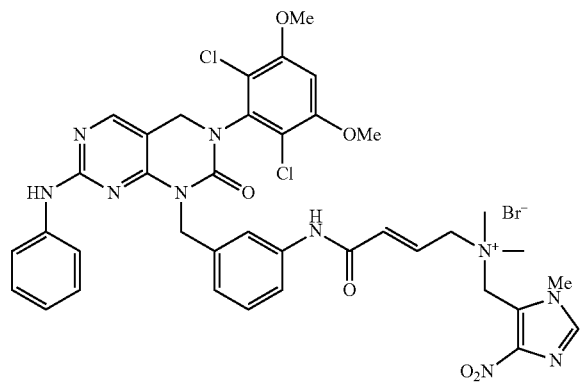
468
469
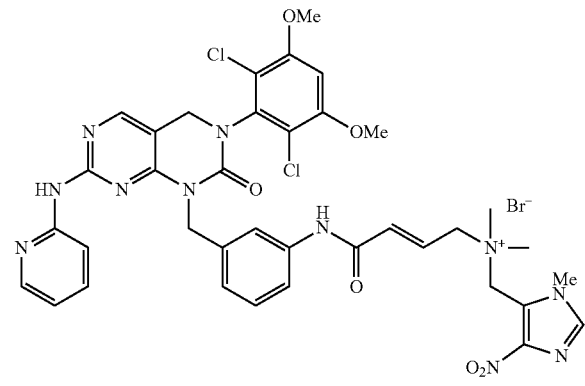
470
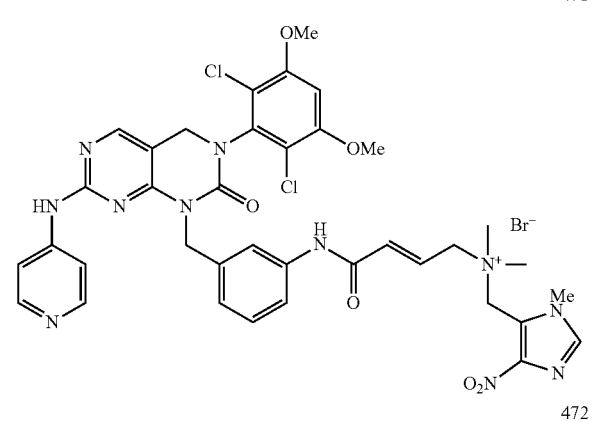
471
472
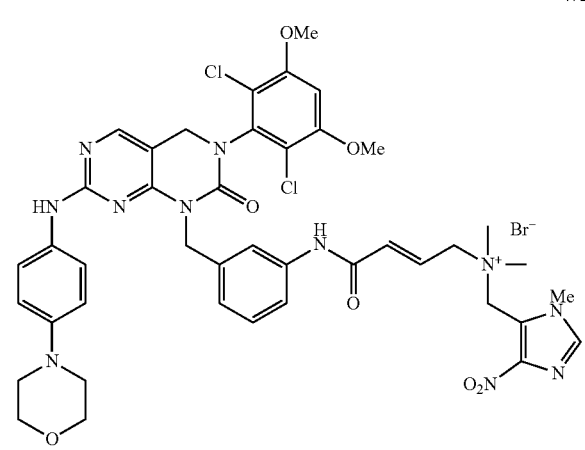

473
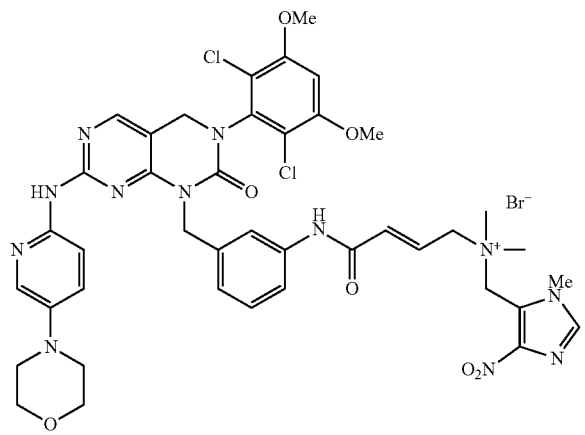
474
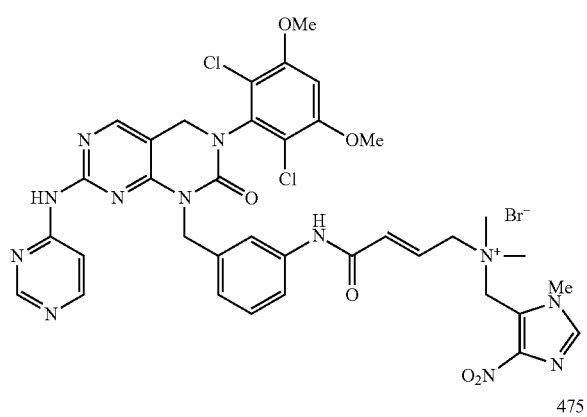
475
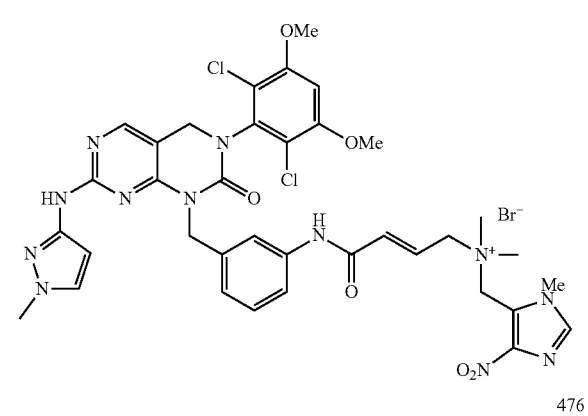
476
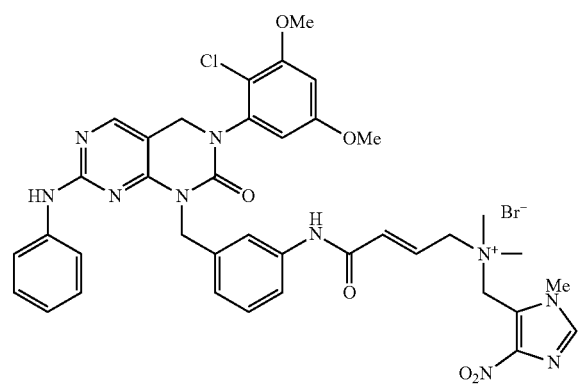
477
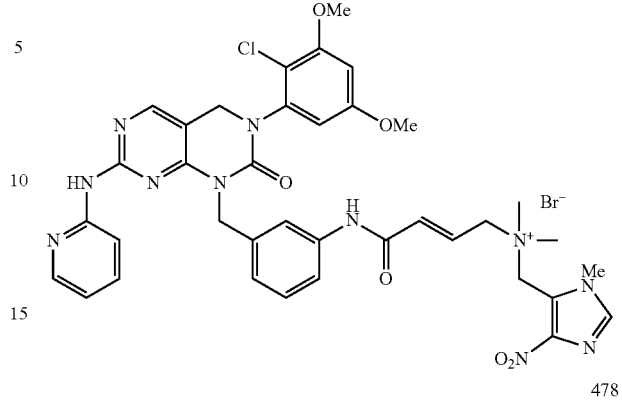
478
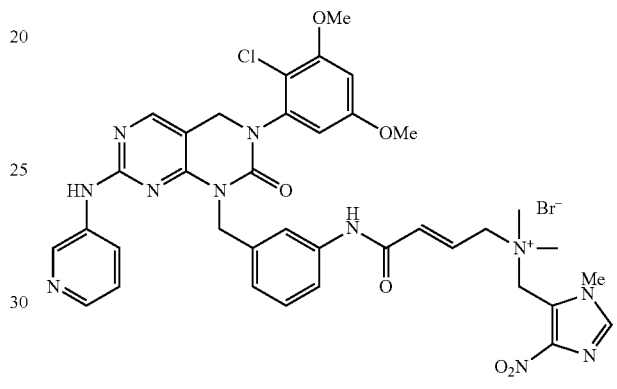
479
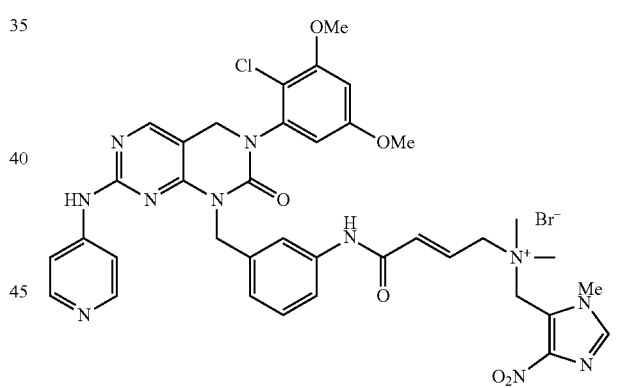
480
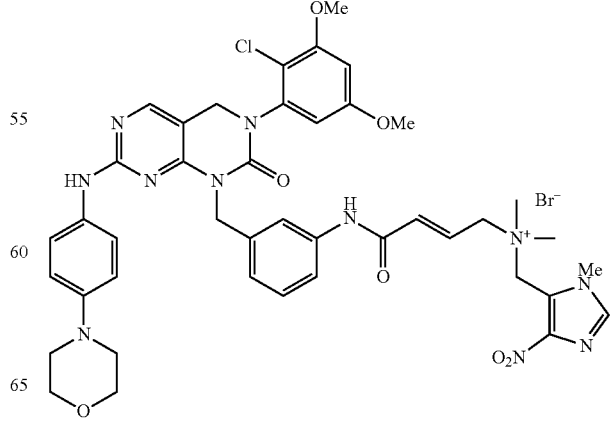

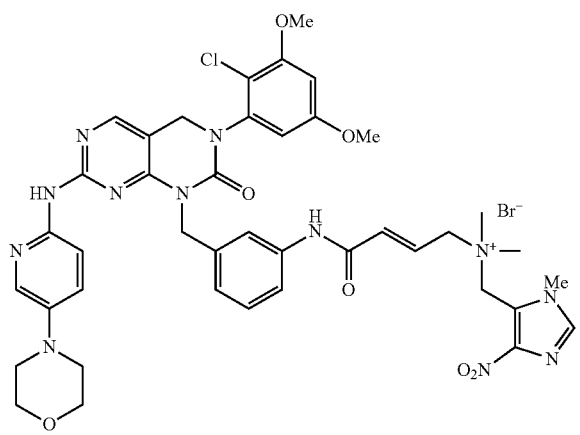
481
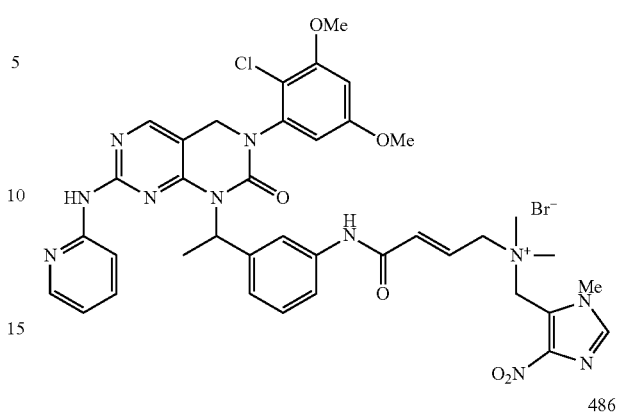
485
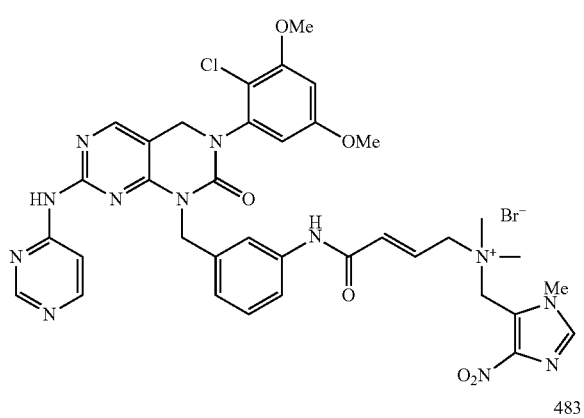
482
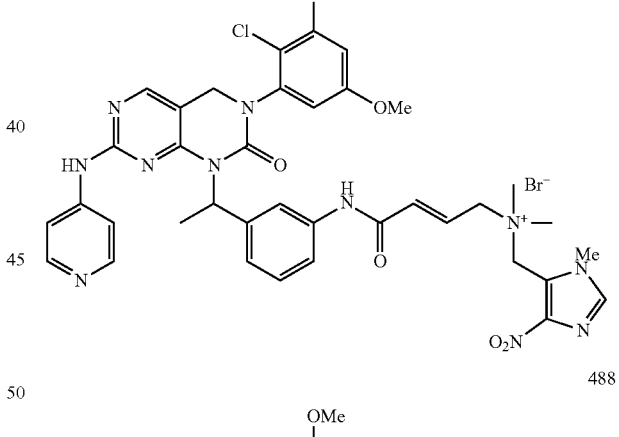
486
487
488
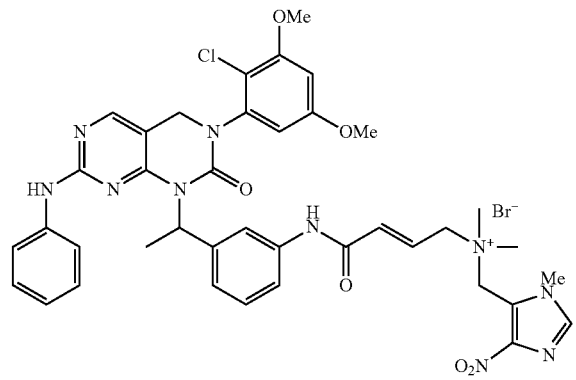
483
484
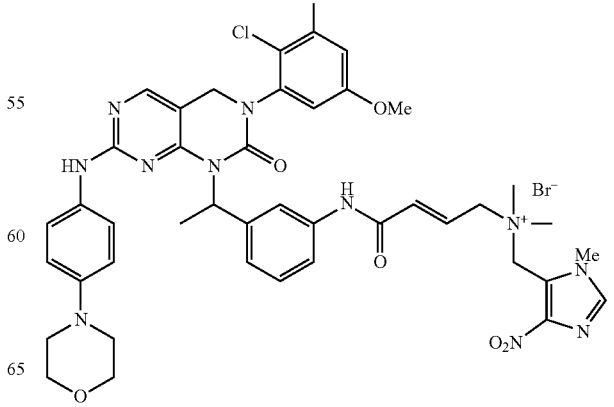

489
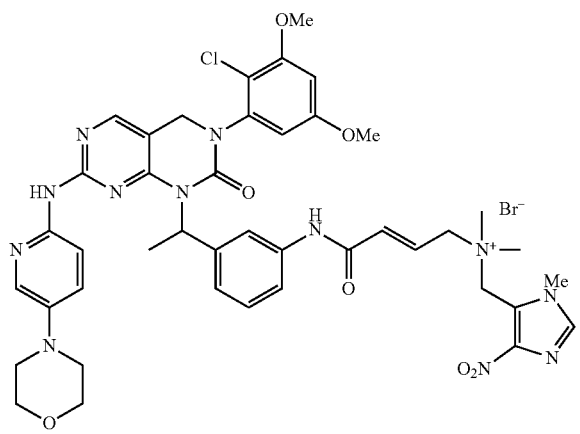
490
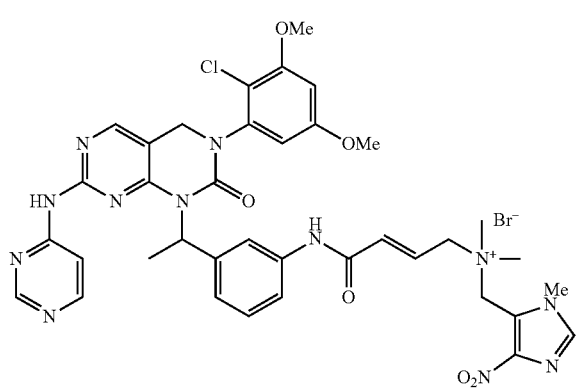
491
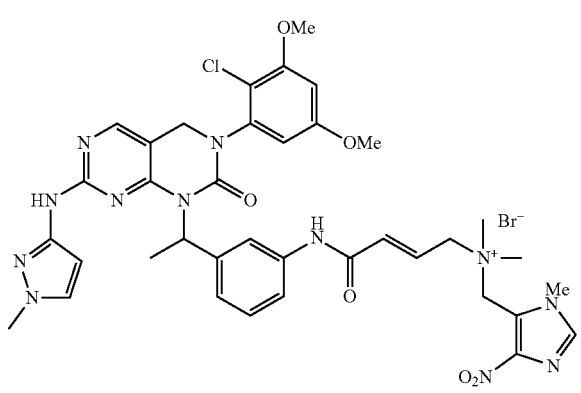
492
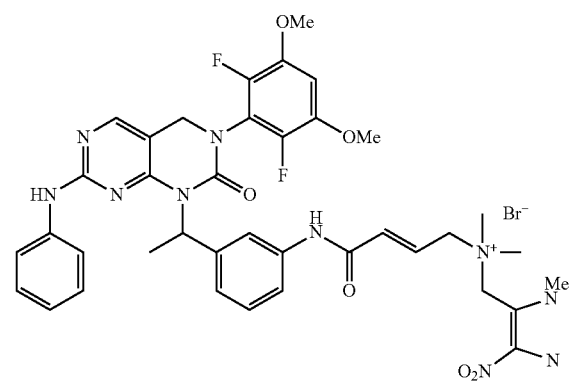
493
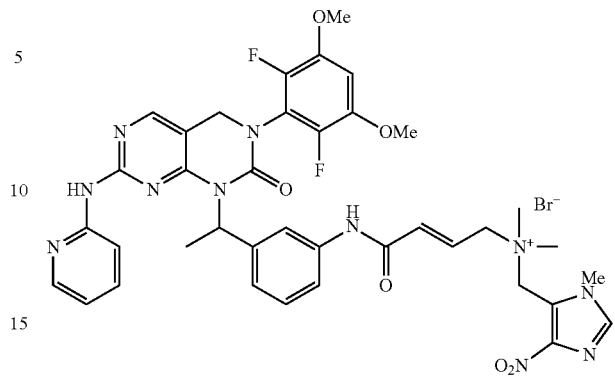
494
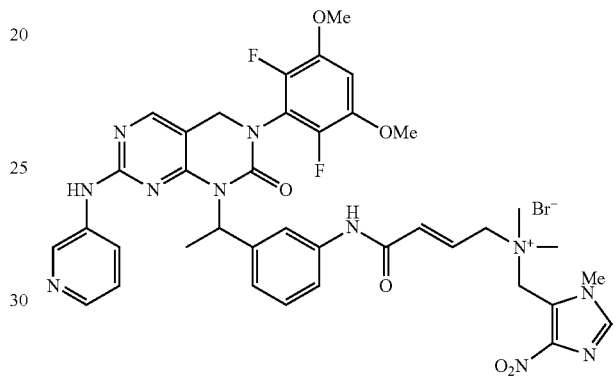
495
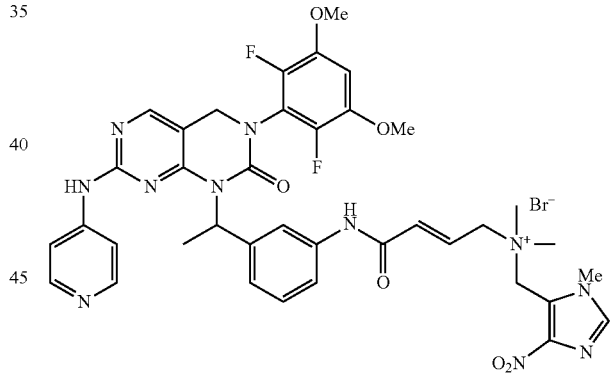
496
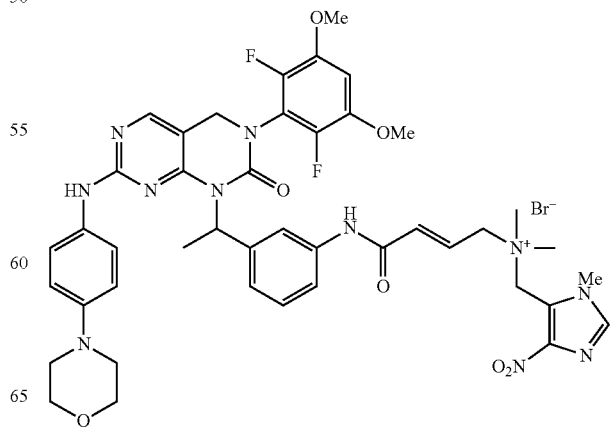

-continued
497
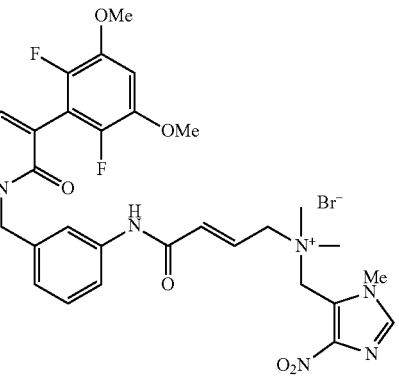
5
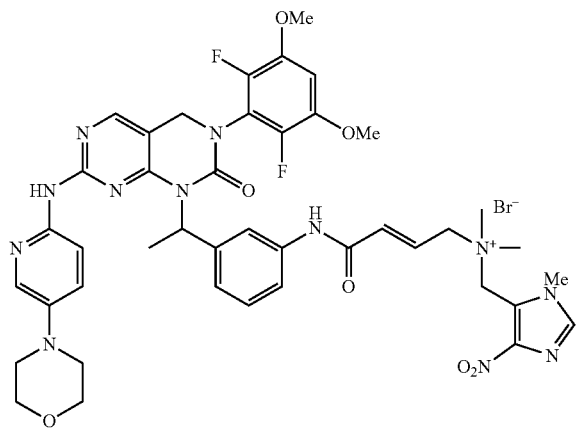
501
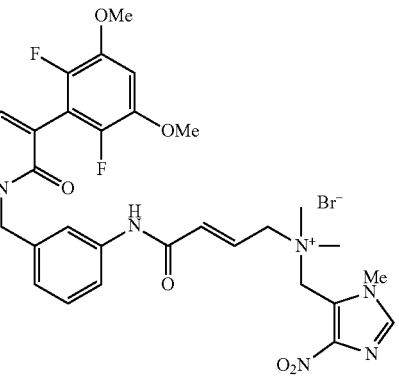
498
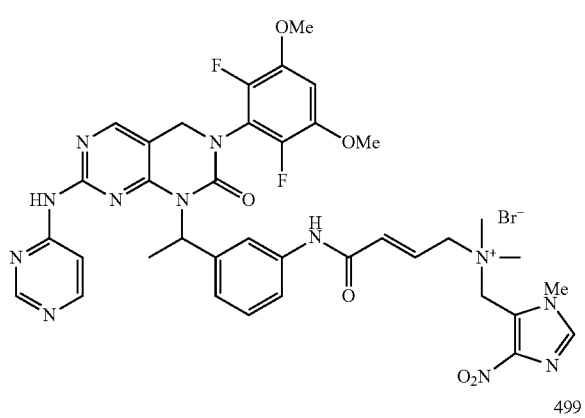
502
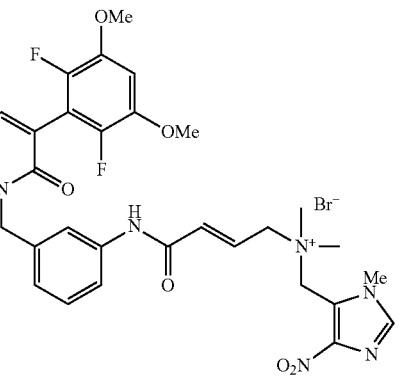
499
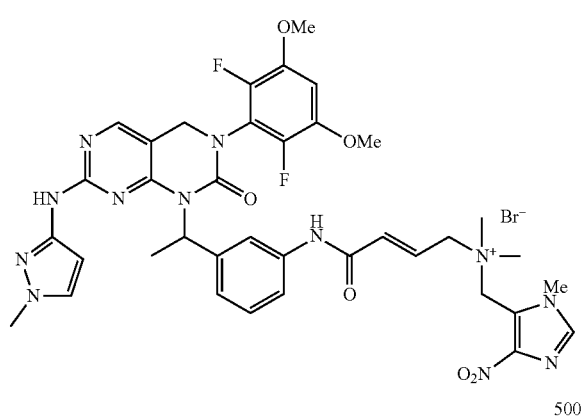
503
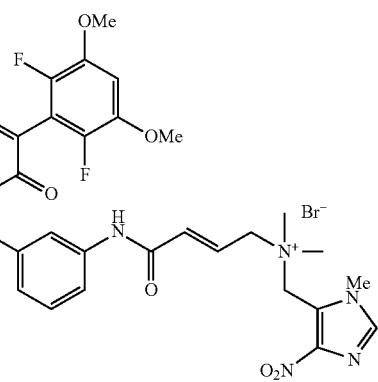
500
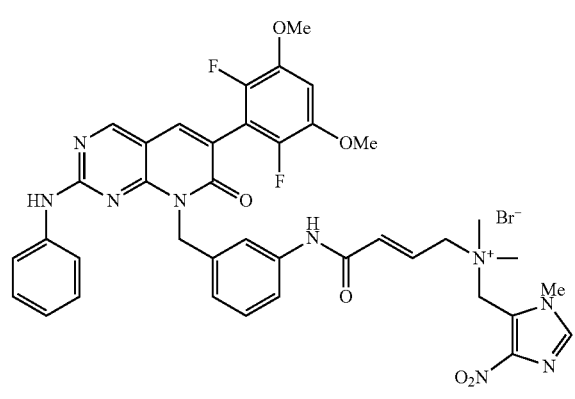
504
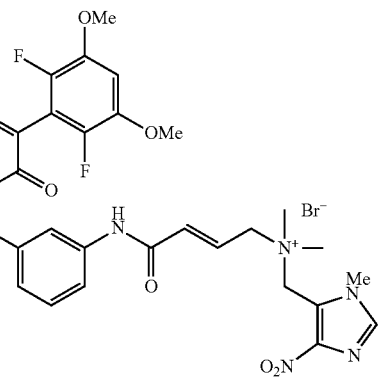

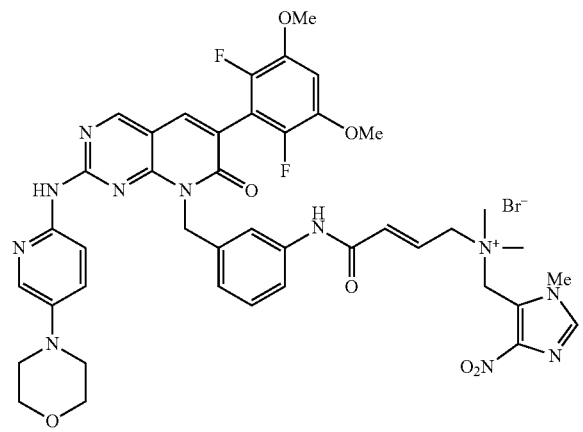
505
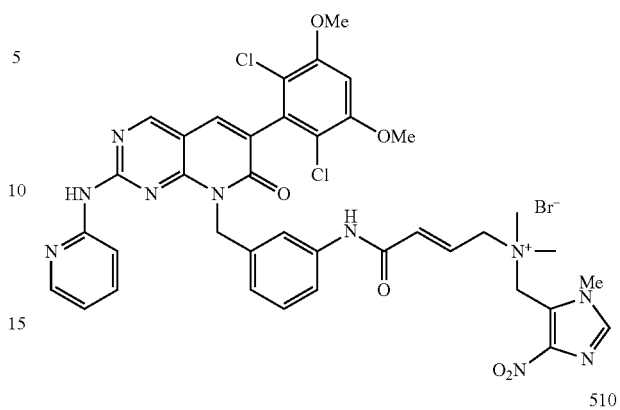
509
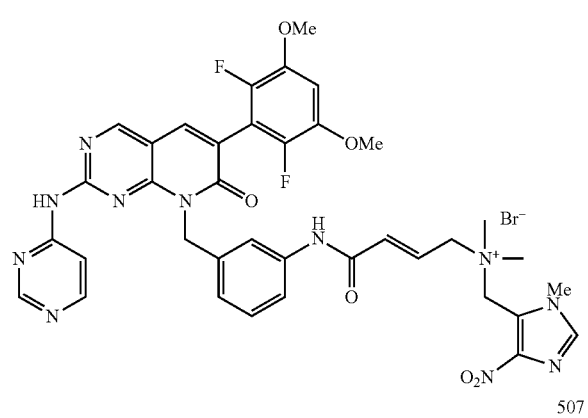
506
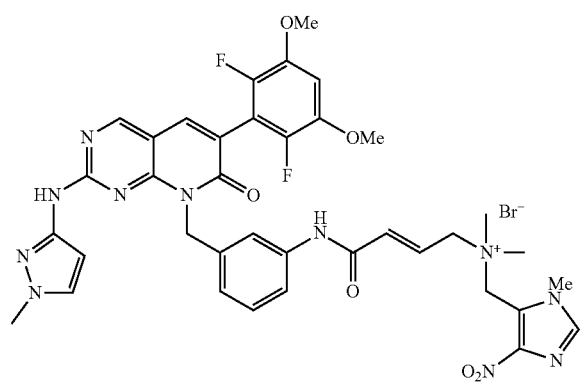
507
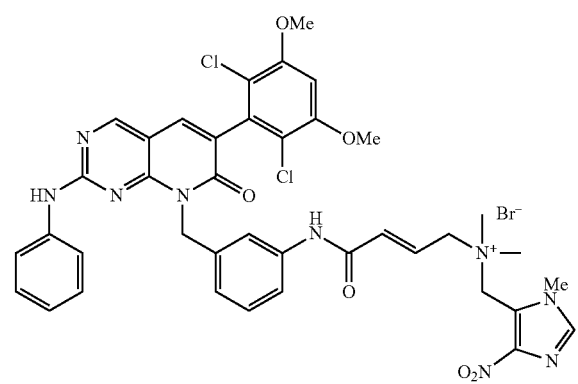
508
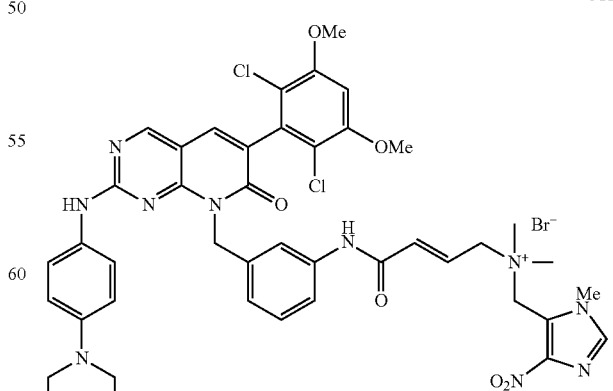
510
511
512

513
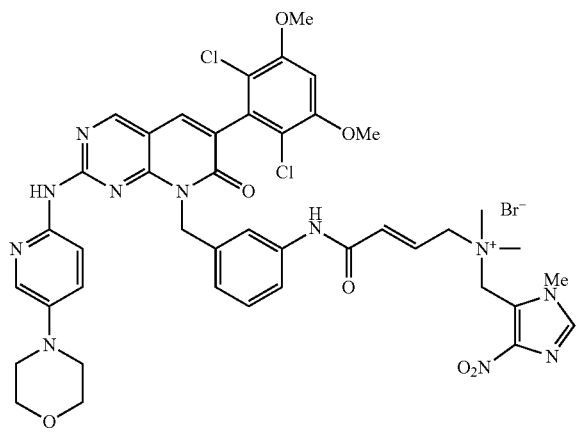
514
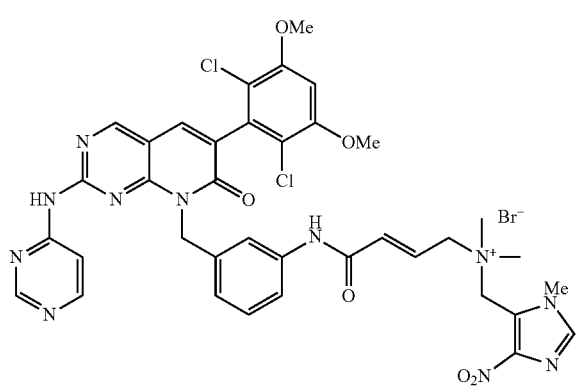
515
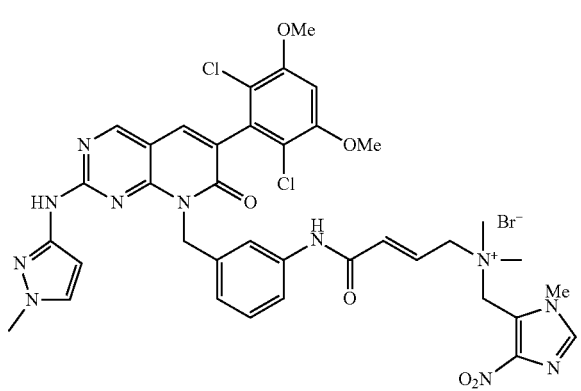
516
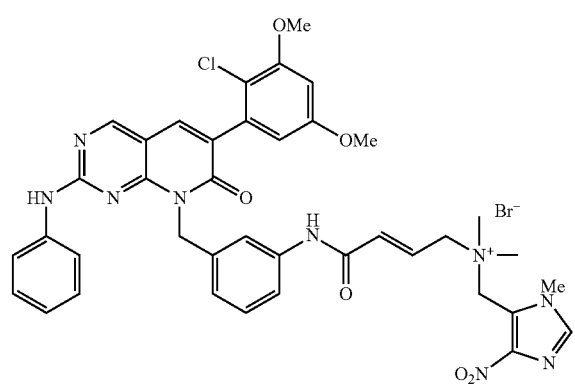
517
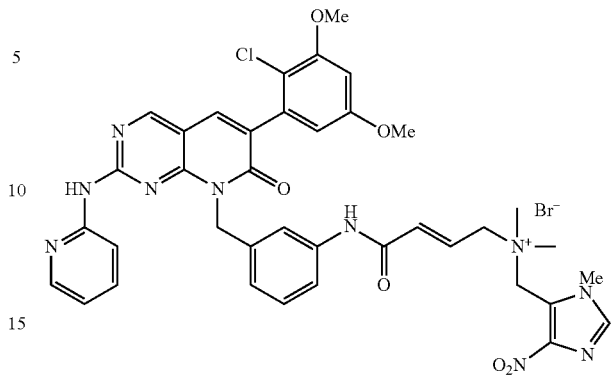
518
519
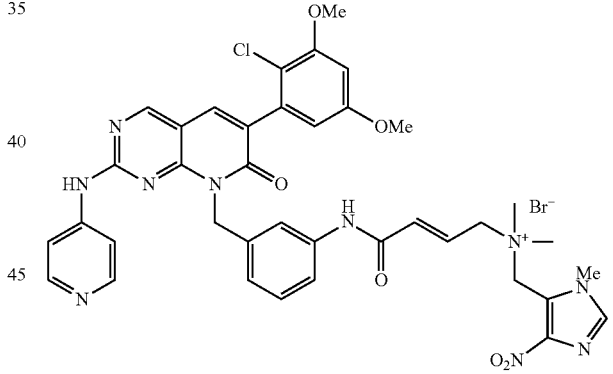
520
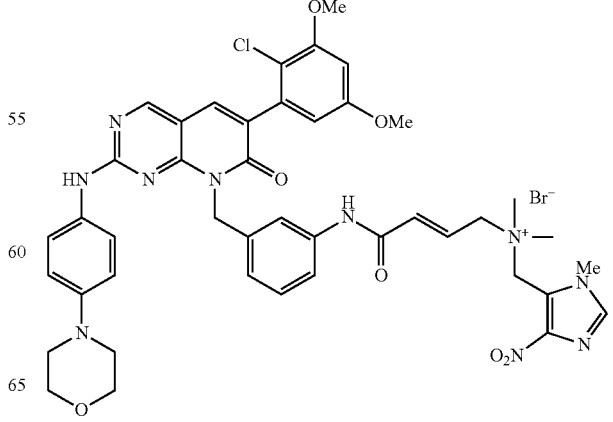

521
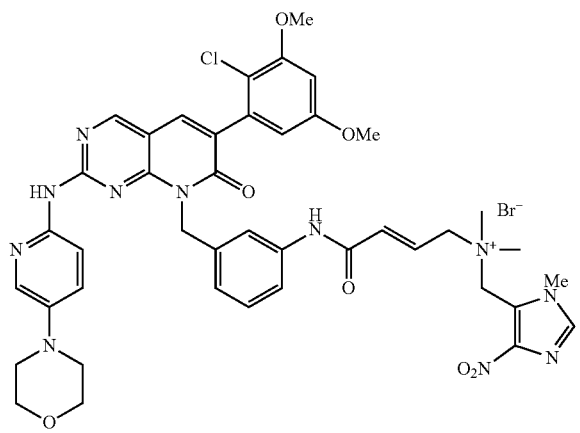
522
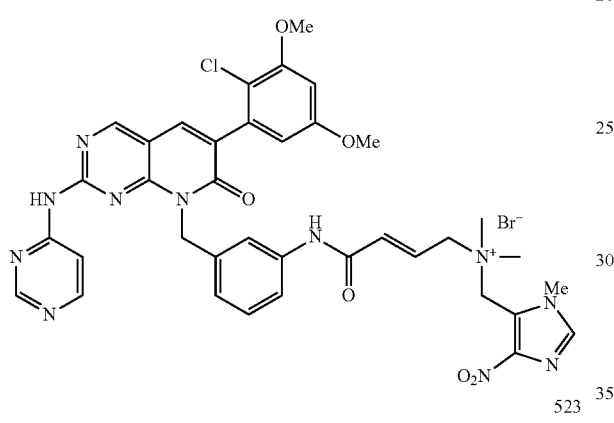
523
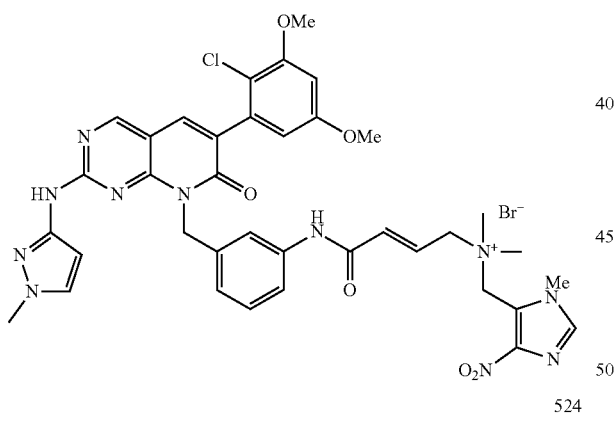
524
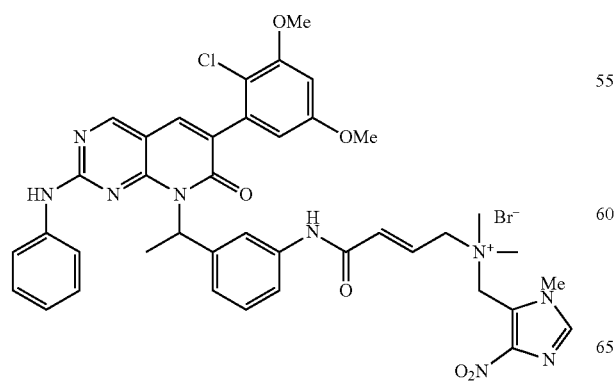
525
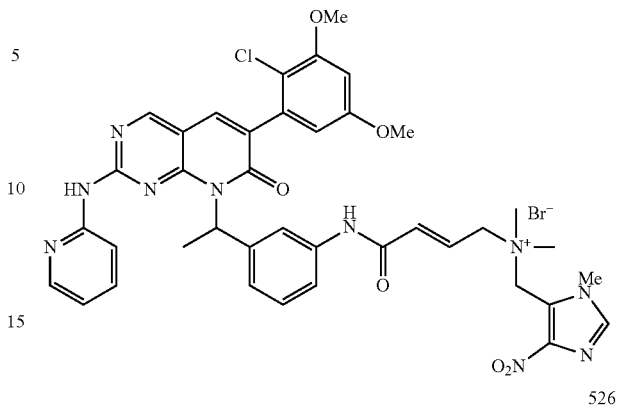
526
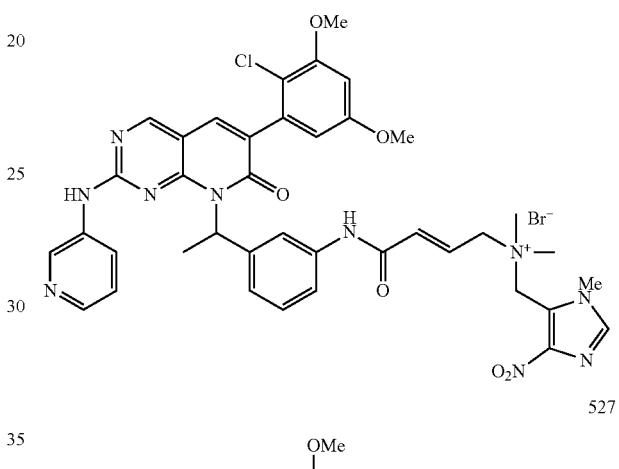
527
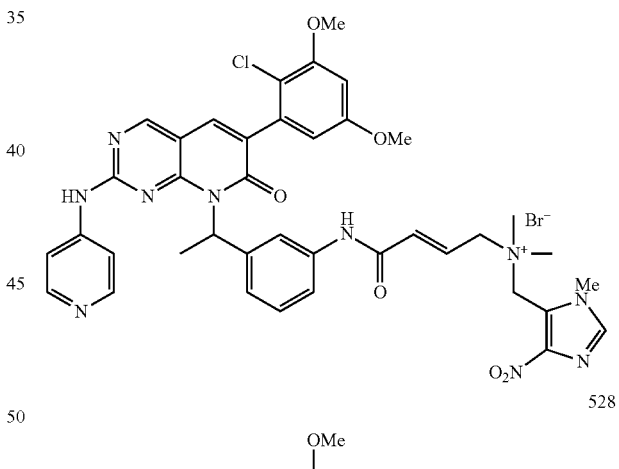
528
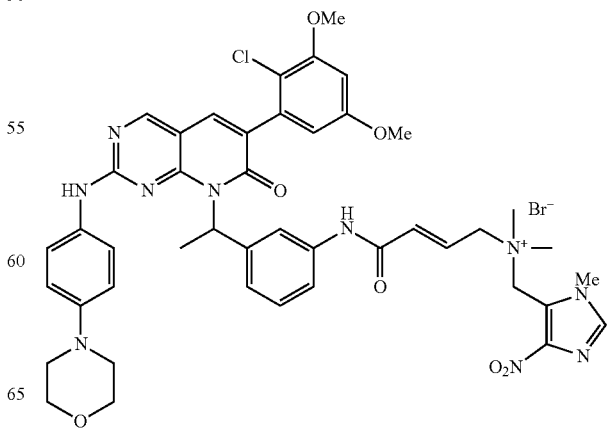

529
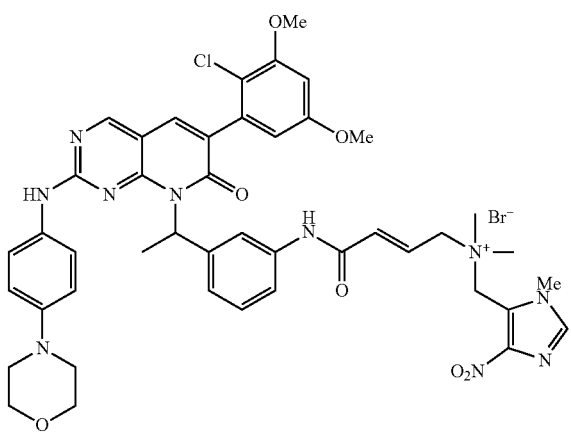
530
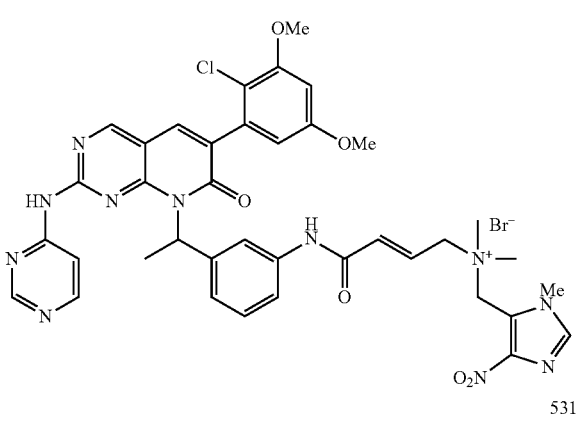
531
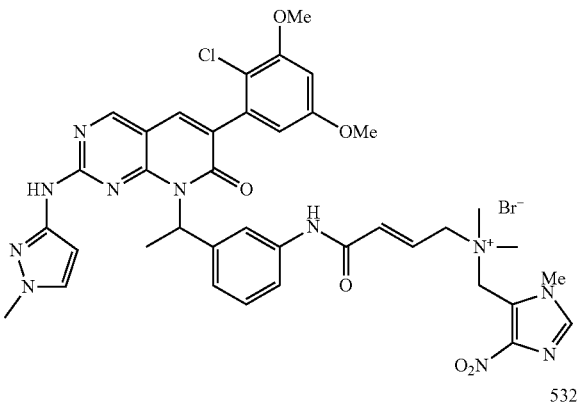
532
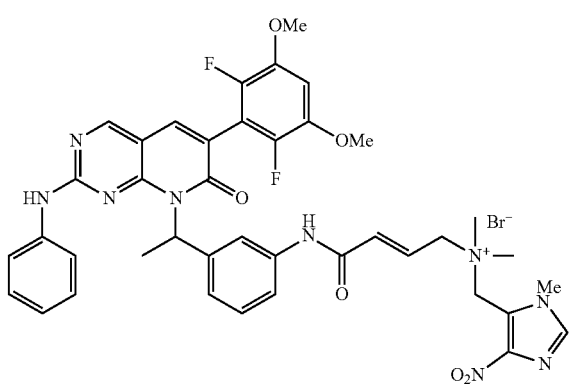
533
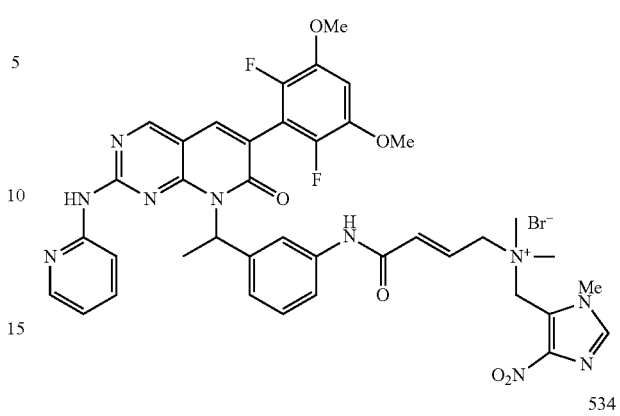
534
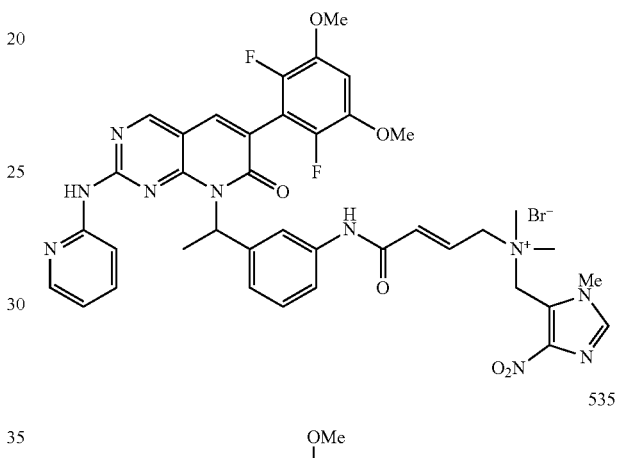
535
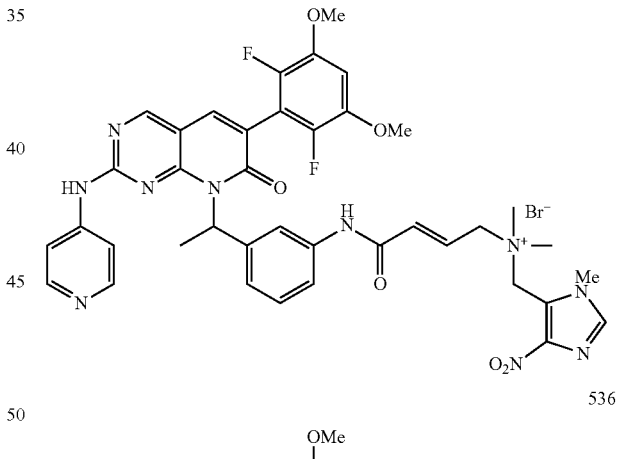
536
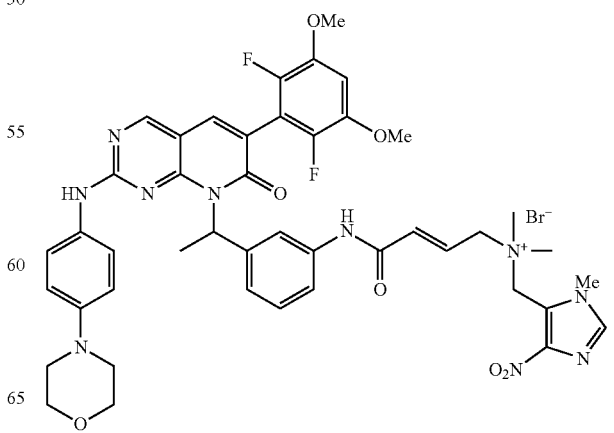

537
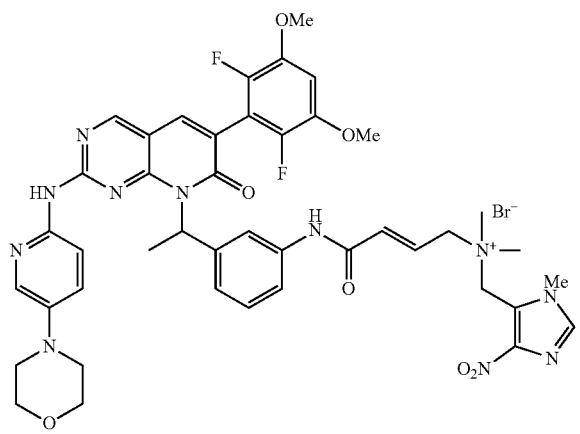
538
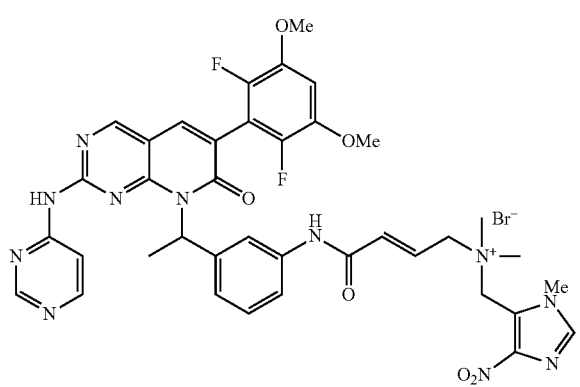
539
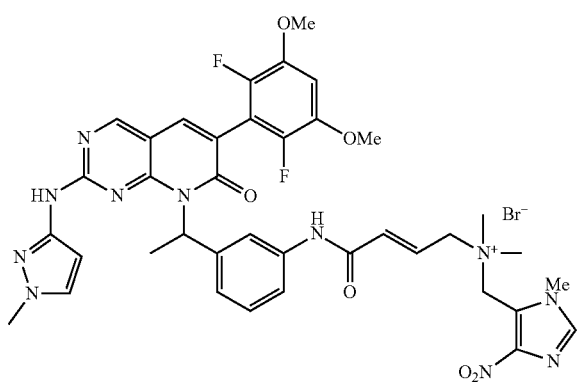
540
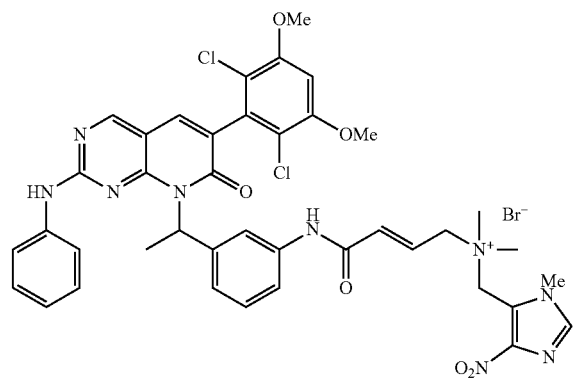
541
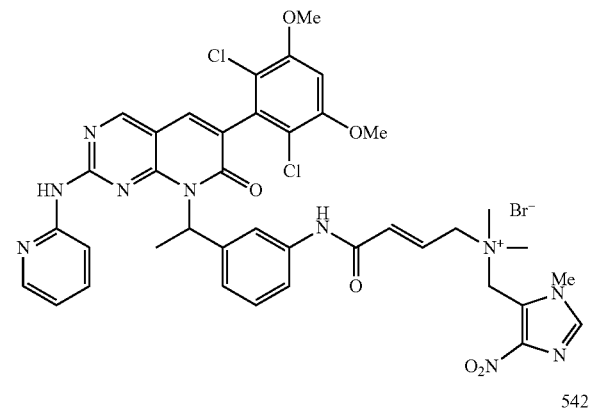
542
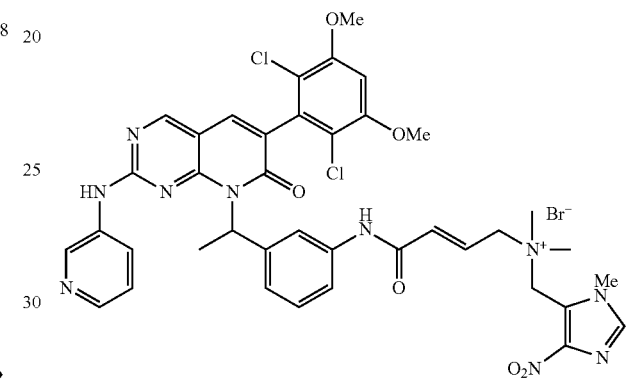
543
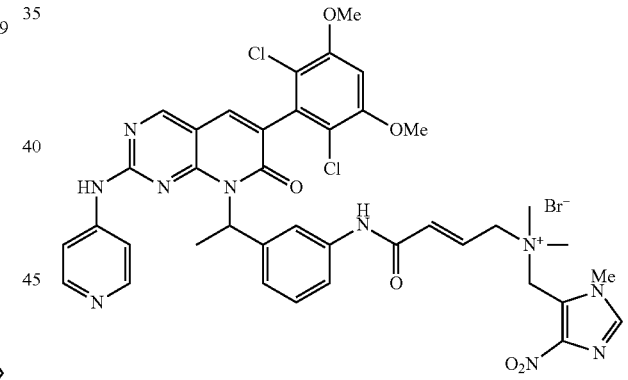
544
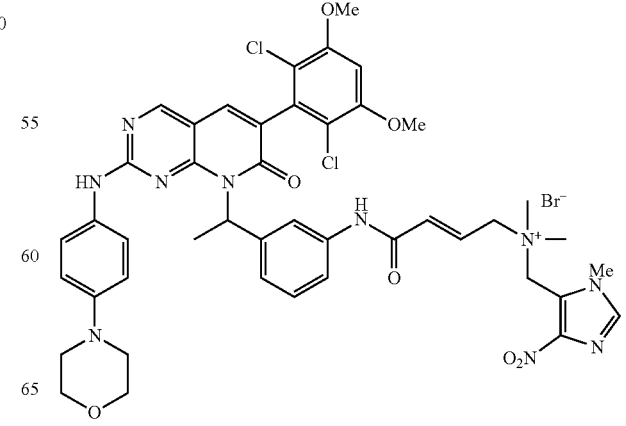

545
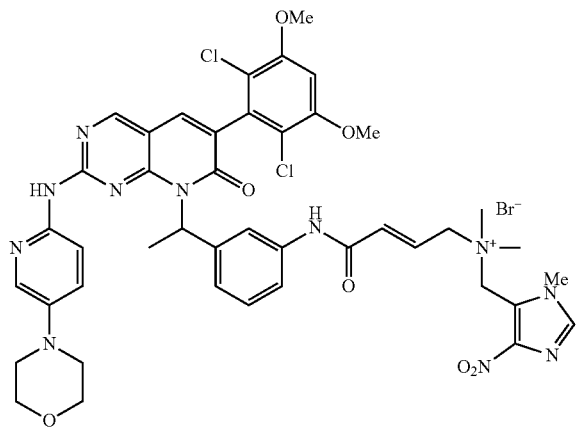
546
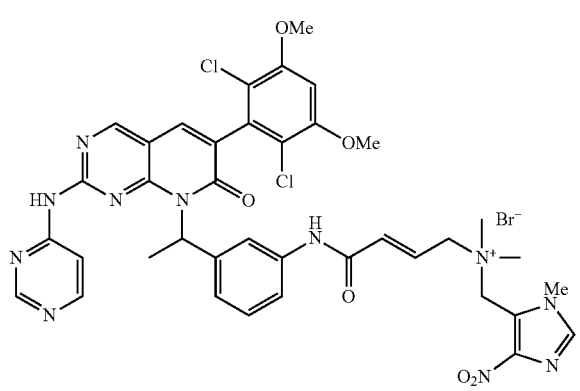
547
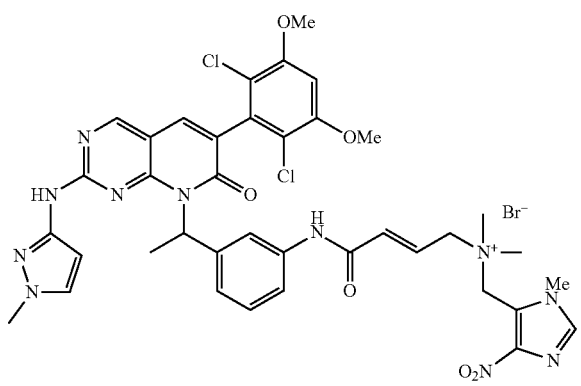
548
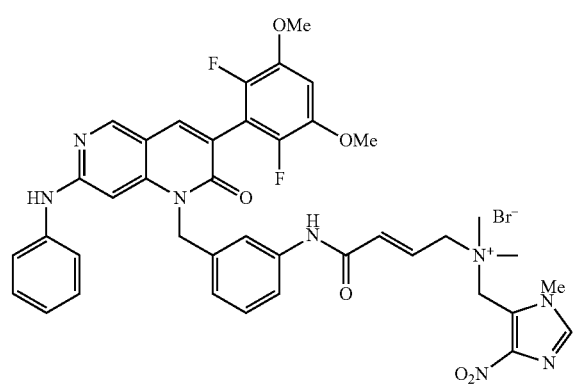
549
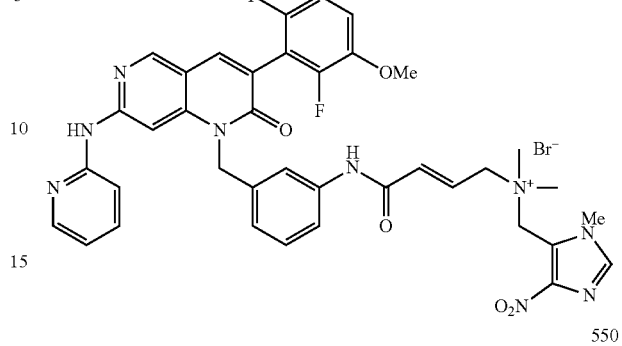
550
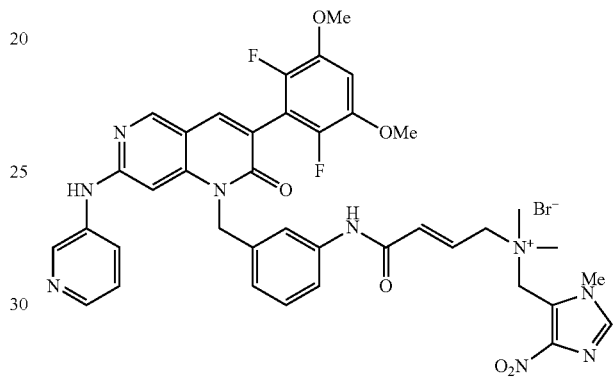
551
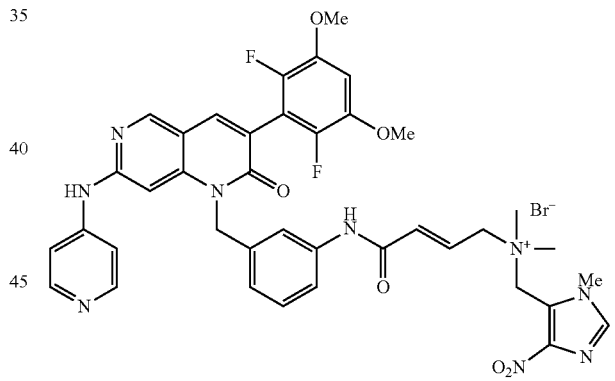
552
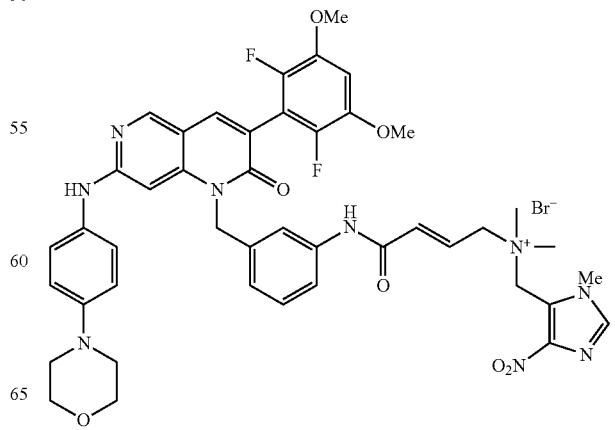

553
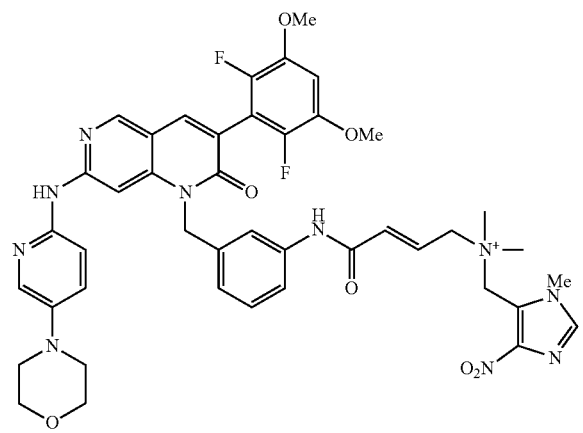
554
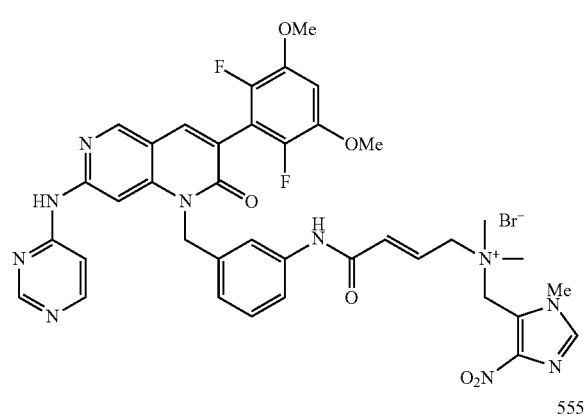
555
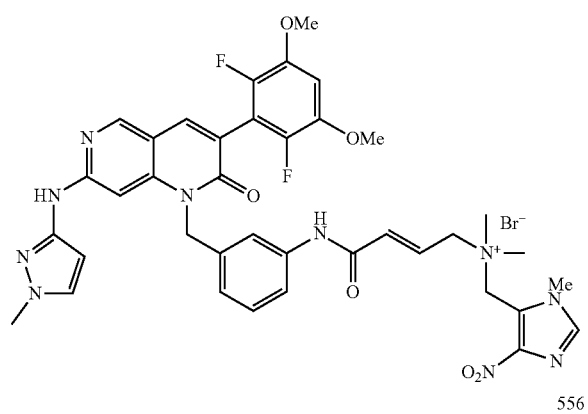
556
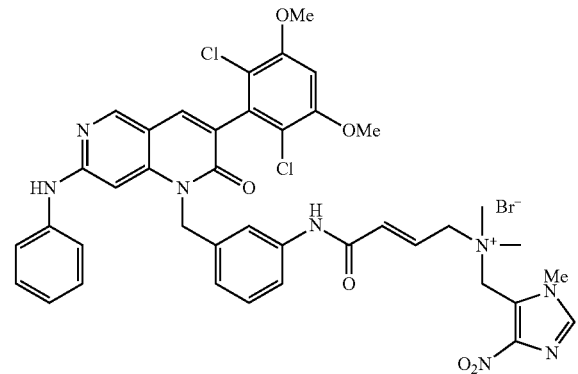
557
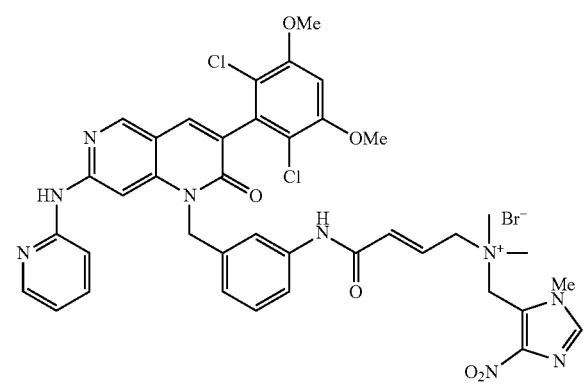
558
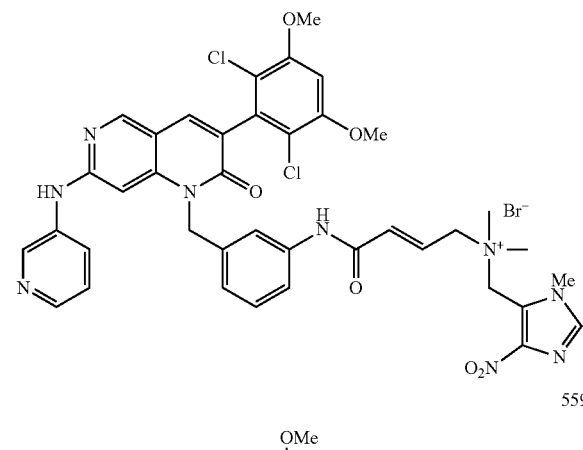
559
560
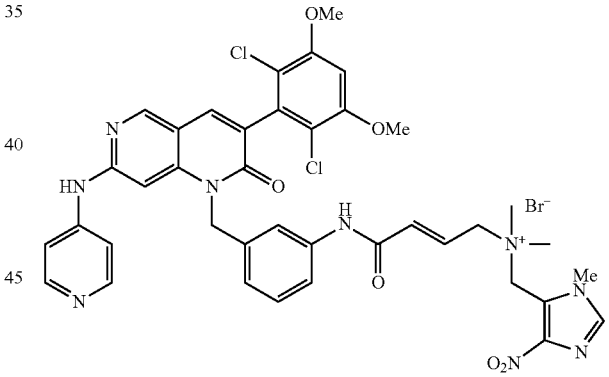

169
-continued
561
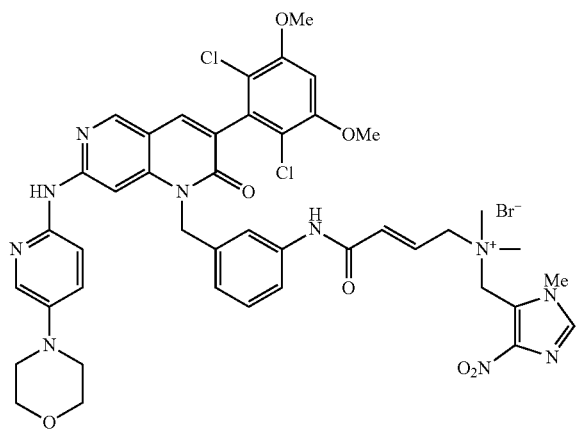
562
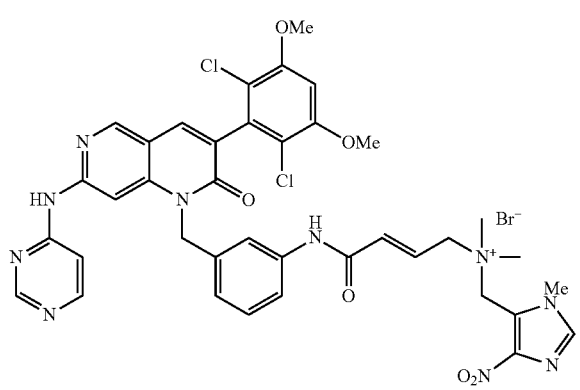
563
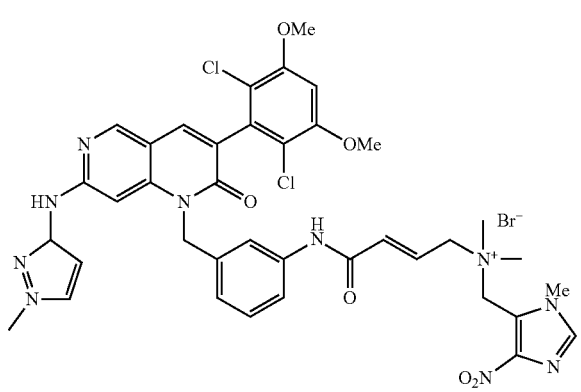
564
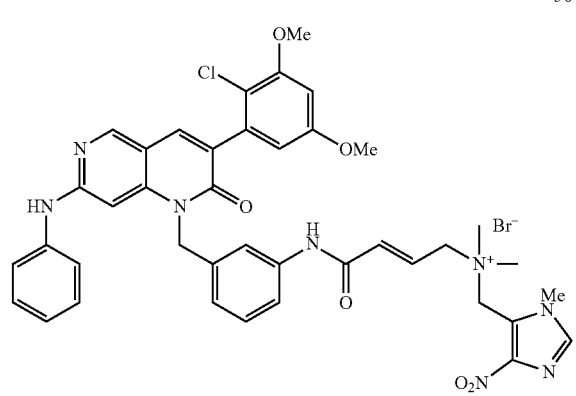
170
-continued
565
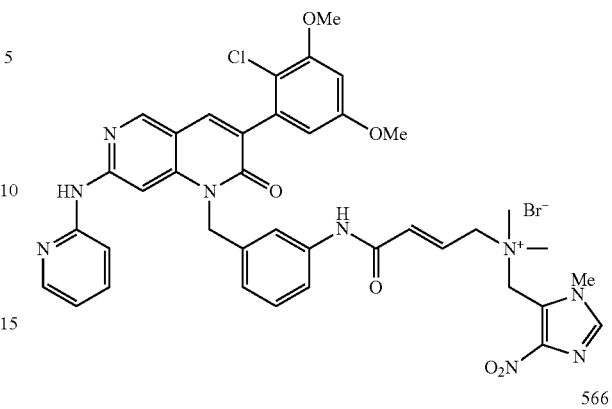
566
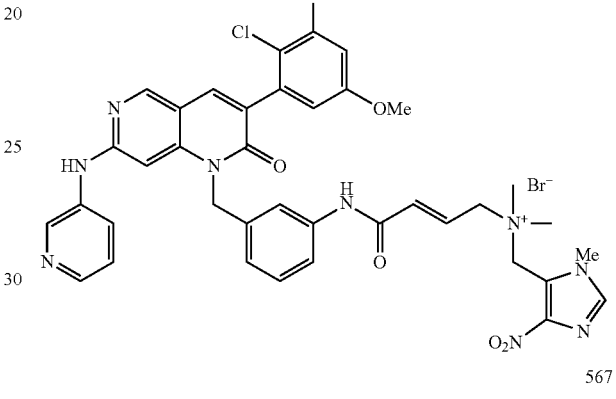
567
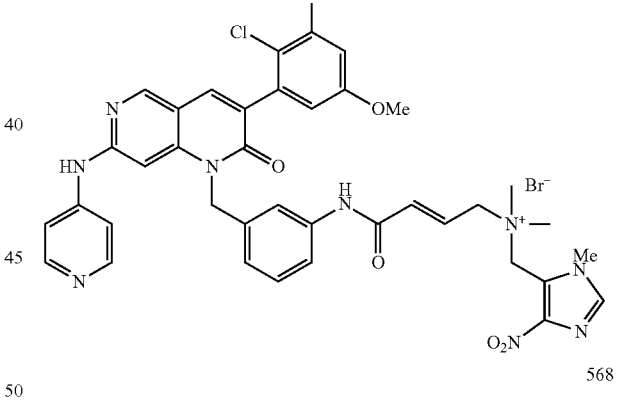
568
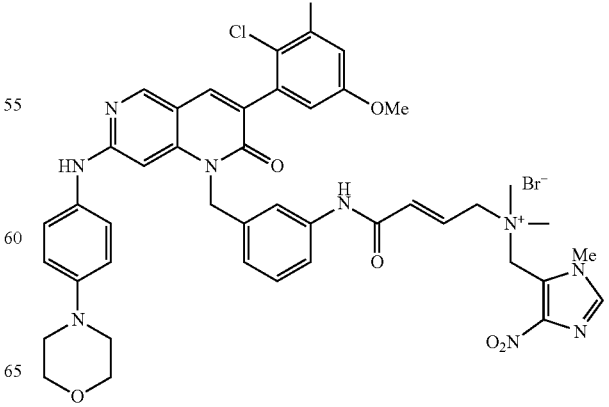

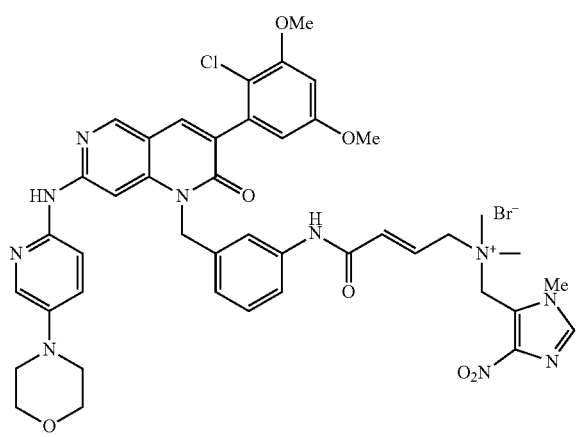
569
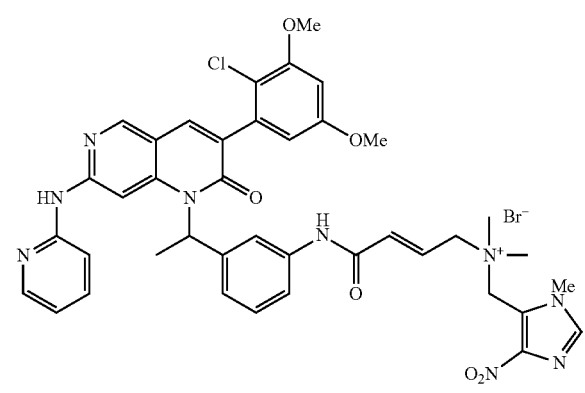
573
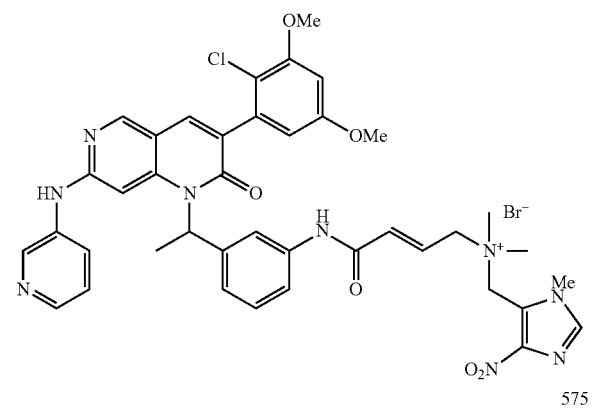
574
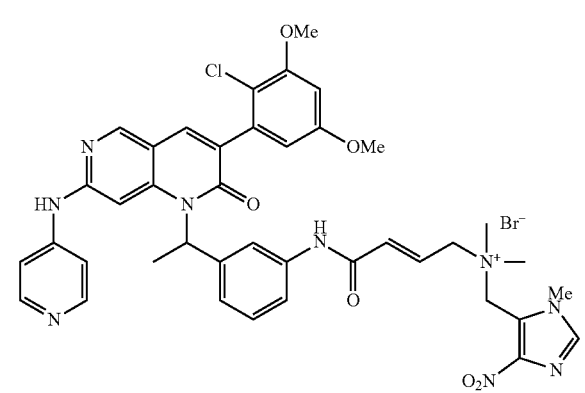
575
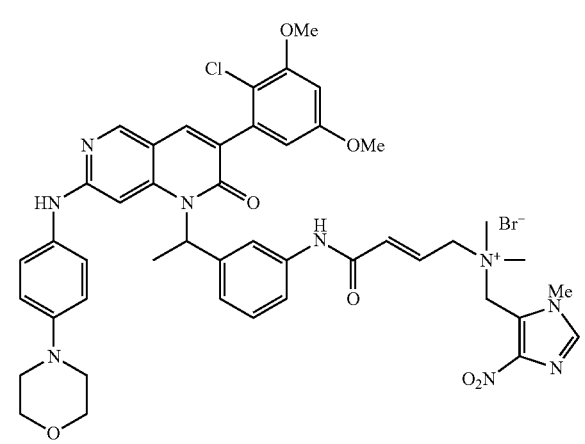
576

577
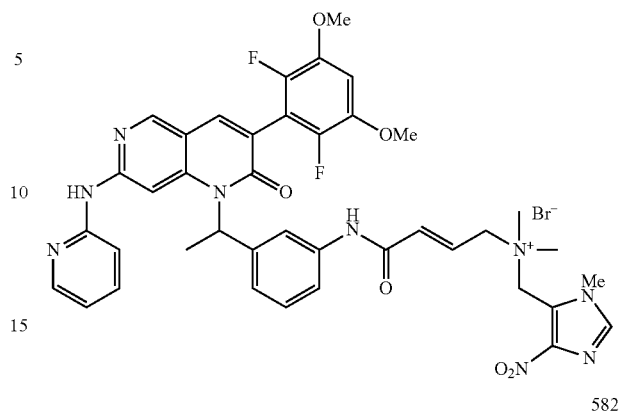
581
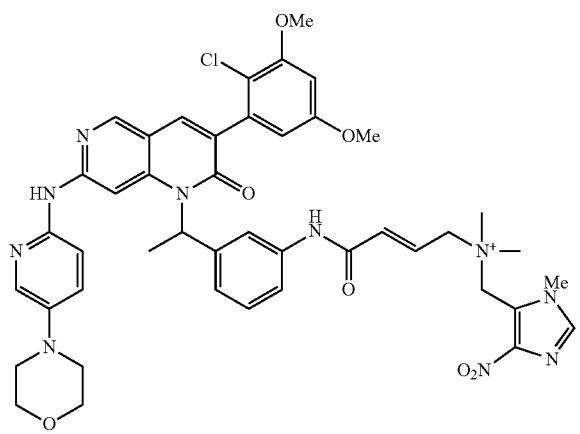
578
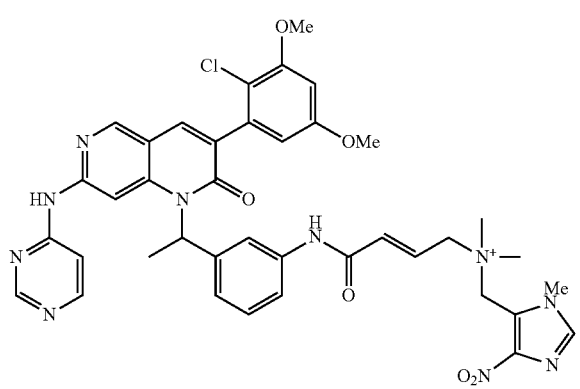
582
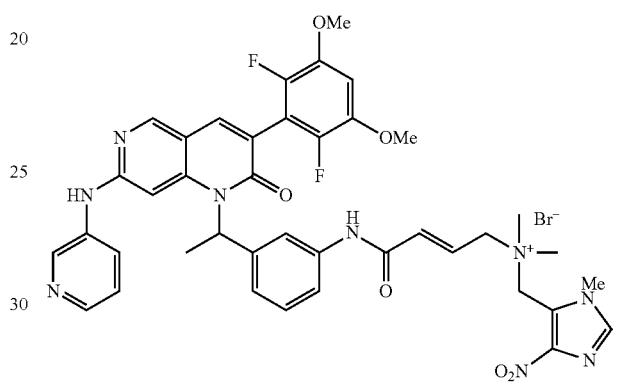
579
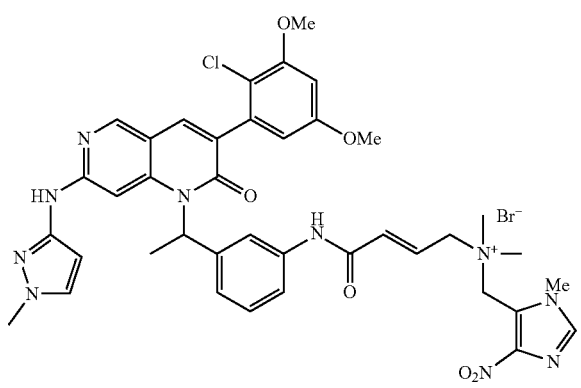
583
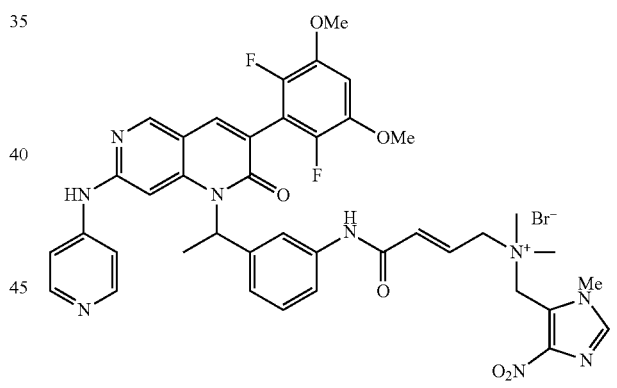
580
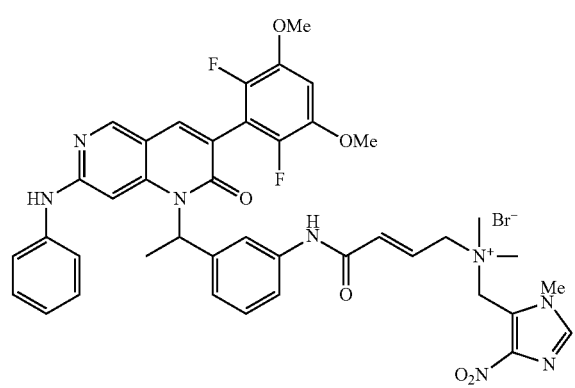
584
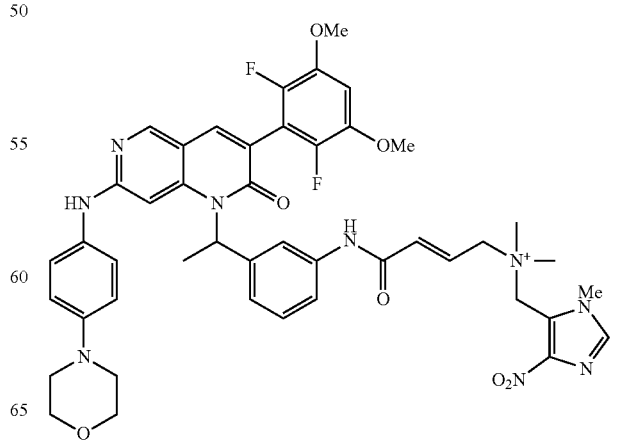

585.
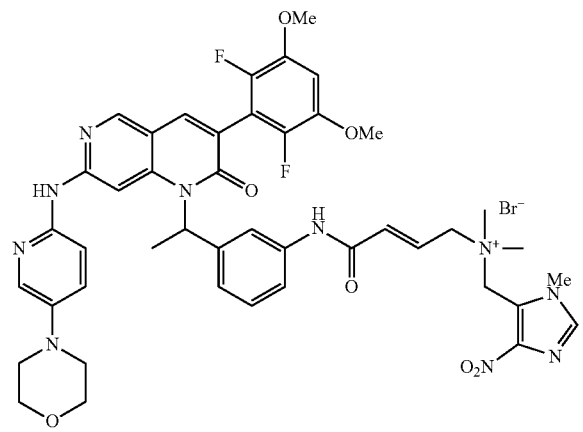
586
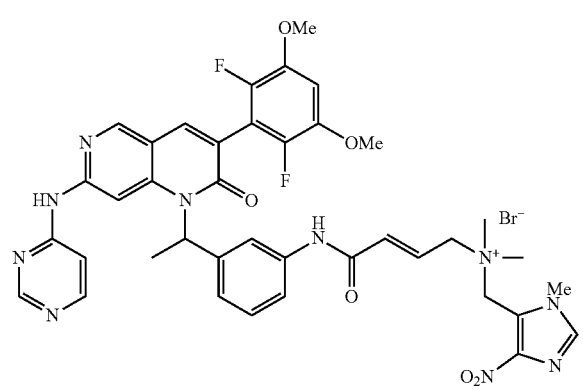
587
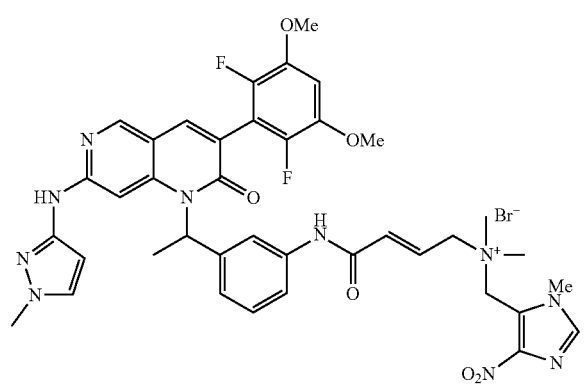
588
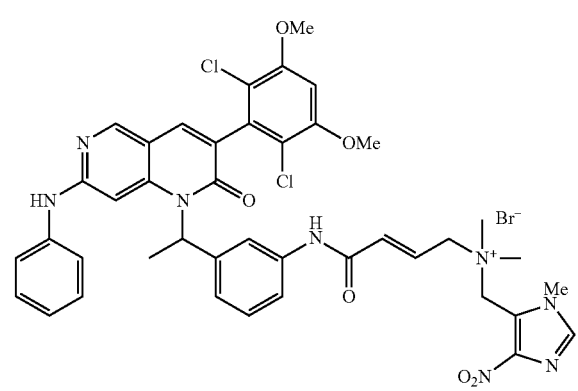
589
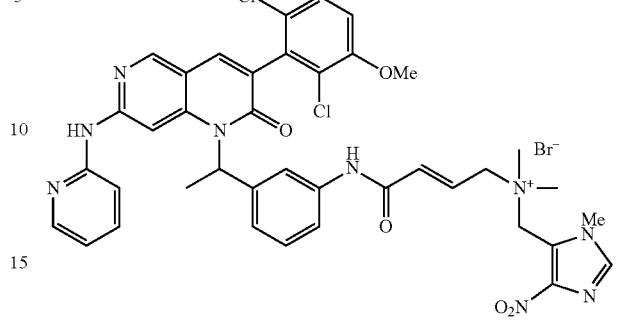
590
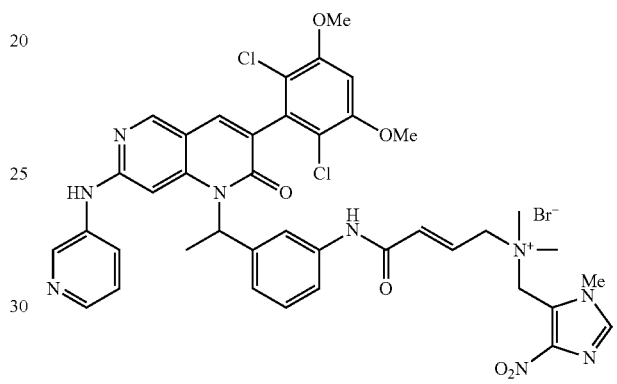
591
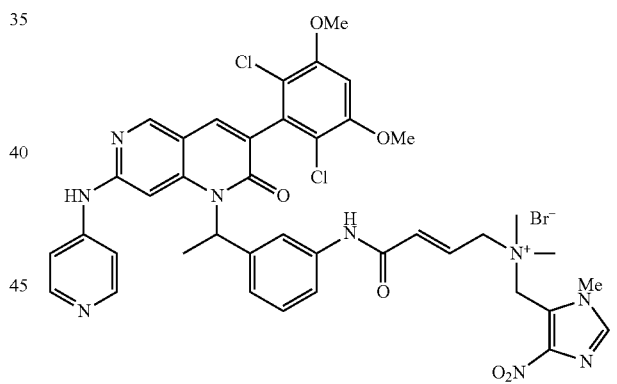
592
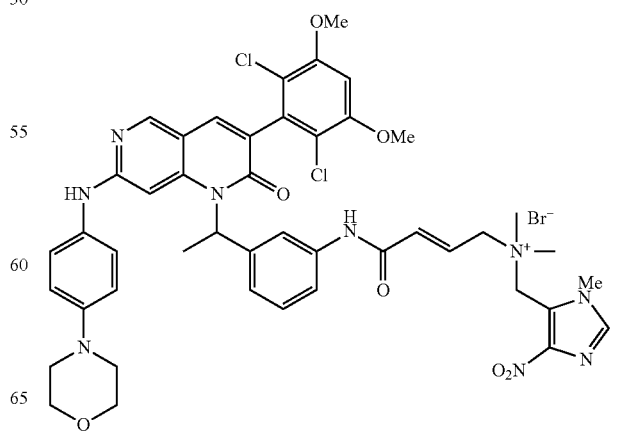

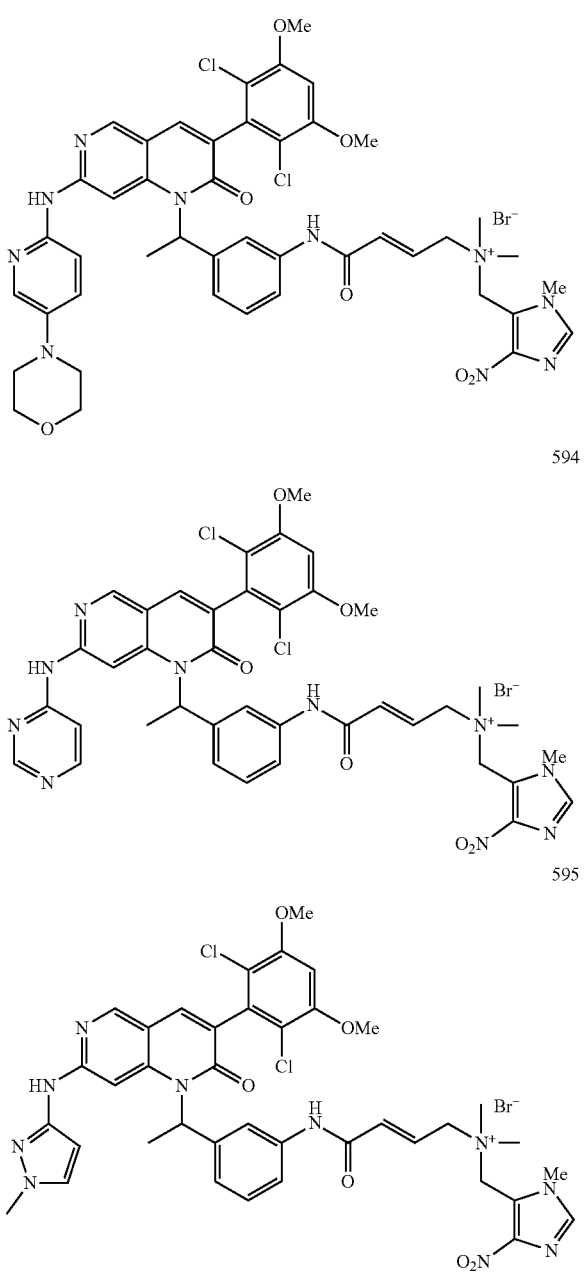

Biology

A range of experiments were conducted to evaluate the therapeutic potential of the compounds of the invention. These experiments include in vitro enzyme inhibition studies and the effect of prodrug compounds on certain cell lines.

Example 85 describes the investigation of inhibition of FGFR1-4 kinases. Compounds of the invention were studied for their ability to inhibit recombinant FGFR1-4 in an isolated enzyme biochemical assay. Most of the compounds exhibited strong pan-inhibition against FGFR1, FGFR2 and FGFR3 with low nanomolar potency. Several compounds were determined to be potent inhibitors of FGFR4 with isolated enzyme $IC_{50}$s<100 nM (e.g. 101, 106, 109, 112, 115 and 118).

Screening of compound 120 for biochemical inhibition of a panel of 456 kinases is described in Example 86. Compound 120 was found to show excellent selectivity for the FGFR family.

The anti-proliferative activity of compounds of the invention was evaluated against a panel of FGFR-driven cancer cell lines (Example 87). All of the selected compounds demonstrated strong inhibitory effects against the proliferation of FGFR1-amplified H520 non-small cell lung cancer cells, FGFR2-amplified SUM52 breast cancer cells and FGFR3-amplified SW780 bladder cancer cells with low nM $IC_{50}$ values. Several compounds demonstrated significantly improved cellular anti-proliferative potency in these cell lines when compared to controls (PD173074 and FIIN-1). Selected compounds also displayed potent anti-proliferative activity against FGFR4-amplified Hep3B hepatocellular carcinoma cells.

Figure 5:
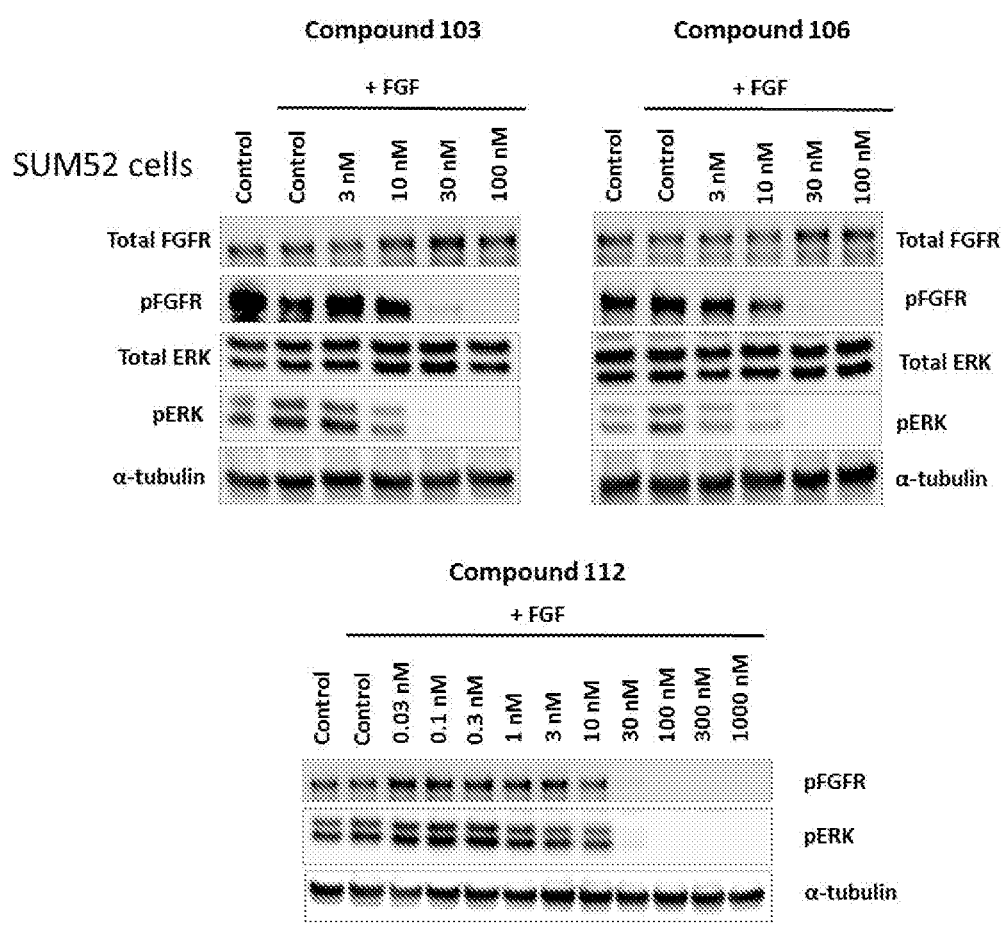
FIG. 5 shows Western blots for phospho-FGFR and phospho-ERK in FGF-stimulated SUM52 cells following exposure to increasing concentrations of compounds 103, 106 and 112.

FIG. 5 shows the results of cellular FGFR inhibition of compounds of the invention as determined by Western blot for FGF ligand-mediated activation of FGFR2 and its downstream signalling partner ERK1/2 in SUM52 cells (Example 88). Compounds 103, 106 and 112 were found to significantly inhibit the phosphorylation of FGFR2 and ERK1/2 in SUM52 cells at nanomolar concentrations, with complete blockade of FGFR2 and ERK1/2 activation observed at a concentration of 30 nM.

Preferred compounds of the invention were designed as irreversible inhibitors of the FGFR family through use of an electrophilic moiety in the inhibitor suitably positioned to target and covalently bind to a cysteine residue in the p-loop region of the FGFR proteins. To confirm the irreversible nature of binding of test compounds of the invention with FGFR1-3, a comparative "drug washout" Western blot assay was performed in the FGFR-amplified cancer cell lines. See Example 89. Here, maintenance of signal inhibition following extensive cell washing is indicative of irreversible receptor binding. PD173074 and FIIN-1 were used as respective reversible and irreversible control compounds.

Figure 6:
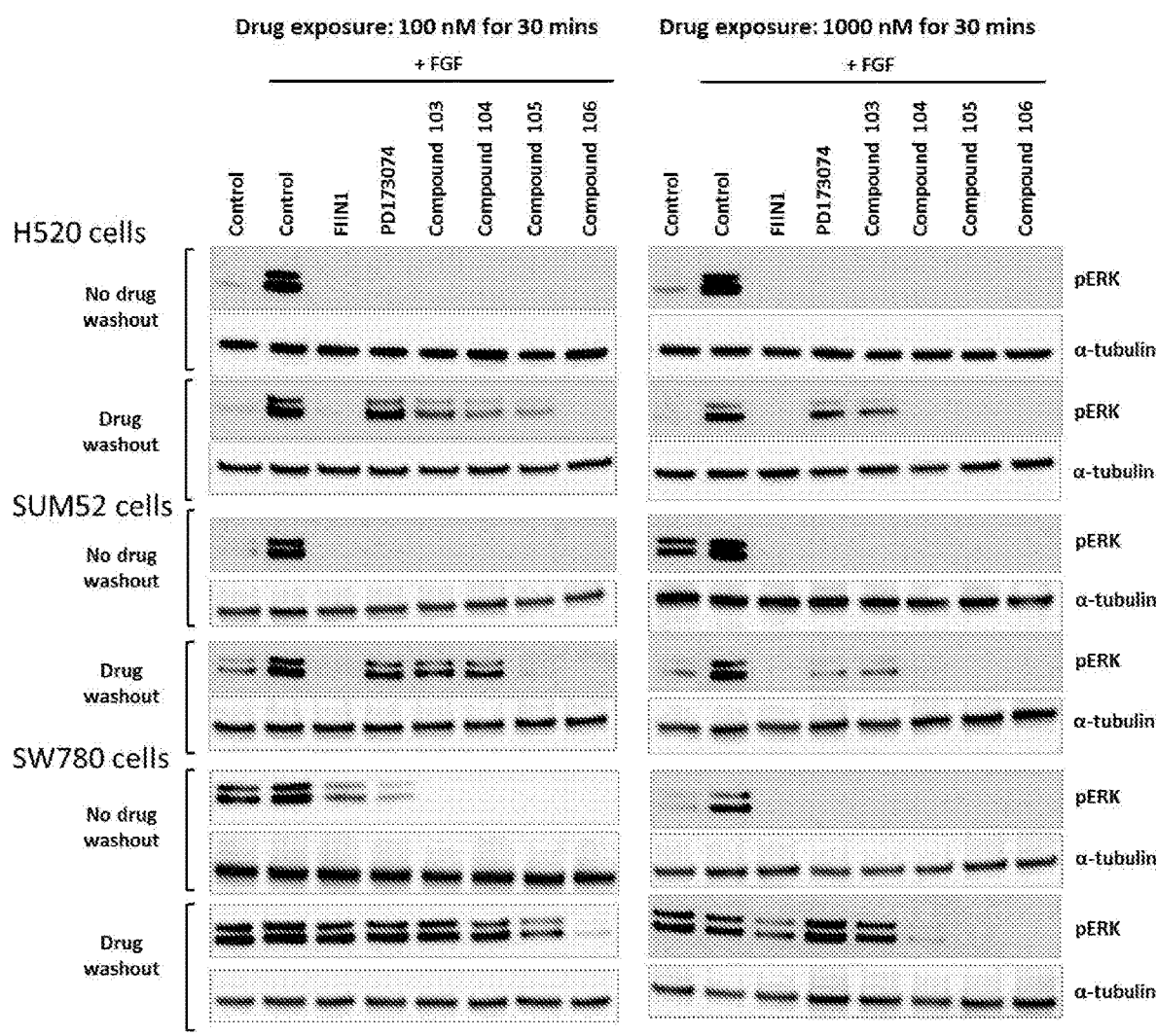
FIG. 6 shows Western blots for phospho-ERK in H520, SUM52 and SW780 cells following exposure to 100 nM of FIIN-1, PD173074, compound 103, 104, 105 and 106 for 30 minutes with and without drug washout prior to FGF-stimulation and cell lysis.

Exposure of the H520, SUM52 and SW780 cell lines to compounds 103, 104, 105 and 106, followed by FGF-stimulation, resulted in complete inhibition of phosphorylation of ERK1/2, consistent with complete inhibition of phosphorylation of the primary FGFR1/2/3 targets (FIG. 6). Compounds 103, 104, 105 and 106 were found to completely inhibit phospho-ERK1/2 in FGFR3-amplified SW780 cells at 100 nM, with FIIN-1 and PD173074 appearing less effective against FGFR3 at this concentration. An identical experiment with an increased drug concentration of 1000 nM FIIN-1 and PD173074 gave complete inhibition of phospho-ERK1/2 in SW780 cells (FIG. 6).

Exposure of the H520, SUM52 and SW780 cell lines to compounds 103, 104, 105 and 106, followed by extensive drug washout prior to FGF-stimulation, demonstrated restoration of phospho-ERK1/2 signalling for compounds 103 and 104 across all three cell lines. For compound 105, phospho-ERK1/2 was fully restored in SW780 cells, remained inhibited in SUM52 cells and was partially inhibited in H520 cells. For compound 106, phospho-ERK1/2 was fully inhibited across all three cell lines. An identical washout assay at the increased concentration of 1000 nM (FIG. 6) demonstrated essential full inhibition of phospho-ERK1/2 for compounds 104, 105 and 106 across all three cell lines. Compound 103 however still showed restoration of phospho-ERK1/2 signalling at this concentration.

By way of comparison, the reversible control compound PD173074 as expected showed restoration of phospho-ERK1/2 following drug washout at both the 100 nM and 1000 nM concentrations (FIG. 6). For FIIN-1, inhibition of phosphorylation of ERK1/2 was conserved in H520 and SUM52 cells despite drug washout, however restoration of phospho-ERK1/2 signalling was observed in SW780 cells following drug washout at both the 100 nM and 1000 nM concentrations (FIG. 6).

Collectively these results are consistent with FIIN-1 acting as an irreversible inhibitor of FGFR1 (H520 cells) and FGFR2 (SUM52), and a reversible inhibitor of FGFR3 (SW780) under the test conditions. The data further demonstrates that compound 103 is a reversible inhibitor of FGFR1-3, but increasing irreversible behaviour in cells is observed going across the series from compound 104 to 105 to 106, with compound 106 acting as a potent irreversible inhibitor of FGFR1/2/3 in cells following a 30 minute exposure to 100 nM, whereas compounds 104 and 105 require a higher exposure concentration of 1000 nM over the 30 minute assay time to fully covalently bind the FGFR1-3 targets.

It is notable that the compound series 103 to 106 contain the identical (S)-pyrrolidin-3-yl linked dimethylaminocrotonamide moiety positioned to covalently bind the FGFR target cysteine. They possess comparable potency for biochemical inhibition of the FGFR1-3 isolated enzymes (Table 1), yet surprisingly they display significant differences in their ability to irreversibly inhibit FGFR1-3 in the cellular wash-out assays. Structurally they differ by substitution at the R1 position of the compound, where going across the series this group changes from Me (103) to iso-propyl (104) to cyclohexyl (105) to phenyl (106), essentially increasing in lipophilicity, steric bulk and aromaticity at this position. The results indicate that these modifications at the R1 group modulate the ability of the (S)-pyrrolidin-3-yl-linked dimethylaminocrotonamide to covalently bind the target cysteine of FGFR1-3 in cells as demonstrated by this drug washout assay, with R1=phenyl having been determined as a preferred example of this phenomenon. Finding that a substituent at a remote position of the molecule has such a large influence on the ability of a common Michael acceptor electrophile to bind a target cysteine in the active site of a kinase in this cellular assay was unexpected.

Figure 7:
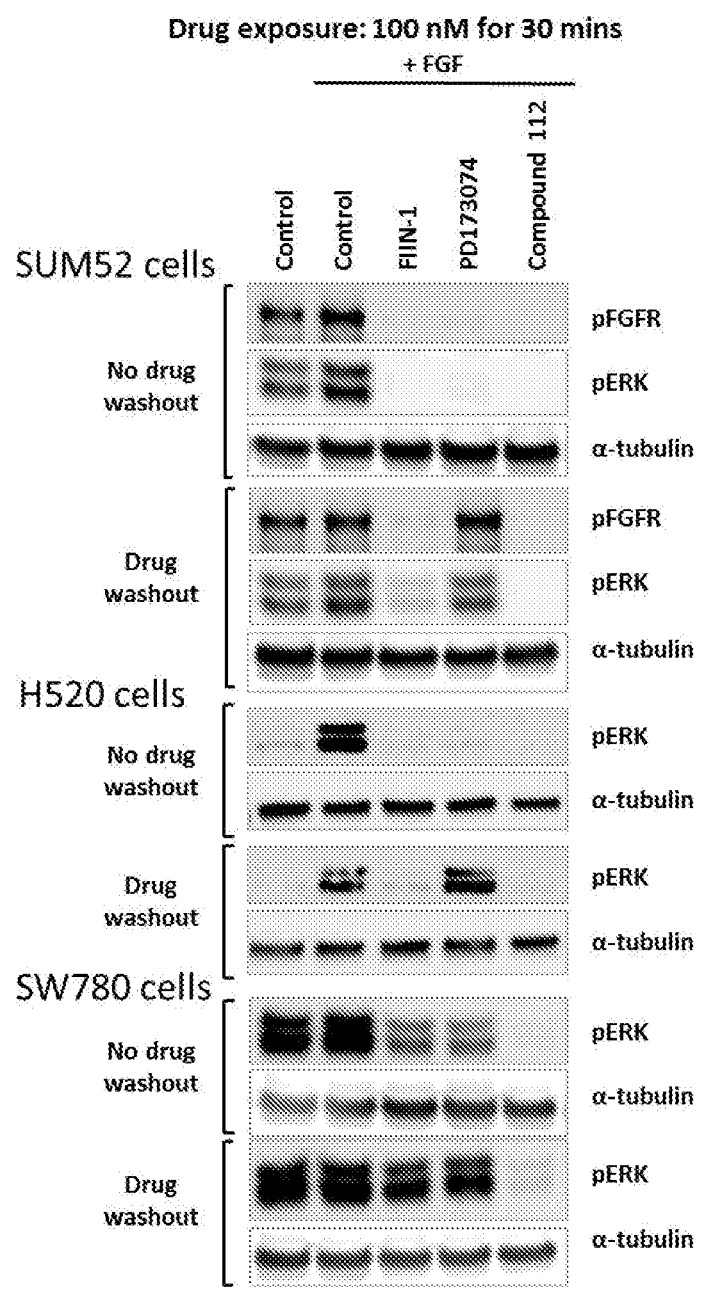
FIG. 7 shows Western blots for phospho-FGFR and phospho-ERK in SUM52 cells and phospho-ERK in H520 and SW780 cells following exposure to 100 nM of FIIN-1, PD173074 and compound 112 for 30 minutes with and without drug washout prior to FGF-stimulation and cell lysis.

Compound 112 represents a further example of a potent irreversible inhibitor of FGFR1-3 in cells (FIG. 7).

Figure 8:
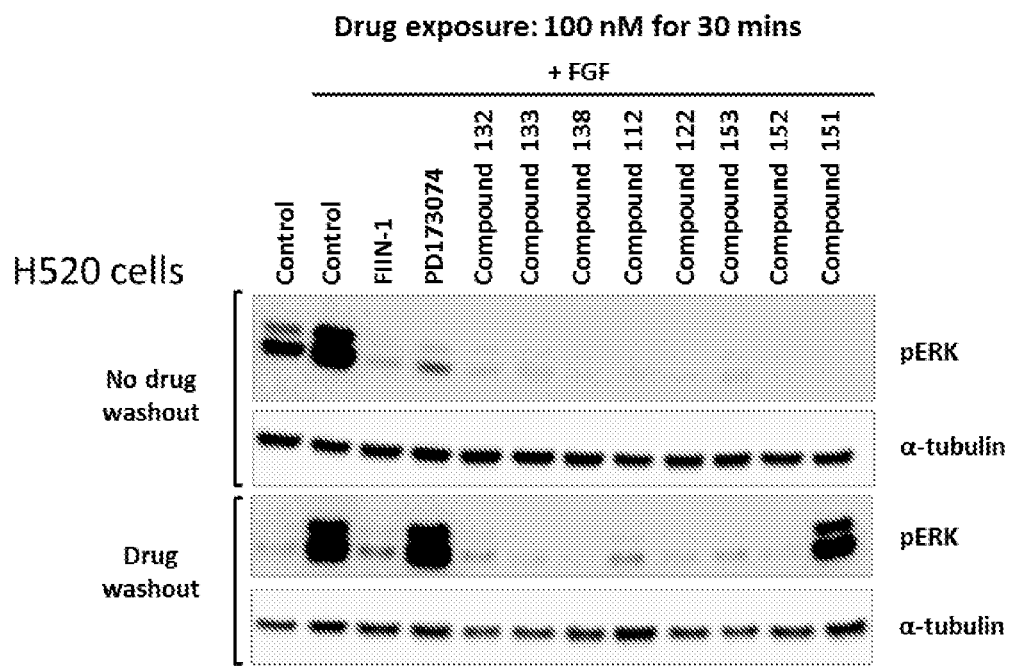
FIG. 8 shows Western blots for phospho-ERK in H520 cells following exposure to 100 nM of FIIN-1, PD173074, compound 132, 133, 138, 112, 122, 153, 152 and 151 for 30 minutes with and without drug washout prior to FGF-stimulation and cell lysis.

FIG. 8 demonstrates that compounds 132, 133, 138, 112, 153 and 152 are potent irreversible inhibitors of FGFR1 in H520 cells. Notably, compound 151 was found to be a potent inhibitor of the target in cells but displays reversible binding characteristics. In this instance, compounds 151 and 153 contain identical R1 (iso-propyl), L-R2 (piperidin-4-yl linked dimethylaminocrotonamide) and Ar (2,6-dibromo-3,5-dimethoxyphenyl) substituents and only differ by the heterocyclic hinge binding scaffold to which they are attached. Yet 151 is a reversible FGFR1 inhibitor and 153 is an irreversible FGFR1 inhibitor. Again, an unexpected finding.

Figure 9:
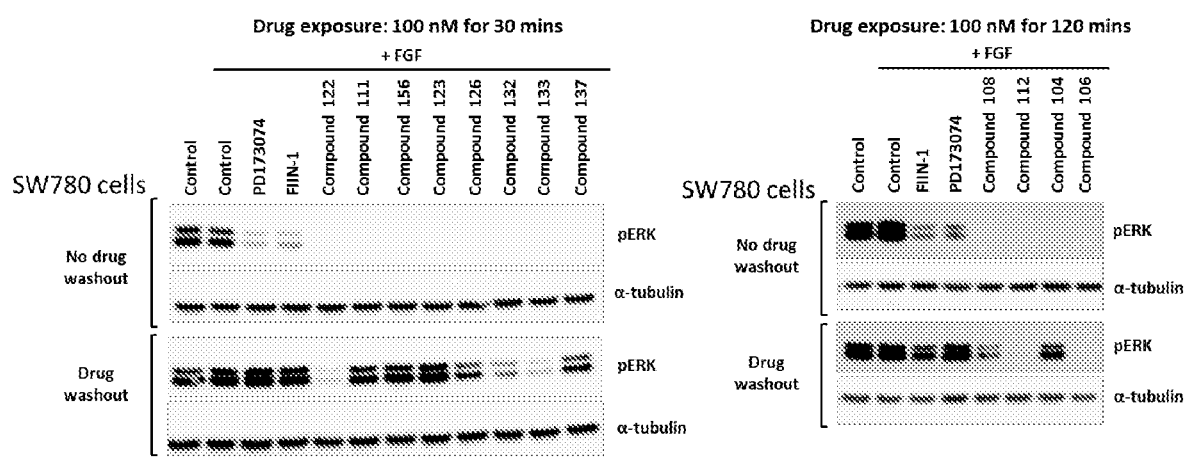
FIG. 9 shows Western blots for phospho-ERK in SW780 cells following exposure to 100 nM of FIIN-1, PD173074, compound 122, 111, 156, 123, 126, 132, 133 and 137 for 30 minutes with and without drug washout prior to FGF-stimulation and cell lysis. It further shows Western blots for phospho-ERK in SW780 cells following exposure to 100 nM of FIIN-1, PD173074, compound 108, 112, 104 and 106 for 120 minutes with and without drug washout prior to FGF-stimulation and cell lysis.

FIG. 9 (left hand side) demonstrates that compounds 122 and 133 are potent irreversible inhibitors of FGFR3 in SW780 cells. Compound 132 displayed partial irreversible character, while compounds 111, 156, 123, 126 and 137 were found to be potent reversible inhibitors of FGFR3.

FIG. 9 (right hand side) shows inhibition of phospho-ERK1/2 in SW780 cells following exposure to compounds 108, 112, 104 and 106, with and without drug washout prior to FGF-stimulation. All the other test compounds were potent inhibitors of FGFR3 in SW780 cells. However, compounds 108 and 104 were determined to be reversible under these test conditions while 112 and 106 were found to be irreversible. Structurally these compounds are related as iso-propyl (108, 104) and phenyl (112, 106) variations at the R1 position of a (S)-pyrrolidin-3-yl-linked dimethylaminocrotonamide and a piperidin-4-yl-linked dimethylaminocrotonamide, again demonstrating surprisingly improved irreversible inhibition of FGFR3 in this cellular assay, conferred by an R1=phenyl substituent for both of these cysteine targeted electrophiles.

Figure 10:
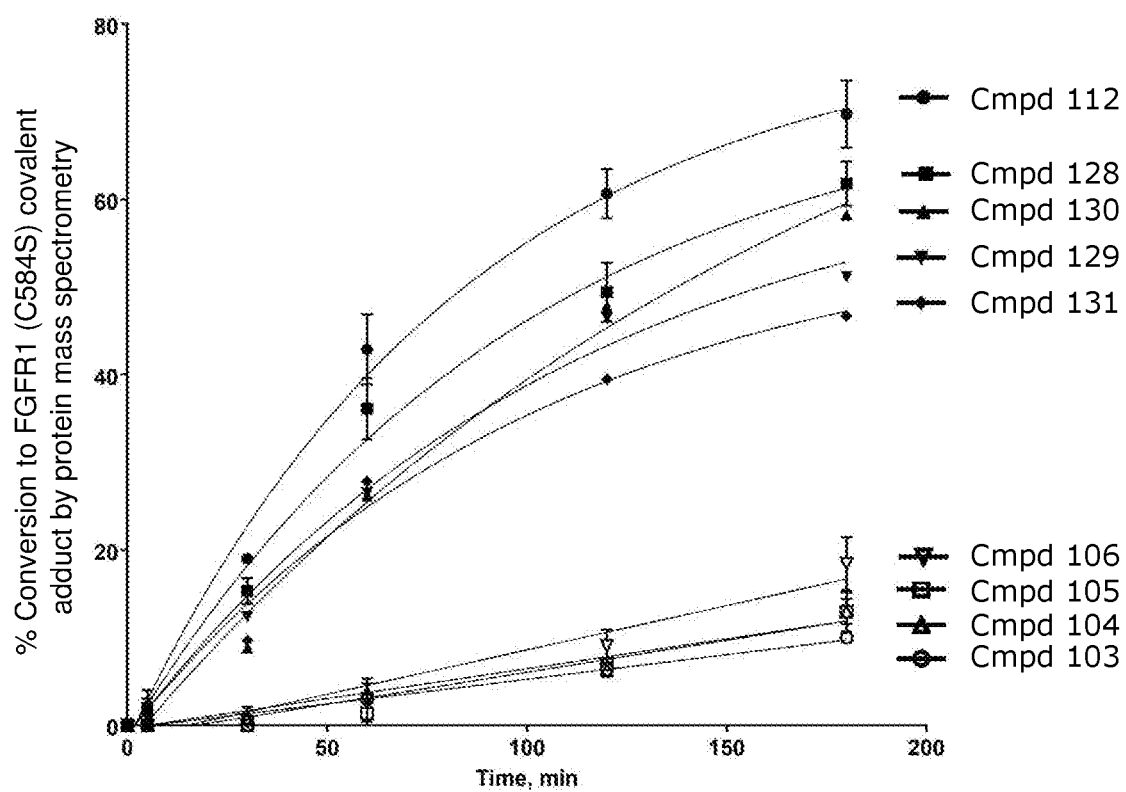
FIG. 10 shows the reaction of compounds 103, 104, 105, 106, 112, 128, 129, 130 and 131 with recombinant FGFR1 (C584S) as a function of time, to form the covalent adduct as detected by protein mass spectrometry.

Example 90 describes the covalent binding reaction of compounds 103, 104, 105, 106, 112, 128, 129, 130 and 131 with recombinant FGFR1 (C584S) by protein mass spectrometry. The percentage conversion to a covalent adduct by mass spectrometry following incubation of the test compounds and FGFR1 for 120 minutes is described in Table 3, while the conversion to a covalent adduct as a function of time is shown for compounds of the invention in FIG. 10. Compound 112 gave the most complete (60%) conversion to the covalent adduct while compound 103 was the least reactive (6% conversion in 120 minutes). It is notable that the series of piperidin-4-yl-linked dimethylaminocrotonamides (112, 130, 128, 129 and 131) were more reactive than the series of (S)-pyrrolidin-3-yl-linked dimethylaminocrotonamides (106, 105, 104 and 103) (FIG. 10). A surprising finding consistent with improved delivery of the dimethylaminocrotonamide Michael acceptor to the target cysteine when linked through a piperidin-4-yl linker. While compounds 103, 104, 105 and 106 displayed similar reactivity towards FGFR1 (C584S), as noted above they displayed significant differences in their ability to irreversibly inhibit FGFR1 in the cellular wash-out assay. A surprising finding consistent with the structure of the compounds modulating their respective cellular uptake and therefore FGFR1 target interaction.

X-ray crystallography was used to investigate the reversible binding mode of compounds 112, 103, 105 and 106 to the active site of a double mutant (C488A, C584S) FGFR1 kinase domain (Example 91 and FIGS. 11A, 11C, 11D and 11E). The applicants surprisingly found that the structural changes made to the ATP-competitive scaffold of the inhibitors is able to modulate the irreversible binding of the compounds by influencing the amount of movement of the crotonamide side chain towards the target cysteine, while simultaneously influencing the rigidity and degree of closure of the p-loop of the kinase, bringing the target cysteine in closer proximity to the reactive electrophilic carbon of the crotonamide moiety.

In each case the inhibitors bind in the active site with the 2,6-dichloro-3,5-dimethoxyphenyl group buried in a hydrophobic pocket forming a single hydrogen bond from the 3-methoxy substituent to Asp641 of the protein. The central heterocyclic system forms a hydrogen bond donor acceptor interaction to Ala564 in the hinge region of the protein backbone. The dimethylamidocrotonamide side chain is presented into solvent accessible space and is in each case directed towards the left hand side of the active site near Glu571, available for nucleophilic attack by the target cysteine in the p-loop of the protein. These interactions are demonstrated for compound 112 in diagram form in FIG. 11B.

In the current protein construct, the target cysteine has been mutated to an alanine, as described previously [Mohammadi et al., Science, 276 (1997) 955-960], facilitating appropriate crystal formation. This prevents trapping an irreversible binding mode for the test compounds allowing us to reveal the reversible binding that occurs prior to covalent bond formation to be revealed. However, these structures allow us to model the likely location of the target cysteine side chain to be modelled. To the applicants' surprise, the site of the modelled cysteine sulfur atom is ~12 Å distant from the reactive crotonamide site (shown with a * in FIGS. 11A, 11B and 11F). Covalent binding to this cysteine as observed in the FGFR1 (C584S) mass spectrometry assay, to provide the irreversible inhibition observed in the washout assay in cells, would require the dynamic movement of the crotonamide side chain of the compounds and/or the "closure" of the p-loop to bring the reactive sites into close proximity. Indeed when the inhibitor position from the compound 106 FGFR1 crystal structure (ligand from FIG. 11E) is overlaid with the reported AZD4547/ FGFR1 (double mutant) crystal structure [Yosaatmadja et al., Acta Cryst. D. Biological Crystallography 2015, D71, 525-33], which demonstrates a closed p-loop conformation, the subsequently modelled cysteine position is now within 3.7 Å of the reactive crotonamide site.

Taken in combination with the findings from the FGFR1 (C584S) mass spectrometry assay and cellular washout assay it was surprisingly found that the structural changes made to the ATP-competitive scaffold of the inhibitors is able to modulate the irreversible binding of the compounds by influencing the amount of movement of the crotonamide side chain towards the target cysteine, while simultaneously influencing the rigidity and degree of closure of the p-loop of the kinase, bringing the target cysteine in closer proximity to the reactive electrophilic carbon of the crotonamide moiety. Further, the data is consistent with these structural changes modulating the cellular uptake of the inhibitors and therefore the potency of irreversible inhibition of FGFR1-3 in cells.

The prodrug forms of compounds of the invention (compounds 200, 201, 202, 203, 204, 205, 206, 207, 208, 209, 210, 211, 212, 213, 215, 216, 217, 218, 219 and 220) were investigated for their ability to inhibit the proliferation of one or more of H520, SUM52 and SW780 cells under oxic conditions (Example 92). In addition, selected compounds were exposed to 4 hours of anoxia to activate the prodrugs and release the FGFR inhibitor through trigger fragmentation, prior to conducting the remainder of the anti-proliferative assay under oxic conditions. The oxic and anoxic anti-proliferative IC50's and their ratio, termed a Hypoxic Cytotoxicity Ratio (HCR), are shown in Table 4.

Comparing prodrug compound 204 to its respective FGFR inhibitor 112 (Table 2), as a representative example, demonstrates that the prodrug is 307-fold, 296-fold and 143-fold less potent with respect to inhibiting the proliferation of H520, SUM52 and SW780 cells respectively than the inhibitor compound 112. Comparable levels of deactivation are observed for all the prodrugs of Table 4. In addition, a four hour exposure to anoxia increases the anti-proliferative potency of prodrug compound 204 by 27-fold in H520 cells and 12-fold in SUM-52 cells. Comparable results are observed for prodrug compounds 201, 203, 205, 206, 207, 208, 209, 210, 211, 212, 213, 215, 216, 217, 218, 219 and 220, with anti-proliferative potency of the prodrugs increasing following exposure to anoxia by between 4 and 106-fold.

Figure 12:
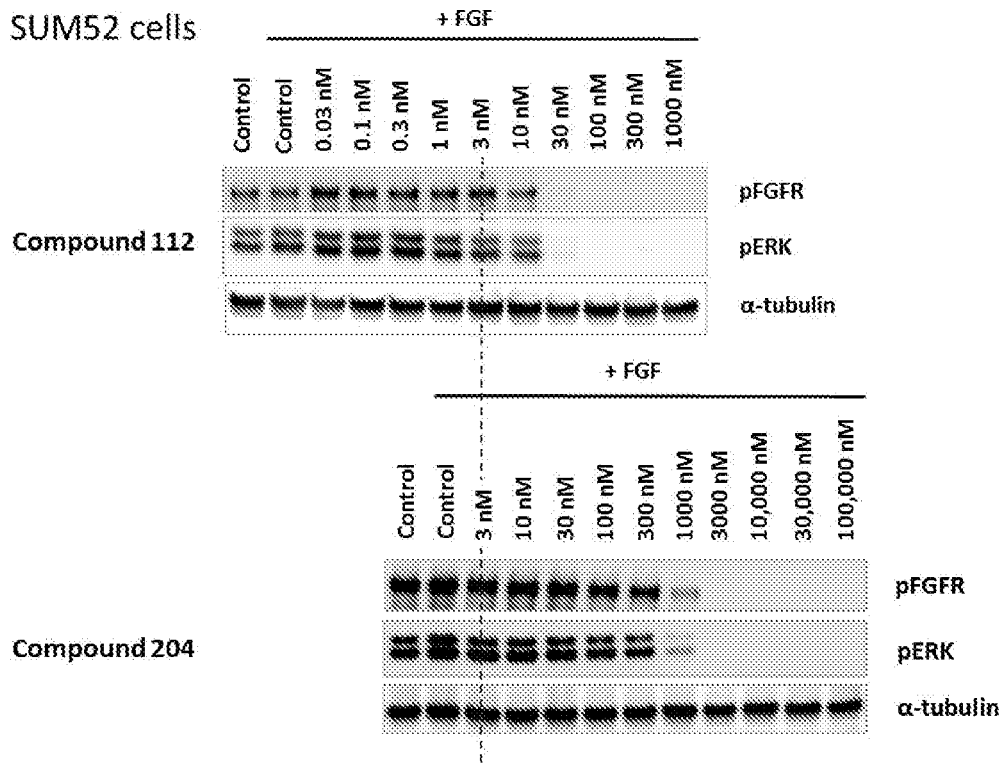
FIG. 12 shows Western blots for phospho-FGFR and phospho-ERK in FGF-stimulated SUM52 cells following exposure to increasing concentrations of compound 112 compared to its NMQ prodrug compound 204.

Example 93 shows the ability of prodrug compound 204 to inhibit FGF-dependent signalling in SUM52 cells for FGF ligand-mediated activation of FGFR2 and its downstream signalling partner ERK1/2. As shown in FIG. 12, prodrug compound 204 was approximately 100-fold less potent at inhibiting the phosphorylation of FGFR2 and ERK1/2 in SUM52 cells than the FGFR inhibitor compound 112 that it is derived from. Compound 204 fully silenced FGF signalling at a concentration of 3000 nM, while its respective FGFR inhibitor compound 112 achieved the same degree of inhibition at a concentration of 30 nM.

Figure 13:
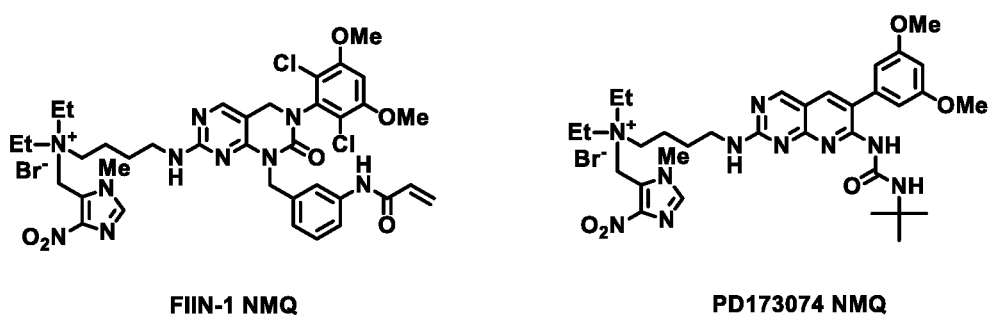
FIG. 13 shows the chemical structures of NMQ prodrugs of FIIN-1 and PD173074.
Figure 14:
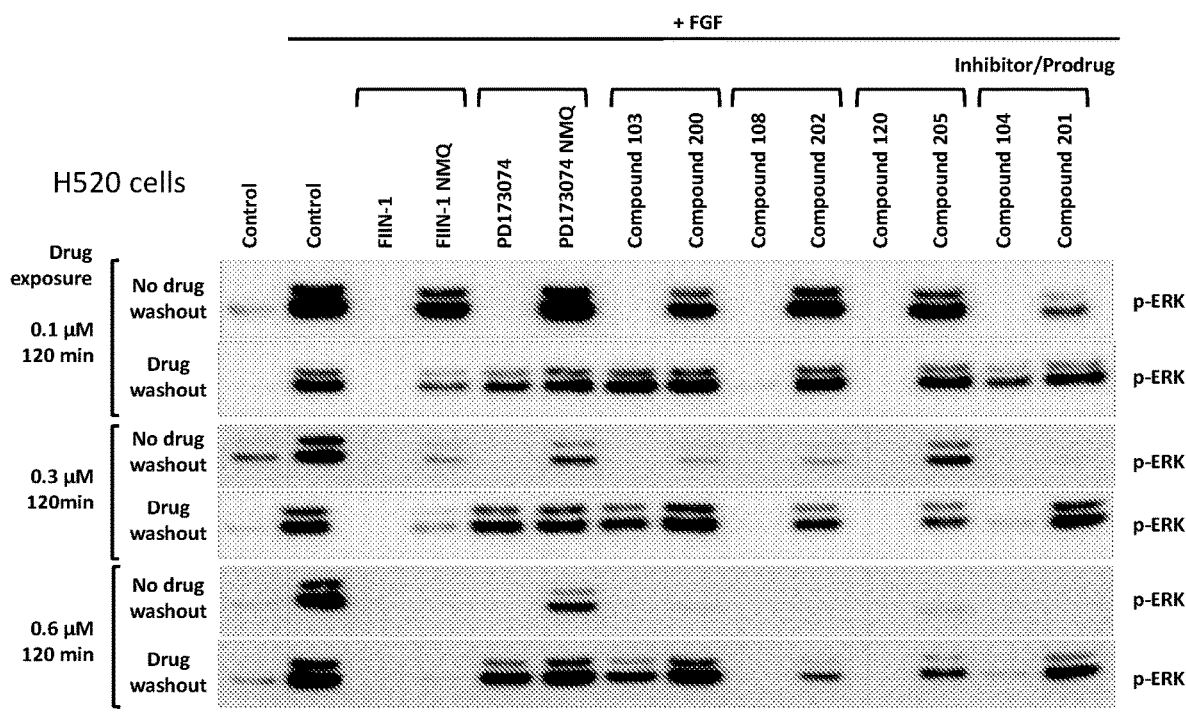
FIG. 14 shows Western blots for phospho-ERK in H520 cells following exposure to 100 nM, 300 nM or 600 nM of FIIN-1, PD173074, compound 103, 108, 120, 104 and their respective NMQ prodrugs FIIN-1 NMQ, PD173074 NMQ, compound 200, 202, 205 and 201, for 120 minutes with and without drug washout prior to FGF-stimulation and cell lysis.

Prodrug compounds 200, 202, 205 and 201, relative to their respective inhibitors (103, 108, 120 and 104), were evaluated in the H520 cell-based Western blot washout assay described in Example 94 to detect reversible or irreversible inhibitors of FGFR1. NMQ prodrugs of FIIN-1 and PD173074 were also prepared, by conjugation of a 4-nitroimidazole trigger on the common diethylaminobutyl side chain of each control compound (FIG. 13), and studied in the Western blot washout assay relative to FIIN-1 and PD173074 as control compounds. A drug exposure time of 2 hours was utilised at a range of test concentrations (100, 300 and 600 nM), with and without drug washout (FIG. 14).

The data indicates that FIIN-1 is an irreversible inhibitor of FGFR1 at all concentrations studied (as described previously). The FIIN-1 NMQ prodrug is cell-excluded in comparison, requiring concentrations of 300 nM to suppress FGFR1 signalling through phospho-ERK1/2. However, the FIIN-1 NMQ prodrug is an irreversible inhibitor of FGFR1 as phospho-ERK1/2 remains suppressed despite washout of the prodrug from cells (most evident at the 600 nM concentration). This result is to be expected as conjugation of the trigger for this prodrug is in a position of the molecule remote from the electrophilic acrylamide moiety and would therefore not be expected to interfere with covalent binding to the target cysteine of FGFR1.

PD173074 was found to be a potent reversible inhibitor of FGFR1 at concentrations as low as 100 nM (as described previously), whereas the NMQ prodrug of PD173074 was demonstrated to be strongly cell excluded, providing partial inhibition of FGF-dependent signalling through phospho-ERK1/2 at a concentration of 600 nM. Drug washout confirmed the partial target inhibition observed was reversible in nature.

The FGFR inhibitor compound 103 was determined to be a potent reversible inhibitor of FGFR1 (as described previously), demonstrating complete inhibition of phospho-ERK1/2 at the lowest concentration tested (100 nM) that could be rescued by washing inhibitor from cells. By way of contrast, the corresponding prodrug compound 200 was unable to silence FGFR1 at 100 nM, requiring 300 nM to achieve significant suppression of phospho-ERK1/2, indicating that the prodrug is partially cell-excluded. In addition, phospho-ERK1/2 was restored following washout of prodrug compound 200 from cells (most evident at the 300 and 600 nM concentrations) indicating that it acts as a reversible inhibitor of FGFR1.

The FGFR inhibitor compounds 108, 120 and 104 all displayed potent, irreversible inhibition of FGFR1 in the H520 washout assay (although 104 was somewhat less effective requiring 300 nM concentrations to achieve this). Their respective prodrugs 202, 205 and 201 were demonstrated to be cell-excluded as they were unable to fully suppress FGFR1 at a concentration of 100 nM (and even 300 nM for compound 205). They were further confirmed to be reversible inhibitors of the target FGFR1 as FGF-dependent signalling of phospho-ERK1/2 was restored at test concentrations as high as 600 nM once the prodrugs were washed from cells.

These findings indicate that the NMQ prodrug technology used by TH-4000 provides the same mechanism of deactivation when applied to the irreversible FGFR1-3 inhibitors of the present invention by ablating the irreversible binding characteristics of the inhibitor, particularly when the prodrug trigger is applied to the dimethylaminocrotonamide function proximal to the electrophilic centre (and not a distant side chain as in FIIN-1). Further, the permanent positive charge resulting on the prodrug complex reduces the ability of the prodrug to enter cells and reversibly bind with the kinase target providing further target deactivation. This is most clearly shown by the inhibitor/prodrug pairings 108/202 and 120/205 in FIG. 14, where potent irreversible FGFR1 inhibitors are rendered both reversible and cell excluded by formation of their prodrug forms. Collectively, these two mechanisms result in significantly less cellular activity for the prodrugs relative to their parent kinase inhibitor.

Example 95 describes pulse and steady state radiolysis studies. Previous studies established that the NMQ prodrug class specifically fragment following one-electron reduction to the intermediate nitro radical anion, releasing the tertiary amine effector molecule with high efficiency [Anderson et al., J Phys Chem 1997, 9704-9]. Two key parameters influence the hypoxia-selectivity of this fragmentation event. First, the inherent one-electron reduction potential (E[1]) of the nitroheterocyclic trigger, a thermodynamic parameter that describes the ability of the trigger to accept one-electron (typically from human oxidoreductases) and concurrently dictates the rate at which molecular oxygen will "back-oxidise" the intermediate radical anion. Secondly, the first-order rate of fragmentation ($k_{frag}$) of the nitro radical anion to release the effector molecule, a kinetic parameter that must be sufficiently slow to permit the rate of back-oxidation to compete efficiently [Smaill et al., WO 2010/104406 A1; Smaill et al., WO 2011/028135 A1]. Only then will fragmentation and release of effector be prevented in normal tissues at physiologically relevant oxygen concentrations (~44% to ~1% $O_2$). Pulse radiolysis of prodrug compounds 200, 202 and 204 compared to TH-4000 as a positive control prodrug has determined that the prodrugs of the present invention demonstrate identical radical chemistry parameters to TH-4000 with E(1) values ranging from −426 to −433 mV (compared to −424 mV for TH-4000) and $k_{frag}$ values ranging from 26 to 32 $s^{-1}$ (compared to 20 $s^{-1}$ for TH-4000). They are therefore predicted to be stable in normoxic tissues while only releasing the FGFR kinase inhibitor selectively in tissues experiencing pathophysiological levels of hypoxia.

Figure 15:
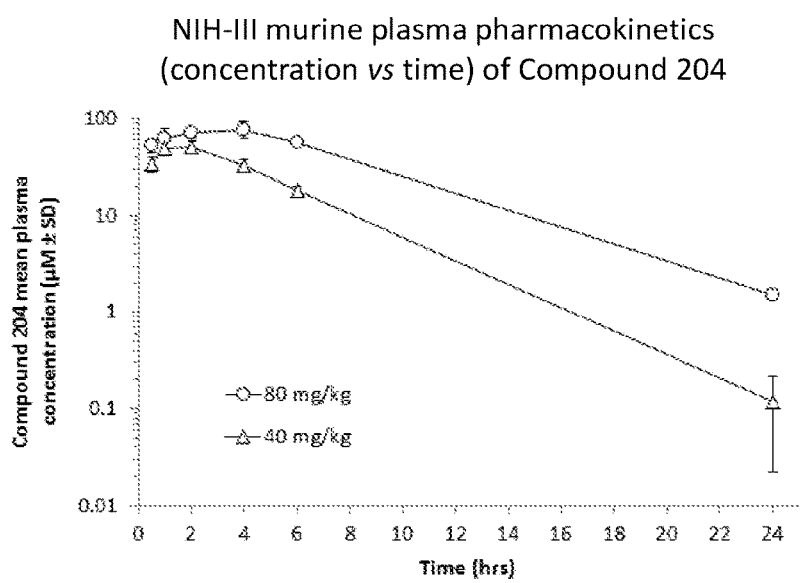
FIG. 15 shows the plasma concentration of compound 204 as a function of time following intraperitoneal administration to NIH-III nude mice at doses of 40 and 80 mg/kg.

Example 96 describes the murine plasma pharmacokinetics of prodrug compound 204 of the invention. There was a linear increase in the maximum plasma concentration and area under the plasma concentration-time curve with an increase in dose of compound 204. The time to maximum plasma concentration was determined to be approximately 2-3 hours (Table 6; FIG. 15), with the plasma half-life of compound 204 ranging from 1.2 to 1.8 hours. A dose of 80 mg/kg provided an observed exposure (AUC0-24) of approximately 900 h·umol/L (Table 6).

Example 97 describes the anti-tumour activity of prodrugs of the invention. The anti-tumour activity of selected prodrug compounds is shown in FIGS. 16 to 20.

Figure 16:
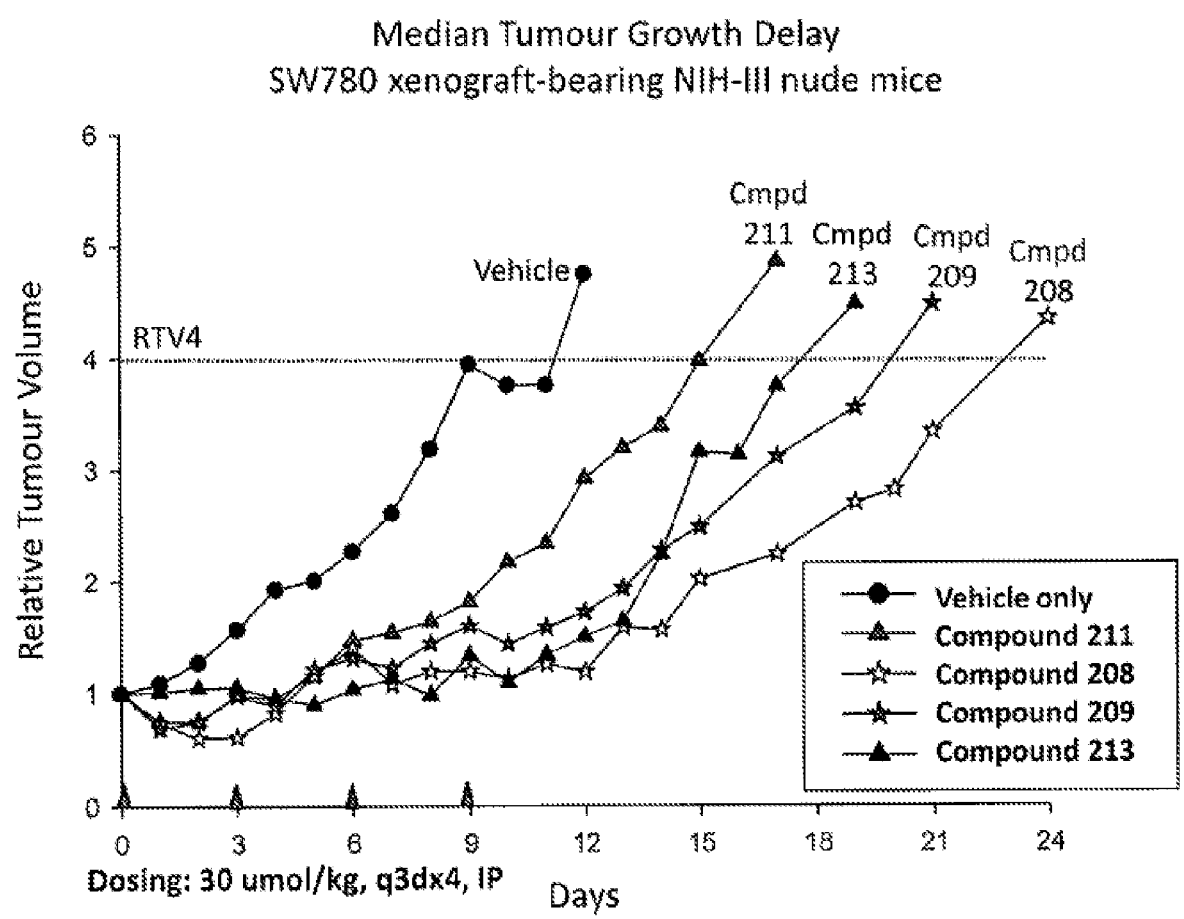
FIG. 16 shows the median tumour growth delay of compound 211, 208, 209 and 213 in SW780 xenograft-bearing NIH-III nude mice following intraperitoneal administration of 30 umol/kg of test compounds on a q3dx4 schedule.

SW780 (FGFR3-amplified bladder cancer) xenograft-bearing NIH-III mice were administered, by intraperitoneal (IP) injection, an equimolar dose and schedule (30 umol/kg, q3dx4) of prodrug compounds 211, 208, 209 and 213 as a solution in water. The median tumour growth delay is shown in FIG. 16 and demonstrates that all of the prodrugs display significant anti-tumour activity, with compound 208 for example approximately doubling the time it takes for control SW780 tumours to reach 4 times relative tumour volume (RTV4; from 12 days to 24 days).

Figure 17:
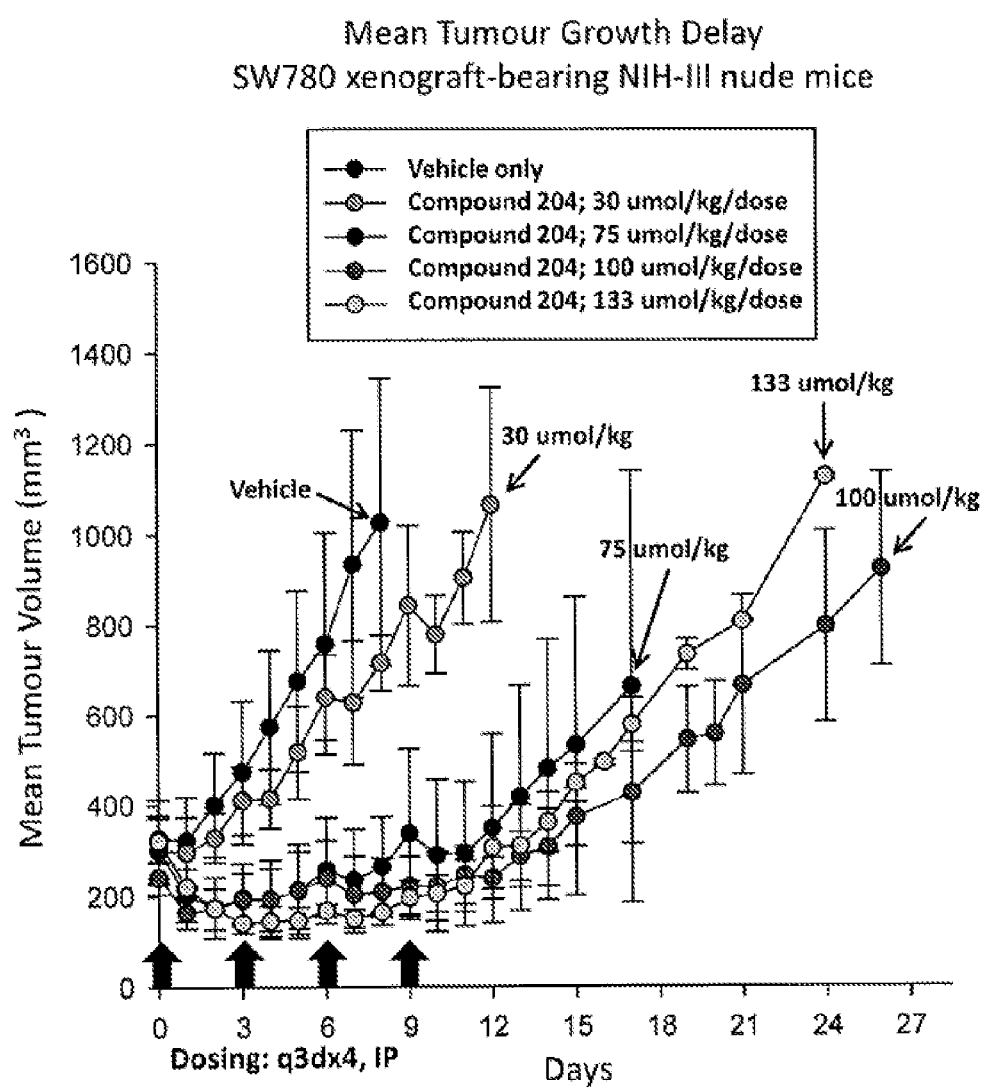
FIG. 17 shows the mean tumour growth delay in SW780 xenograft-bearing NIH-III nude mice following intraperitoneal administration of increasing doses of compound 204 on a q3dx4 schedule.

Dose-dependent efficacy of prodrug compound 204 is shown in FIG. 17. Here, SW780 xenograft-bearing NIH-III mice were administered doses of compound 204 ranging from 30 to 133 umol/kg/dose (q3dx4; IP) as a solution in water. The higher doses tested regressed the tumours and provided a significant tumour growth delay, with tumours for example taking approximately 26 days to reach RTV4 at the 100 umol/kg dose.

Figure 18:
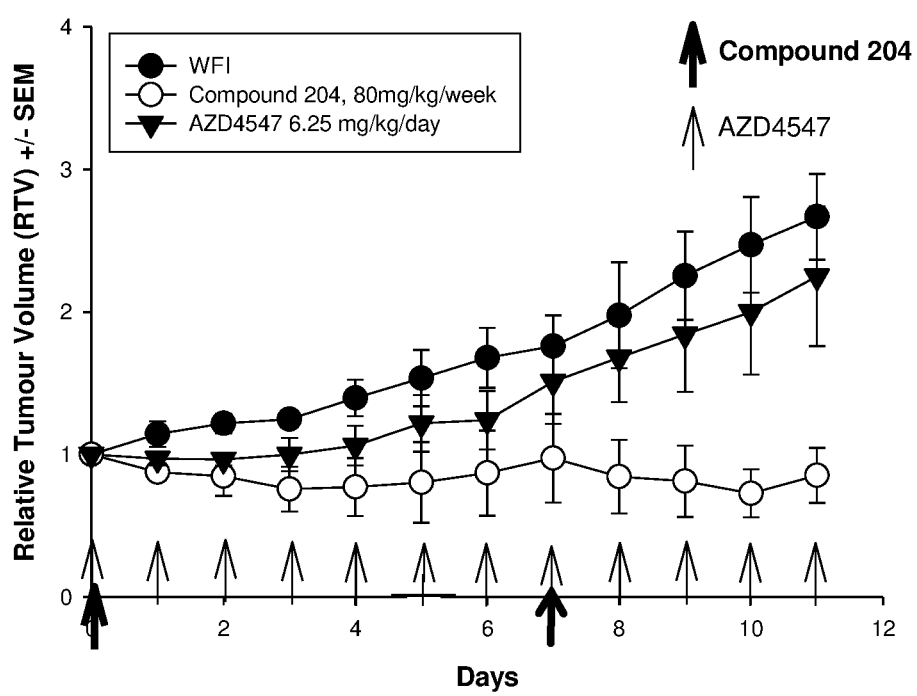
FIG. 18 shows a comparison of the mean tumour growth delay in SNU-16 xenograft-bearing NIH-III nude mice following intraperitoneal administration of two doses of compound 204 at 80 mg/kg/week relative to daily oral administration of AZD4547 for twelve days at 6.25 mg/kg/day.

Compound 204 was also assessed for efficacy against the SNU-16 (FGFR2-amplified) gastric cancer xenograft model relative to the clinical comparator compound AZD4547 known in the prior art (FIG. 18). SNU-16-bearing NIH-III nude mice were administered either vehicle, AZD4547 (6.25 mg/kg, qdx12; PO) or compound 204 (80 mg/kg, q7dx2; IP). Control tumours grew rapidly, reaching 2.5 times initial volume by day 11, while compound 204-treated tumours regressed following each drug administration. Treated tumours had failed to return to starting volume by day 11 when the experiment was terminated. Conversely, AZD4547 treated tumours demonstrated progressive growth despite daily oral administration at 6.25 mg/kg, a dose selected from the prior art to approximate a plasma exposure in mice achieved in human clinical studies (Cancer Res 2012; 72: 2045-56; Invest New Drugs 2017; 35:451-462).

Figure 19:
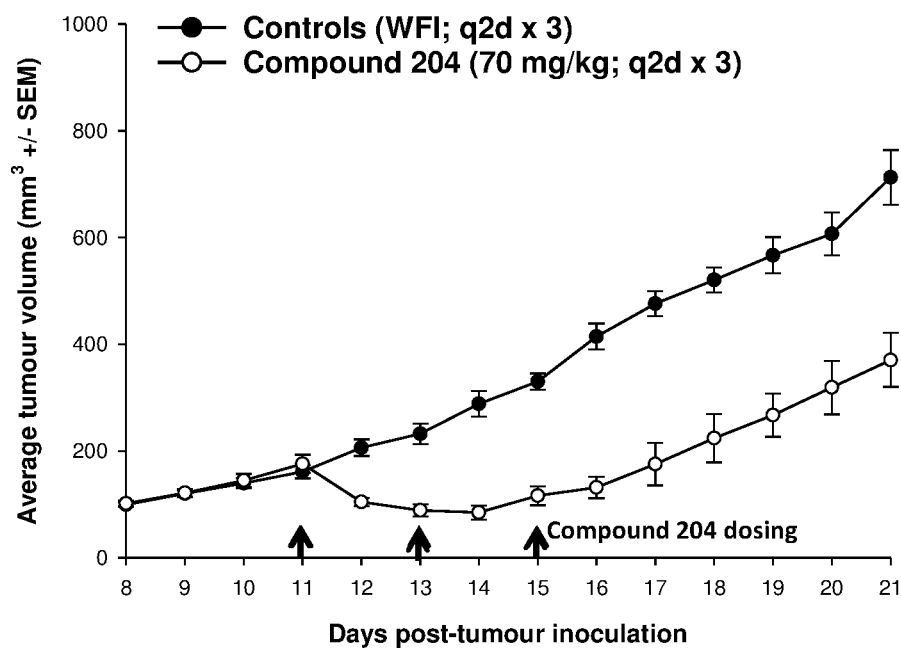
FIG. 19 shows the mean tumour growth delay in 4T1 xenograft-bearing BALB/c immunocompetant mice following intraperitoneal administration of 70 mg/kg compound 204 on a q2dx3 schedule.
Figure 20:
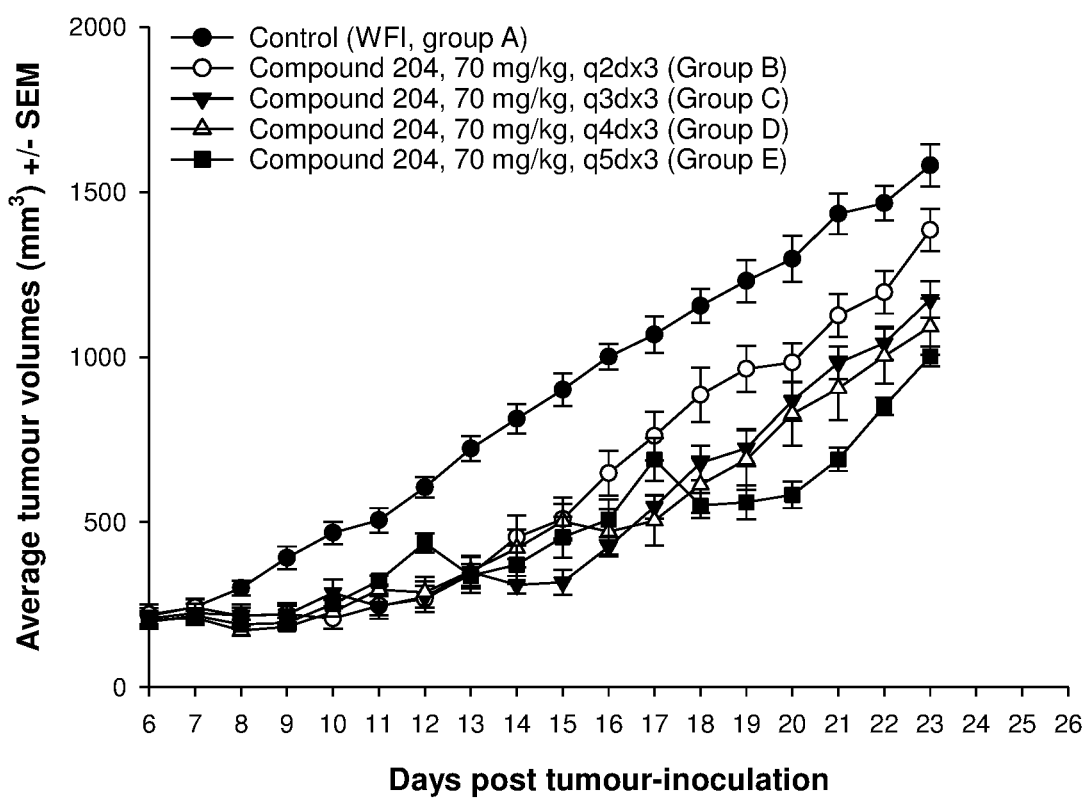
FIG. 20 shows the mean tumour growth delay in 4T1 xenograft-bearing BALB/c immunocompetant mice following intraperitoneal administration of 70 mg/kg compound 204 on a q2dx3, q3dx3, q4dx3 and q5dx3 schedule.

Compound 204 was also assessed for efficacy against the murine 4T1 xenograft model in BALB/c immunocompetant mice (FIG. 19). Schedule dependence of compound 204 in this xenograft model was also assessed (FIG. 20). Compound 204 was administered intraperitoneally at 70 mg/kg every two (q2dx3; group B), three (q3dx3; group C), four (q4dx3; group D) or five days (q5dx3; group E), with a total of 3 doses/schedule. Tumour measurements and body weight were recorded every day for 23 days, until all tumours increased their volume 4-fold ($RTV^4$) from day0 of experimental assignment. The median survival time was 16 days (controls), 18 days (q2dx3), 20 days (q3dx3), 21 days (q4dx3) and 22 days (q5dx3). The Dunnett's test demonstrated statistically significant difference between control and q3dx3, q4dx3 and q5dx3 survival curves (P=<0.05). Tumour Growth Inhibition (TGI %) on day 13 ranged between 51% and 53% (P<0.001; groups B÷E) compared to the control group.

Figure 21:
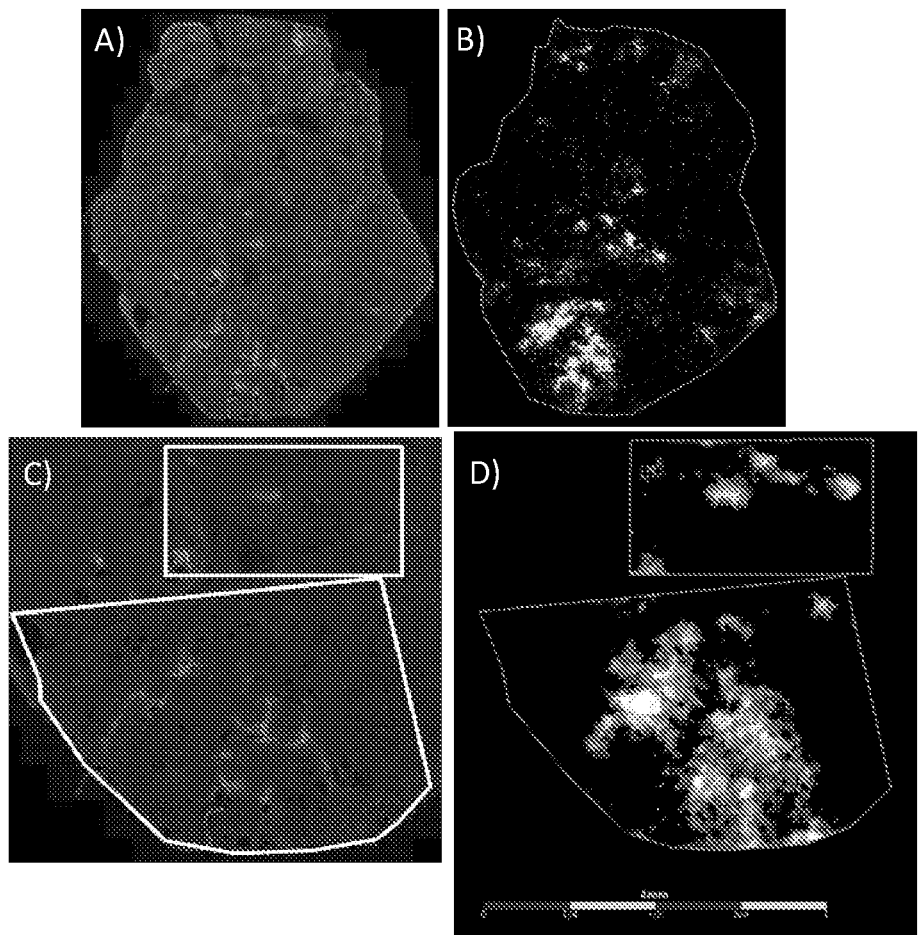
FIG. 21A shows a full tumour cross-section displaying hypoxia in a SiHa xenograft harvested from an NIH-III nude mouse administered EF5 followed 3 hours later by compound 204.
FIG. 21B shows low resolution MALDI imaging mass spectrometry for compound 112 in a SiHa xenograft harvested from an NIH-III nude mouse administered EF5 followed 3 hours later by compound 204.
FIG. 21C shows a magnified portion of a tumour cross-section displaying hypoxia in a SiHa xenograft harvested from an NIH-III nude mouse administered EF5, followed 3 hours later by compound 204.
FIG. 21D shows high resolution MALDI imaging mass spectrometry for compound 112 in a magnified portion of a SiHa xenograft harvested from an NIH-III nude mouse administered EF5, followed 3 hours later by compound 204.
Figure 22:
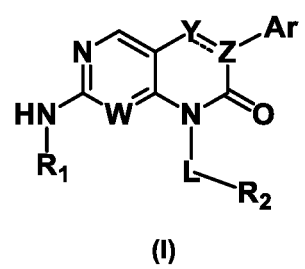
FIG. 22 shows the general chemical structure of the compounds of the invention.

Example 98 shows the geometric relationship of metabolite (compound 112) release from prodrug compound 204 and tumour hypoxia as imaged by EF5 immunostaining. In this study SiHa xenograft-bearing NIH-III mice were administered EF5 and then 3 hours later prodrug compound 204 (86 mg/kg, IP). After 24 hours tumours were collected and sister sections imaged. Areas of hypoxia imaged by EF5 immunostaining (full tumour, FIG. 21A; magnified tumour area, FIG. 21C) were found to be co-ordinate with areas showing the highest concentrations of compound 112 by MALDI imaging mass spectrometry (low resolution full tumour, FIG. 21B; high resolution magnified tumour area, FIG. 21D). The results are consistent with hypoxia-selective metabolism of prodrug compound 204 and release of FGFR inhibitor compound 112 in SiHa tumours.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

General Chemistry Experimental Information

All reagents and solvents were obtained from commercial sources. Flash chromatography was performed using silica gel (300 mesh). All reactions were monitored by TLC, using silica gel plates with fluorescence F254 and UV light visualization. $^1$H NMR was recorded on a Brucker AV-400 spectrometer at 400 MHz or a Brucker AV-500 spectrometer at 125 MHz. $^{13}$C NMR spectra was recorded on a Brucker AV-500 spectrometer at 125 MHz. Coupling constants (J) are expressed in hertz (Hz). Chemical shifts (δ) are reported in parts per million (ppm). The high resolution of ESI-MS was recorded on an Applied Biosystems Q-STAR Elite ESI-LC-MS/MS mass spectrometer. The purity of compounds was determined to be over 95% using reverse-phase HPLC analysis. HPLC instrument: Dionex Summit HPLC (Column: Diamonsil C18, 5.0 mm, 4.6×250 mm (Agilent Technologies); detector: PDA-100 photodiode array; injector: ASI-100 autoinjector; pump: p-680A). The flow rate was 1.0 mL/min and mobile phase was MeOH in H$_2$O with 0.1% modifier (ammonia v/v).

Example 1: (E)-3-(2,6-dichloro-3,5-dimethoxyphenyl)-1-(1-(4-(dimethylamino)-but-2-enoyl)piperidin-4-yl)-7-(isopropylamino)-3,4-dihydropyrimido[4,5-d]pyrimidin-2(1H)-one (108)

A synthetic route for the preparation of compound 108 is outlined in Scheme 7.

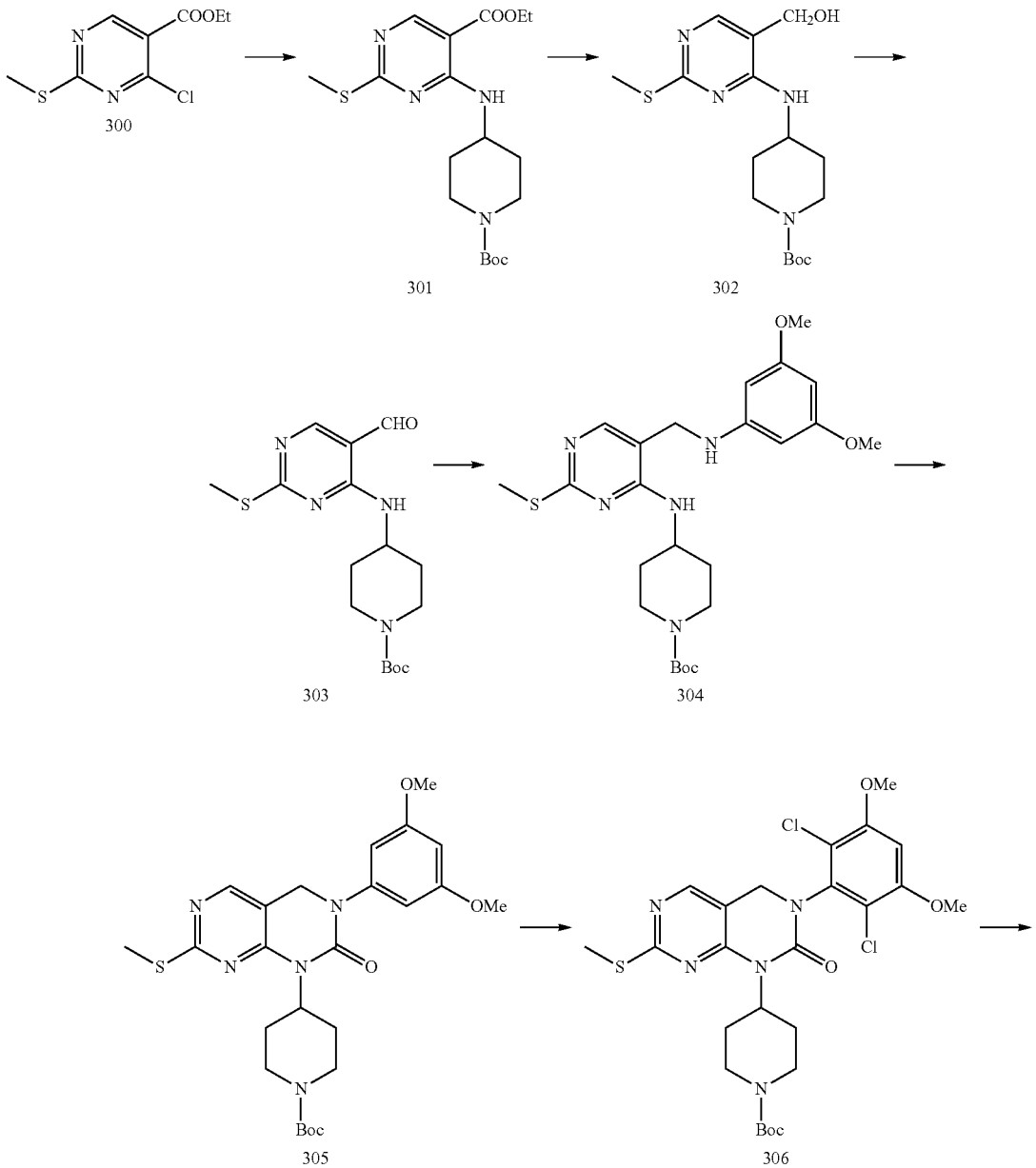

-continued

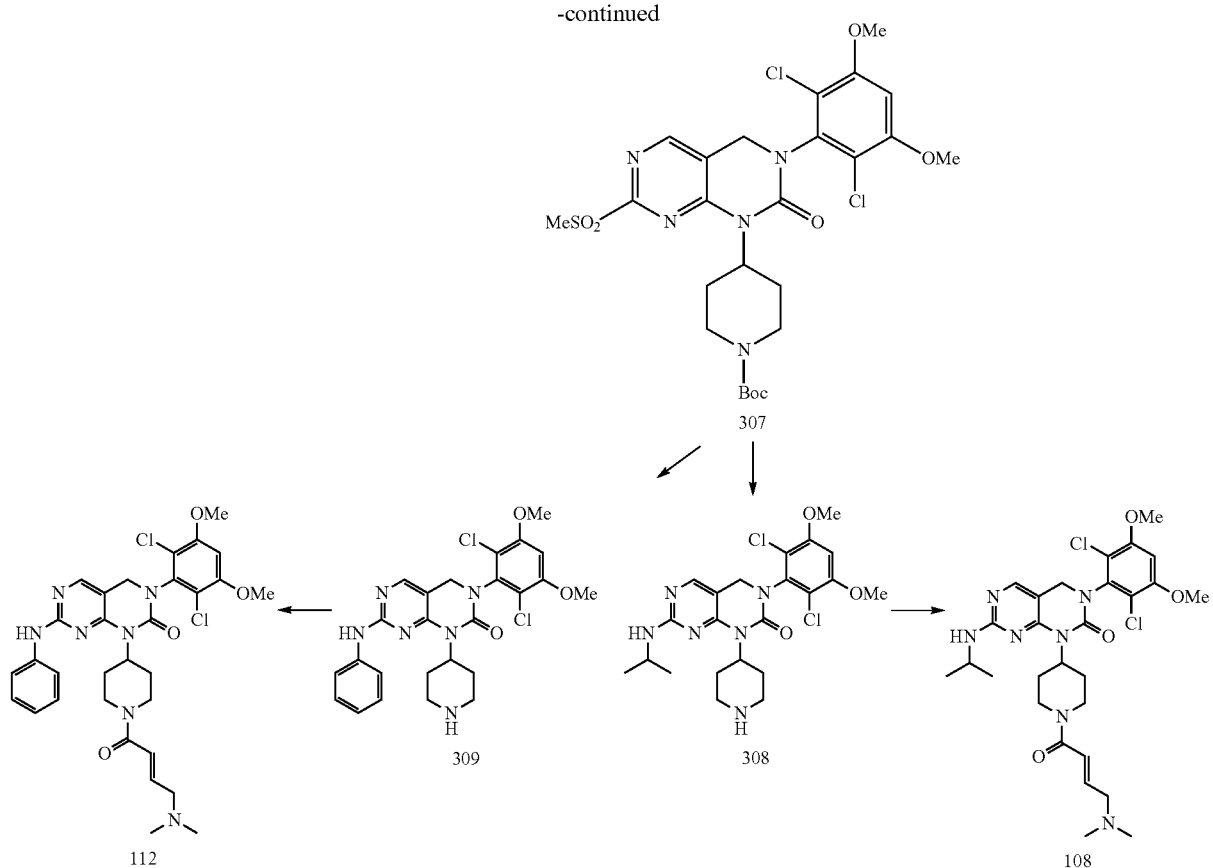

Ethyl 4-((1-(tert-butoxycarbonyl)piperidin-4-yl)amino)-2-(methylthio)-pyrimidine-5-carboxylate (301)

To a solution of ethyl 4-chloro-2-(methylthio)pyrimidine-5-carboxylate (300) (21 g, 90.3 mmol) and tert-butyl 4-aminopiperidine-1-carboxylate (21.7 g, 108.3 mmol) in DMF (300 mL) was added $K_2CO_3$ (25 g, 180.9 mmol). The reaction was heated to 60° C. overnight. After the mixture was cooled to room temperature, it was added to ice-water. The precipitate was filtered, and the filtered cake was washed with cool water and dried in a vacuum oven to afford 301 (31.1 g, 86.9%). $^1$H NMR (400 MHz, $CDCl_3$) δ 8.63 (s, 1H), 8.50 (d, J=7.2 Hz, 1H), 4.31 (q, J=7.2 Hz, 2H), 4.27-4.21 (m, 1H), 4.00-3.97 (m, 2H), 3.02 (t, J=11.4 Hz, 2H), 2.51 (s, 3H), 2.03-1.99 (m, 2H), 1.54-1.49 (m, 2H), 1.46 (s, 9H), 1.36 (t, J=7.2 Hz, 3H).

Tert-butyl 4-((5-(hydroxymethyl)-2-(methylthio)-pyrimidin-4-yl)amino)-piperidine-1-carboxylate (302)

A suspension of $LiAlH_4$ (4.41 g, 116.0 mmol) in dry THF (70 mL) was added to a stirred solution of 301 (23 g, 58.0 mmol) in dry THF (160 mL) at −40° C. under argon. The mixture was warmed to 0° C. After the reaction was completed, 4.4 mL of $H_2O$ was added dropwise. After that, 15% aqueous NaOH (4.4 mL) was added, followed by a further 13.2 mL of water. The resulting mixture was stirred at room temperature for 20 min and filtered through a pad of Celite. The Celite was washed with $CH_2Cl_2$, and the washes were combined and then dried in vacuo. $CH_2Cl_2$ was added to the residue and washed with saturated aqueous $NaHCO_3$. The organic layer was separated, washed with brine, dried with $Na_2SO_4$ and concentrated in vacuo. The resulting crude product was purified by column chromatography giving 302 (11.72 g, 57%). $^1$H NMR (400 MHz, $CDCl_3$) δ 7.63 (s, 1H), 5.95 (d, J=7.2 Hz, 1H), 4.48 (s, 2H), 4.21-4.14 (m, 1H), 3.99-3.96 (m, 2H), 2.95 (t, J=11.4 Hz, 2H), 2.47 (s, 3H), 2.03-1.99 (m, 2H), 1.45 (s, 9H), 1.43-1.37 (m, 2H).

Tert-butyl 4-((5-formyl-2-(methylthio)pyrimidin-4-yl)amino)piperidine-1-carboxylate (303)

Compound 302 (11.72 g, 33.1 mmol) was dissolved in $CH_2Cl_2$ (250 mL) and $MnO_2$ (17.3 g, 198 mmol) was added in three portions. The mixture was stirred at room temperature overnight. The mixture was filtered through a pad of Celite. The filtrate was concentrated and the resulting crude product was purified by column chromatography to afford 303 (11 g, 94%). $^1$H NMR (400 MHz, $CDCl_3$) δ 9.70 (s, 1H), 8.59 (d, J=6.8 Hz, 1H), 8.31 (s, 1H), 4.34-4.25 (m, 1H), 4.03-4.01 (m, 1H), 3.01 (t, J=11.4 Hz, 2H), 2.54 (s, 3H), 2.04-2.00 (m, 2H), 1.54-1.50 (m, 2H), 1.47 (s, 9H).

Tert-butyl 4-((5-(((3,5-dimethoxyphenyl)amino)methyl)-2-(methylthio)-pyrimidin-4-yl)amino)piperidine-1-carboxylate (304)

To a solution of compound 303 (10.8 g, 30.6 mmol) and 3,5-dimethoxyaniline (7.04 g, 46.0 mmol) in anhydrous $CH_3OH$ (150 mL) were added $CH_3COOH$ (0.76 ml). The mixture was stirred at room temperature overnight. After the completion of the reaction, NaBH₄ (3.5 g, 92 mmol) was added to the reaction mixture at 0° C. in three portions. The resulting mixture was concentrated, partitioned between CH₂Cl₂ and saturated NaHCO₃ and extracted with CH₂Cl₂. The organic phase was separated and concentrated. The crude compound was purified by column chromatography to afford 304 (12.7 g, 85%). ¹H NMR (400 MHz, CDCl₃) δ 7.85 (s, 1H), 5.97 (s, 1H), 5.89 (m, 2H), 4.18-4.16 (m, 1H), 4.06 (s, 2H), 3.93 (m, 2H), 3.75 (s, 6H), 2.97-2.91 (m, 2H), 2.50 (s, 3H), 1.99-1.95 (m, 2H), 1.45 (s, 9H), 1.40-1.35 (m, 2H).

Tert-butyl 4-(3-(3,5-dimethoxyphenyl)-7-(methyl-thio)-2-oxo-3,4-dihydropyrimido[4,5-d]pyrimidin-1(2H)-yl)piperidine-1-carboxylate (305)

Compound 304 (9.10 g, 18.6 mmol) was dissolved in CH₂Cl₂ (110 mL) and DIEA (9.62 mL, 55.3 mmol) was added dropwise a solution of triphosgene (1.84 g, 6.2 mmol) in anhydrous CH₂Cl₂ (10 ml) at 0° C. The mixture was warmed to room temperature. After the reaction was over, aqueous saturated NaHCO₃ was poured into the mixture. The organic layer was separated, washed with brine, dried with Na₂SO₄, filtered, and concentrated in vacuo. The crude product was subjected to column chromatography to give 305 (8.6 g, 89.6%) ¹H NMR (400 MHz, CDCl₃) δ 8.09 (s, 1H), 6.45-6.44 (m, 2H), 6.39 (m, 1H), 4.83 (s, 1H), 4.61 (s, 2H), 4.32-4.28 (m, 2H), 3.79 (s, 6H), 2.81-2.72 (m, 4H), 2.54 (s, 3H), 1.99-1.95 (m, 2H), 1.46 (s, 9H).

Tert-butyl 4-(3-(2,6-dichloro-3,5-dimethoxyphenyl)-7-(methylthio)-2-oxo-3,4-dihydropyrimido[4,5-d]pyrimidin-1(2H)-yl)piperidine-1-carboxylate (306)

To a solution of compound 305 (4.85 g, 9.41 mmol) in anhydrous CH₃CN (60 ml) was added SO₂Cl₂ (1.52 mL, 18.82 mmol) dropwise. The mixture was stirred in ice-water bath for 30 min and quenched by addition of saturated aqueous NaHCO₃. The mixture was basified with saturated aqueous NaHCO₃ and extracted with CH₂Cl₂. The organic layer was separated, dried over Na₂SO₄, and concentrated in vacuo. The resulting crude product was dissolved in CH₂Cl₂ (60 mL). DIPEA (1.5 mL, 9.44 mmol) and Di-tert-butyl dicarbonate (4 mL, 9.44 mmol) were added to the mixture. The mixture was stirred at room temperature for 4 hours. After removal of CH₂Cl₂, the crude product was purified by column chromatography to afford 306 (3.96 g, 72%). ¹H NMR (400 MHz, CDCl₃) δ 8.09 (s, 1H), 6.59 (s, 1H), 4.88 (m, 1H), 4.53 (s, 2H), 4.31-4.20 (m, 2H), 3.93 (s, 6H), 2.74-2.71 (m, 4H), 2.54 (s, 3H), 1.75 (m, 2H), 1.45 (s, 9H).

Tert-butyl 4-(3-(2,6-dichloro-3,5-dimethoxyphenyl)-7-(methylsulfonyl)-2-oxo-3,4-dihydropyrimido[4,5-d]pyrimidin-1(2H)-yl)piperidine-1-carboxylate (307)

To a solution of compound 306 (3.3 g, 5.7 mmol) in CH₂Cl₂ (50 ml) was added 3-chloroperbenzoic acid (2.78 g, 12.0 mmol). The mixture was stirred at room temperature for 5 hours. The solution was diluted with CH₂Cl₂ and washed with saturated aqueous NaHCO₃ three times. The organic layer was separated, washed with brine, dried with Na₂SO₄ and concentrated in vacuo. The resulting material was subjected to column chromatography affording 307 (2.8 g, 81%) ¹H NMR (500 MHz, CDCl₃) δ 8.40 (s, 1H), 6.61 (s, 1H), 4.93-4.87 (m, 1H), 4.68 (s, 2H), 4.32-4.20 (m, 2H), 3.94 (s, 6H), 2.81 (m, 2H), 2.70-2.64 (m, 2H), 1.77-1.74 (m, 2H), 1.60-1.55 (m, 2H), 1.45 (s, 9H).

(E)-3-(2,6-dichloro-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (108)

To a solution of 307 (0.9 g, 1.46 mmol) in 1,4-dioxane (10 mL) was added isopropylamine (0.37 ml, 4.38 mmol). The mixture was stirred at 110° C. in a sealed tube for 5 h. The mixture was cooled to room temperature and concentrated in vacuo. The crude product was dissolved in CH₂Cl₂ (10 mL), then TFA (1.0 mL) was added. The resulting mixture was stirred at room temperature for 4 hours. The mixture was basified with saturated aqueous NaHCO₃. The organic layer was separated, washed with brine, dried with Na₂SO₄, filtered and concentrated. The resulting crude material (308) was used without any further purification. Trans-4-Dimethylaminocrotonic acid hydrochloride (0.21 g, 1.3 mmol) and HATU (0.57 g, 1.5 mmol) were added to a flask charged with the crude compound, followed by adding CH₃CN (10 ml) and DIEA (0.49 ml, 3.0 mmol). The resulting mixture was stirred at room temperature overnight. The reaction mixture was diluted with CH₂Cl₂, basified with saturated aqueous NaHCO₃ and extracted with CH₂Cl₂. The organic layer was separated, washed with brine, dried with Na₂SO₄, filtered, and concentrated in vacuo. The crude product was purified by column chromatography to give compound 108 (0.42 g, 69%). ¹H NMR (500 MHz, DMSO-d₆) δ 7.96 (s, 1H), 6.97 (s, 2H), 6.63-6.59 (m, 2H), 4.83 (s, 1H), 4.62-4.46 (m, 1H), 4.37 (s, 2H), 4.15 (d, J=13.6 Hz, 1H), 3.95 (s, 6H), 3.90-3.68 (m, 1H), 3.10-3.05 (m, 1H), 3.01 (d, J=4.4 Hz, 2H), 2.61-2.59 (m, 3H), 2.13 (s, 6H), 1.71-1.68 (m, 2H), 1.11 (d, J=6.4 Hz, 6H). ¹³C NMR (125 MHz, DMSO-d₆) δ 163.78, 160.57, 156.60, 154.68, 154.12, 151.46, 141.68, 137.99, 122.29, 113.15, 98.11, 59.91, 56.84, 45.00, 44.79, 42.21, 41.78, 29.18, 28.05, 22.35. HRMS (ESI) for C₂₈H₃₇Cl₂N₇O₄ [M+H]⁺ calcd: 606.2357, found: 606.2353. HPLC analysis: MeOH—H₂O (85:15) 5.91 min, 97.16% purity.

Example 2: (E)-3-(2,6-dichloro-3,5-dimethoxyphenyl)-1-(1-(4-(dimethyl-amino)-but-2-enoyl)piperidin-4-yl)-7-(phenylamino)-3,4-dihydropyrimido[4,5-d]pyrimidin-2(1H)-one (112)

A synthetic route for the preparation of compound 112 is outlined in Scheme 7 (see Example 1).

3-(2,6-dichloro-3,5-dimethoxyphenyl)-7-(phenylamino)-1-(piperidin-4-yl)-3,4-dihydropyrimido[4,5-d]pyrimidin-2(1H)-one (309)

Aniline (0.3 ml, 2.92 mmol) was added to a solution of 307 (0.9 g, 1.46 mmol) in 1,4-dioxane (10 mL), followed by adding TFA (0.12 ml, 1.61 mmol). The reaction mixture was stirred at 110° C. for 18 hours in a sealed tube. The mixture was cooled to room temperature and concentrated in vacuo. The crude product was dissolved in CH₂Cl₂ (10 mL), then TFA (1.0 mL) was added. The resulting mixture was stirred at room temperature for 4 h. The mixture was basified with saturated aqueous NaHCO₃. The organic layer was separated, washed with brine and concentrated in vacuo. The resultant crude material was purified by column chromatography furnishing the title compound 309 (0.62 g, 80%). ¹H NMR (400 MHz, CDCl₃) δ 9.56 (s, 1H), 8.16 (s, 1H), 7.75-7.73 (m, 2H), 7.30-7.26 (m, 2H), 6.98 (s, 1H), 6.96-

6.94 (m, 1H), 4.71-4.66 (m, 1H), 4.48 (s, 2H), 3.96 (s, 6H), 3.06-3.04 (m, 2H), 2.56-2.42 (m, 4H), 1.62-1.59 (m, 2H).

(E)-3-(2,6-dichloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (112)

To a solution of 309 (0.49 g, 0.9 mmol), trans-4-dimethylaminocrotonic acid hydrochloride (0.2 g, 1.2 mmol) and HATU (0.5 g, 1.4 mmol) in $CH_3CN$ (12 ml) was added DIPEA (0.46 ml, 2.75 mmol). The resulting mixture was stirred at room temperature overnight. The reaction mixture was diluted with $CH_2Cl_2$, basified with saturated aqueous $NaHCO_3$. The organic layer was separated, washed with brine and concentrated. The crude material was purified by column chromatography to give compound 112 (0.47 g, 79.4%). $^1$H NMR (500 MHz, DMSO-$d_6$) δ 9.61 (s, 1H), 8.19 (s, 1H), 7.69 (d, J=8.0 Hz, 2H), 7.45-7.22 (m, 2H), 6.98 (s, 1H), 6.94 (t, J=7.3 Hz, 1H), 6.73-6.46 (m, 2H), 4.87 (m, 1H), 4.61 (d, J=12.6 Hz, 1H), 4.48 (s, 2H), 4.19 (d, J=13.9 Hz, 1H), 3.95 (s, 6H), 3.08 (t, J=13.4 Hz, 1H), 3.01 (d, J=4.2 Hz, 2H), 2.63 (t, J=12.9 Hz, 1H), 2.47-2.35 (m, 2H), 2.13 (s, 6H), 1.77 (d, J=11.9 Hz, 2H). $^{13}$C NMR (125 MHz, DMSO-$d_6$) δ 163.97, 158.92, 156.82, 154.71, 154.10, 151.03, 141.92, 140.17, 137.76, 128.46, 122.35, 121.60, 113.17, 102.74, 98.20, 59.93, 56.87, 52.54, 45.31, 45.03, 44.80, 41.78, 29.07, 28.08. HRMS (ESI) for $C_{31}H_{35}Cl_2N_7O_4$ [M+H]$^+$ calcd: 640.2200, found: 640.2204. HPLC analysis: MeOH—$H_2O$ (85:15) 6.36 min, 97.59% purity.

Example 3: (S,E)-3-(2,6-dichloro-3,5-dimethoxyphenyl)-1-(1-(4-(dimethylamino)-but-2-enoyl) piperidin-3-yl)-7-(methylamino)-3,4-dihydropyrimido[4,5-d]pyrimidin-2(1H)-one (100)

Compound 100 was prepared according to the general method of Scheme 1.

$[α]_D^{20}$ 5.405 (c 0.37, $CH_2Cl_2$). $^1$H NMR (500 MHz, DMSO-$d_6$) δ 8.00 (s, 1H), 7.09 (s, 1H), 6.98 (s, 1H), 6.74-6.46 (m, 2H), 4.77-4.24 (m, 4.5H), 4.23-4.00 (m, 1.5H), 3.95 (s, 6H), 3.14-2.91 (m, 3H), 2.96-2.72 (m, 3H), 2.64 (s, 1H), 2.14 (d, J=16.6 Hz, 6H), 1.79 (d, J=13.3 Hz, 2H), 1.41 (d, J=12.5 Hz, 1H). $^{13}$C NMR (125 MHz, DMSO-$d_6$) δ 164.09, 161.79, 156.50, 154.67, 151.25, 141.53, 137.87, 122.63, 113.17, 99.46, 98.18, 59.79, 56.85, 55.97, 54.83, 44.88, 44.81, 39.09, 39.02, 27.85, 18.49. HRMS (ESI) for $C_{26}H_{33}Cl_2N_7O_4$ [M+H]$^+$ calcd: 578.2044, found: 578.2038. HPLC analysis: MeOH—$H_2O$ (90:10) 5.28 min, 95.92% purity.

Example 4: (S,E)-3-(2,6-dichloro-3,5-dimethoxyphenyl)-1-(1-(4-(dimethylamino)-but-2-enoyl) piperidin-3-yl)-7-(methylamino)-3,4-dihydropyrimido[4,5-d]-pyrimidin-2(1H)-one (101)

Compound 101 was prepared according to the general method of Scheme 1.

$[α]_D^{20}$ −10.000 (c 0.20, $CH_2Cl_2$). $^1$H NMR (500 MHz, DMSO-$d_6$), δ 8.00 (s, 1H), 7.10 (s, 1H), 6.98 (s, 1H), 6.59 (d, J=6.0 Hz, 2H), 4.58 (d, J=30.9 Hz, 1H), 4.41 (s, 3H), 4.07-4.01 (m, 2H), 3.95 (s, 6H), 3.15-2.89 (m, 3H), 2.79 (s, 3H), 2.64 (s, 1H), 2.12 (d, J=17.1 Hz, 6H), 1.80 (s, 2H), 1.42 (s, 1H). $^{13}$C NMR (125 MHz, DMSO-$d_6$) δ 164.12, 161.83, 156.55, 154.69, 154.19, 151.28, 141.89, 137.90, 122.43, 113.20, 98.17, 59.91, 56.86, 55.99, 54.86, 47.39, 45.01, 44.83, 41.80, 27.87, 24.94, 18.51. HRMS (ESI) for $C_{26}H_{33}Cl_2N_7O_4$ [M+H]$^+$ calcd: 578.2044, found: 578.2039. HPLC analysis: MeOH—$H_2O$ (85:15) 5.02 min, 97.35% purity.

Example 5: (R,E)-3-(2,6-dichloro-3,5-dimethoxyphenyl)-1-(1-(4-(dimethylamino)-but-2-enoyl)pyrrolidin-3-yl)-7-(methylamino)-3,4-dihydropyrimido[4,5-d]-pyrimidin-2(1H)-one (102)

Compound 102 was prepared according to the general method of Scheme 1.

$[α]_D^{20}$ 10.000 (c 0.22, $CH_2Cl_2$). $^1$H NMR (500 MHz, DMSO-$d_6$), δ 8.11-7.95 (m, 1H), 7.11 (s, 1H), 7.07-6.94 (m, 1H), 6.60 (dtd, J=15.3, 6.1, 3.0 Hz, 1H), 6.36 (dd, J=25.9, 15.2 Hz, 1H), 5.47 (s, 1H), 4.42 (d, J=2.6 Hz, 2H), 3.95 (s, 6H), 3.91-3.79 (m, 1H), 3.73 (s, 2H), 3.57 (d, J=8.9 Hz, 1H), 3.00 (dd, J=9.8, 6.0 Hz, 2H), 2.76 (d, J=5.5 Hz, 3H), 2.58 (s, 1H), 2.22 (d, J=8.8 Hz, 1H), 2.13 (d, J=8.6 Hz, 6H). $^{13}$C NMR (125 MHz, DMSO-$d_6$) δ 163.20, 163.10, 161.74, 154.70, 151.15, 141.23, 141.19, 137.73, 123.74, 123.15, 113.12, 98.22, 59.85, 59.75, 56.87, 55.99, 54.86, 51.65, 50.17, 47.04, 45.15, 45.01, 44.98, 44.78, 44.09, 39.02, 28.21, 27.74, 26.12, 18.51. HRMS (ESI) for $C_{25}H_{31}Cl_2N_7O_4$ [M+H]$^+$ calcd: 564.1887, found: 564.1887. HPLC analysis: MeOH—$H_2O$ (75:25) 7.28 min, 96.74% purity.

Example 6: (S,E)-3-(2,6-dichloro-3,5-dimethoxyphenyl)-1-(1-(4-(dimethylamino)-but-2-enoyl)pyrrolidin-3-yl)-7-(methylamino)-3,4-dihydropyrimido[4,5-d]-pyrimidin-2(1H)-one (103)

Compound 103 was prepared according to the general method of Scheme 1.

$[α]_D^{20}$ −14.81 (c 0.405, $CH_2Cl_2$). $^1$H NMR (400 MHz, CDCl$_3$-d) δ 7.91 (d, J=7.0 Hz, 1H), 6.88 (dt, J=15.2, 6.1 Hz, 1H), 6.58 (d, J=5.5 Hz, 1H), 6.27 (ddt, J=23.0, 15.2, 1.6 Hz, 1H), 5.61 (q, J=8.5 Hz, 1H), 5.15 (q, J=5.0 Hz, 0.6H), 5.06 (d, J=5.4 Hz, 0.4H), 4.45 (dd, J=8.6, 0.8 Hz, 2H), 4.16 (s, 0.6H), 3.99 (ddd, J=12.7, 8.1, 5.0 Hz, 1.4H), 3.94-3.90 (m, 6.3H), 3.86 (t, J=9.4 Hz, 0.7H), 3.57 (ddt, J=46.0, 12.3, 8.1 Hz, 1H), 3.06 (td, J=6.6, 1.6 Hz, 2H), 2.95 (dd, J=5.1, 1.5 Hz, 3H), 2.77 (d, J=8.3 Hz, 1H), 2.31 (dtd, J=13.0, 8.7, 4.7 Hz, 0.3H), 2.23 (d, J=5.8 Hz, 6H), 2.17 (ddd, J=11.8, 8.3, 3.4 Hz, 0.7H). $^{13}$C NMR (125 MHz, DMSO-$d_6$) δ 164.79, 164.41, 162.21, 162.11, 157.34, 157.07, 155.23, 155.15, 154.00, 153.87, 151.79, 151.60, 142.07, 141.91, 138.21, 138.17, 123.69, 123.19, 114.92, 114.80, 114.74, 97.47, 60.82, 56.84, 56.81, 52.34, 50.65, 47.67, 46.02, 45.57, 45.47, 44.78, 29.00, 28.57, 26.60. HRMS (ESI) for $C_{25}H_{31}Cl_2N_7O_4$ [M+H]$^+$ calcd: 564.1887, found: 564.1884. HPLC analysis: MeOH—$H_2O$ (75:25) 7.27 min, 96.04% purity.

Example 7: (S,E)-3-(2,6-dichloro-3,5-dimethoxyphenyl)-1-(1-(4-(dimethylamino)-but-2-enoyl) pyrrolidin-3-yl)-7-(isopropylamino)-3,4-dihydropyrimido[4,5-d]-pyrimidin-2(1H)-one (104)

Compound 104 was prepared according to the general method of Scheme 1.

$^1$H NMR (400 MHz, CDCl$_3$-d) δ 7.89 (d, J=6.1 Hz, 1H), 6.99-6.78 (m, 1H), 6.59 (d, J=5.4 Hz, 1H), 6.33 (dd, J=33.9, 15.2 Hz, 1H), 5.61 (p, J=8.5 Hz, 1H), 4.95 (dd, J=32.7, 7.8 Hz, 1H), 4.65-4.33 (m, 2H), 4.30-3.77 (m, 10H), 3.75-3.43 (m, 1H), 3.15 (dd, J=15.4, 6.2 Hz, 2H), 2.76 (q, J=8.4, 7.1 Hz, 1H), 2.31 (d, J=12.8 Hz, 6H), 2.24-2.09 (m, 1H), 1.24

(dd, J=6.4, 3.1 Hz, 6H). HRMS (ESI) for C27H35Cl2N7O4 [M+H]+ calcd: 592.2200, found: 592.2214.

Example 8: (S,E)-7-(cyclohexylamino)-3-(2,6-dichloro-3,5-dimethoxyphenyl)-1-(1-(4-(dimethylamino)but-2-enoyl)pyrrolidin-3-yl)-3,4-dihydropyrimido[4,5-d]pyrimidin-2(1H)-one (105)

Compound 105 was prepared according to the general method of Scheme 1.
$^1$H NMR (500 MHz, DMSO-$d_6$) δ 7.99 (s, 1H), 6.96 (d, J=1.8 Hz, 2H), 6.60 (ddt, J=12.6, 6.4, 3.1 Hz, 1H), 6.48-6.24 (m, 1H), 5.71-5.20 (m, 1H), 4.40 (s, 2H), 3.94 (s, 6H), 3.78-3.67 (m, 7H), 2.99 (dd, J=14.2, 7.1 Hz, 2H), 2.11 (d, J=10.3 Hz, 6H), 1.83-1.02 (m, 10H). HRMS (ESI) for C30H39Cl2N7O4 [M+H]+ calcd: 632.2513, found: 632.2517.

Example 9: (S,E)-3-(2,6-dichloro-3,5-dimethoxyphenyl)-1-(1-(4-(dimethylamino)-but-2-enoyl)pyrrolidin-3-yl)-7-(phenylamino)-3,4-dihydropyrimido[4,5-d]-pyrimidin-2(1H)-one (106)

Compound 106 was prepared according to the general method of Scheme 1.
$^1$H NMR (400 MHz, CDCl$_3$-d) δ 8.10-7.99 (m, 1H), 7.64-7.49 (m, 2.0H), 7.32 (ddd, J=8.5, 7.3, 1.8 Hz, 2.0H), 7.22 (s, 0.6H), 7.05 (ddt, J=7.3, 5.8, 1.3 Hz, 1.4H), 6.92 (dq, J=15.2, 6.1 Hz, 1H), 6.60 (d, J=5.9 Hz, 1H), 6.48-6.20 (m, 1H), 5.74-5.50 (m, 1H), 4.71-4.45 (m, 2H), 4.31-4.13 (m, 0.6H), 4.13-4.00 (m, 1.4H), 4.00-3.91 (m, 6.4H), 3.88 (d, J=9.5 Hz, 0.6H), 3.76-3.45 (m, 1H), 3.06 (ddd, J=21.2, 6.1, 1.6 Hz, 2H), 2.76 (dt, J=12.6, 8.8 Hz, 1H), 2.25 (s, 3H), 2.20 (s, 4H). HRMS (ESI) for C30H33Cl2N7O4 [M+H]+ calcd: 626.2044, found: 626.2058.

Example 10: (E)-3-(2,6-dichloro-3,5-dimethoxyphenyl)-1-(1-(4-(dimethylamino)-but-2-enoyl)piperidin-4-yl)-7-(methylamino)-3,4-dihydropyrimido[4,5-d]-pyrimidin-2(1H)-one (107)

Compound 107 was prepared according to the general method of Scheme 1.
$^1$H NMR (400 MHz, CDCl$_3$-d) δ 7.97 (s, 1H), 7.36 (d, J=1.2 Hz, 1H), 6.89 (dt, J=15.0, 6.1 Hz, 1H), 6.68 (s, 1H), 6.63-6.40 (m, 1H), 5.40 (d, J=1.2 Hz, 1H), 5.17 (d, J=5.1 Hz, 1H), 5.04 (d, J=11.9 Hz, 1H), 4.88 (d, J=12.8 Hz, 1H), 4.54 (d, J=7.6 Hz, 2H), 4.20 (d, J=13.0 Hz, 1H), 4.02 (s, 6H), 3.57 (d, J=1.3 Hz, 1H), 3.34-3.12 (m, 3H), 3.05 (d, J=4.9 Hz, 3H), 2.92 (d, J=12.6 Hz, 2H), 2.78 (t, J=12.9 Hz, 1H), 2.35 (d, J=1.3 Hz, 6H). $^{13}$C NMR (125 MHz, DMSO-$d_6$) δ 164.02, 161.78, 156.64, 154.68, 151.37, 141.71, 137.99, 122.36, 113.17, 98.12, 59.92, 56.85, 56.00, 51.95, 45.26, 44.99, 44.79, 27.84, 18.52. HRMS (ESI) for C26H33Cl2N7O4 [M+H]+ calcd: 578.2044, found: 578.2029. HPLC analysis: MeOH—H$_2$O (80:20) 5.83 min, 97.04% purity.

Example 11: (E)-3-(2,6-dichloro-3,5-dimethoxyphenyl)-1-(1-(4-(dimethylamino)-but-2-enoyl)piperidin-4-yl)-7-((tetrahydrofuran-3-yl)amino)-3,4-dihydropyrimido[4,5-d]pyrimidin-2(1H)-one (109)

Compound 109 was prepared according to the general method of Scheme 1.
$^1$H NMR (500 MHz, DMSO-$d_6$) δ 8.01 (s, 1H), 7.43 (brs, 1H), 6.98 (s, 1H), 6.84-6.40 (m, 2H), 4.85-4.83 (m, 1H), 4.56 (d, J=12.5 Hz, 1H), 4.40 (s, 2H), 4.29-4.12 (m, 2H), 3.96 (s, 6H), 3.82 (t, J=7.4 Hz, 2H), 3.68 (s, 3H), 3.64-3.49 (m, 1H), 3.10 (m, 1H), 3.03 (d, J=4.6 Hz, 2H), 2.72-2.53 (m, 3H), 2.14 (s, 6H), 2.08 (s, 1H), 1.86 (s, 1H), 1.72-1.69 (m, 2H). $^{13}$C NMR (125 MHz, DMSO-$d_6$) δ 163.87, 160.88, 165.61, 151.33, 141.78, 137.93, 122.31, 113.15, 98.14, 72.55, 66.46, 59.91, 56.85, 54.87, 51.72, 44.99, 44.77, 41.75, 32.11, 29.18, 28.06. HRMS (ESI) for C29H37Cl2N7O5 [M+H]+ calcd: 634.2306, found: 634.2304. HPLC analysis: MeOH—H$_2$O (80:20) 5.23 min, 95.76% purity.

Example 12: (E)-7-(cyclohexylamino)-3-(2,6-dichloro-3,5-dimethoxyphenyl)-1-(1-(4-(dimethylamino)but-2-enoyl)piperidin-4-yl)-3,4-dihydropyrimido[4,5-d]-pyrimidin-2(1H)-one (110)

Compound 110 was prepared according to the general method of Scheme 1.
$^1$H NMR (500 MHz, DMSO-$d_6$) δ 7.96 (s, 1H), 7.06 (brs, 1H), 6.97 (s, 1H), 6.64-6.56 (m, 2H), 4.79 (s, 1H), 4.59 (d, J=13.2 Hz, 1H), 4.37 (s, 2H), 4.17 (d, J=13.4 Hz, 1H), 3.95 (s, 6H), 3.54 (brs, 1H), 3.09-3.03 (m, 1H), 3.01 (d, J=4.6 Hz, 2H), 2.63-2.58 (m, 2H), 2.13 (s, 6H), 1.84 (brs, 2H), 1.69 (brs, 4H), 1.52 (brs, 1H), 1.23 (brs, 4H), 1.14-1.09 (m, 1H), 1.07-1.04 (m, 1H). $^{13}$C NMR (125 MHz, DMSO-$d_6$) δ 160.58, 154.66, 141.80, 137.99, 122.26, 113.16, 98.13, 59.92, 56.83, 55.97, 54.83, 44.98, 44.79, 32.43, 25.35, 24.71, 18.49. HRMS (ESI) for C31H41Cl2N7O4 [M+H]+ calcd: 646.2670, found: 646.2666. HPLC analysis: MeOH—H$_2$O (85:15) 7.79 min, 97.70% purity.

Example 13: (E)-3-(2,6-dichloro-3,5-dimethoxyphenyl)-1-(1-(4-(dimethylamino)-but-2-enoyl)piperidin-4-yl)-7-((tetrahydro-2H-pyran-4-yl)amino)-3,4-dihydropyrimido[4,5-d]pyrimidin-2(1H)-one (111)

Compound 111 was prepared according to the general method of Scheme 1.
$^1$H NMR (500 MHz, DMSO-$d_6$) δ 7.98 (s, 1H), 7.19 (s, 1H), 6.97 (s, 1H), 6.75-6.39 (m, 2H), 4.80 (s, 1H), 4.58 (s, 1H), 4.38 (s, 2H), 4.17 (d, J=13.5 Hz, 1H), 3.95 (s, 6H), 3.90-3.68 (m, 3H), 3.43-3.40 (m, 3H), 3.21-2.97 (m, 3H), 2.64-2.56 (m, 2H), 2.13 (s, 6H), 1.77-1.70 (m, 4H), 1.64-1.37 (m, 2H). $^{13}$C NMR (125 MHz, DMSO-$d_6$) δ 160.55, 154.68, 151.49, 142.04, 137.96, 122.27, 113.15, 98.13, 66.02, 59.92, 56.85, 47.27, 45.01, 41.69, 32.49. HRMS (ESI) for C30H39Cl2N7O5 [M+H]+ calcd: 648.2462, found: 648.2463. HPLC analysis: MeOH—H$_2$O (85:15) 4.58 min, 98.30% purity.

Example 14: (E)-3-(2,6-dichloro-3,5-dimethoxyphenyl)-1-(1-(4-(dimethylamino)-but-2-enoyl)piperidin-4-yl)-7-((3-methoxyphenyl)amino)-3,4-dihydropyrimido[4,5-d]pyrimidin-2(1H)-one (113)

Compound 113 was prepared according to the general method of Scheme 1.
$^1$H NMR (500 MHz, DMSO-$d_6$) δ 9.59 (s, 1H), 8.19 (s, 1H), 7.35 (s, 1H), 7.32 (dd, J=8.0, 1.9 Hz, 1H), 7.19 (t, J=8.1 Hz, 1H), 6.98 (s, 1H), 6.74-6.57 (m, 2H), 6.55 (dd, J=8.2, 2.5 Hz, 1H), 4.90 (ddt, J=11.7, 7.8, 4.0 Hz, 1H), 4.59 (d, J=13.0 Hz, 1H), 4.48 (s, 2H), 4.19 (d, J=13.6 Hz, 1H), 3.95 (s, 6H), 3.73 (s, 3H), 3.10 (t, J=13.4 Hz, 1H), 3.01 (d, J=4.8 Hz, 2H), 2.66 (t, J=12.8 Hz, 1H), 2.42 (q, J=13.4 Hz, 2H), 2.13 (s, 6H), 1.78 (d, J=12.0 Hz, 2H). $^{13}$C NMR (125 MHz, DMSO-$d_6$) δ 163.98, 159.52, 158.85, 156.78, 154.69, 154.02, 150.88, 141.78, 141.32, 137.72, 129.17, 122.34, 113.18, 111.60, 106.28, 105.59, 102.73, 98.22, 59.89, 56.85, 54.97, 54.82, 52.42, 44.98, 44.77. HRMS (ESI) for C$_{32}$H$_{37}$Cl$_2$N$_7$O$_5$ [M+H]$^+$ calcd: 670.2306, found: 670.2281. HPLC analysis: MeOH—H$_2$O (85:15) 6.77 min, 95.36% purity.

Example 15: (E)-3-(2,6-dichloro-3,5-dimethoxyphenyl)-1-(1-(4-(dimethylamino)-but-2-enoyl)piperidin-4-yl)-7-(m-tolylamino)-3,4-dihydropyrimido[4,5-d]-pyrimidin-2(1H)-one (114)

Compound 114 was prepared according to the general method of Scheme 1.
$^1$H NMR (500 MHz, DMSO-d$_6$) δ 9.52 (s, 1H), 8.18 (s, 1H), 7.66-7.50 (m, 1H), 7.46 (s, 1H), 7.17 (t, J=7.8 Hz, 1H), 6.98 (s, 1H), 6.77 (d, J=7.5 Hz, 1H), 6.70-6.50 (m, 2H), 4.92-4.85 (m, 1H), 4.59 (d, J=12.8 Hz, 1H), 4.47 (s, 2H), 4.18 (d, J=13.5 Hz, 1H), 3.95 (s, 6H), 3.10-3.07 (m, 1H), 3.05 (d, J=5.2 Hz, 2H), 2.63-2.60 (m, 1H), 2.47-2.39 (m, 2H), 2.29 (s, 3H), 2.16 (s, 6H), 1.78 (d, J=11.9 Hz, 2H). $^{13}$C NMR (125 MHz, DMSO-d$_6$) δ 163.91, 158.97, 156.80, 154.70, 154.08, 150.95, 141.36, 140.07, 137.74, 137.48, 128.27, 122.64, 122.40, 119.58, 116.40, 113.17, 102.55, 98.22, 59.76, 56.86, 55.97, 54.83, 52.37, 44.85, 44.77, 21.34, 18.49. HRMS (ESI) for C$_{32}$H$_{37}$Cl$_2$N$_7$O$_4$ [M+H]$^+$ calcd: 654.2357, found: 654.2342. HPLC analysis: MeOH—H$_2$O (80:20) 12.44 min, 96.11% purity.

Example 16: (E)-3-(2,6-dichloro-3,5-dimethoxyphenyl)-1-(1-(4-(dimethylamino)-but-2-enoyl)piperidin-4-yl)-7-((3-fluorophenyl)amino)-3,4-dihydropyrimido[4,5-d]pyrimidin-2(1H)-one (115)

Compound 115 was prepared according to the general method of Scheme 1.
$^1$H NMR (500 MHz, DMSO-d$_6$) δ 9.85 (s, 1H), 8.23 (s, 1H), 7.73 (d, J=12.4 Hz, 1H), 7.51-7.39 (m, 1H), 7.31 (q, J=8.0 Hz, 1H), 6.99 (s, 1H), 6.83-6.70 (m, 1H), 6.67-6.48 (m, 2H), 4.92-4.87 (m, 1H), 4.61 (d, J=12.7 Hz, 1H), 4.50 (s, 2H), 4.20 (d, J=14.1 Hz, 1H), 3.95 (s, 6H), 3.11-3.07 (m, 1H), 3.01 (d, J=4.6 Hz, 2H), 2.68-2.62 (m, 1H), 2.46-2.37 (m, 2H), 2.13 (s, 6H), 1.81-1.79 (m, 2H). $^{13}$C NMR (125 MHz, DMSO-d$_6$) δ 163.99, 163.22, 161.31, 158.60, 156.69, 154.70, 154.07, 150.81, 142.17, 142.08, 141.88, 137.66, 129.97, 129.90, 122.29, 114.67, 113.15, 107.75, 107.58, 105.49, 105.28, 103.35, 98.24, 59.90, 56.86, 52.58, 44.99, 44.75, 29.07, 28.06. HRMS (ESI) for C$_{31}$H$_{34}$Cl$_2$FN$_7$O$_4$ [M+H]$^+$ calcd: 658.2106, found: 658.2108. HPLC analysis: MeOH—H$_2$O (85:15) 7.42 min, 95.97% purity.

Example 17: (E)-3-(2,6-dichloro-3,5-dimethoxyphenyl)-7-((3,5-difluorophenyl)-amino)-1-(1-(4-(dimethylamino)but-2-enoyl)piperidin-4-yl)-3,4-dihydropyrimido[4,5-d]pyrimidin-2(1H)-one (116)

Compound 116 was prepared according to the general method of Scheme 1.
$^1$H NMR (500 MHz, DMSO-d$_6$) δ 10.05 (s, 1H), 8.26 (s, 1H), 7.59-7.42 (m, 2H), 6.99 (s, 1H), 6.75 (tt, J=9.2, 2.4 Hz, 1H), 6.66-6.50 (m, 2H), 4.88 (tt, J=11.9, 4.0 Hz, 1H), 4.59 (d, J=12.9 Hz, 1H), 4.51 (s, 2H), 4.20 (d, J=13.5 Hz, 1H), 3.95 (s, 6H), 3.16-3.03 (m, 1H), 3.01 (d, J=5.1 Hz, 2H), 2.66 (d, J=13.6 Hz, 1H), 2.46-2.31 (m, 2H), 2.13 (s, 6H), 1.82 (d, J=12.0 Hz, 2H). $^{13}$C NMR (125 MHz, DMSO-d$_6$) δ 164.02, 163.50, 163.37, 161.58, 161.45, 158.35, 156.98, 154.71, 154.05, 150.66, 142.97, 141.84, 137.58, 122.28, 113.15, 103.98, 101.41, 101.17, 98.27, 96.16, 59.88, 56.87, 55.97, 54.82, 52.66, 44.98, 44.73, 18.49. HRMS (ESI) for C$_{31}$H$_{33}$Cl$_2$F$_2$N$_7$O$_4$, [M+H]$^+$ calcd: 676.2012, found: 676.2017. HPLC analysis: MeOH—H$_2$O (85:15) 9.43 min, 98.01% purity.

Example 18: (E)-3-(2,6-dichloro-3,5-dimethoxyphenyl)-7-((3,4-difluorophenyl)-amino)-1-(1-(4-(dimethylamino)but-2-enoyl)piperidin-4-yl)-3,4-dihydropyrimido[4,5-d]pyrimidin-2(1H)-one (117)

Compound 117 was prepared according to the general method of Scheme 1.
$^1$H NMR (500 MHz, DMSO-d$_6$) δ 9.84 (s, 1H), 8.22 (s, 1H), 7.89-7.86 (m, 1H), 7.43-7.33 (m, 2H), 6.99 (s, 1H), 6.64-6.56 (m, 2H), 4.88-4.84 (m, 1H), 4.61-4.59 (m, 1H), 4.49 (s, 2H), 4.20-4.18 (m, 1H), 3.95 (s, 6H), 3.12-3.06 (m, 1H), 3.02-3.01 (m, 2H), 2.67-2.62 (m, 1H), 2.45-2.36 (m, 2H), 2.13 (s, 6H), 1.79-1.78 (m, 2H). $^{13}$C NMR (125 MHz, DMSO-d$_6$) δ 163.97, 158.53, 156.92, 154.71, 154.08, 150.84, 141.87, 137.66, 137.45, 137.38, 122.31, 117.16, 117.02, 115.08, 113.15, 107.77, 107.59, 103.41, 98.24, 59.89, 56.87, 52.58, 44.98, 44.75, 29.09, 28.05. HRMS (ESI) for C$_{31}$H$_{33}$Cl$_2$F$_2$N$_7$O$_4$ [M+H]$^+$ calcd: 676.2012, found: 676.2025. HPLC analysis: MeOH—H$_2$O (85:15) 7.80 min, 98.38% purity.

Example 19: (E)-3-(2,6-dichloro-3,5-dimethoxyphenyl)-1-(1-(4-(dimethylamino)-but-2-enoyl)piperidin-4-yl)-7-((4-fluoro-3-methoxyphenyl)amino)-3,4-dihydropyrimido[4,5-d]pyrimidin-2(1H)-one (118)

Compound 118 was prepared according to the general method of Scheme 1.
$^1$H NMR (500 MHz, DMSO-d$_6$) δ 9.52 (s, 1H), 8.18 (s, 1H), 7.41 (ddd, J=8.9, 3.9, 2.6 Hz, 1H), 7.34 (d, J=7.8 Hz, 1H), 7.12 (dd, J=11.5, 8.9 Hz, 1H), 6.98 (s, 1H), 6.79-6.46 (m, 2H), 5.00-4.77 (m, 1H), 4.59 (d, J=12.9 Hz, 1H), 4.47 (d, J=2.0 Hz, 2H), 4.18 (d, J=13.5 Hz, 1H), 3.95 (s, 6H), 3.81 (s, 3H), 3.09-3.04 (m, 1H), 3.01 (d, J=4.2 Hz, 2H), 2.64-2.59 (m, 1H), 2.47-2.37 (m, 2H), 2.13 (s, 6H), 1.76 (d, J=11.9 Hz, 2H). $^{13}$C NMR (125 MHz, DMSO-d$_6$) δ 163.94, 158.85, 156.85, 154.69, 153.95, 150.96, 147.88, 146.76, 146.67, 145.98, 141.88, 137.72, 136.91, 122.29, 115.39, 115.24, 113.15, 111.08, 111.04, 106.01, 102.89, 98.22, 59.90, 56.86, 56.02, 52.38, 44.98, 44.74. HRMS (ESI) for C$_{32}$H$_{36}$Cl$_2$FN$_7$O$_5$ [M+H]$^+$ calcd: 688.2212, found: 688.2216. HPLC analysis: MeOH—H$_2$O (85:15) 6.05 min, 95.08% purity.

Example 20: (E)-7-((3-chloro-4-fluorophenyl)amino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (119)

Compound 119 was prepared according to the general method of Scheme 1.
$^1$H NMR (500 MHz, DMSO-d$_6$) δ 9.80 (s, 1H), 8.22 (s, 1H), 7.99-7.97 (m, 1H), 7.60-7.58 (m, 1H), 7.34 (t, J=9.1 Hz, 1H), 6.99 (s, 1H), 6.63-6.56 (m, 2H), 4.89-4.83 (m, 1H), 4.58 (d, J=12.8 Hz, 1H), 4.49 (s, 2H), 4.18 (d, J=13.6 Hz, 1H), 3.95 (s, 6H), 3.14-3.09 (m, 1H), 3.03-3.00 (m, 2H), 2.69-2.65 (m, 1H), 2.45-2.37 (m, 2H), 2.12 (s, 6H), 1.79 (s, 2H). $^{13}$C NMR (125 MHz, DMSO-d$_6$) δ 163.93, 158.52, 156.89, 154.69, 154.10, 153.07, 151.15, 150.80, 141.87, 137.64, 137.54, 122.25, 119.99, 119.19, 119.14, 118.18, 118.73, 116.66, 116.49, 113.13, 103.33, 98.25, 59.88, 56.86, 52.49, 44.97, 44.72, 29.01, 28.00. HRMS (ESI) for $C_{31}H_{33}Cl_3FN_7O_4$ [M+H]$^+$ calcd: 692.1716, found: 692.1717. HPLC analysis: MeOH—H$_2$O (85:15) 9.43 min, 98.38% purity.

Example 21: (E)-3-(2,6-dichloro-3,5-dimethoxyphenyl)-1-(1-(4-(dimethylamino)-but-2-enoyl)piperidin-4-yl)-7-((4-fluorophenyl)amino)-3,4-dihydropyrimido[4,5-d]pyrimidin-2(1H)-one (120)

Compound 120 was prepared according to the general method of Scheme 1.
$^1$H NMR (500 MHz, d$_6$-DMSO) δ 9.62 (s, 1H), 8.18 (s, 1H), 7.84-7.57 (m, 2H), 7.13 (t, J=8.9 Hz, 2H), 6.98 (s, 1H), 6.61 (m, 2H), 4.84 (td, J=11.7, 5.8 Hz, 1H), 4.60 (d, J=12.8 Hz, 1H), 4.47 (s, 2H), 4.18 (d, J=13.6 Hz, 1H), 3.95 (s, 6H), 3.09 (dd, J=16.9, 10.8 Hz, 1H), 3.04-2.97 (m, 1H), 2.64 (t, J=12.8 Hz, 1H), 2.46-2.29 (m, 2H), 2.13 (s, 6H), 1.76 (d, J=12.0 Hz, 1H). $^{13}$C NMR (125 MHz, d$_6$-DMSO), δ 163.92, 158.85, 158.18, 156.83, 156.28, 154.69, 154.07, 151.02, 141.88, 137.74, 136.48, 122.29, 120.83, 120.76, 115.02, 114.85, 113.17, 102.78, 98.21, 59.90, 56.85, 55.97, 54.83, 52.52, 44.97, 44.76, 18.49. HRMS (ESI) for $C_{31}H_{34}Cl_2FN_7O_4$ [M+H]$^+$ calcd: 658.2106, found: 658.2088. HPLC analysis: MeOH—H$_2$O (85:15) 6.55 min, 98.47% purity.

Example 21: (E)-3-(2,6-dichloro-3,5-dimethoxyphenyl)-1-(1-(4-(dimethylamino)-but-2-enoyl)piperidin-4-yl)-7-((2-methoxyphenyl)amino)-3,4-dihydropyrimido[4,5-d]pyrimidin-2(1H)-one (121)

Compound 121 was prepared according to the general method of Scheme 1.
$^1$H NMR (500 MHz, DMSO-d$_6$) δ 8.15 (d, J=5.4 Hz, 2H), 8.02-7.87 (m, 1H), 7.08-6.96 (m, 3H), 6.93 (td, J=7.5, 7.0, 2.0 Hz, 1H), 6.75-6.53 (m, 2H), 4.87-4.69 (m, 1H), 4.56 (d, J=12.8 Hz, 1H), 4.47 (s, 2H), 4.13 (d, J=13.6 Hz, 1H), 3.95 (s, 6H), 3.84 (s, 3H), 3.19 (d, J=5.9 Hz, 2H), 3.03 (d, J=13.6 Hz, 1H), 2.60 (t, J=13.2 Hz, 1H), 2.39 (d, J=12.3 Hz, 2H), 2.26 (s, 6H), 1.72 (d, J=11.8 Hz, 2H). $^{13}$C NMR (125 MHz, DMSO-d$_6$), δ 163.71, 159.01, 156.85, 154.68, 154.06, 150.99, 149.69, 137.74, 128.18, 123.76, 123.29, 121.15, 120.17, 113.15, 110.89, 102.85, 98.21, 59.36, 56.85, 55.97, 55.64, 54.82, 52.41, 44.75, 44.41, 28.94, 27.93, 18.48. HRMS (ESI) for $C_{32}H_{37}Cl_2N_7O_5$ [M+H]$^+$ calcd: 670.2310, found: 670.2308. HPLC analysis: MeOH—H$_2$O (85:15) 7.83 min, 97.47% purity.

Example 22: (E)-3-(2,6-dichloro-3,5-dimethoxyphenyl)-1-(1-(4-(dimethylamino)-but-2-enoyl)piperidin-4-yl)-7-((4-methoxyphenyl)amino)-3,4-dihydropyrimido[4,5-d]pyrimidin-2(1H)-one (122)

Compound 122 was prepared according to the general method of Scheme 1.
$^1$H NMR (400 MHz, DMSO-d$_6$) δ 9.42 (s, 1H), 8.15 (s, 1H), 7.75-7.47 (m, 2H), 6.99 (s, 1H), 6.93-6.79 (m, 2H), 6.81-6.40 (m, 2H), 5.07-4.71 (m, 1H), 4.61 (d, J=12.6 Hz, 1H), 4.46 (s, 2H), 4.19 (d, J=13.5 Hz, 1H), 3.96 (s, 6H), 3.72 (s, 3H), 3.21-2.93 (m, 3H), 2.72-2.59 (m, 1H), 2.46-2.42 (m, 2H), 2.16 (s, 6H), 1.76 (d, J=11.9 Hz, 2H). $^{13}$C NMR (125 MHz, DMSO-d$_6$) δ 162.87, 159.11, 156.74, 154.69, 154.39, 154.15, 151.08, 137.78, 133.24, 131.89, 129.07, 120.96, 113.69, 113.20, 113.30, 102.07, 98.19, 57.21, 56.87, 55.16, 52.24, 45.39, 44.79, 42.19, 29.00, 27.99. HRMS (ESI) for $C_{32}H_{37}Cl_2N_7O_5$ [M+H]$^+$ calcd: 670.2306, found: 670.2312. HPLC analysis: MeOH—H$_2$O (80:20) 9.04 min, 99.37% purity.

Example 23: (E)-3-(2,6-dichloro-3,5-dimethoxyphenyl)-7-(methylamino)-1-(1-(4-morpholinobut-2-enoyl)piperidin-4-yl)-3,4-dihydropyrimido[4,5-d]pyrimidin-2(1H)-one (123)

Compound 123 was prepared according to a synthetic route similar to the general method of Scheme 1.
$^1$H NMR (500 MHz, DMSO-d$_6$) δ 7.98 (s, 1H), 7.03 (s, 1H), 6.97 (s, 1H), 6.71-6.45 (m, 2H), 4.87-4.82 (m, 1H), 4.53 (d, J=11.7 Hz, 1H), 4.38 (s, 2H), 4.14 (d, J=13.6 Hz, 1H), 3.95 (s, 6H), 3.57-3.55 (m, 4H), 3.08-3.07 (m, 3H), 2.84-2.70 (m, 3.22H), 2.61 (d, J=12.9 Hz, 2.41H), 2.34 (d, J=4.7 Hz, 4.36H), 1.69 (d, J=12.0 Hz, 2H). HRMS (ESI) for $C_{28}H_{35}Cl_2N_7O_5$ [M+H]$^+$ calcd: 620.2150, found: 620.2152.

Example 24: (E)-3-(2,6-dichloro-3,5-dimethoxyphenyl)-7-(methylamino)-1-(1-(4-(piperidin-1-yl)but-2-enoyl)piperidin-4-yl)-3,4-dihydropyrimido[4,5-d]pyrimidin-2(1H)-one (124)

Compound 124 was prepared according to a synthetic route similar to the general method of Scheme 1.
$^1$H NMR (500 MHz, DMSO-d$_6$) δ 7.98 (s, 1H), 7.03 (s, 1H), 6.97 (s, 1H), 6.76-6.40 (m, 2H), 4.97-4.78 (m, 1H), 4.53 (d, J=11.6 Hz, 1H), 4.38 (s, 2H), 4.13 (d, J=13.6 Hz, 1H), 3.95 (s, 6H), 3.12-3.08 (m, 1H), 3.03 (d, J=4.6 Hz, 2H), 2.82-2.68 (m, 3H), 2.59-2.62 (m, 2H), 2.34-2.22 (m, 4H), 1.71-1.68 (m, 2H), 1.51-1.46 (m, 4.6H), 1.37-1.36 (m, 2.4H). HRMS (ESI) for $C_{29}H_{37}Cl_2N_7O_4$ [M+H]$^+$ calcd: 618.2357, found: 618.2354.

Example 25: (E)-N-(3-(3-(2,6-dichloro-3,5-dimethoxyphenyl)-7-(methylamino)-2-oxo-3,4-dihydropyrimido[4,5-d]pyrimidin-1(2H)-yl)propyl)-4-(dimethylamino)-but-2-enamide (125)

Compound 125 was prepared according to a synthetic route similar to the general method of Scheme 1.
$^1$H NMR (500 MHz, DMSO-d$_6$) δ 7.97 (brs, 2H), 7.03 (brs, 1H), 6.99 (s, 1H), 6.52 (dt, J=15.4, 6.1 Hz, 1H), 5.99 (dt, J=15.5, 1.6 Hz, 1H), 4.44 (s, 2H), 3.99-3.96 (m, 2H), 3.95 (s, 6H), 3.18-3.13 (m, 2H), 2.96 (dd, J=6.2, 1.5 Hz, 2H), 2.79 (d, J=4.7 Hz, 3H), 2.12 (s, 6H), 1.75 (t, J=7.3 Hz, 2H). $^{13}$C NMR (125 MHz, DMSO-d$_6$) δ 164.41, 162.00, 155.63, 154.71, 154.00, 150.91, 138.97, 137.78, 125.99, 113.19, 98.22, 59.69, 56.83, 55.97, 54.82, 44.98, 44.78, 36.32, 28.15, 27.76, 18.45. HRMS (ESI) for $C_{24}H_{31}Cl_2N_7O_4$ [M+H]$^+$ calcd: 552.1887, found: 552.1888. HPLC analysis: MeOH—H$_2$O (80:20) 5.30 min, 95.44% purity.

Example 26: (E)-N-(4-(3-(2,6-dichloro-3,5-dimethoxyphenyl)-7-(methylamino)-2-oxo-3,4-dihydropyrimido[4,5-d]pyrimidin-1(2H)-yl)cyclohexyl)-4-(dimethylamino)but-2-enamide (126)

Compound 126 was prepared according to a synthetic route similar to the general method of Scheme 1.
$^1$H NMR (500 MHz, DMSO-d$_6$) δ 7.97 (s, 1H), 7.86 (d, J=7.8 Hz, 1H), 7.07 (d, J=5.2 Hz, 1H), 6.97 (s, 1H), 6.53 (dt, J=15.5, 6.1 Hz, 1H), 6.10-5.91 (m, 1H), 4.57-4.52 (m, 1H), 4.38 (s, 2H), 3.95 (s, 6H), 3.61 (s, 1H), 3.01 (d, J=4.6 Hz, 2H), 2.82 (d, J=4.7 Hz, 3H), 2.60 (q, J=12.4 Hz, 2H), 2.13 (s, 6H), 1.89 (d, J=12.2 Hz, 2H), 1.66 (d, J=12.0 Hz, 2H),

Example 27: (E)-N-(3-((3-(2,6-dichloro-3,5-dimethoxyphenyl)-7-(methylamino)-2-oxo-3,4-dihydropyrimido[4,5-d]pyrimidin-1(2H)-yl)methyl)phenyl)-4-(dimethylamino)but-2-enamide (127)

Compound 127 was prepared according to the general method of Scheme 4.
$^1$H NMR (400 MHz, CDCl$_3$-d) δ 7.90 (s, 1H), 7.60 (d, J=53.2 Hz, 2H), 7.31 (s, 1H), 7.26 (d, J=5.0 Hz, 2H), 6.96 (dt, J=15.2, 6.1 Hz, 1H), 6.60 (s, 1H), 6.11 (d, J=15.3 Hz, 1H), 5.34 (s, 1H), 5.28 (s, 2H), 4.57 (s, 2H), 3.95 (s, 6H), 3.14 (d, J=6.1 Hz, 2H), 3.00 (d, J=5.0 Hz, 3H), 2.32 (s, 6H). HRMS (ESI) for C$_{28}$H$_{31}$Cl$_2$N$_7$O$_4$ [M+H]$^+$ calcd: 600.1887, found: 600.1892.

Example 28: (E)-3-(2-chloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (128)

Compound 128 was prepared according to the general method of Scheme 1.
$^1$H NMR (400 MHz, DMSO-d$_6$) δ 9.57 (s, 1H), 8.17 (s, 1H), 7.82-7.61 (m, 2H), 7.49-7.17 (m, 2H), 7.08-6.89 (m, 1H), 6.86-6.51 (m, 4H), 4.89 (td, J=10.0, 8.1, 6.0 Hz, 1H), 4.64 (t, J=13.5 Hz, 2H), 4.44 (d, J=13.8 Hz, 1H), 4.20 (s, 1H), 3.86 (s, 3H), 3.79 (s, 3H), 3.23-3.00 (m, 3H), 2.75-2.57 (m, 1H), 2.24 (s, 6H), 1.77 (d, J=12.0 Hz, 2H), 1.24 (s, 3H). HRMS (ESI) for C$_{31}$H$_{36}$ClN$_7$O$_4$ [M+H]$^+$ calcd: 606.2603, found: 606.2604.

Example 29: (E)-3-(2,6-dichloro-3,5-dimethoxyphenyl)-1-(1-(4-(dimethylamino)-but-2-enoyl) piperidin-4-yl)-7-((4-morpholinophenyl)amino)-3,4-dihydropyrimido[4,5-d]pyrimidin-2(1H)-one (129)

Compound 129 was prepared according to the general method of Scheme 1.
$^1$H NMR (400 MHz, DMSO-d$_6$) δ 9.38 (s, 1H), 8.13 (s, 1H), 7.69-7.45 (m, 2H), 6.98 (s, 1H), 6.94-6.83 (m, 2H), 6.68-6.53 (m, 2H), 4.85 (t, J=12.0 Hz, 1H), 4.60 (d, J=12.8 Hz, 1H), 4.45 (d, J=3.8 Hz, 2H), 4.20 (d, J=13.6 Hz, 1H), 3.95 (s, 6H), 3.79-3.64 (m, 4H), 3.18-2.97 (m, 7H), 2.73-2.60 (m, 1H), 2.43 (s, 2H), 2.13 (s, 6H), 1.75 (d, J=11.9 Hz, 2H). HRMS (ESI) for C$_{35}$H$_{42}$Cl$_2$N$_8$O$_5$ [M+H]$^+$ calcd: 725.2728, found: 725.2725.

Example 30: (E)-3-(2-chloro-3,5-dimethoxyphenyl)-1-(1-(4-(dimethylamino)but-2-enoyl) piperidin-4-yl)-7-((4-morpholinophenyl)amino)-3,4-dihydropyrimido[4,5-d]pyrimidin-2(1H)-one (130)

Compound 130 was prepared according to the general method of Scheme 1.
$^1$H NMR (400 MHz, DMSO-d$_6$) δ 9.35 (s, 1H), 8.12 (s, 1H), 7.72-7.45 (m, 2H), 6.88 (d, J=9.1 Hz, 2H), 6.81-6.54 (m, 4H), 4.87 (t, J=12.0 Hz, 1H), 4.63 (t, J=11.6 Hz, 2H), 4.48-4.33 (m, 1H), 4.20 (s, 1H), 3.86 (s, 3H), 3.79 (s, 3H), 3.73 (t, J=4.8 Hz, 4H), 3.16-2.96 (m, 7H), 2.79-2.58 (m, 1H), 2.17 (s, 6H), 1.75 (d, J=11.8 Hz, 2H), 1.25 (s, 2H). HRMS (ESI) for C$_{35}$H$_{43}$ClN$_8$O$_5$ [M+H]$^+$ calcd: 691.3131, found: 691.3125.

Example 31: (E)-3-(3,5-dimethoxyphenyl)-1-(1-(4-(dimethylamino)but-2-enoyl)-piperidin-4-yl)-7-((4-morpholinophenyl)amino)-3,4-dihydropyrimido[4,5-d]-pyrimidin-2(1H)-one (131)

Compound 131 was prepared according to the general method of Scheme 1.
$^1$H NMR (400 MHz, DMSO-d$_6$) δ 9.32 (s, 1H), 8.12 (s, 1H), 7.83-7.45 (m, 2H), 7.11-6.80 (m, 2H), 6.73-6.55 (m, 2H), 6.52 (d, J=2.2 Hz, 2H), 6.40 (t, J=2.3 Hz, 1H), 4.91-4.77 (m, 1H), 4.62 (d, J=3.3 Hz, 3H), 4.21 (d, J=13.2 Hz, 1H), 3.74 (s, 10H), 3.16-2.92 (m, 7H), 2.78-2.54 (m, 1H), 2.19 (s, 6H), 1.78 (d, J=11.8 Hz, 2H), 1.25 (s, 2H). HRMS (ESI) for C$_{35}$H$_{44}$N$_8$O$_5$ [M+H]$^+$ calcd: 657.3521, found: 657.3516.

Example 32: (E)-3-(2,6-dibromo-3,5-dimethoxyphenyl)-1-(1-(4-(dimethylamino)-but-2-enoyl)piperidin-4-yl)-7-(isopropylamino)-3,4-dihydropyrimido[4,5-d]-pyrimidin-2(1H)-one (151)

Compound 151 was prepared according to a synthetic route similar to the general method of Scheme 1.
$^1$H NMR (400 MHz, CDCl$_3$-d) δ 7.86 (s, 1H), 6.81 (dt, J=15.2, 6.0 Hz, 1H), 6.53 (s, 1H), 6.44 (dt, J=15.2, 1.6 Hz, 1H), 5.02-4.92 (m, 1H), 4.89 (d, J=7.7 Hz, 1H), 4.80 (d, J=12.4 Hz, 1H), 4.46 (d, J=5.7 Hz, 2H), 4.22-3.98 (m, 2H), 3.92 (s, 6H), 3.14 (d, J=12.9 Hz, 1H), 3.06 (dd, J=6.0, 1.5 Hz, 2H), 2.74 (dd, J=39.3, 13.1 Hz, 3H), 2.25 (s, 6H), 1.81 (d, J=12.1 Hz, 2H), 1.24 (d, J=6.6 Hz, 6H). HRMS (ESI) for C$_{28}$H$_{37}$Br$_2$N$_7$O$_4$ [M+H]$^+$ calcd: 696.1328, found: 696.1334.

Example 33: Synthesis of (E)-6-(2,6-dichloro-3,5-dimethoxyphenyl)-8-(1-(4-(dimethylamino)but-2-enoyl)piperidin-4-yl)-2-(methylamino)pyrido[2,3-d]-pyrimidin-7(8H)-one (132)

A synthetic route for the preparation of compound 132 is outlined in Scheme 8.

Scheme 8:

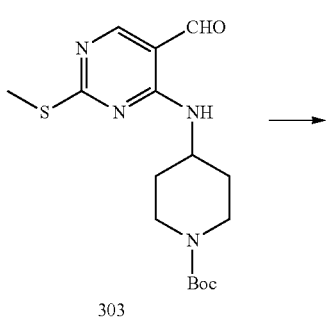

303

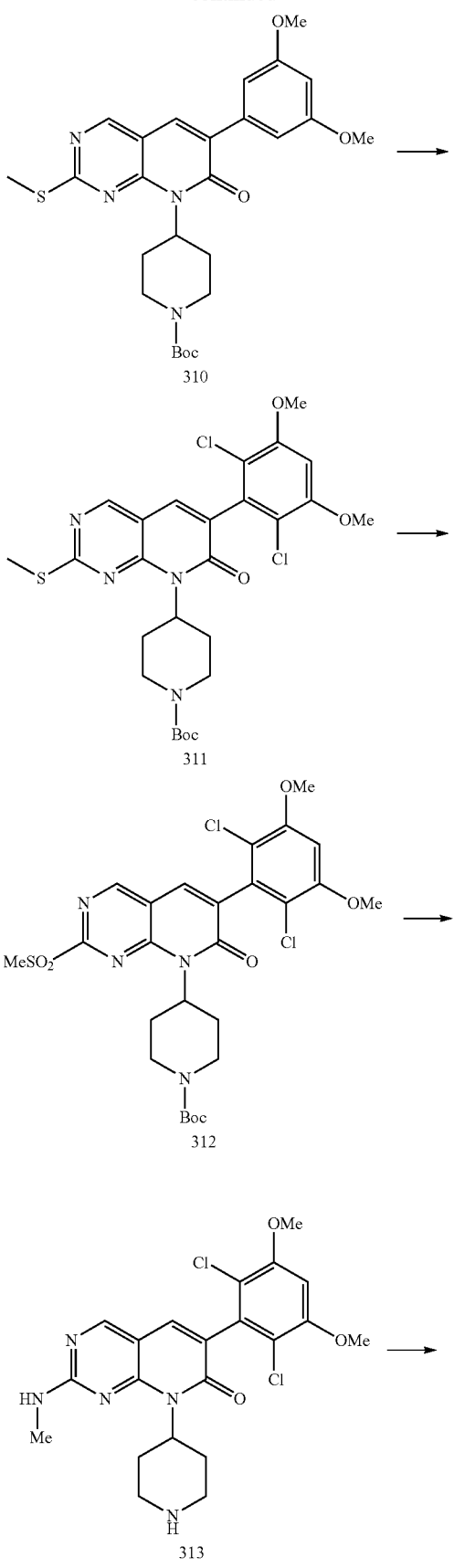

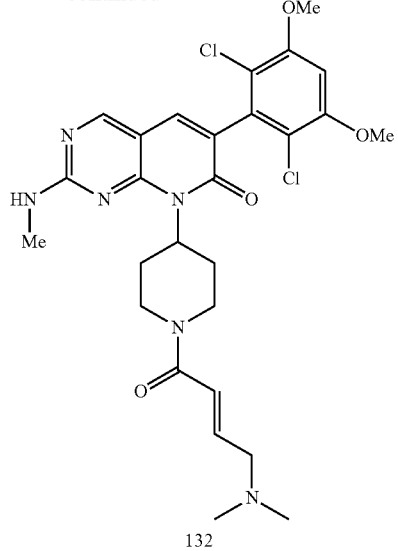

To a solution of compound 303 (6.0 g, 17.0 mmol) and methyl 2-(3,5-dimethoxyphenyl)acetate (4.29 g, 20.4 mmol) in DMF was added K$_2$CO$_3$ (7.0 g, 51 mmol). The mixture was stirred at 110° C. for 10 hours. When the reaction was complete, water was added to the mixture and the aqueous layer was extracted with CH$_2$Cl$_2$. The organic layer was separated, dried over Na$_2$SO$_4$ and concentrated to afford the crude product. The residue was purified by column chromatography to give compound 310 (6.8 g, 78%). $^1$H NMR (400 MHz, CDCl$_3$-d) δ 8.63 (s, 1H), 7.66 (s, 1H), 6.78 (d, J=2.3 Hz, 2H), 6.51 (t, J=2.3 Hz, 1H), 5.64 (s, 1H), 4.33 (d, J=45.4 Hz, 2H), 3.83 (s, 6H), 3.21-2.76 (m, 4H), 2.62 (s, 3H), 1.68 (d, J=11.8 Hz, 2H), 1.49 (s, 9H). MS (ESI) m/z 513.2 [M+H]$^+$.

Compound 310 (3.0 g, 5.86 mmol) was dissolved in anhydrous CH$_3$CN (50 mL) and SO$_2$Cl$_2$ (0.95 mL, 11.72 mmol) was added to the solution dropwise. The reaction mixture was stirred in an ice-water bath for 30 min and quenched by dropwise addition of saturated NaHCO$_3$. The mixture was diluted with CH$_2$Cl$_2$ and washed with saturated NaHCO$_3$. The organic layer was separated, dried over Na$_2$SO$_4$, and concentrated in vacuo to give the crude material. The crude product was dissolved in CH$_2$Cl$_2$ (40 mL). DIEA (1.0 mL, 5.86 mmol) and di-tert-butyl dicarbonate (1.3 mL, 5.86 mmol) were added to the mixture. The mixture was stirred at room temperature for 4 hours. After removal of CH$_2$Cl$_2$, the crude product was purified by column chromatography to afford compound 311 (2.2 g, 65%). MS (ESI) m/z 582.1 [M+H]$^+$.

Compound 311 (2.0 g, 3.44 mmol) was dissolved in anhydrous CH$_2$Cl$_2$ (20 mL). m-CPBA (1.66 g, 7.22 mmol) was added to the solution. The reaction mixture was stirred for 5 hours. The solution was diluted with CH$_2$Cl$_2$ and then washed with NaHCO$_3$ solution. The organic layer was separated, washed with brine, dried with Na$_2$SO$_4$ and concentrated in vacuo. The resulting crude product was subjected to column chromatography giving compound 312 (1.7 g, 82%). $^1$H NMR (400 MHz, DMSO-d$_6$) δ 9.34 (s, 1H), 8.17 (s, 1H), 7.04 (s, 1H), 5.49 (s, 1H), 4.15 (s, 2H), 3.98 (s, 6H), 3.47 (s, 3H), 2.90 (d, J=18.7 Hz, 2H), 2.75-2.59 (m, 2H), 1.67 (d, J=11.8 Hz, 2H), 1.42 (s, 9H). MS (ESI) m/z 614.1 [M+H]$^+$.

Methylamine hydrochloride (0.18 g, 2.7 mmol) and DIEA (0.49 mL, 2.7 mmol) was added to a solution of compound 312 (0.85 g, 1.4 mmol). The reaction mixture was stirred for 5 h at 110° C. in a sealed tube. After cooling to room temperature, the reaction mixture was concentrated in vacuo to give the crude product. The crude product was dissolved in $CH_2Cl_2$ (20 mL), then TFA (2.0 mL) was added to the solution and the resulting mixture was stirred at room temperature for 4 h. The reaction mixture was basified with saturated aqueous $NaHCO_3$ and extracted with $CH_2Cl_2$. The organic layer was separated filtered and concentrated to give the crude product 313, which was used in the next step without further purification (0.43 g, 67%). MS (ESI) m/z 465.1 $[M+H]^+$.

The crude product 313 (0.4 g, 0.86 mmol), trans-4-Dimethylaminocrotonic acid hydrochloride (0.18 g, 1.1 mmol) and HATU (0.49 g, 1.3 mmol) were added to a 25 mL flask followed by addition of $CH_3CN$ (10 mL) and DIEA (0.46 mL, 2.6 mmol). The resulting mixture was stirred at room temperature overnight. The reaction mixture was diluted with $CH_2Cl_2$, basified with saturated aqueous $NaHCO_3$ and extracted with $CH_2Cl_2$. The organic layer was separated and concentrated in vacuo. The crude material was purified by column chromatography to give the title compound 132 (420 mg, 85%). $^1$H NMR (500 MHz, DMSO-$d_6$) δ 8.64 (d, J=44.9 Hz, 1H), 7.79 (d, J=43.9 Hz, 1H), 7.65 (s, 1H), 6.96 (s, 1H), 6.75-6.49 (m, 2H), 5.58 (s, 1H), 4.57 (d, J=12.9 Hz, 1H), 4.19 (d, J=13.3 Hz, 1H), 3.94 (s, 6H), 3.23-2.58 (m, 9H), 2.14 (s, 6H), 1.63 (d, J=21.2 Hz, 2H). HRMS (ESI) for $C_{27}H_{32}Cl_2N_6O_4$ $[M+H]^+$ calcd: 575.1935, found: 575.1940.

Example 34: (E)-6-(2,6-dichloro-3,5-dimethoxyphenyl)-8-(1-(4-(dimethylamino)-but-2-enoyl)piperidin-4-yl)-2-(isopropylamino)pyrido[2,3-d]pyrimidin-7(8H)-one (133)

Compound 133 was prepared according to the general method of Scheme 2.
$^1$H NMR (500 MHz, DMSO-$d_6$) δ 8.66 (s, 0.2H), 8.60 (s, 0.8H), 7.87 (d, J=7.8 Hz, 0.8H), 7.70 (s, 0.2H), 7.63 (s, 1H), 6.96 (s, 1H), 6.65 (s, 2H), 5.64 (brs, 1H), 4.59 (d, J=11.6 Hz, 1H), 4.20 (d, J=13.7 Hz, 1H), 3.95 (s, 7H), 3.16-2.68 (m, 6H), 2.14 (s, 6H), 1.63 (d, J=19.7 Hz, 2H), 1.19-1.13 (m, 6H). HRMS (ESI) for $C_{29}H_{36}Cl_2N_6O_4$ $[M+H]^+$ calcd: 603.2248, found: 603.2238.

Example 35: (E)-6-(2,6-dichloro-3,5-dimethoxyphenyl)-8-(1-(4-(dimethylamino)-but-2-enoyl)piperidin-4-yl)-2-((tetrahydrofuran-3-yl)amino)pyrido[2,3-d]-pyrimidin-7(8H)-one (134)

Compound 134 was prepared according to the general method of Scheme 2.
$^1$H NMR (500 MHz, DMSO-$d_6$) δ 8.68 (s, 0.1H), 8.63 (s, 0.9H), 8.22 (s, 0.8H), 8.01 (s, 0.2H), 7.67 (s, 1H), 6.97 (s, 1H), 6.76-6.55 (m, 2H), 5.57 (s, 1H), 4.60 (s, 1H), 4.40-4.14 (m, 2H), 3.95 (s, 6H), 3.84 (s, 2H), 3.67 (s, 2H), 3.17 (s, 1H), 3.02 (d, J=4.8 Hz, 2H), 2.66 (d, J=30.7 Hz, 2H), 2.14 (s, 8H), 1.97 (d, J=38.2 Hz, 1H), 1.63 (s, 2H). HRMS (ESI) for $C_{30}H_{36}Cl_2N_6O_5$ $[M+H]^+$ calcd: 631.2197, found: 631.2177.

Example 36: (E)-6-(2,6-dichloro-3,5-dimethoxyphenyl)-8-(1-(4-(dimethylamino)-but-2-enoyl) piperidin-4-yl)-2-((tetrahydro-2H-pyran-4-yl)amino)pyrido[2,3-d]-pyrimidin-7(8H)-one (135)

Compound 135 was prepared according to the general method of Scheme 2.

$^1$H NMR (500 MHz, DMSO-$d_6$) δ 8.83-8.54 (m, 1H), 8.00 (d, J=7.9 Hz, 0.8H), 7.82 (s, 0.2H), 7.66 (d, J=7.5 Hz, 1H), 6.97 (s, 1H), 6.83-6.55 (m, 2H), 5.51 (s, 1H), 4.65 (s, 1H), 4.25-4.03 (m, 2H), 3.95 (s, 6H), 3.86 (s, 3H), 3.16 (d, J=7.0 Hz, 3H), 2.97-2.62 (m, 3H), 2.23 (s, 6H), 1.93-1.47 (m, 7H). HRMS (ESI) for $C_{31}H_{38}Cl_2N_6O_5$ $[M+H]^+$ calcd: 645.2354, found: 645.2353.

Example 37: (E)-2-(cyclohexylamino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (136)

Compound 136 was prepared according to the general method of Scheme 2.
$^1$H NMR (500 MHz, DMSO-$d_6$) δ 8.59 (s, 1H), 7.89 (d, J=8.1 Hz, 1H), 7.63 (s, 1H), 6.97 (s, 1H), 6.75-6.53 (m, 2H), 4.67-4.57 (m, 1H), 4.23 (d, J=14.0 Hz, 1H), 3.95 (s, 6H), 3.67 (brs, 1H), 3.13-3.10 (m, 1H), 3.02 (d, J=4.9 Hz, 2H), 2.84-2.65 (m, 3H), 2.14 (s, 6H), 1.87 (brs, 2H), 1.73-1.65 (s, 4.6H), 1.51 (brs, 1H), 1.37-1.25 (m, 4.4H), 1.15-1.09 (d, J=11.2 Hz, 1H). HRMS (ESI) for $C_{32}H_{40}Cl_2N_6O_4$ $[M+H]^+$ calcd: 643.25609, found: 643.25611.

Example 38: (E)-6-(2,6-dichloro-3,5-dimethoxyphenyl)-8-(1-(4-(dimethylamino)-but-2-enoyl)piperidin-4-yl)-2-(((tetrahydro-2H-pyran-4-yl)methyl)amino)-pyrido[2,3-d]pyrimidin-7(8H)-one (137)

Compound 137 was prepared according to the general method of Scheme 2.
$^1$H NMR (500 MHz, DMSO-$d_6$) δ 8.66 (s, 0.1H), 8.60 (s, 0.9H), 8.08 (s, 0.9H), 7.90 (s, 0.1H), 7.64 (s, 1H), 6.97 (s, 1H), 6.82-6.45 (m, 2H), 5.56 (s, 1H), 4.62 (s, 1H), 4.21 (d, J=12.0 Hz, 1H), 3.95 (s, 6H), 3.83 (s, 2H), 3.24-3.13 (m, 4H), 3.03 (d, J=4.1 Hz, 2H), 2.73 (d, J=73.1 Hz, 3H), 2.14 (s, 6H), 1.84 (s, 1H), 1.76-1.50 (m, 4H), 1.29-1.05 (m, 3H). HRMS (ESI) for $C_{32}H_{40}Cl_2N_6O_5$ $[M+H]^+$ calcd: 659.2510, found: 659.2511.

Example 39: (E)-6-(2,6-dichloro-3,5-dimethoxyphenyl)-8-(1-(4-(dimethylamino)-but-2-enoyl)piperidin-4-yl)-2-(phenylamino)pyrido[2,3-d]pyrimidin-7(8H)-one (138)

Compound 138 was prepared according to the general method of Scheme 2.
$^1$H NMR (500 MHz, DMSO-$d_6$) δ 10.17 (s, 1H), 8.83 (s, 1H), 7.77 (s, 1H), 7.74 (d, J=7.8 Hz, 2H), 7.35 (s, 2H), 7.03 (s, 1H), 6.98 (s, 1H), 6.63 (s, 2H), 5.63 (s, 1H), 4.65 (s, 1H), 4.23 (d, J=13.4 Hz, 1H), 3.95 (s, 6H), 3.15-3.05 (m, 1H), 3.04-2.99 (m, 2H), 2.71-2.60 (m, 3H), 2.14 (s, 6H), 1.70-1.68 (m, 2H). HRMS (ESI) for $C_{32}H_{34}Cl_2N_6O_4$ $[M+H]^+$ calcd: 637.2091, found: 637.2086.

Example 40: (E)-6-(2,6-dichloro-3,5-dimethoxyphenyl)-8-(1-(4-(dimethylamino)-but-2-enoyl)piperidin-4-yl)-2-((4-fluorophenyl)amino)pyrido[2,3-d]pyrimidin-7(8H)-one (139)

Compound 139 was prepared according to the general method of Scheme 2.
$^1$H NMR (500 MHz, DMSO-$d_6$) δ 10.17 (s, 1H), 8.81 (d, J=2.2 Hz, 1H), 7.77 (d, J=2.1 Hz, 1H), 7.73 (s, 2H), 7.19 (s, 2H), 6.98 (d, J=2.2 Hz, 1H), 6.63 (s, 2H), 5.58 (s, 1H), 4.64 (s, 1H), 4.21 (d, J=13.6 Hz, 1H), 3.95 (s, 6H), 3.12-3.08 (m, 1H), 3.03 (s, 2H), 2.66-2.58 (m, 3H), 2.14 (s, 6H), 1.68 (d, J=11.0 Hz, 2H). HRMS (ESI) for $C_{32}H_{33}Cl_2FN_6O_4$ [M+H]$^+$ calcd: 655.1997, found: 655.1989.

Example 41: (E)-6-(2,6-dichloro-3,5-dimethoxyphenyl)-8-(1-(4-(dimethylamino)-but-2-enoyl)piperidin-4-yl)-2-((3-methoxyphenyl)amino)pyrido[2,3-d]pyrimidin-7(8H)-one (140)

Compound 140 was prepared according to the general method of Scheme 2.

$^1$H NMR (500 MHz, DMSO-d$_6$) δ 10.14 (s, 1H), 8.82 (s, 1H), 7.76 (s, 1H), 7.34-7.25 (m, 4H), 6.96 (s, 1H), 6.77-6.52 (m, 2H), 5.67 (s, 1H), 4.62 (d, J=12.1 Hz, 1H), 4.22 (d, J=13.4 Hz, 1H), 3.94 (s, 6H), 3.74 (s, 3H), 3.12 (d, J=13.4 Hz, 1H), 3.08-2.93 (m, 2H), 2.66 (d, J=14.0 Hz, 3H), 2.13 (s, 6H), 1.87-1.58 (m, 2H). HRMS (ESI) for $C_{33}H_{36}Cl_2N_6O_5$ [M+H]$^+$ calcd: 667.2197, found: 667.2165.

Example 42: (E)-6-(2,6-dichloro-3,5-dimethoxyphenyl)-8-(1-(4-(dimethylamino)-but-2-enoyl)piperidin-4-yl)-2-((4-fluoro-3-methoxyphenyl)amino)pyrido[2,3-d]-pyrimidin-7(8H)-one (141)

Compound 141 was prepared according to the general method of Scheme 2.

$^1$H NMR (500 MHz, DMSO-d$_6$) δ 10.09 (s, 1H), 8.82 (s, 1H), 7.77 (s, 1H), 7.45 (s, 1H), 7.36 (s, 1H), 7.20 (s, 1H), 6.98 (s, 1H), 6.62 (s, 2H), 5.60 (s, 1H), 4.63 (s, 1H), 4.21 (d, J=13.6 Hz, 1H), 3.95 (s, 6H), 3.83 (s, 3H), 3.10-3.05 (m, 1H), 3.02 (d, J=4.2 Hz, 2H), 2.64 (brs, 3H), 2.13 (s, 6H), 1.69-1.67 (m, 2H). HRMS (ESI) for $C_{33}H_{35}Cl_2FN_6O_5$ [M+H]$^+$ calcd: 685.2103, found: 685.2103.

Example 43: (E)-2-((3-chloro-4-fluorophenyl)amino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (142)

Compound 142 was prepared according to the general method of Scheme 2.

$^1$H NMR (500 MHz, DMSO-d$_6$) δ 10.36 (s, 1H), 8.86 (s, 1H), 8.13 (brs, 1H), 7.80 (s, 1H), 7.62 (s, 1H), 7.42 (s, 1H), 6.98 (s, 1H), 6.65-6.61 (m, 2H), 5.67-5.50 (m, 1H), 4.64 (d, J=12.6 Hz, 1H), 4.23 (d, J=13.0 Hz, 1H), 3.95 (s, 6H), 3.23-3.08 (m, 1H), 3.01 (d, J=4.6 Hz, 2H), 2.68-2.59 (m, 3H), 2.14 (s, 6H), 1.72-1.70 (m, 2H). HRMS (ESI) for $C_{32}H_{32}Cl_3FN_6O_4$ [M+H]$^+$ calcd: 689.1607, found: 689.1609.

Example 44: (E)-3-(2,6-dichloro-3,5-dimethoxyphenyl)-1-(1-(4-(dimethylamino)but-2-enoyl)piperidin-4-yl)-7-(methylamino)-1,6-naphthyridin-2(1H)-one (148)

Compound 148 was prepared according to the general method of Scheme 3.

M.p. 209-212° C. $^1$H NMR [(CD$_3$)$_2$SO] δ 8.38 (s, 1H), 7.61 (s, 1H), 7.02 (br, 1H), 7.01 (s, 1H), 6.66-6.58 (m, 2H), 6.50 (s, 1H), 4.60-4.55 (m, 1H), 4.20-4.16 (m, 1H), 3.37 (s, 6H), 3.27-3.19 (m, 2H), 3.03 (d, J=4.7 Hz, 2H), 2.83-2.60 (m, 4H), 2.14 (s, 6H), 1.70-1.68 (m, 2H). HRMS (ESI) calc: for $C_{28}H_{33}Cl_2N_5O_4$ (M+H) m/z 574.1982, found: 574.1994.

Example 45: (E)-3-(2,6-dichloro-3,5-dimethoxyphenyl)-1-(1-(4-(dimethylamino)but-2-enoyl)piperidin-4-yl)-7-(isopropylamino)-1,6-naphthyridin-2(1H)-one (149)

Compound 149 was prepared according to the general method of Scheme 3.

M.p. 243-246° C. $^1$H NMR [(CD$_3$)$_2$SO] δ 8.36 (s, 1H), 7.59 (s, 1H), 6.95 (s, 1H), 6.90 (br, 1H), 6.67-6.57 (m, 2H), 6.55 (s, 1H), 4.60-4.58 (m, 1H), 4.21-4.12 (m, 2H), 3.94 (s, 6H), 3.27-3.12 (m, 1H), 3.02 (d, J=4.7 Hz, 2H), 2.75-2.55 (m, 4H), 2.14 (s, 6H), 1.70-1.67 (m, 2H), 1.17 (d, J=6.4 Hz, 6H). HRMS (ESI) calc: for $C_{30}H_{37}Cl_2N_5O_4$ (M+H) m/z 602.2295, found: 602.2296.

Example 46: (E)-6-(2,6-dibromo-3,5-dimethoxyphenyl)-8-(1-(4-(dimethylamino)-but-2-enoyl)piperidin-4-yl)-2-(phenylamino)pyrido[2,3-d]pyrimidin-7(8H)-one (152)

Compound 152 was prepared according to a synthetic route similar to the general method of Scheme 2.

$^1$H NMR (500 MHz, DMSO-d$_6$) δ 10.18 (s, 1H), 8.83 (s, 1H), 7.74 (d, J=8.1 Hz, 2H), 7.69 (s, 1H), 7.35 (s, 2H), 7.03 (s, 1H), 6.92 (s, 1H), 6.63 (s, 2H), 5.64 (brs, 1H), 4.66 (m, 1H), 4.23 (d, J=13.6 Hz, 1H), 3.95 (s, 6H), 3.09 (t, J=13.8 Hz, 1H), 3.05-2.99 (m, 2H), 2.65 (brs, 3H), 2.14 (s, 6H), 1.69 (d, J=10.5 Hz, 2H). HRMS (ESI) for $C_{32}H_{34}Br_2N_6O_4$ [M+H]$^+$ calcd: 727.1064, found: 727.1070.

Example 47: (E)-6-(2,6-dibromo-3,5-dimethoxyphenyl)-8-(1-(4-(dimethylamino)-but-2-enoyl)piperidin-4-yl)-2-(isopropylamino)pyrido[2,3-d]pyrimidin-7(8H)-one (153)

Compound 153 was prepared according to a synthetic route similar to the general method of Scheme 2.

$^1$H NMR (500 MHz, DMSO-d$_6$) δ 8.63 (d, J=31.6 Hz, 1H), 7.84 (s, 0.08H), 7.67 (s, 0.2H), 7.55 (s, 1H), 6.91 (s, 1H), 6.64 (s, 2H), 5.54 (brs, 1H), 4.92-4.56 (m, 1H), 4.21 (s, 1H), 3.94 (s, 7H), 3.16-2.69 (m, 6H), 2.14 (s, 6H), 1.63 (d, J=22.8 Hz, 2H), 1.17 (d, J=22.6 Hz, 6H). HRMS (ESI) for $C_{29}H_{36}Br_2N_6O_4$ [M+H]$^+$ calcd: 693.1220, found: 693.1229.

Example 48: (E)-N-(3-((6-(2,6-dichloro-3,5-dimethoxyphenyl)-2-(methylamino)-7-oxopyrido[2,3-d]pyrimidin-8(7H)-yl)methyl)phenyl)-4-(dimethylamino)but-2-enamide (143)

A synthetic route for the preparation of compound 143 is outlined in Scheme 9.

Scheme 9:

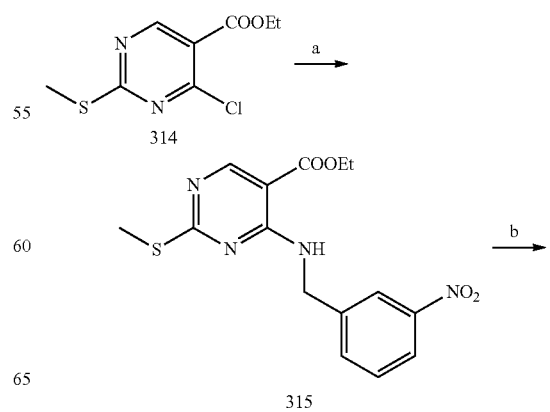

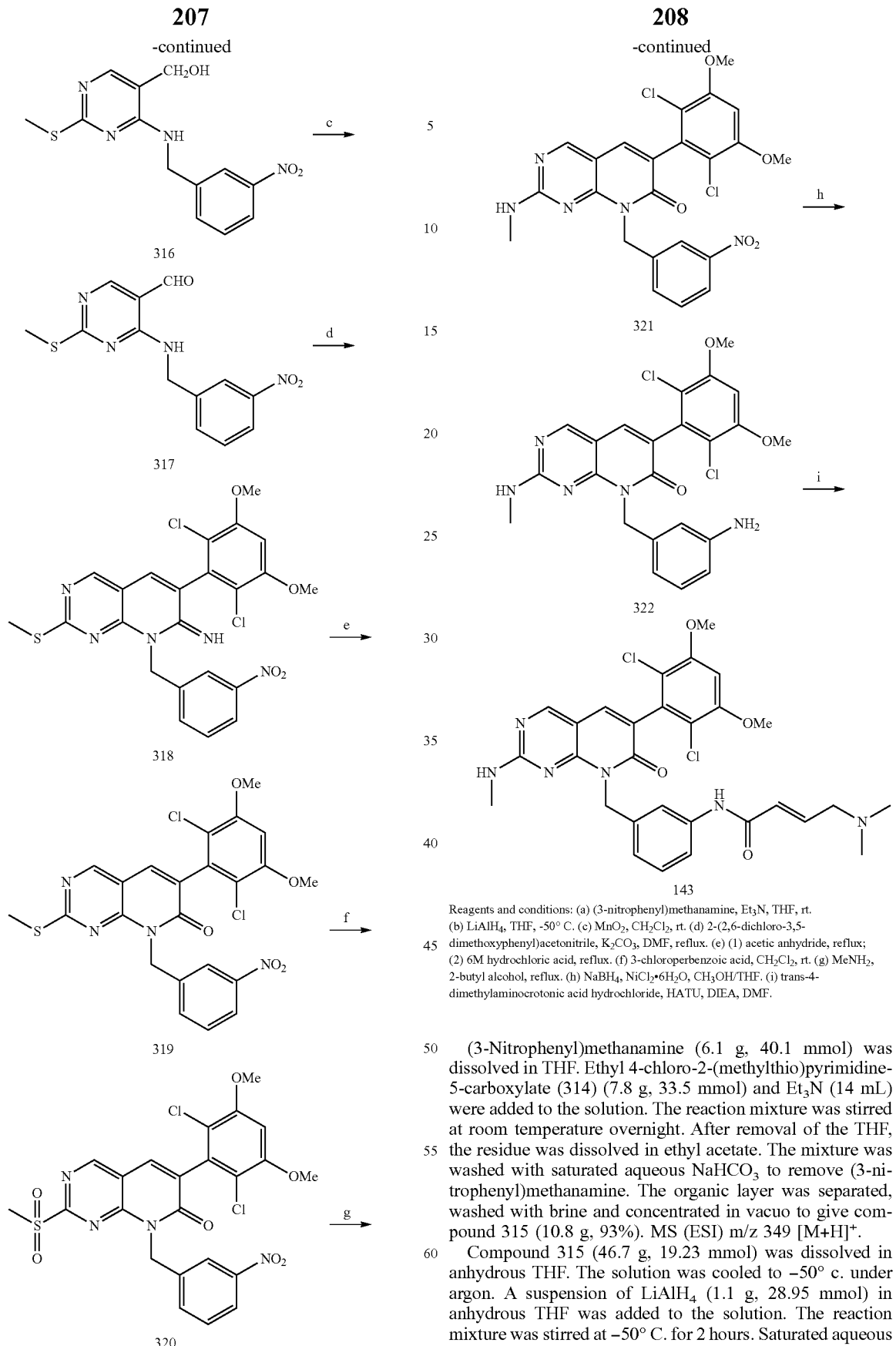

Reagents and conditions: (a) (3-nitrophenyl)methanamine, Et₃N, THF, rt. (b) LiAlH₄, THF, -50° C. (c) MnO₂, CH₂Cl₂, rt. (d) 2-(2,6-dichloro-3,5-dimethoxyphenyl)acetonitrile, K₂CO₃, DMF, reflux. (e) (1) acetic anhydride, reflux; (2) 6M hydrochloric acid, reflux. (f) 3-chloroperbenzoic acid, CH₂Cl₂, rt. (g) MeNH₂, 2-butyl alcohol, reflux. (h) NaBH₄, NiCl₂·6H₂O, CH₃OH/THF. (i) trans-4-dimethylaminocrotonic acid hydrochloride, HATU, DIEA, DMF.

(3-Nitrophenyl)methanamine (6.1 g, 40.1 mmol) was dissolved in THF. Ethyl 4-chloro-2-(methylthio)pyrimidine-5-carboxylate (314) (7.8 g, 33.5 mmol) and Et₃N (14 mL) were added to the solution. The reaction mixture was stirred at room temperature overnight. After removal of the THF, the residue was dissolved in ethyl acetate. The mixture was washed with saturated aqueous NaHCO₃ to remove (3-nitrophenyl)methanamine. The organic layer was separated, washed with brine and concentrated in vacuo to give compound 315 (10.8 g, 93%). MS (ESI) m/z 349 [M+H]⁺.

Compound 315 (46.7 g, 19.23 mmol) was dissolved in anhydrous THF. The solution was cooled to −50° c. under argon. A suspension of LiAlH₄ (1.1 g, 28.95 mmol) in anhydrous THF was added to the solution. The reaction mixture was stirred at −50° C. for 2 hours. Saturated aqueous NH₄Cl was added to the reaction mixture. The resulting mixture was filtered through Celite. The Celite was washed with CH₂Cl₂. The organic layer was separated, washed with brine and concentrated in vacuo. The crude product was purified by column to give compound 316 (2.3 g, 39%). $^1$H NMR (400 MHz, DMSO-d6) δ 8.21 (s, 1H), 8.09 (d, J=8.1 Hz, 1H), 7.88 (s, 1H), 7.79 (d, J=7.5 Hz, 1H), 7.61 (t, J=7.3 Hz, 2H), 5.15 (t, J=5.1 Hz, 1H), 4.69 (d, J=5.8 Hz, 2H), 4.38 (d, J=5.2 Hz, 2H), 2.31 (s, 3H). MS (ESI) m/z 307 [M+H]$^+$.

MnO$_2$ (782 mg) was added to a stirred solution of compound 316 (306 mg) in CH$_2$Cl$_2$. The reaction mixture was stirred at room temperature overnight. The mixture was filtered through Celite and the solution was concentrated in vacuo. The crude product was subjected to column chromatography to give compound 317 (284 mg, 93%). $^1$H NMR (400 MHz, CDCl$_3$-d) δ 9.76 (s, 1H), 9.09 (s, 1H), 8.38 (s, 1H), 8.17 (d, J=26.4 Hz, 2H), 7.65 (s, 1H), 7.53 (s, 1H), 4.88 (d, J=6.0 Hz, 2H), 2.48 (s, 3H). MS (ESI) m/z 305 [M+H]$^+$.

To a solution of compound 317 (204 mg) and 2-(2,6-dichloro-3,5-dimethoxyphenyl)acetonitrile (200 mg) in DMF was added K$_2$CO$_3$ (400 mg). The reaction mixture was heated at reflux overnight. After removal of DMF, CH$_2$Cl$_2$ was added to dissolve the residue. The mixture was washed with water. The organic layer was separated, washed with brine and concentrated. The resulting product was purified by column chromatography to afford compound 318 (100 mg, 28%). $^1$H NMR (400 MHz, CDCl$_3$) δ 8.46 (s, 1H), 8.26 (s, 1H), 8.10 (d, J=7.4 Hz, 1H), 7.84 (d, J=7.5 Hz, 1H), 7.48 (t, J=8.0 Hz, 1H), 7.16 (s, 1H), 6.88 (s, 1H), 6.69 (s, 1H), 5.99 (s, 2H), 3.98 (s, 6H), 2.56 (s, 3H). MS (ESI) m/z 532 [M+H]$^+$.

Compound 318 (460 mg) was dissolved in acetic anhydride. The mixture was heated at reflux for 30 minutes. After removal of the acetic anhydride, 6 M hydrochloric acid was added to dissolve the residue. The reaction mixture was heated at reflux for 30 minutes. After cooling to room temperature, the reaction mixture was basified with saturated aqueous NaHCO$_3$ and extracted with CH$_2$Cl$_2$. The organic phase was separated, dried and concentrated in vacuo. The resulting residue was purified by column chromatography to afford compound 319 (378 mg, 80%). $^1$H NMR (400 MHz, DMSO) δ 8.97 (s, 1H), 8.13 (d, J=8.9 Hz, 2H), 8.07 (s, 1H), 7.80 (d, J=7.7 Hz, 1H), 7.65 (t, J=7.7 Hz, 1H), 7.03 (s, 1H), 5.71 (s, 2H), 3.98 (s, 6H), 2.56 (s, 3H). MS (ESI) m/z 533 [M+H]$^+$.

Compound 319 (100 mg) and m-CPBA (71 mg) were dissolved in CH$_2$Cl$_2$. The reaction mixture was stirred at room temperature overnight. Saturated aqueous Na$_2$S$_2$O$_3$ was added to the reaction mixture. The organic layer was separated, dried and concentrated in vacuo. The residue was purified by column chromatography to give compound 320 (76 mg, 72%). MS (ESI) m/z 565 [M+H]$^+$.

Compound 320 (76 mg) and methylamine hydrochloride (18 mg) were dissolved in 2-butyl alcohol. Et$_3$N (55 µL) was added to the solution. The reaction was heated at reflux overnight. After removal of the solvent, the residue was dissolved in CH$_2$Cl$_2$ and saturated aqueous NaHCO$_3$ was added. The organic layer was separated, washed with brine and concentrated. The resulting product was subjected to column chromatography to giving compound 321 (57 mg, 81%). $^1$H NMR (400 MHz, DMSO) δ 8.75 (s, 1H), 8.65 (s, 1H), 8.22 (s, 1H), 8.11 (d, J=7.2 Hz, 1H), 7.98 (s, 1H), 7.86 (d, J=7.7 Hz, 1H), 7.78 (s, 1H), 7.65 (d, J=7.1 Hz, 1H), 6.99 (s, 1H), 5.63 (s, 1H), 5.56 (s, 1H), 3.96 (s, 6H), 2.88 (d, J=3.9 Hz, 3H). MS (ESI) m/z 516 [M+H]$^+$.

Compound 321 (500 mg) and NiCl$_2$.6H$_2$O (576 mg) were dissolved in CH$_3$OH/THF (1:1, v/v). NaBH$_4$ (367 mg) was added to the reaction mixture at 0° C. in three portions. The reaction mixture was stirred for 30 minutes. After the completion of the reaction, saturated aqueous NH$_4$Cl was added. The resulting mixture was filtered through Celite. The Celite was washed with CH$_2$Cl$_2$. The organic layer was separated, washed with brine and concentrated in vacuo. The crude product was purified by column chromatography to give compound 322 (176 mg, 37%). $^1$H NMR (400 MHz, DMSO) δ 8.72 (s, 1H), 8.62 (s, 1H), 7.95 (s, 1H), 7.87 (d, J=4.9 Hz, 1H), 7.71 (s, 1H), 6.98 (s, 1H), 6.89 (t, J=7.8 Hz, 1H), 6.55 (s, 1H), 6.48 (d, J=7.4 Hz, 1H), 6.39 (d, J=7.5 Hz, 1H), 5.33 (d, J=18.8 Hz, 2H), 4.96 (s, 2H), 3.95 (s, 6H), 2.88 (d, J=6.1 Hz, 3H). MS (ESI) m/z 486 [M+H]$^+$.

Compound 322 (176 mg), trans-4-Dimethylaminocrotonic acid hydrochloride (89 mg) and HATU (176 mg) were dissolved in DMF (0.2 mL). DIEA (0.26 mL) was added to the solution. The reaction mixture was stirred at room temperature overnight. Water was added to the mixture and the mixture was then extracted with CH$_2$Cl$_2$. The organic layer was concentrated in vacuo. The residue was purified by column chromatography to give the title compound 143 (100 mg, 47%). $^1$H NMR (400 MHz, DMSO) δ 9.98 (s, 1H), 8.75 (s, 1H), 8.64 (s, 1H), 7.89 (d, J=4.4 Hz, 1H), 7.72 (d, J=14.4 Hz, 2H), 7.51 (d, J=7.7 Hz, 1H), 7.21 (t, J=7.9 Hz, 1H), 7.03 (d, J=7.4 Hz, 1H), 6.98 (s, 1H), 6.69 (dt, J=15.3, 5.9 Hz, 1H), 6.24 (d, J=15.4 Hz, 1H), 5.45 (d, J=20.7 Hz, 2H), 3.95 (s, 6H), 3.03 (d, J=5.5 Hz, 2H), 2.87 (d, J=4.5 Hz, 3H), 2.16 (s, 6H). MS (ESI) m/z 597 [M+H]$^+$.

Example 49: (E)-N-(3-((6-(2,6-dichloro-3,5-dimethoxyphenyl)-2-(ethylamino)-7-oxopyrido[2,3-d]pyrimidin-8(7H)-yl)methyl)phenyl)-4-(dimethylamino)but-2-enamide (144)

Compound 144 was prepared according to the general method of Scheme 5.

$^1$H NMR (400 MHz, DMSO) δ 9.99 (s, 1H), 8.73 (s, 1H), 8.64 (s, 1H), 7.97 (t, J=5.7 Hz, 1H), 7.79 (s, 1H), 7.73 (s, 1H), 7.69 (s, 1H), 7.61-7.43 (m, 1H), 7.21 (t, J=7.9 Hz, 1H), 6.97 (d, J=10.3 Hz, 2H), 6.70 (dt, J=15.4, 5.9 Hz, 1H), 6.24 (d, J=15.4 Hz, 1H), 5.45 (s, 2H), 3.95 (s, 6H), 3.04 (d, J=4.9 Hz, 2H), 2.17 (s, 6H), 1.17-1.00 (m, 3H). MS (ESI) m/z 611 [M+H]$^+$.

Example 50: (E)-N-(3-((6-(2,6-dichloro-3,5-dimethoxyphenyl)-2-(isopropylamino)-7-oxopyrido[2,3-d]pyrimidin-8(7H)-yl)methyl)phenyl)-4-(dimethylamino)but-2-enamide (145)

Compound 145 was prepared according to the general method of Scheme 5.

$^1$H NMR (400 MHz, DMSO) δ 9.99 (s, 1H), 8.72 (s, 1H), 8.63 (s, 1H), 7.86 (d, J=7.4 Hz, 1H), 7.73 (s, 2H), 7.62 (s, 1H), 7.45 (d, J=7.7 Hz, 1H), 7.20 (t, J=7.8 Hz, 1H), 6.98 (s, 1H), 6.94 (d, J=7.7 Hz, 1H), 6.70 (dt, J=15.0, 5.7 Hz, 1H), 6.24 (d, J=15.6 Hz, 1H), 5.43 (s, 2H), 4.07 (d, J=5.9 Hz, 1H), 3.95 (s, 6H), 3.04 (d, J=5.7 Hz, 2H), 2.16 (s, 6H), 1.11 (t, J=16.3 Hz, 6H). MS (ESI) m/z 625 [M+H]$^+$.

Example 51: (E)-N-(3-(1-(6-(2,6-dichloro-3,5-dimethoxyphenyl)-2-(methylamino)-7-oxopyrido[2,3-d]pyrimidin-8(7H)-yl)ethyl)phenyl)-4-(dimethylamino)but-2-enamide (146)

Compound 146 was prepared according to the general method of Scheme 5.

$^1$H NMR (400 MHz, DMSO) δ 10.08 (s, 1H), 8.73 (s, 1H), 8.60 (s, 1H), 7.69 (s, 2H), 7.57 (d, J=20.9 Hz, 2H), 7.21 (t, J=7.7 Hz, 1H), 6.96 (s, 2H), 6.73-6.61 (m, 1H), 6.30 (d,

J=15.3 Hz, 1H), 3.95 (s, 6H), 3.41 (s, 4H), 2.90 (s, 2H), 2.43 (s, 6H), 1.91 (s, 3H). MS (ESI) m/z 611 [M+H]$^+$.

Example 52: (E)-3-(2,6-dibromo-3,5-dimethoxyphenyl)-1-(1-(4-(dimethylamino)but-2-enoyl)piperidin-4-yl)-7-(isopropylamino)-1,6-naphthyridin-2(1H)-one (155)

Compound 155 was prepared according to a synthetic route similar to the general method of Scheme 3.

M.p. 251-254° C. $^1$H NMR [(CD$_3$)$_2$SO] δ 8.36 (s, 1H), 7.50 (s, 1H), 6.89 (s, 1H), 6.85 (br, 1H), 6.67-6.57 (m, 2H), 6.55 (s, 1H), 4.60-4.58 (m, 1H), 4.22-3.98 (m, 2H), 3.93 (s, 6H), 3.20-3.14 (m, 1H), 3.02 (d, J=4.7 Hz, 2H), 2.76-2.59 (m, 4H), 2.14 (s, 6H), 1.70-1.67 (m, 2H), 1.17 (d, J=6.4 Hz, 6H). HRMS (ESI) calc. for C$_{30}$H$_{37}$Br$_2$N$_5$O$_4$ (M+H) m/z 690.1285, found: 690.1287.

Example 53: (E)-3-(2,6-dichloro-3,5-dimethoxyphenyl)-1-(1-(4-(dimethylamino)but-2-enoyl)piperidin-4-yl)-7-(pyridin-2-ylamino)-3,4-dihydropyrimido[4,5-d]pyrimidin-2(1H)-one (157)

A synthetic route for the preparation of compound 157 is outlined in Scheme 10.

Scheme 10:

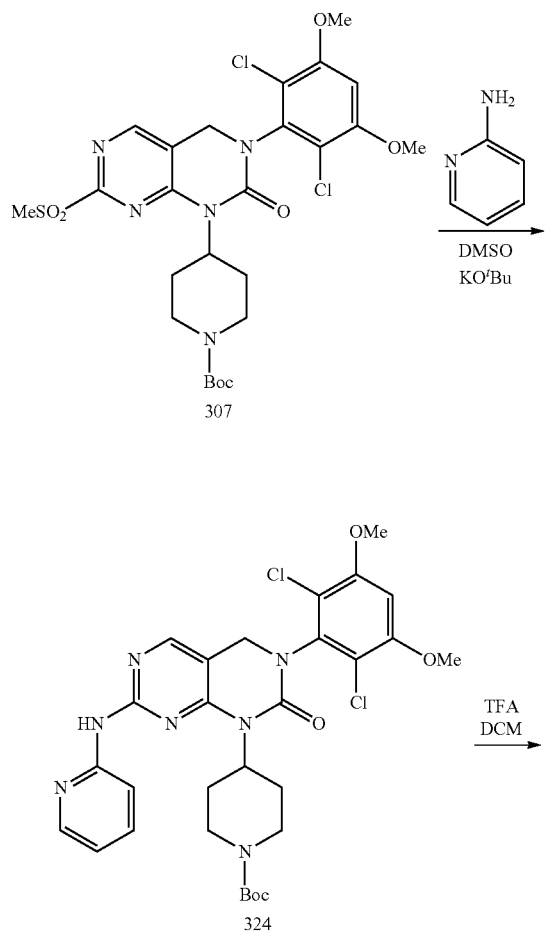

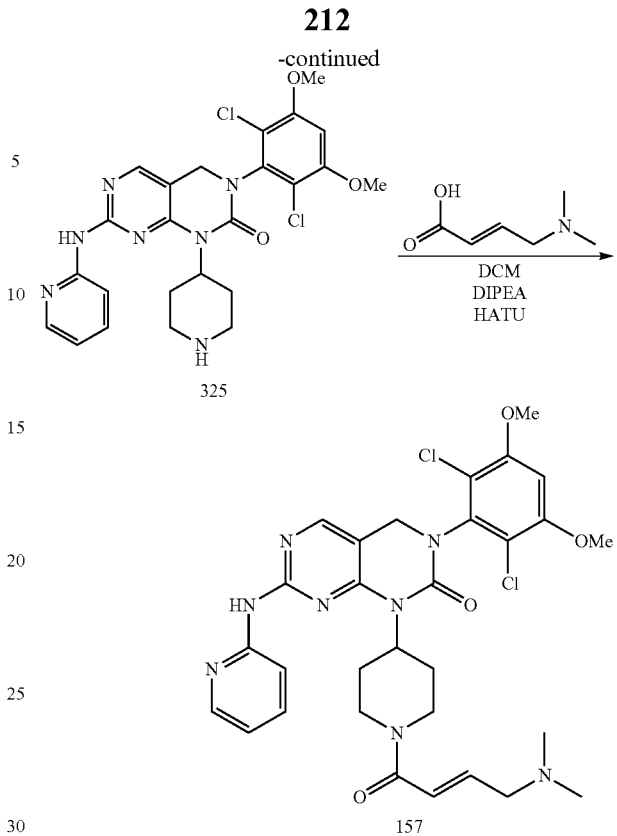

tert-butyl 4-(3-(2,6-dichloro-3,5-dimethoxyphenyl)-2-oxo-7-(pyridin-2-ylamino)-3,4-dihydropyrimido[4,5-d]pyrimidin-1(2H)-yl)piperidine-1-carboxylate (324)

A mixture of 307 (514 mg, 0.83 mmol) and 2-aminopyridine (157 mg, 1.66 mmol) and KO$^t$Bu (186 mg, 1.65 mmol) in DMSO (2 mL) was stirred at 20° C. for 2 hr. TLC and mass spec showed the reaction was complete. The reaction mixture was diluted with H$_2$O (100 mL) and stirred for 30 min. The resulting precipitate was filtered and washed with water before being dried at 100° C. to give essentially pure 324 (508 mg, 97%). $^1$H NMR [CD$_3$)$_2$SO] δ 9.80 (s, 1H), 8.29-8.24 (m 1H), 8.24 (s, 1H), 8.12 (d, J=8.5 Hz, 1H), 7.78-7.74 (m, 1H), 7.00-6.97 (m, 2H), 4.83-4.76 (m, 1H), 4.51 (s, 2H), 4.15-4.04 (brm, 2H), 3.96 (s, 6H), 2.88-2.71 (brm, 2H), 2.50-2.39 (m, 2H), 1.70-1.67 (m, 2H), 1.40 (s, 9H).

3-(2,6-dichloro-3,5-dimethoxyphenyl)-1-(piperidin-4-yl)-7-(pyridin-2-ylamino)-3,4-dihydropyrimido[4,5-d]pyrimidin-2(1H)-one (325)

To a solution of compound 324 (507 mg, 0.8 mmol) in DCM (15 mL) was added TFA (2 mL). The reaction mixture was stirred overnight at 20° C. The solvents and the excess TFA were evaporated at room temperature and the resulting oily residue was stirred in saturated aq KHCO$_3$ (20 mL). The resulting solid was collected by filtration and washed with water, dried and recrystallized from DCM/petroleum ether to give 325 (333 mg, 78%). $^1$H NMR[CD$_3$)$_2$SO] δ 9.76 (s, 1H), 8.30-8.24 (m, 1H), 8.24 (s, 1H), 7.77-7.73 (m, 1H), 7.02-6.99 (m, 2H), 4.69 (brm, 1H), 4.50 (s, 2H), 3.96 (s, 6H), 3.10-3.08 (m, 2H), 2.67-2.54 (m, 4H), 1.62-1.60 (m, 2H).

(E)-3-(2,6-dichloro-3,5-dimethoxyphenyl)-1-(1-(4-(dimethylamino)but-2-enoyl)piperidin-4-yl)-7-(pyridin-2-ylamino)-3,4-dihydropyrimido[4,5-d]pyrimidin-2(1H)-one (157)

A mixture of compound 325 (319 mg, 0.6 mmol), (E)-4-(dimethylamino)but-2-enoic acid (130 mg, 0.98 mmol, 1.6 eq) and DIPEA (0.41 mL, 2.3 mmol, 3.8 eq) in DCM (15 mL) was stirred at 20° C. for 2 hr. TLC and mass spec. showed the reaction was complete. The solvent was removed at room temperature and the residue was stirred in saturated KHCO$_3$. The resulting precipitate was collected by filtration, washed with H$_2$O and purified by chromatography on SiO$_2$ gel eluting initially with DCM/EtOAc (50:50) followed by DCM/MeOH 0-2% then DCM/MeOH 2-3% with 1% aq NH$_3$ to elute the desired product. Combined fractions of the desired product were evaporated to dryness and recrystallized from DCM/petroleum ether to give 157 (282 mg, 99%), mp (DCM/pet.ether) 224-227° C.; HPLC 95.6%; $^1$H NMR NMR[CD$_3$)$_2$SO] δ 9.80 (s, 1H), 8.28-8.27 (m, 1H), 8.24 (s, 1H), 8.10 (d, J=8.5 Hz, 1H), 7.77-7.29 (m, 1H), 6.98 (s, 1H), 6.98-6.98 (m, 1H), 6.66-6.57 (m, 2H), 4.90-4.84 (m, 1H), 4.61-4.58 (m, 2H), 4.51 (s, 2H), 4.19-4.16 (m, 2H), 3.95 (s, 6H), 3.10-3.03 (m, 4H), 2.14 (s, 6H), 1.78-1.75 (m, 2H), HRMS calcd. for C$_{30}$H$_{34}$Cl$_2$N$_8$O$_4$: ESI m/z 641.2153; found 641.2152.

Example 54: (E)-3-(2,6-dichloro-3,5-dimethoxyphenyl)-1-(1-(4-(dimethylamino)but-2-enoyl)piperidin-4-yl)-7-(pyridin-3-ylamino)-3,4-dihydropyrimido[4,5-d]pyrimidin-2(1H)-one (158)

Compound 158 was prepared according to the general method of Scheme 1.
MP (DCM/Petrolium ether) 207-209° C.; $^1$H NMR [(CD$_3$)$_2$SO] δ 9.79 (s, 1H), 8.83 (d, J=2.2 Hz, 1H), 8.22 (s, 1H), 8.16-8.13 (m, 2H), 7.32 (dd, J=8.5, 4.8 Hz, 1H), 6.99 (s, 1H), 6.65-6.55 (m, 2H), 4.90-4.8 (m, 1H), 4.61-4.57 (brm, 1H), 4.49 (s, 2H), 4.23-4.18 (brm, 1H), 3.95 (s, 6H), 3.10 (d, J=4.6 Hz, 2H), 2.64-2.60 (m, 2H), 2.44-2.33 m (2H), 2.13 (s, 6H), 1.79-1.76 (m, 2H). HPLC 98.1%, HRMS calcd. for C$_{30}$H$_{34}$Cl$_2$N$_8$O$_4$: m/z 641.2152 found 641.2149.

Example 55: (E)-3-(2,6-dichloro-3,5-dimethoxyphenyl)-1-(1-(4-(dimethylamino)but-2-enoyl)piperidin-4-yl)-7-(pyridin-4-ylamino)-3,4-dihydropyrimido[4,5-d]pyrimidin-2(1H)-one (159)

Compound 159 was prepared according to the general method of Scheme 1.
MP (DCM/petroleum ether) >300° C., $^1$H NMR [(CD$_3$)$_2$SO] δ 10.07 (s, 1H), 8.36 (dd, J=5.0, 1.4 Hz, 2H), 8.29 (s, 1H), 7.69 (dd, J=4.9, 1.5 Hz, 2H), 6.99 (s, 1H), 3.69-6.57 (m, 2H), 4.92-4.81 (m, 1H), 4.64-4.61 (m, 1H), 4.52 (s, 2H), 4.23-4.20 (m, 1H), 3.95 (s, 6H), 3.08 (d, J=5.4 Hz, 2H), 2.73-2.66 (m, 2H), 2.46-2.39 (m, 2H), 2.18 (s, 6H), 1.82-1.80 (m, 2H), HPLC 99.3%, HRMS calcd. for C$_{30}$H$_{34}$Cl$_2$N$_8$O$_4$: m/z 641.2152 found 641.2152.

Example 56: (E)-3-(2,6-dichloro-3,5-dimethoxyphenyl)-1-(1-(4-(dimethylamino)but-2-enoyl)piperidin-4-yl)-7-((1-methyl-1H-pyrazol-3-yl)amino)-3,4-dihydropyrimido[4,5-d]pyrimidin-2(1H)-one (160)

Compound 160 was prepared according to the general method of Scheme 1.
MP 203° C. gas evolved, $^1$H NMR [(CD$_3$)$_2$SO] δ 9.67 (s, 1H), 8.12 (s, 1H), 7.50 (d, J=2.1 Hz, 1H), 6.98 (s, 1H), 6.65-6.56 (m, 2H), 6.44 (d, J=2.1 Hz, 1H), 4.89-4.81 (m, 1H), 4.60-4.56 (m, 1H), 4.45 (s, 2H), 4.19-4.15 (m, 1H), 3.95 (s, 6H), 3.73 (s, 3H), 3.03-3.02 (m, 2H), 2.65-2.37 (m, 4H), 2.14 (s, 6H), 1.74-1.71 M, 2H). HRMS calcd. for C$_{29}$H$_{35}$Cl$_2$N$_9$O$_4$: m/z 644.2261 found 644.2266.

Example 57: (E)-3-(2,6-dichloro-3,5-dimethoxyphenyl)-1-(1-(4-(dimethylamino)but-2-enoyl)piperidin-4-yl)-7-((6-morpholinopyridin-3-yl)amino)-3,4-dihydropyrimido[4,5-d]pyrimidin-2(1H)-one (161)

Compound 161 was prepared according to the general method of Scheme 1.
$^1$H NMR [(CD$_3$)$_2$SO] δ 9.38 (brs, 1H), 8.34 (d, J=2.5 Hz, 1H), 8.12 (s, 1H), 7.92 (dd, J=9.1, 2.7 Hz, 1H), 6.98 (s 1H), 6.81 (d, J=9.1 Hz, 1H), 6.64-6.54 (m, 2H), 4.85-4.76 (m, 1H), 4.59-4.56 (s, 1H), 4.45 (d, J=1.6 hz, 2H), 4.19-4.15 (m, 1H), 3.95 (s, 6H), 3.71-3.69 (m, 4H), 3.36-3.34 9m, 4H), 3.14-3.00 (m, 3H), 2.65-2.58 (m, 1H), 2.44-2.36 (m, 2H), 2.13 (s, 6H), 1.75-1.73 (m, 2H); HPLC 96.8%.

Example 58: (E)-3-(2,6-dichloro-3,5-dimethoxyphenyl)-1-(1-(4-(dimethylamino)but-2-enoyl)piperidin-4-yl)-7-(pyrimidin-4-ylamino)-3,4-dihydropyrimido[4,5-d]pyrimidin-2(1H)-one (162)

Compound 162 was prepared according to the general method of Scheme 1.
$^1$H NMR [(CD$_3$)$_2$SO] δ 10.52 (s, 1H), 8.78 (s, 1H), 8.56 (d, J=5.9 Hz, 1H), 8.33 (s, 1H), 8.13 (dd, J=5.9, 1.0 Hz, 1H), 7.00 (s, 1H), 6.84 (d, J=15.1 Hz, 1H), 6.60 (td, J=14.2, 6.8 Hz, 1H), 4.93-4.85 (m, 1H), 4.62-4.58 (m, 1H), 4.56 (s, 2H), 4.22-4.16 (m, 1H), 3.95 (s, 6H), 3.57 (brm, 2H), 3.20-3.13 (m, 2H), 2.76-2.73 (m, 2H), 1.83-1.79 (m, 2H), $^1$H signal for N(CH$_3$)$_2$ obscured by DMSO signal. LCMS (M$^{+1}$) 642.2.

Example 59: (E)-4-(4-(3-(2,6-dichloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (204)

A synthetic route for the preparation of compound 204 is outlined in Scheme 11.

Scheme 11:

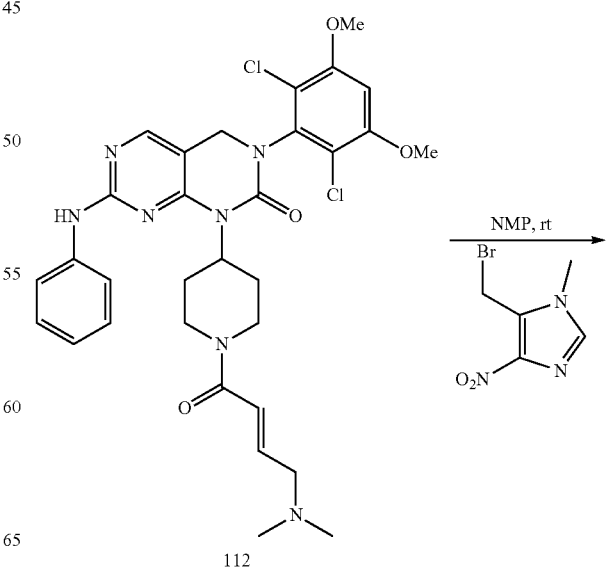

112

215
-continued

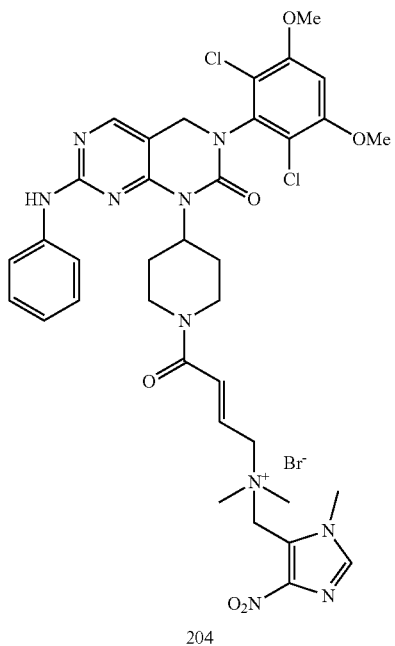

204

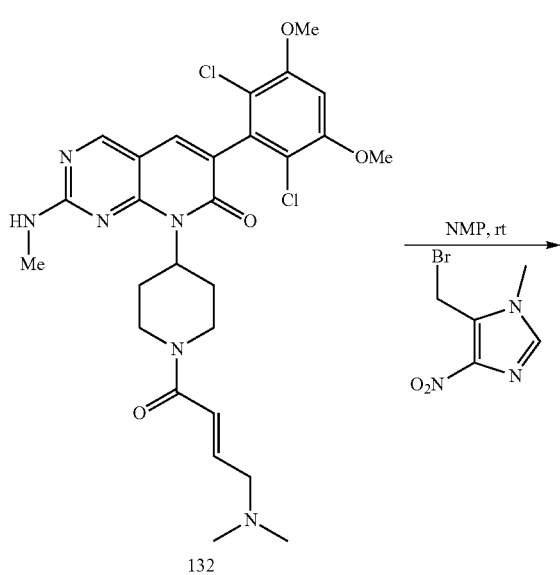

132

216
-continued

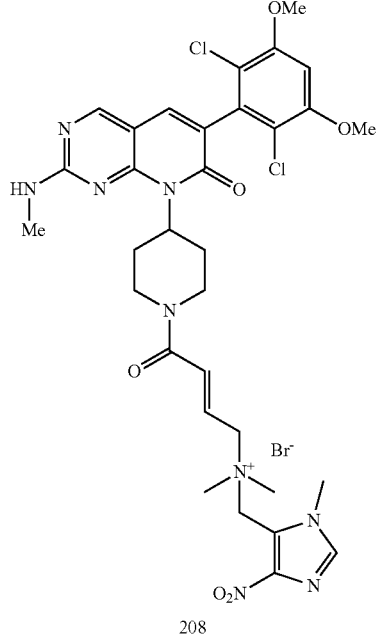 [SMILES: CNc1ncc2cc(-c3c(Cl)c(OC)cc(OC)c3Cl)c(=O)n(C3CCN(C(=O)/C=C/C[N+](C)(C)Cc4c([N+](=O)[O-])ncn4C)CC3)c2n1 ; [Br-]]

208

Compound 112 (451 mg, 704.1 mmol) was dissolved in dry NMP (4.5 mL) and 5-(bromomethyl)-1-methyl-4-nitro-1H-imidazole (178.1 mg, 809.4 mmol) was added. The mixture was stirred at room temperature under nitrogen for 48 hours. CH$_2$Cl$_2$ (1.5 mL) was added to dilute the mixture followed by diethylether (5 mL). The precipitate was collected by filtration and dried in a vacuum oven overnight. The crude product was triturated with CH$_2$Cl$_2$/ether (3:2, v/v) to afford compound 204 (459.2 mg, 76%), m.p. 189-192° C. $^1$H NMR (400 MHz, DMSO-d$_6$) δ 9.62 (s, 1H), 8.20 (s, 1H), 8.12 (s, 1H), 7.70-7.68 (m, 2H), 7.30-7.27 (m, 2H), 7.06 (d, J=14.8 Hz, 1H), 6.99 (s, 1H), 6.97-6.93 (m, 1H), 6.80-6.73 (m, 1H), 5.00 (br, 2H), 4.93-4.87 (m, 1H), 4.64-4.61 (m, 1H), 4.49-4.48 (m, 2H), 4.28-4.26 (m, 2H), 4.17-4.13 (m, 1H), 3.95 (s, 6H), 3.84 (s, 3H), 3.18-3.12 (m, 1H), 3.06 (s, 6H), 2.74-2.67 (m, 2H), 2.45-2.42 (m, 1H), 1.83-1.80 (m, 2H). HRMS (ESI) for C$_{36}$H$_{41}$Cl$_2$N$_{10}$O$_6$ [M]$^+$ calcd: 779.2582, found: 779.2581.

Example 60: (E)-4-(4-(6-(2,6-dichloro-3,5-dimethoxyphenyl)-2-(methylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (208)

A synthetic route for the preparation of compound 208 is outlined in Scheme 11.

Compound 132 (0.3 g, 0.52 mmol) was dissolved in dry NMP (1.0 mL) and 5-(bromomethyl)-1-methyl-4-nitro-1H-imidazole (0.11 g, 0.52 mmol) was added. The mixture was stirred at room temperature under nitrogen for 24 hours. CH$_2$Cl$_2$ (0.5 mL) was added to dilute the mixture followed by diethylether (5 mL). The precipitate was collected by filtration and dried in a vacuum oven overnight. The crude product was triturated with CH$_2$Cl$_2$/ether (3:1, v/v) to afford compound 208 (333 mg, 80%). $^1$H NMR (400 MHz, DMSO-d$_6$) δ 8.70 (s, 0.22H), 8.61 (s, 0.78H), 8.13 (s, 1H), 7.90 (d, J=5.2 Hz, 0.78H), 7.74 (s, 0.22H), 7.66 (s, 1H), 7.09 (d, J=14.9 Hz, 1H), 6.97 (s, 1H), 6.77 (dt, J=14.7, 7.3 Hz, 1H), 5.64 (s, 1H), 5.01 (s, 2H), 4.59 (d, J=10.6 Hz, 1H), 4.28

(d, J=7.5 Hz, 2H), 4.15 (d, J=13.6 Hz, 1H), 3.94 (s, 6H), 3.85 (s, 3H), 3.07 (s, 7H), 2.87-2.79 (m, 6H), 1.67 (s, 2H). HRMS (ESI) for $C_{32}H_{38}Cl_2N_9O_6$ [M]$^+$ calcd: 714.2317, found: 714.2326.

Example 61: (S,E)-4-(3-(3-(2,6-dichloro-3,5-dimethoxyphenyl)-7-(methylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (200)

Compound 200 was prepared according to the general method of Scheme 1.
M.p. 195-198° C. $^1$H NMR [(CD$_3$)$_2$SO] δ 8.12 (d, J=2.2 Hz, 1H), 8.03 (s, 1H), 7.12 (br, 1H), 6.99 (br, 1H), 6.86-6.72 (m, 2H), 5.51 (br, 1H), 4.99 (br, 2H), 4.42 (s, 2H), 4.31-4.25 (m, 2H), 3.95 (s, 6H), 3.92-3.87 (m, 3H), 3.84 (d, J=3.0 Hz, 3H), 3.78-3.61 (m, 2H), 3.01 (s, 6H), 2.78-2.75 (d, J=5.8 Hz, 3H), 2.63-2.56 (m, 1H), 2.29-2.27 (m, 1H). HRMS (ESI) calc: for $C_{30}H_{37}Cl_2N_{10}O_6$ (M$^+$) m/z 703.2269, found: 703.2291.

Example 62: (S,E)-4-(3-(3-(2,6-dichloro-3,5-dimethoxyphenyl)-7-(isopropylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (201)

Compound 201 was prepared according to the general method of Scheme 1.
M.p. 184-187° C. $^1$H NMR [(CD$_3$)$_2$SO] δ 8.12 (d, J=1.9 Hz, 1H), 8.03 (s, 1H), 7.04 (br, 1H), 6.99 (br, 1H), 6.86-6.75 (m, 2H), 5.51 (br, 1H), 4.99 (br, 2H), 4.42 (s, 2H), 4.32-4.25 (m, 2H), 3.95 (s, 6H), 3.91-3.86 (m, 3H), 3.84 (d, J=3.2 Hz, 3H), 3.77-3.61 (m, 2H), 3.01 (s, 6H), 2.64-2.52 (m, 1H), 2.33-2.11 (m, 1H), 1.19-1.07 (m, 6H). HRMS (ESI) calc: for $C_{32}H_{41}Cl_2N_{10}O_6$ (M$^+$) m/z 731.2582, found: 731.2590.

Example 63: (E)-4-(4-(3-(2,6-dichloro-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (202)

Compound 202 was prepared according to the general method of Scheme 1.
M.p. 171-174° C. $^1$H NMR [(CD$_3$)$_2$SO] δ 8.13 (s, 1H), 7.98 (s, 1H), 7.07 (d, J=14.8 Hz, 1H), 7.05 (br, 1H), 6.97 (s, 1H), 6.80-6.74 (m, 1H), 5.00 (br, 2H), 4.89 (br, 1H), 4.57-4.55 (m, 1H), 4.38 (s, 2H), 4.29-4.26 (m, 2H), 4.13-4.09 (m, 1H), 3.95 (s, 6H), 3.84 (5, 3H), 3.19-3.12 (m, 2H), 3.06 (s, 6H), 2.72-2.55 (m, 3H), 1.77-1.72 (m, 2H), 1.13 (d, J=6.4 Hz, 6H). HRMS (ESI) calc: for $C_{33}H_{43}Cl_2N_{10}O_6$ (M$^+$) m/z 745.2756, found: 745.2739.

Example 64: (E)-4-(4-(3-(2,6-dichloro-3,5-dimethoxyphenyl)-2-oxo-7-((tetrahydro-2H-pyran-4-yl)amino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (203)

Compound 203 was prepared according to the general method of Scheme 1.
M.p. 157-160° C. $^1$H NMR [(CD$_3$)$_2$SO] δ 8.13 (s, 1H), 8.02 (s, 1H), 7.51 (br, 1H), 7.09 (d, J=14.8 Hz, 1H), 6.98 (s, 1H), 6.81-6.74 (m, 1H), 4.99 (br, 2H), 4.85 (br, 1H), 4.61-4.58 (m, 1H), 4.41 (s, 2H), 4.28 (br, 2H), 4.14-4.11 (m, 1H), 3.95 (s, 6H), 3.86 (br, 3H), 3.84 (s, 3H), 3.32 (br, 2H), 3.18-3.12 (m, 1H), 3.06 (s, 6H), 2.72-2.66 (m, 2H), 2.55-2.54 (m, 1H), 1.82-1.75 (m, 4H), 1.54-1.49 (m, 2H). HRMS (ESI) calc: for $C_{35}H_{45}Cl_2N_{10}O_7$ (M$^+$) m/z 787.2844, found: 787.2843.

Example 65: (E)-4-(4-(3-(2,6-dichloro-3,5-dimethoxyphenyl)-7-((4-fluorophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (205)

Compound 205 was prepared according to the general method of Scheme 1.
M.p. 162-165° C. $^1$H NMR [(CD$_3$)$_2$SO] δ 9.65 (br, 1H), 8.19 (s, 1H), 8.12 (s, 1H), 7.69-7.66 (m, 2H), 7.15-7.11 (m, 2H), 7.06 (d, J=14.8 Hz, 1H), 6.99 (s, 1H), 6.80-6.73 (m, 1H), 5.00 (br, 2H), 4.90-4.84 (m, 1H), 4.63-4.60 (m, 1H), 4.48 (d, J=3.2 Hz, 2H), 4.27-4.26 (m, 2H), 4.22-4.11 (m, 1H), 3.95 (s, 6H), 3.84 (s, 3H), 3.18-3.12 (m, 2H), 3.06 (s, 6H), 2.73-2.66 (m, 1H), 2.45-2.40 (m, 1H), 1.81-1.78 (m, 2H). HRMS (ESI) calc: for $C_{36}H_{40}Cl_2FN_{10}O_6$ (M$^+$) m/z 797.2507, found: 797.2488.

Example 66: (E)-4-(4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (206)

Compound 206 was prepared according to the general method of Scheme 1.
$^1$H NMR (400 MHz, DMSO-d$_6$) δ 9.42 (s, 1H), 8.14 (d, J=9.3 Hz, 2H), 7.82-7.44 (m, 2H), 7.06 (d, J=14.8 Hz, 1H), 6.98 (s, 1H), 6.95-6.83 (m, 2H), 6.75 (dt, J=14.9, 7.3 Hz, 1H), 5.00 (s, 2H), 4.87 (t, J=11.9 Hz, 1H), 4.61 (d, J=12.7 Hz, 1H), 4.46 (d, J=4.0 Hz, 2H), 4.26 (d, J=7.5 Hz, 2H), 4.12 (d, J=12.7 Hz, 1H), 3.95 (s, 6H), 3.84 (s, 3H), 3.71 (s, 3H), 3.06 (s, 7H), 2.78-2.63 (m, 2H), 2.43 (d, J=14.8 Hz, 1H), 1.79 (d, J=11.8 Hz, 2H). HRMS (ESI) for $C_{37}H_{43}Cl_2N_{10}O_7$ [M]$^+$ calcd: 809.2688, found: 809.2695.

Example 67: (E)-4-(4-(3-(2,6-dibromo-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (207)

Compound 207 was prepared according to a synthetic route similar to the general method of Scheme 1.
$^1$H NMR (400 MHz, DMSO-d$_6$) δ 8.12 (s, 1H), 7.99 (s, 1H), 7.07 (d, J=14.8 Hz, 2H), 6.90 (s, 1H), 6.76 (dt, J=14.8, 7.4 Hz, 1H), 5.02-4.91 (m, 3H), 4.56 (d, J=12.5 Hz, 1H), 4.39 (s, 2H), 4.27 (t, J=6.6 Hz, 2H), 4.11 (d, J=13.2 Hz, 1H), 3.94 (s, 7H), 3.84 (s, 3H), 3.15 (t, J=13.5 Hz, 1H), 3.06 (d, J=3.7 Hz, 6H), 2.78-2.54 (m, 3H), 1.73 (s, 2H), 1.28-1.11 (m, 6H). HRMS (ESI) for $C_{33}H_{43}Br_2N_{10}O_6$ [M]$^+$ calcd: 833.17283, found: 833.17302.

Example 68: (E)-4-(4-(6-(2,6-dichloro-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (209)

Compound 209 was prepared according to the general method of Scheme 2.

$^1$H NMR (400 MHz, DMSO-$d_6$) δ 8.67 (s, 0.2H), 8.61 (s, 0.8H), 8.13 (s, 1H), 7.90 (d, J=7.8 Hz, 0.8H), 7.67 (s, 0.2H), 7.65 (s, 1H), 7.11 (d, J=14.8 Hz, 1H), 6.97 (s, 1H), 6.80 (s, 1H), 5.62 (s, 1H), 5.01 (s, 2H), 4.61 (d, J=10.8 Hz, 1H), 4.28 (d, J=9.0 Hz, 2H), 4.16 (d, J=13.4 Hz, 1H), 3.94 (s, 7H), 3.84 (s, 3H), 3.28-3.20 (m, 2H), 3.07 (d, J=7.5 Hz, 7H), 2.79-2.73 (m, 1H), 1.71-1.65 (m, 2H), 1.17 (s, 6H). HRMS (ESI) for $C_{34}H_{42}Cl_2N_9O_6$ [M]$^+$ calcd: 742.2630, found: 742.2634.

Example 69: (E)-4-(4-(6-(2,6-dibromo-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (210)

Compound 210 was prepared according to a synthetic route similar to the general method of Scheme 2.

$^1$H NMR (400 MHz, DMSO-$d_6$) δ 8.67 (s, 0.28H), 8.61 (s, 0.72H), 8.13 (s, 1H), 7.89 (d, J=7.6 Hz, 1H), 7.57 (s, 1H), 7.10 (d, J=14.7 Hz, 1H), 6.91 (s, 1H), 6.80 (s, 1H), 5.62 (s, 1H), 5.01 (s, 2H), 4.61 (d, J=10.7 Hz, 1H), 4.28 (d, J=8.5 Hz, 2H), 4.16 (d, J=13.6 Hz, 1H), 3.94 (s, 7H), 3.84 (s, 3H), 3.06 (s, 7H), 2.76-2.67 (m, 3H), 1.67 (s, 2H), 1.18 (s, 6H). HRMS (ESI) for $C_{34}H_{42}Br_2N_9O_6$ [M]$^+$ calcd: 830.1625, found: 830.1627.

Example 70: (E)-4-(4-(6-(2,6-dichloro-3,5-dimethoxyphenyl)-7-oxo-2-(phenylamino)pyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (211)

Compound 211 was prepared according to the general method of Scheme 2.

$^1$H NMR (400 MHz, DMSO-$d_6$) δ 10.20 (s, 1H), 8.84 (s, 1H), 8.12 (s, 1H), 7.79 (s, 1H), 7.74 (s, 2H), 7.36 (s, 2H), 7.15-7.01 (m, 2H), 6.98 (s, 1H), 6.79 (dt, J=14.6, 7.2 Hz, 1H), 5.66 (s, 1H), 5.01 (s, 2H), 4.67 (d, J=11.3 Hz, 1H), 4.28 (s, 2H), 4.18 (d, J=13.4 Hz, 1H), 3.95 (s, 6H), 3.84 (s, 3H), 3.18-3.07 (m, 8H), 2.76-2.70 (m, 2H), 1.75 (d, J=11.0 Hz, 2H). HRMS (ESI) for $C_{37}H_{40}Cl_2N_9O_6$ [M]$^+$ calcd: 776.2473, found: 76.2480.

Example 71: (E)-4-(4-(6-(2,6-dibromo-3,5-dimethoxyphenyl)-7-oxo-2-(phenylamino)pyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (212)

Compound 212 was prepared according to a synthetic route similar to the general method of Scheme 2.

$^1$H NMR (400 MHz, DMSO-$d_6$) δ 10.20 (s, 1H), 8.84 (s, 1H), 8.12 (s, 1H), 7.75 (s, 2H), 7.71 (s, 1H), 7.36 (s, 2H), 7.09-7.04 (m, 2H), 6.92 (s, 1H), 6.79 (dt, J=14.5, 7.2 Hz, 1H), 5.66 (s, 1H), 5.01 (s, 2H), 4.67 (d, J=11.5 Hz, 1H), 4.28 (s, 2H), 4.18 (d, J=13.8 Hz, 1H), 3.95 (s, 6H), 3.84 (s, 3H), 3.15 (t, J=13.2 Hz, 1H), 3.07 (s, 6H), 2.88-2.57 (m, 3H), 1.74 (d, J=11.1 Hz, 2H). HRMS (ESI) for $C_{37}H_{40}Br_2N_9O_6$ [M]$^+$ calcd: 864.14682, found: 864.14691.

Example 72: (E)-4-((3-((6-(2,6-dichloro-3,5-dimethoxyphenyl)-2-(isopropylamino)-7-oxopyrido[2,3-d]pyrimidin-8(7H)-yl)methyl)phenyl)amino)-N,N-dimethyl-N-((1-methyl-4-nitro-1H-imidazol-5-yl)methyl)-4-oxobut-2-en-1-aminium bromide (213)

Compound 213 was prepared according to the general method of Scheme 5.

$^1$H NMR (400 MHz, DMSO-$d_6$) δ 10.30 (s, 1H), 8.73 (s, 0.22H), 8.64 (s, 0.72H), 8.13 (s, 1H), 7.88 (d, J=7.7 Hz, 1H), 7.74 (s, 1H), 7.66 (s, 1H), 7.54 (d, J=8.3 Hz, 1H), 7.26 (t, J=7.9 Hz, 1H), 7.08-6.96 (m, 2H), 6.89 (dt, J=15.0, 7.4 Hz, 1H), 6.55 (d, J=15.1 Hz, 1H), 5.45 (s, 2H), 5.02 (s, 2H), 4.37 (d, J=7.4 Hz, 2H), 4.07-3.99 (m, 1H), 3.95 (s, 6H), 3.85 (s, 3H), 3.08 (s, 6H), 1.39-1.00 (m, 6H). HRMS (ESI) for $C_{36}H_{40}O_2N_9O_6$ [M]$^+$ calcd: 764.2473, found: 764.2468.

Example 73: (E)-4-((4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)cyclohexyl)amino)-N,N-dimethyl-N-((1-methyl-4-nitro-1H-imidazol-5-yl)methyl)-4-oxobut-2-en-1-aminium bromide (214)

Compound 214 was prepared according to the general method of Scheme 1.

$^1$H NMR (400 MHz, DMSO-$d_6$) δ 9.41 (s, 1H), 8.29 (d, J=7.8 Hz, 1H), 8.12 (s, 2H), 7.82-7.48 (m, 2H), 6.99 (s, 1H), 6.95 (d, J=9.0 Hz, 2H), 6.77 (dt, J=14.9, 7.4 Hz, 1H), 6.36 (d, J=15.1 Hz, 1H), 5.00 (s, 2H), 4.59 (t, J=12.4 Hz, 1H), 4.45 (s, 2H), 4.32 (d, J=7.4 Hz, 2H), 3.96 (s, 6H), 3.85 (s, 3H), 3.74 (s, 4H), 3.06 (s, 6H), 2.58 (d, J=14.3 Hz, 1H), 1.93 (dd, J=14.1, 7.9 Hz, 2H), 1.74 (d, J=11.8 Hz, 2H), 1.36 (q, J=12.5 Hz, 3H). HRMS (ESI) for $C_{38}H_{45}Cl_2N_{10}O_7$ [M]$^+$ calcd: 823.2844, found: 823.2844.

Example 74: (E)-4-(4-(3-(2,6-dichloro-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (215)

Compound 215 was prepared according to the general method of Scheme 3.

Compound 149 (253 mg, 420 mmol) was dissolved in dry NMP (2.5 mL) and 5-(bromomethyl)-1-methyl-4-nitro-1H-imidazole (92.3 mg, 420 mmol) was added. The mixture was stirred at room temperature under nitrogen for 24 hours. The mixture was diluted with dichloromethane (1 mL) and the crude product was precipitated by addition of diethylether (4 mL), collected by filtration and dried in a desiccator overnight. The crude product was triturated with $CH_2Cl_2$/ether (3:2, v/v) to afford compound 215 (243 mg, 70%) as a pale yellow powder. m.p. 202-205° C. $^1$H NMR [(CD$_3$)$_2$SO] δ 8.37 (s, 1H), 8.12 (s, 1H), 7.60 (s, 1H), 7.09 (d, J=14.8 Hz, 1H), 6.95 (s, 1H), 6.87 (br, 1H), 6.81-6.74 (m, 1H), 6.57 (s, 1H), 5.00 (br, 2H), 4.62-4.59 (m, 1H), 4.27 (d, J=7.3 Hz, 2H), 4.17-4.14 (m, 2H), 3.93 (s, 6H), 3.84 (s, 3H), 3.27-3.21 (m, 1H), 3.07 (s, 6H), 2.83-2.55 (m, 4H), 1.75-1.72 (m, 2H), 1.18 (d, J=6.4 Hz, 6H). HRMS (ESI) calc: for $C_{35}H_{43}Cl_2N_8O_6$ (M$^+$) m/z 741.2677, found: 741.2679.

Example 75: (E)-4-(4-(3-(2,6-dibromo-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (216)

Compound 216 was prepared according to a synthetic route similar to the general method of Scheme 3.
M.p. 219° C. $^1$H NMR [(CD$_3$)$_2$SO] δ 8.37 (s, 1H), 8.12 (s, 1H), 7.52 (s, 1H), 7.09 (d, J=14.9 Hz, 1H), 6.89 (s, 1H), 6.85 (br, 1H), 6.81-6.74 (m, 1H), 6.57 (s, 1H), 5.01 (br, 2H), 4.62-4.59 (m, 2H), 4.27 (d, J=7.4 Hz, 2H), 4.16-4.13 (m, 2H), 3.93 (s, 6H), 3.84 (s, 3H), 3.27-3.21 (m, 1H), 3.07 (s, 6H), 2.86-2.77 (m, 1H), 2.67-2.57 (m, 2H), 1.75-1.71 (m, 2H), 1.18 (d, J=6.4 Hz, 6H). HRMS (ESI) calc: for C$_{35}$H$_{43}$Br$_2$N$_8$O$_6$ (M$^+$) m/z 829.1667, found: 829.1668.

Example 76: (E)-4-(4-(3-(2-chloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (217)

Compound 217 was prepared according to a synthetic route similar to the general method of Scheme 1.
M.p. 181-184° C. $^1$H NMR [(CD$_3$)$_2$SO] δ 9.59 (br, 1H), 8.18 (s, 1H), 8.12 (s, 1H), 7.70 (d, J=7.8 Hz, 2H), 7.28 (t, J=7.2 Hz, 2H), 7.07 (d, J=15.0 Hz, 1H), 6.94 (t, J=7.0 Hz, 1H), 6.79-6.72 (m, 3H), 5.00 (br, 2H), 4.92 (br, 1H), 4.69-4.63 (m, 2H), 4.47-4.42 (m, 1H), 4.28-4.26 (m, 2H), 4.14 (br, 1H), 3.86 (s, 3H), 3.84 (s, 3H), 3.79 (s, 3H), 3.18-3.12 (m, 1H), 3.06 (s, 6H), 2.72-2.67 (m, 2H), 2.60-2.55 (m, 1H), 1.81-1.79 (m, 2H). HRMS (ESI) calc: for C$_{36}$H$_{42}$ClN$_{10}$O$_6$ (M$^+$) m/z 745.2972, found: 745.2982.

Example 77: (E)-4-(4-(3-(2,6-dichloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (218)

Compound 218 was prepared according to the general method of Scheme 1.
M.p.>295° C. $^1$H NMR [(CD$_3$)$_2$SO] δ 9.40 (br, 1H), 8.14 (s, 1H), 8.12 (s, 1H), 7.55 (d, J=9.1 Hz, 2H), 7.07 (d, J=14.8 Hz, 1H), 6.98 (s, 1H), 6.89 (d, J=9.2 Hz, 2H), 6.78-6.72 (m, 1H), 5.01 (br, 2H), 4.92-4.86 (m, 1H), 4.63-4.60 (m, 1H), 4.50-4.41 (m, 2H), 4.27-4.25 (m, 2H), 4.15-4.12 (m, 1H), 3.95 (s, 6H), 3.83 (s, 3H), 3.74-3.72 (m, 4H), 3.18-3.12 (m, 1H), 3.06 (s, 6H), 3.04-3.01 (m, 4H), 2.69-2.55 (m, 3H), 1.81-1.78 (m, 2H). HRMS (ESI) calc: for C$_{40}$H$_{48}$Cl$_2$N$_{11}$O$_7$ (M$^+$) m/z 864.3110, found: 864.3114.

Example 78: (E)-4-(4-(3-(2-chloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (219)

Compound 219 was prepared according to a synthetic route similar to the general method of Scheme 1.
M.p. 241-244° C. $^1$H NMR [(CD$_3$)$_2$SO] δ 9.36 (br, 1H), 8.12 (s, 1H), 7.55 (d, J=8.8 Hz, 2H), 7.08 (d, J=14.8 Hz, 1H), 6.88 (d, J=8.8 Hz, 2H), 6.76-6.72 (m, 3H), 5.01 (br, 2H), 4.94-4.88 (m, 1H), 4.66-4.60 (m, 2H), 4.45-4.40 (m, 2H), 4.27-4.26 (m, 2H), 4.16-4.13 (m, 1H), 3.86 (s, 3H), 3.84 (s, 3H), 3.79 (s, 3H), 3.74-3.72 (m, 4H), 3.18-3.11 (m, 1H), 3.06 (s, 6H), 3.04-3.01 (m, 4H), 2.73-2.55 (m, 3H), 1.80-1.77 (m, 2H). HRMS (ESI) calc: for C$_{40}$H$_{49}$ClN$_{11}$O$_7$ (M$^+$) m/z 830.3500, found: 830.3500.

Example 79: (E)-4-(4-(3-(3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (220)

Compound 220 was prepared according to a synthetic route similar to the general method of Scheme 1.
M.p. 192-195° C. $^1$H NMR [(CD$_3$)$_2$SO] δ 9.33 (br, 1H), 8.13 (s, 1H), 8.12 (s, 1H), 7.56 (d, J=9.1 Hz, 2H), 7.09 (d, J=14.8 Hz, 1H), 6.88 (d, J=9.1 Hz, 2H), 6.78-6.71 (m, 1H), 6.52 (d, J=2.2 Hz, 2H), 6.41 (t, J=2.2 Hz, 1H), 5.01 (br, 2H), 4.89-4.83 (m, 1H), 4.66-4.58 (m, 3H), 4.28-4.26 (m, 2H), 4.16-4.13 (m, 1H), 3.84 (s, 3H), 3.74 (s, 6H), 3.73-3.72 (m, 4H), 3.18-3.11 (m, 1H), 3.06 (s, 6H), 3.03-3.01 (m, 4H), 2.71-2.54 (m, 3H), 1.81 (br, 2H). HRMS (ESI) calc: for C$_{40}$H$_{50}$N$_{11}$O$_7$ (M$^+$) m/z 796.3889, found: 796.3894.

Example 80: (E)-4-(4-(3-(2,6-dichloro-3,5-dimethoxyphenyl)-2-oxo-7-(pyridin-2-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (221)

Compound 221 was prepared according to the general method of Scheme 1.
$^1$H NMR [(CD$_3$)$_2$SO] δ 9.81 (s, 1H), 8.30-8.27 (m, 1H), 8.25 (s, 1H), 8.12-8.10 (m 2H), 7.77-7.73 (m, 1H), 7.07 (d, J=14.8 Hz, 1H), 7.00-6.79 (m, 2H), 6.80-6.73 (m, 1H), 5.00 (br, 1H), 4.94-4.87 (m, 1H), 4.63-4.60 (m, 1H), 4.57-4.80 (m, 2H), 4.31-4.23 (m, 2H), 4.17-4.09 (m, 1H), 3.95 (s, 6H), 3.84 (s, 3H), 3.21-3.14 (m, 1H), 3.06 (s, 6H), 2.76-2.66 (m, 2H), 2.55-2.44 (m, 2H obscured by DMSO signal), 1.82-1.79 (m, 2H).

Example 81: (E)-4-(4-(3-(2,6-dichloro-3,5-dimethoxyphenyl)-2-oxo-7-(pyridin-3-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (222)

Compound 222 was prepared according to the general method of Scheme 1.
$^1$H NMR [(CD$_3$)$_2$SO] δ 10.12 (s, 1H), 9.05 (s, 1H), 8.35-8.32 (m, 2H), 8.28 (s, 1H), 8.12 (s, 1H), 7.61 (dd, J=8.01, 5.11 Hz, 1H), 7.07 (d, J=14.8 Hz, 1H), 6.76 (td, J=14.8, 7.2 Hz, 1H), 4.97-4.82 (m, 4H), 4.52-4.51 (m, 2H), 4.51 (s, 2H), 4.23-4.18 (m, 1H), 3.89 (s, 6H), 3.76 (s, 3H), 3.17 (t, J=12.6 Hz, 1H), 3.01 (s, 6H), 2.75 (t, J=13.0 Hz, 1H), 2.43-2.33 (m, 2H), 1.81-1.78 (m, 2H). HPLC 99.3%.

Example 82: (E)-4-(4-(3-(2,6-dichloro-3,5-dimethoxyphenyl)-2-oxo-7-(pyridin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (223)

Compound 223 was prepared according to the general method of Scheme 1.

$^1$H NMR δ 11.29 (s, 1H), 8.61 (d, J=7.2 Hz, 2H), 8.44 (s, 1H 8.2 (d, J=6.4 Hz, 2H), 7.07 (d, J=14.8 Hz, 1H), 6.99 (s, 1H), 6.77 (td, J=14.8, 7.3 Hz, 1H), 5.01 (br, 1H), 4.94-4.86 (m, 1H), 4.63-4.64 (brm, 1H), 4.60 (s, 2H), 4.26 (d, J=7.3 Hz, 2H), 4.16-4.13 (m, 1H), 3.95 (s, 6H), 3.83 (s, 3H), 3.29-3.19 (m, 2H), 3.05 (brs, 6H), 2.80-2.75 (m, 2H), 2.49-2.35 (m, 2H), 1.87-1.85 (m, 2H), HPLC 99.8%.

Example 83: (E)-4-(4-(3-(2,6-dichloro-3,5-dimethoxyphenyl)-7-((1-methyl-1H-pyrazol-3-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (224)

Compound 224 was prepared according to the general method of Scheme 1.

$^1$H NMR [(CD$_3$)$_2$SO] δ 9.69 (s, 1H), 8.13 (d, J=2.8 Hz, 2H), 7.51 (d, J=2.0 Hz, 1H), 7.06 (d, J=14.8 Hz, 1H), 6.98 (s, 1H), 6.81-6.74 (m, 1H), 6.45 (d, J=2.1 Hz, 1H), 5.00 (br 2H), 4.92-4.84 (m, 1H), 4.62-4.56 (m, 1H), 4.49-4.42 (m, 2H), 4.27-4.26 (m, 2H), 4.15-4.11 (m, 1H), 3.95 (s, 6H), 3.83 (s, 3H), 3.73 (s, 3H), 3.37 (br s, 2H), 3.06 (s, 6H), 2.72-2.65 (m, 2H), 1.79-1.75 (m, 2H).

Example 84: (E)-3-(2,6-dichloro-3,5-dimethoxyphenyl)-1-(1-(4-(dimethylamino)but-2-enoyl)piperidin-4-yl)-7-(phenylamino)-1,6-naphthyridin-2(1H)-one (232)

Compound 232 was prepared according to the general method of Scheme 3.

M.p. 230-233° C. $^1$H NMR [(CD$_3$)$_2$SO] δ 9.42 (br, 1H), 8.55 (s, 1H), 7.75 (s, 1H), 7.66 (d, J=8.0 Hz, 2H), 7.30 (t, J=7.6 Hz, 2H), 7.00-6.93 (m, 3H), 6.68-6.58 (m, 2H), 4.67-4.62 (m, 1H), 4.25-4.22 (m, 1H), 3.95 (s, 6H), 3.20-3.14 (m, 2H), 3.03 (d, J=4.8, 2H), 2.77-2.58 (m, 3H), 2.14 (s, 6H), 1.77-1.74 (m, 2H). HRMS (ESI) C$_{33}$H$_{35}$Cl$_2$N$_5$O$_4$ (M+H) m/z 636.2139, found: 636.2150.

General Biology Experimental Information

In Vitro Kinase Enzyme Assay

FGFR1-4 and the Z-Lyte Kinase Assay Kit were purchased from Invitrogen. The concentration gradients from $5.1\times10^{-11}$ to $1.0\times10^{-6}$ mol/L were used for all the test compounds. The experiments were performed according to the instructions of the manufacturer.

Growth and Maintenance of Cell Lines

All cell lines used were cultured as monolayers in 75 cm$^2$ (T-75) or 175 cm$^2$ (T-175) tissue culture flasks containing RPMI 1640 supplemented with 10% FBS (v/v) (H520, SUM52 and SW780) or α-MEM supplemented with 5% FBS (v/v) (PC-9, H1661, H1975, H460 and H1299) in a humidified incubator (37° C., 5% CO$_2$). Cells were harvested when the monolayer achieved 80% density. The total number of cells was determined by diluting 100 μL of the cell suspension in 9.9 mL of saline and counting on a Z2 Coulter Particle Count and Size Analyzer. Cells were seeded into fresh T-75 or T-175 flasks at low cell density and were sub-cultured every 7 days. Cells were grown for a period of no longer than 2 months.

Cell Proliferation Assays

The cancer cells were counted and an appropriate volume of cells was transferred to 15 mL RPMI1640+10% FBS (or α-MEM supplemented with 5% FBS) to give the correct cell density for seeding into 96-well plates (2000 cells/well; total volume of 150 μl/well). Cells were incubated overnight at 37° C. to allow attachment. All drugs were prepared as stocks in DMSO and stored at –80° C. Working solutions of each drug were made in RPMI+10% FBS (or α-MEM supplemented with 5% FBS) at 3 times the required final concentration for the top well. A 3-fold serial dilution was performed along the plate. Following drug addition, cells were incubated in the presence of drug (37° C., 5% CO$_2$) for a period of 5 days (with the exception of H520 cells which were incubated for 7 days). The plates were removed from the incubator and the cells were fixed by adding 50 μL of cold 40% (w/v) TCA solution per well. The plates were incubated for 1 hour at 4° C. The plates were subsequently washed (3×) with running tap water before being stained with 50 μL of 0.4% (w/v) SRB. The plates were incubated in the dark 30 (min). Excess stain was removed by rinsing the plates (4×) in water containing 1% (v/v) acetic acid. The stain was solubilised by adding 100 μL of 10 mM unbuffered Tris (pH 10.5) to each well and the plates were left on a shaker in the dark at R.T for at least 1 hour. The absorbance values were determined for each well by an EL808 Absorbance Microplate Reader (490 nm; reference filter 450 nm). The IC$_{50}$ values were determined by the KC4 microplate data analysis software (KC4TM, Bio-Tek).

Western Blot Analysis and Washout Assay

Cells were seeded on the day prior to drug treatment (1 million cells/well; 6-well plate). For SW780 and SUM52, cells were seeded in 3 ml RPMI 1640+10% FBS and incubated for 6 hr to allow adherence. Media was then aspirated, cells washed with PBS and 3 ml of fresh, serum-free RPMI 1640 was added to serum-starve the cells overnight (18 hours) (all subsequent steps used serum-free media). Serum starvation was not performed in experiments using H520 cells; instead cells were seeded in RPMI 1640+ 10% FBS and incubated overnight.

Drug Exposure—No Washout:

Drug stocks were prepared in media using 1 mM or 10 mM DMSO stock solutions. Media was aspirated from each well and replaced with 2 ml of drug-free media for control wells or 2 ml of diluted drug for treated wells. Cells were exposed to drug for 30 min. Recombinant FGF (50 ng/well) was added to each well 15 minutes prior to the end of the drug exposure and protein was extracted as below.

Drug Exposure—with Washout:

Cells were exposed to drug for 30 min as above. Media was aspirated and each well was washed with 5 ml drug-free media. The wash media was aspirated and replaced with 2 ml drug-free media and cells incubated for a further 30 minutes, after which the wash protocol was repeated. Cells were incubated for a further 90 minutes in drug-free media. Recombinant FGF (50 ng/well) was added to each well 15 minutes prior to the end of the drug-free incubation and protein was extracted as below.

Protein Extraction and Western Blotting:

Cell lysates were prepared in 250 μL of RIPA lysis buffer containing protease inhibitor (1:100). After incubation on ice (30 min) and centrifugation (13,000 rpm, 5 min, 4° C.) the supernatants containing the proteins were stored (–20° C.) until required. Bicinchoninic acid (BCA) assay was used to determine the protein concentration of individual cell lysate samples. Western blots were prepared using the following primary antibodies: p-p44/42 MAPK (pERK1/2) (Thr202/Tyr204) rabbit monoclonal (Cell Signalling Technology #9101); pFGFR mouse monoclonal (Cell signalling Technology #34765); and α-Tubulin mouse monoclonal (Sigma-Aldrich #T6074).

Murine Plasma Pharmacokinetics Assay

Compound 204 was formulated in water for injection at 2 or 4 mg/ml to be administered by intraperitoneal injection at 0.02 ml/g body weight to achieve a 40 or 80 mg/kg dose. Specific pathogen-free female NIH-III mice (Crl:NIH Lyst$^{bg}$ Foxn1$^{nu}$ Btk$^{xid}$) were obtained from the Vernon Jansen Unit (VJU), The University of Auckland. To minimize exogenous infection, mice were maintained in individually ventilated cages at 6 mice per cage (Sealsafe Plus Mouse AERO, Tecniplast) and handled in accordance with the Guide for the Care and Use of Laboratory Animals, The University of Auckland. Mice had access to water and food ad libitum. Following dosing, at the specified time points (0.5, 1, 2, 4, 6 and 24 hours, n=3 per time point) mice were anaesthetised (isoflurane inhalation) and blood collected through cardiac puncture. Mice were subsequently culled via cervical dislocation whilst anaesthetized. Blood was collected in ice cold tubes (BD Microtainer® containing K$_2$EDTA) and centrifuged (7 minutes at 6,500 rpm) to separate the plasma fraction. Plasma samples were stored at −80° C. until analysis. Control mice were injected with vehicle only and plasma collected as described. Prior to analysis by LC-MS/MS, calibration standards were prepared in control mouse plasma with a synthetic standard of Compound 204. Plasma samples expected to be outside the range of these standards were diluted in control mouse plasma. Standards and samples were mixed with 3 volumes of ice-cold acetonitrile containing internal standard (2 uL) and then centrifuged at 13000 rpm for 10 minutes at 4° C. The resulting supernatant was diluted in 2 volumes of 0.01% formic acid in water and 10 uL injected onto the LC-MS/MS system using an established quantitative analysis method. Pharmacokinetic parameters resulting from model fit of Compound 204 plasma concentration-time data were then derived where $T_{max}$=time at maximum concentration, $T_{max\text{-}obs}$=time at maximum observed concentration, $C_{max\text{-}obs}$=maximum concentration observed, $C_{max}$=maximum concentration determined by model, $T_{1/2}$=half-life of Compound 204 in plasma during elimination phase, $AUC_{0\text{-}24}$=observed area under the mean concentration-time curve, $AUC_{0\text{-}inf}$=area under the concentration-time curve of the model fit.

In Vivo Efficacy Experimental

Studies in NIH-III Nude Mice:

Specific pathogen-free homozygous female NIH-III nude mice (Charles River Laboratories, Wilmington, Mass.) were inoculated subcutaneously with a single cell suspension of SW780 cells (8×10$^6$ cells/100 μL with Matrigel; right flank) or SNU-16 cells (10×10$^6$ cells/100 μL; right flank). When tumour xenografts were established (typically 7-14 days for SW780 and 21-28 days for SNU-16) mice were randomized to treatment groups. Test compounds of the present invention were prepared in Water for Injection (WFI). Mice were dosed by intraperitoneal injection (0.01-0.03 ml/g) using the stated schedules and dose levels. AZD4547 was formulated as a 1% (v/v) solution of polyoxyethylenesorbitan monooleate (Tween-80) in deionized water and administered by oral gavage. Tumour size and body weights were measured at regular intervals. Tumour volume was calculated as n (length×width$^2$)/6. The time for tumours to increase in volume 4-fold relative to pre-treatment volume (RTV$^4$) was determined, and the % Tumour Growth Inhibition (% TGI) was calculated as the median percentage increase in RTV$^4$ for treated versus control.

Studies in BALB/c mice: 4T1 murine syngeneic breast cancer cells (7.5×10$^6$ cells/mouse) were implanted into the subcutaneous space, in the right flank of immunocompetent BALB/c female mice. Treatment with Compound 204 started at the stated day post cell-implant. Compound 204 was administered intraperitoneally at the stated dose and schedule in Water for Injection. Tumour measurements and body weight were recorded every day, until all tumours increased their volume 4-fold (RTV$^4$) from day0 of experimental assignment.

General Pulse Radiolysis Experimental Information

Pulse radiolysis was used to monitor the 1-electron reduction and stability of the compounds in real time. A linear accelerator delivering short pulses of high energy electrons (2-3 Gy in 200 ns of 4 MeV) equipped with a fast spectrophotometric detection system was used (Anderson et al, J. Phys. Chem. A, 101, 9704-9709, 1997). Prodrugs were dissolved in N$_2$O-saturated solutions containing formate ions, as above, which, following pulse radiolysis, resulted in the rapid formation of the radical anions of the compounds within a few microseconds. The rate of fragmentation was determined by analysing kinetic transients at wavelengths corresponding to the formation of the benzyl-type radical of the trigger moiety (Bays et al., J. Am. Chem. Soc., 105, 320-324, 1983; Anderson et al, J. Phys. Chem. A, 101, 9704-9709, 1997).

General FGFR1 Protein X-Ray Crystallography Experimental Information

Recombinant protein production and X-ray crystallography was carried out as described previously [Yosaatmadja et al., Acta Cryst. D. Biological Crystallography 2015, D71, 525-33]. In brief, DNA encoding the FGFR1 kinase domain harbouring C488A, C584S mutations, was cloned into the pETDuet vector (Merck) along with the complete gene for PTP1B phosphatase. Protein was produced by incubation in Terrific Broth medium supplemented with ampicillin at 18° C., and with IPTG induction. The protein was purified by immobilised metal affinity chromatography followed by anion exchange chromatography. Protein was concentrated to ~40 mg/ml in a buffer comprising 20 mM TRis-HCl pH 7.8, 20 mM NaCl, 5 mM EDTA, 2 mM TCEP, and was flash-cooled after supplementing with 50% glycerol. For X-ray crystallography, protein was thawed and buffer exchanged to remove glycerol. Crystals were grown by mixing 1 μL of protein solution (7.5 mg/ml) with 1 μL of crystallization buffer comprising 20% (w/v) MPEG 5000, 0.25 M ammonium sulfate, 0.1 M sodium cacodylate. Crystals were grown from drops using the hanging drop vapour diffusion method and required a microseeding step. After one week, crystals were glutaraldehyde crosslinked by placing crystal-containing drops over 3 μL of 25% glutaraldehyde solution for 30 min. Compound 21 was soaked into preformed/crosslinked crystals for 18 hours by placing crystals into a solution comprising the crystallization solution supplemented to 5 mM compound 21 in DMSO. Crystals were transferred to a 70:30 mixture of Paratone N and mineral oils, placed in nylon loops, and flash-cooled in liquid nitrogen. Data were collected at the Australian Synchrotron MX1 beamline using the Blu-Ice software package. Data were processed using XDS and Aimless software packages. The structure was solved by molecular replacement using PHASER and PDB model 4WUN, and refined with REFMAC before visualization and manual fitting in COOT. Molecules of compound 112 were modelled into electron density with some atoms of the acrylamide arm not able to be modelled, presumably being unconstrained and mobile in the crystal.

FGFR1 (C584S) Covalent Binding Protein Mass Spectrometry Assay

The previously cloned C488A/C584S FGFR1 construct was modified by site-directed mutagenesis to provide a gene encoding the C584S FGFR1 kinase domain with the cysteine at amino acid C488 reinstated. Expression and purification of this protein followed the protocol described above but with the addition of 10% glycerol to all buffers and a change of buffer pH to a value of 8.5. Protein for mass spectrometry was concentrated to ~40 mg/ml and was mixed 1:1 (v/v) with glycerol, and then frozen at −20° C. or flash cooled in liquid nitrogen and stored at −80° C. until needed.

Protein samples were buffer exchanged to remove glycerol (the final buffer comprised 20 mM Tris-HCl pH 8.5, 10% (v/v) glycerol, 20 mM NaCl, 5 mM EDTA, 2 mM TCEP) and were mixed with each inhibitor at 1:10 molar ratio (protein:inhibitor). Final protein concentration was 20 µM. Samples were incubated for 3 hr at 37° C., with 10 µL samples removed at specific time points between 5 and 180 min. Samples were mixed with 90 µL of 0.1% formic acid to quench the reaction followed by flash cooling in liquid nitrogen. Samples were stored at −80° C. until needed. All experiments were carried out in triplicate.

Samples were subjected to liquid chromatography mass spectrometry (LC-MS) to show mass changes attributable to irreversible inhibition. Mass spectrometry experiments were performed at the University of Auckland Mass Spectrometry Center using an electrospray QSTAR® XL ESI quadrupole Time-of-Flight (QToF) MS system (Applied Biosystems) operated in positive ionization mode. The instrument was calibrated using Renin Substrate Standard (SCIEX), over the m/z range 100-2000. Protein/inhibitor samples were thawed and 2 µL volumes injected into a liquid chromatography (LC) BIOshell™ A400 Protein C4 HPLC column (10 cm×2.1 mm, 3.4 µm) attached to the mass spectrometer. A 30 min linear solvent gradient from 25% to 65% mobile phase buffer B was applied over 21 min (mobile phase A: 0.1% formic acid in water; mobile phase B: 0.1% formic acid in acetonitrile) with the flow rate set at 0.012 mL/min. The buffer B concentration was raised to 98% from 21 to 25 min. Following elution, samples were directly injected into the mass spectrometer for separation and mass analysis. Mass spectrometry data were processed and analysed using the PeakView™ 2.1 software and the Bio Tool Kit plug-in (SCIEX) and covered an m/z range of 330-1600. Deconvolution calculations allowed visualisation of intact mass protein peaks and allowed peak area measurement to assess the percentage of protein covalently modified by each inhibitor at each time point. Data was plotted using GraphPad Prism 7 (GraphPad).

C584S FGFR1 Kinase Domain Sequences

```
Cloned gene sequence
ATGGGCCACCACCACCACCACCACTCTGCTGAAAACCTGTACTTCCAGGGTGCTGGTGTTTC

TGAATACGAACTGCCGGAAGACCCGCGTTGGGAACTGCCGCGTGACCGTCTGGTTCTGGGTAAACC

GCTGGGTGAAGGTTGCTTCGGTCAGGTTGTTCTGGCTGAAGCTATCGGTCTGGACAAAGACAAACC

GAACCGTGTTACCAAAGTTGCTGTTAAAATGCTGAAATCTGACGCTACCGAAAAAGACCTGTCTGAC

CTGATCTCTGAAATGGAAATGATGAAAATGATCGGTAAACACAAAAACATCATCAACCTGCTGGGTG

CTTGCACCCAGGACGGTCCGCTGTACGTTATCGTTGAATACGCTTCTAAAGGTAACCTGCGTGAATA

CCTGCAGGCTCGTCGTCCGCCGGGTCTGGAATACTCTTACAACCCGTCTCACAACCCGGAAGAACAG

CTGTCTTCTAAAGACCTGGTTTCTTGCGCTTACCAGGTTGCTCGTGGTATGGAATACCTGGCTTCTA

AAAAATGCATCCACCGTGACCTGGCTGCTCGTAACGTTCTGGTTACCGAAGACAACGTTATGAAAAT

CGCTGACTTCGGTCTGGCTCGTGACATCCACCACATCGACTACTACAAAAAAACCACCAACGGTCGT

CTGCCGGTTAAATGGATGGCTCCGGAAGCTCTGTTCGACCGTATCTACACCCACCAGTCTGACGTTT

GGTCTTTCGGTGTTCTGCTGTGGGAAATCTTCACCCTGGGTGGTTCTCCGTACCCGGGTGTTCCGGT

TGAAGAACTGTTCAAACTGCTGAAAGAAGGTCACCGTATGGACAAACCGTCTAACTGCACCAACGAA

CTGTACATGATGATGCGTGACTGCTGGCACGCTGTTCCGTCTCAGCGTCCGACCTTCAAACAGCTGG

TTGAAGACCTGGACCGTATCGTTGCTCTGACCTCTAACCAGGAATAA

Translated FGFR1 kinase domain sequence before rTEV cleavage:
MGHHHHHHSAENLYFQGAGVSEYELPEDPRWELPRDRLVLGKPLGEGCFGQVVLAEAIGLDKD

KPNRVTKVAVKMLKSDATEKDLSDLISEMEMMKMIGKHKNIINLLGACTQDGPLYVIVEYASKGNLR

EYLQARRPPGLEYSYNPSHNPEEQLSSKDLVSCAYQVARGMEYLASKKCIHRDLAARNVLVTEDNVM

KIADFGLARDIHHIDYYKKTTNGRLPVKWMAPEALFDRIYTHQSDVWSFGVLLWEIFTLGGSPYPGV

PVEELFKLLKEGHRMDKPSNCTNELYMMMRDCWHAVPSQRPTFKQLVEDLDRIVALTSNQE

Translated FGFR1 kinase domain sequence after rTEV cleavage:
GAGVSEYELPEDPRWELPRDRLVLGKPLGEGCFGQVVLAEAIGLDKDKPNRVTKVAVKMLKSD

ATEKDLSDLISEMEMMKMIGKHKNIINLLGACTQDGPLYVIVEYASKGNLREYLQARRPPGLEYSYN

PSHNPEEQLSSKDLVSCAYQVARGMEYLASKKCIHRDLAARNVLVTEDNVMKIADFGLARDIHHIDY

YKKTTNGRLPVKWMAPEALFDRIYTHQSDVWSFGVLLWEIFTLGGSPYPGVPVEELFKLLKEGHRMD

KPSNCTNELYMMMRDCWHAVPSQRPTFKQLVEDLDRIVALTSNQE
```

EF5 Immunostaining and MALDI Imaging Mass Spectrometry Assay

SiHa cervical tumour cells were implanted into the flanks of female NIH-III mice to form subcutaneous xenografts. Once tumours reached a size of 800-1000 mm$^3$, mice were treated with the hypoxia marker EF5 (60 mg/kg, intraperitoneal injection) and three hours later they received a single dose of vehicle or Compound 204 (86 mg/kg, intraperitoneal injection). Tumours were then collected 24 hours later, immediately frozen in liquid nitrogen and stored at −80° C. until further analysis. Vehicle and drug-treated SiHa tumours were sectioned at 12 um and collected by melting. Five serial sections were collected from each sample such that sections 1, 3 and 5 were mounted on a standard glass slide for optical microscopy, while sections 2 and 4 were mounted on ITO coated glass slides for MALDI imaging. Slides were stored at −80° C. until required.

For MALDI Imaging:

Sections were desiccated for 1-1.5 hours, washed with Ammonium Formate (50 mM, 3×10s) and allowed to air dry. Acid matrix solution (10 mg/ml in 66% ACN/0.1% TFA) was applied by robotic spray (TM-sprayer, HTX Technologies) and allowed to air dry. Imaging mass spectrometry was performed at 30 um spatial resolution using a MALDI FT-ICR mass spectrometer (Bruker Solarix-XR 7T) operating in positive ion mode. MALDI imaging data were normalised (Root Mean Square method), and the distribution of Compound 112 plotted at the predicted m/z (640.2200)+/− 0.001%. Mass error was <1 ppm.

For EF5 Immunostaining:

Sections were air-dried for 3h and fixed in 95% EtOH for 3 minutes (twice). They were washed in dH$_2$O for 5 minutes, in Tris-Buffered saline (TBS) for 10 minutes and blocked with 10% goat serum in TBS and 1% Tween-20, for 1 h, at room temperature. Sections were then incubated with Alexa488-ELK3-51 antibody (Hypoxia-Imaging.org, University of Pennsylvania, US) that recognises EF5 adducts in hypoxic cells and counterstained with DAPI. Images were acquired using the Metasystems VSlide slide scanner (BIRU, UoA).

Example 85: Biochemical Inhibition of FGFR1-4 Kinase

Compounds of the invention were studied for their ability to inhibit recombinant FGFR1-4 in an isolated enzyme biochemical assay as described above in the general biology experimental information. Results are shown in Table 1.

TABLE 1

| | Isolate Enzyme Inhibition IC$_{50}$ (nM) | | | |
|---|---|---|---|---|
| Compound | FGFR1 | FGFR2 | FGFR3 | FGFR4 |
| 100 | 3.6 | 7.0 | 125 | 829 |
| 101 | 4.1 | 4.0 | 39 | 73 |
| 102 | 9.7 | 15 | 703 | >1000 |
| 103 | 3.1 | 3.3 | 17 | 287 |
| 104 | 1.1 | 23 | 35 | 906 |
| 105 | 1.2 | 16 | 33 | 729 |
| 106 | 1.1 | 26 | 17 | 94 |
| 107 | 0.7 | 1.4 | 8.1 | 452 |
| 108 | 1.1 | 2.0 | 9.8 | 296 |
| 109 | 1.2 | 2.7 | 15 | 79 |
| 110 | 1.1 | 2.0 | 8.2 | 180 |
| 111 | 1.3 | 2.0 | 10 | 166 |
| 112 | 1.1 | 0.8 | 6.2 | 69 |
| 114 | | 1.6 | 5.0 | 186 |
| 115 | 1.2 | 1.8 | 7.0 | 44 |

TABLE 1-continued

| | Isolate Enzyme Inhibition IC$_{50}$ (nM) | | | |
|---|---|---|---|---|
| Compound | FGFR1 | FGFR2 | FGFR3 | FGFR4 |
| 118 | | 2.3 | 2.4 | 9.6 |
| 122 | | 2.3 | 3.7 | 270 |
| 123 | 0.7 | 2.7 | 8.3 | |
| 124 | 0.8 | 1.9 | 12 | |
| 125 | 1.8 | 6.5 | 51 | >1000 |
| 126 | 0.5 | 1.5 | 6.8 | |
| 127 | 1.0 | 2.7 | 35 | |
| 132 | 0.7 | 1.0 | 4.9 | |
| 133 | 1.0 | 1.5 | 11 | |
| 134 | 1.1 | 1.6 | 11 | |
| 135 | 0.9 | 1.2 | 6.3 | |
| 136 | 1.1 | 1.3 | 6.7 | |
| 137 | 0.7 | 1.8 | 6.2 | |
| 138 | 1.1 | 1.1 | 5.1 | |
| 139 | 0.3 | 1.1 | 6.0 | |
| 140 | 0.7 | 0.9 | 4.9 | |
| 141 | 0.7 | 1.5 | 5.5 | |
| 143 | 0.8 | 0.9 | 8.0 | |
| 144 | 0.9 | 1.6 | 6.7 | |
| 145 | 1.3 | 2.5 | 6.9 | |
| 146 | 1.2 | 1.2 | 6.2 | |
| 151 | 4.2 | 3.5 | 35 | |
| 152 | 0.7 | 1.1 | 2.0 | |
| 153 | 0.8 | 1.0 | 7.6 | |

FGFR1-4 isolated enzyme activity was determined using the FRET-based Z-Lyte kinase inhibition assay. The data are the means from 3 independent experiments.

Example 86: Biochemical Kinase Selectivity Screening

Compound 120 was screened for biochemical inhibition of a panel of 456 kinases (DiscoveRx KINOMEscan) at a set concentration of 1 uM. This determined that compound 120 displays excellent selectivity for the FGFR family with a S(35) selectivity score of 0.082 indicating that a concentration of 1 uM provides a Percent Control <35 for only 8.2% of the non-mutant kinases studied (33/403).

Example 87: Anti-Proliferative Activity in FGFR1-4 Amplified Cancer Cell Lines

The anti-proliferative activity of compounds of the invention was evaluated against a panel of FGFR-driven cancer cell lines as described above in the general biology experimental information. Results are shown in Table 2.

TABLE 2

| | Cellular Anti-proliferative IC$_{50}$ (nM) | | | |
|---|---|---|---|---|
| Compound | H520 | SUM52 | SW780 | Hep3B |
| 100 | 40 | 3.3 | 28 | 245 |
| 101 | 218 | 9 | 59 | 163 |
| 102 | 838 | 51 | 700 | 1433 |
| 103 | 77 | 4.8 | 31 | 48 |
| 104 | 17 | 1.4 | 11 | 12 |
| 105 | 68 | 2.1 | 4 | 80 |
| 106 | 11 | 0.5 | 5 | 5.5 |
| 107 | 56 | 2.0 | 5.2 | |
| 108 | 4.9 | 0.7 | 12 | |
| 109 | 70 | 4.0 | 32 | |
| 110 | 14 | 0.8 | 15 | |
| 111 | 7.8 | 0.6 | 3.3 | |
| 112 | 4.1 | 0.7 | 9.7 | |
| 113 | 19 | 1.0 | 5.4 | |
| 114 | 5.3 | 1.1 | 15 | |

TABLE 2-continued

| Compound | Cellular Anti-proliferative IC$_{50}$ (nM) | | | |
|---|---|---|---|---|
| | H520 | SUM52 | SW780 | Hep3B |
| 115 | 6.5 | 1.1 | 9.0 | |
| 120 | 8.7 | 0.8 | 16 | |
| 121 | 40 | 3.3 | 28 | |
| 122 | 3.0 | 0.8 | 0.3 | |
| PD173074 | 281 | 12 | 84 | |
| FIIN-1 | 121 | 2.9 | 277 | |

Example 88: Inhibition of FGF-Dependent Signalling in FGFR1-3 Amplified Cancer Cell Lines The potent cellular FGFR inhibition of compounds of the invention was determined by Western blot for FGF ligand-mediated activation of FGFR2 and its down-stream signalling partner ERK1/2 in SUM52 cells as described above in the general biology experimental information. The results are shown in FIG. 5.

Example 89: Irreversible Inhibition of FGF-Dependent Signalling in FGFR1-3 Amplified Cancer Cell Lines Compounds of the invention were studied for their ability to irreversibly inhibit FGFR1-3 signalling in cells. The H520, SUM52 and SW780 cell lines were exposed to test compounds at the stated concentrations, with and without extensive drug removal (washout), prior to FGF-stimulation, cell lysis and Western blotting as described above in the general biology experimental information. The results are shown in FIGS. 6 to 9.

Example 90: Covalent Binding to Recombinant FGFR1 by Protein Mass Spectrometry Compounds of the invention were studied for their ability to covalently bind and therefore irreversibly inhibit the single mutant (C584S) FGFR1 kinase domain recombinant protein by protein mass spectrometry according to methodology described above in the general biology experimental information. The results are shown in Table 3 and FIG. 10.

TABLE 3

| Compound | % Conversion to FGFR1 (C584S) covalent adduct after 120 minutes incubation |
|---|---|
| 112 | 60 |
| 128 | 48 |
| 130 | 46 |
| 129 | 46 |
| 131 | 39 |
| 106 | 11 |
| 105 | 8 |
| 104 | 8 |
| 103 | 6 |

Example 91: Inhibitor-Bound FGFR1 Protein X-Ray Crystallography

Figure 11:
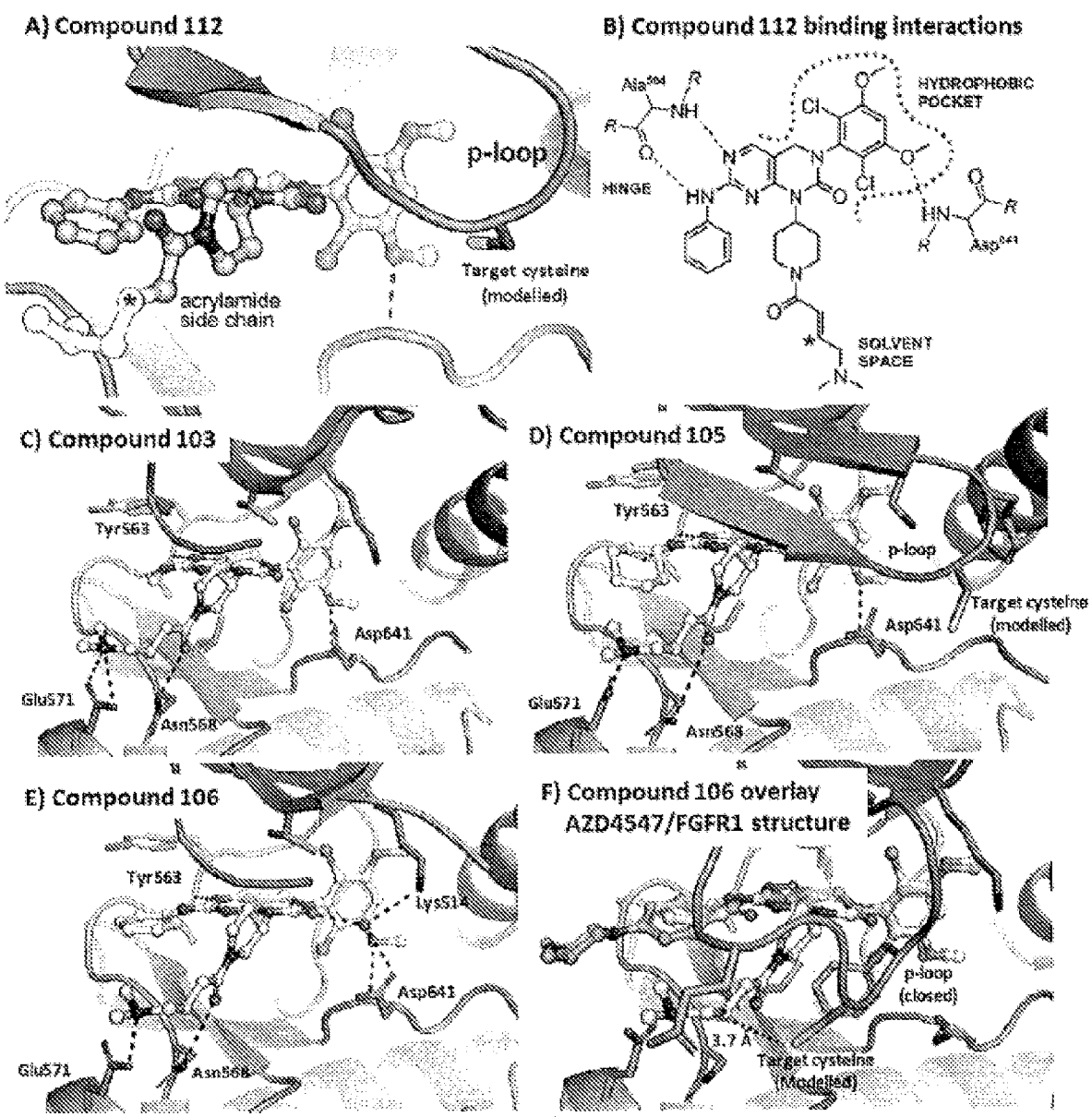
FIG. 11A shows a protein X-ray crystal structure of compound 112 bound in the active site of a double mutant construct of FGFR1.
FIG. 11B shows a diagram of the binding interactions observed in a protein X-ray crystal structure of compound 112 bound in the active site of a double mutant construct of FGFR1.
FIG. 11C shows a protein X-ray crystal structure of compound 103 bound in the active site of a double mutant construct of FGFR1.
FIG. 11D shows a protein X-ray crystal structure of compound 105 bound in the active site of a double mutant construct of FGFR1.
FIG. 11E shows a protein X-ray crystal structure of compound 106 bound in the active site of a double mutant construct of FGFR1.
FIG. 11F shows an overlay of compound 106 on the reported crystal structure of AZD4547 bound in the active site of a double mutant construct of FGFR1.

Inhibitor-bound protein X-ray crystal structures of compounds 112, 103, 105 and 106 with a double mutant (C488A, C584S) FGFR1 kinase domain have been determined according to methodology described above in the general biology experimental information. The reversible binding mode of compounds 112, 103, 105 and 106 to the active site of FGFR1 is shown in FIGS. 11A, 11C, 11D and 11E respectively. A diagram demonstrating the interactions between compound 112 and FGFR1 is shown in FIG. 11B.

Example 92: Oxic and Anoxic Anti-Proliferative Activity of the Prodrugs in FGFR-Dependent Cancer Cell Lines The prodrug forms of compounds of the present invention (compounds 200, 201, 202, 203, 204, 205, 206, 207, 208, 209, 210, 211, 212, 213, 215, 216, 217, 218, 219 and 220) were investigated for their ability to inhibit the proliferation of one or more of H520, SUM52 and SW780 cells under oxic conditions. In addition selected examples were exposed to 4 hours of anoxia to activate the prodrugs and release the FGFR inhibitor through trigger fragmentation, prior to conducting the remainder of the anti-proliferative assay under oxic conditions as described in the general biology experimental information. The oxic and anoxic anti-proliferative IC50's and their ratio, termed a Hypoxic Cytotoxicity Ratio (HCR), are shown in Table 4.

TABLE 4

| | Cellular Anti-proliferative IC$_{50}$ (nM) | | | | | | | | |
|---|---|---|---|---|---|---|---|---|---|
| | H520 | | | SUM52 | | | SW780 | | |
| Compound | Oxic | Anoxic | HCR | Oxic | Anoxic | HCR | Oxic | Anoxic | HCR |
| 200 | 3665 | | | 229 | | | 2635 | | |
| 201 | 902 | | | 612 | 38 | 16 | 1994 | | |
| 202 | 1732 | | | 737 | | | 2122 | | |
| 203 | | | | 961 | 37 | 26 | | | |
| 204 | 1257 | 47 | 27 | 207 | 17 | 12 | 1388 | | |
| 205 | 668 | | | 23 | 4 | 6 | 1470 | | |
| 206 | | | | 8 | 1 | 8 | | | |
| 207 | | | | 404 | 8 | 53 | | | |
| 208 | 4152 | | | 13 | 3 | 5 | 2581 | | |
| 209 | 1477 | 41 | 36 | 269 | 4 | 68 | 1568 | | |
| 210 | | | | 35 | 4 | 9 | | | |
| 211 | 817 | 41 | 20 | 199 | 12 | 16 | 754 | | |
| 212 | | | | 13 | 2 | 8 | | | |
| 213 | | | | 40 | 7 | 5 | | | |

TABLE 4-continued

| | Cellular Anti-proliferative IC$_{50}$ (nM) | | | | | | | | |
|---|---|---|---|---|---|---|---|---|---|
| | H520 | | | SUM52 | | | SW780 | | |
| Compound | Oxic | Anoxic | HCR | Oxic | Anoxic | HCR | Oxic | Anoxic | HCR |
| 215 | 4022 | 209 | 19 | 1188 | 11 | 106 | 3505 | | |
| 216 | | | | 346 | 6 | 59 | | | |
| 217 | | | | 24 | 4 | 7 | | | |
| 218 | | | | 14 | 3 | 4 | | | |
| 219 | | | | 52 | 2 | 22 | | | |
| 220 | | | | 1719 | 36 | 48 | | | |

Example 93: Inhibition of FGF-Dependent Signalling for Prodrug Compound 204 in FGFR2 Amplified SUM52 Cells The ability of prodrug compound 204 to inhibit FGF-dependent signalling in SUM52 cells was determined by Western blot for FGF ligand-mediated activation of FGFR2 and its down-stream signalling partner ERK1/2 as described above in the general biology experimental information. The results are shown in FIG. 12.

Example 94: Inhibition of FGF-Dependent Signalling for Prodrug Compounds in FGFR1 Amplified H520 Cells with and without Drug Washout Prodrug compounds 200, 202, 205 and 201, relative to their respective inhibitors (103, 108, 120 and 104), were evaluated in the H520 cell-based Western blot washout assay described in Example 64 to detect reversible or irreversible inhibitors of FGFR1. NMQ prodrugs of FIIN-1 and PD173074 were also prepared (FIG. 13), and studied in the Western blot washout assay relative to FIIN-1 and PD173074 as control compounds. A drug exposure time of 2 hours was utilised at a range of test concentrations (100, 300 and 600 nM), with and without drug washout. The results are shown in FIG. 14.

Example 95: Pulse Radiolysis of Prodrugs of the Invention

The one-electron reduction potential (E(1)) and first order rate of fragmentation ($k_{frag}$) of prodrug compounds 200, 202 and 204 compared to TH-4000 as a positive control prodrug was measured by pulse radiolysis as described above in the general pulse radiolysis experimental information. The results are shown in Table 5.

TABLE 5

| Compound | E(1) (mV) | $k_{frag}$ (s$^{-1}$) |
|---|---|---|
| TH-4000 | −424 | 20 |
| 200 | −426 | 32 |
| 202 | −428 | 26 |
| 204 | −433 | 30 |

Example 96: Murine Plasma Pharmacokinetics of Prodrug Compound 204

The plasma pharmacokinetic parameters of prodrug compound 204 have been determined following administration at 40 and 80 mg/kg to NIH-III nude mice as described in the general biology experimental information. The results are shown in Table 6. The plasma concentration of compound 204 as a function of time is shown in FIG. 15.

TABLE 6

| | Dose (mg/kg) | |
|---|---|---|
| | 40 | 80 |
| $T_{max}$ (h) | 1.75 ± 0.06 | 2.58 ± 0.36 |
| $T_{max-obs}$ (h) | 2 | 4 |
| $C_{max-obs}$ (µmol/L) | 51.77 ± 7.46 | 77.31 ± 14.72 |
| $C_{max}$ (µmol/L) | 54.93 ± 2.38 | 86.43 ± 10.41 |
| $T_{1/2}$ (h) | 1.21 ± 0.06 | 1.79 ± 0.36 |
| AUC$_{0-24}$ (h · µmol/L) | 381.87 | 914.20 |
| AUC$_{0-inf}$ (h · µmol/L) | 261.59 ± 10.75 | 605.67 ± 103.04 |

Example 97: Anti-Tumour Activity of Prodrugs of the Invention

The anti-tumour activity of selected prodrug compounds in human and murine xenograft-bearing NIH-III nude mice and BALB/c immunocompetant mice, respectively, was determined as described above in the general biology experimental information. The results are shown in FIGS. 16 to 20.

Example 98: MALDI Imaging Mass Spectrometry of FGFR Inhibitor Release in SiHa Xenograft-Bearing NIH-III Mice Administered Prodrug Compound 204

The hypoxia-dependent metabolism of prodrug Compound 204 leading to release of FGFR inhibitor Compound 112 in a SiHa xenograft-bearing NIH-III nude mice administered prodrug Compound 204 was determined by MALDI Imaging Mass Spectrometry as described above in the general biology experimental information. The results are shown in FIGS. 21A to 21D.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A compound of Formula (I):

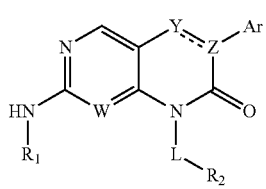

where:

W is N or CH;

Y is N, CH or CH$_2$;

Z is N or C;

Ar is a phenyl group substituted at the 2-position and at least one of the 3-, 5- and 6-positions with halogen, alkyl or alkoxy;

====== denotes either a single bond or a double bond;

R$_1$ is hydrogen, or is selected from the group comprising C1-C6 alkyl, C3-C6 cycloalkyl, heterocyclyl, aryl, and heteroaryl each of which is optionally substituted with hydroxy, alkyl, alkenyl, alkynyl, alkoxy, acetyl, thiol, alkylthio, arylthio, aralkylthio, halogen, carboxylic acid, carboxylate alkyl ester, carboxamide, alkylcarboxamide, dialkylcarboxamide, alkylsulfonyl, alkylsulfoxide, haloalkyl, haloalkoxy, amino, alkylamino, dialkylamino, morpholinyl, thiomorpholinyl, piperazinyl, N-alkylpiperazinyl, N-acetylpiperazinyl, N-alkylsulfonylpiperazinyl, pyrrolidinyl, piperidinyl, imidazolyl, or nitro;

L is a radical of selected from the group comprising Formulae (A)-(G):

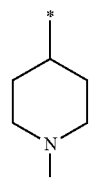

(A)

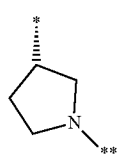

(B)

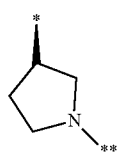

(C)

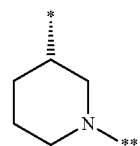

(D)

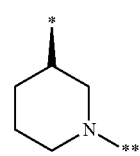

(E)

-continued (F)
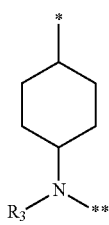

(G)
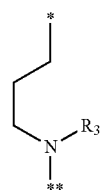

where:
* is a point of attachment to the heterocyclic nitrogen atom of Formula (I);
** is a point of attachment to R₂; and
R₃ is selected from hydrogen and C1-C6 alkyl;
R₂ is a radical of Formula (L):

(L)
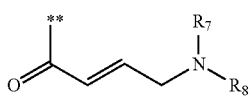

where:
R₇ and R₈ are independently C1-C6 alkyl or may together form a non-aromatic heterocyclic ring; and
** is a point of attachment to L;
or a nitroarylmethyl quaternary prodrug thereof, a pharmaceutically acceptable salt thereof, or a solvate thereof.

2. A compound as claimed in claim 1, wherein R₁ is C1-C6 alkyl or is a radical selected from the group comprising Formulae (M)-(FF):

(M)

(N)
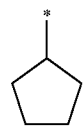

(O)
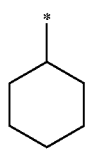

(P)
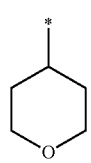

-continued (Q)
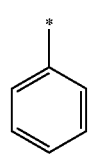

(R)
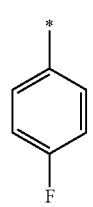

(S)
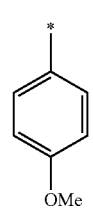

(T)
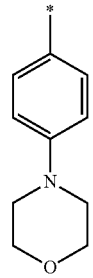

(U)
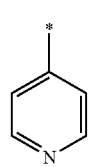

(W)
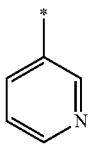

(Y)
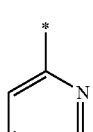

(Z)
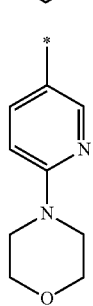

(AA) 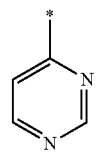
(BB) 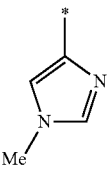
(CC) 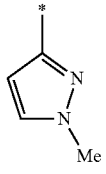
(DD) 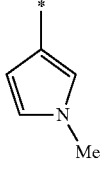
(EE) 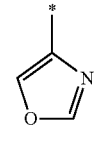
(FF) 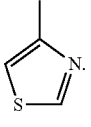
3. A compound as claimed in claim 1, wherein Ar is a radical selected from the group comprising Formulae (GG)-(FFF):
(GG) 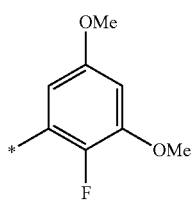
(HH) 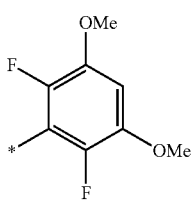
(JJ) 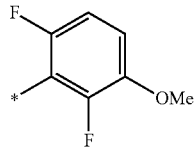
(KK) 
(LL)
(MM)
(NN)
(OO)
(PP)
(QQ)
(RR)

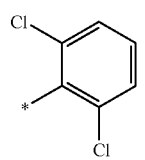 (SS)
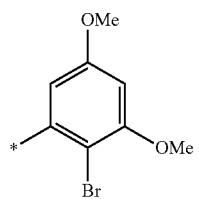 (TT)
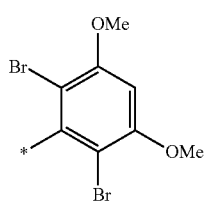 (UU)
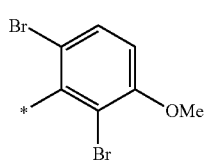 (VV)
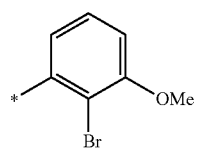 (WW)
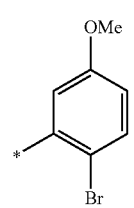 (YY)
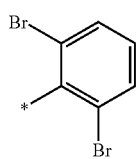 (ZZ)
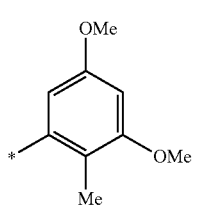 (AAA)
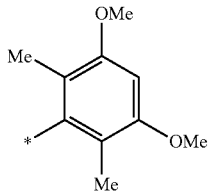 (BBB)
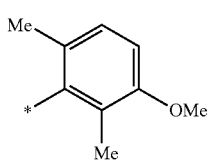 (CCC)
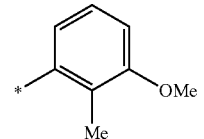 (DDD)
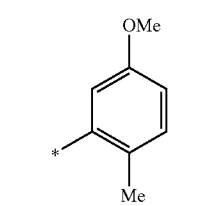 (EEE)
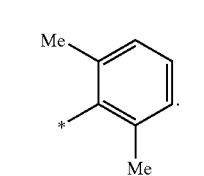 (FFF)
4. A compound as claimed in claim 1, having a formula selected from the group comprising Formulae (II) to (V):
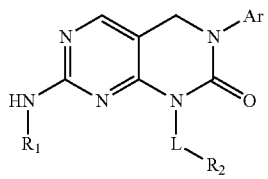 (II)
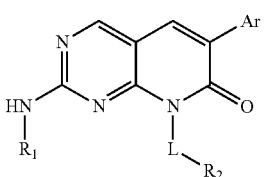 (III)
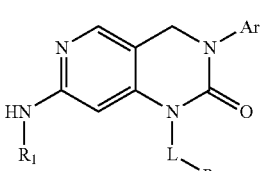 (IV)

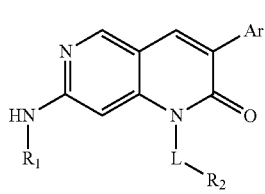

(V)

wherein Ar, R$_1$ and R$_2$ are as defined in claim 1.

5. A compound as claimed in claim 1, wherein R$_1$ is alkylamino.

6. A compound as claimed in claim 5, wherein alkylamino is —(CH$_2$)$_n$NR$_{10}$R$_{11}$ and n is an integer from 1-6, R$_{10}$ is H or alkyl, and R$_{11}$ is H or alkyl, or R$_{10}$ and R$_{11}$ taken together form a non-aromatic heterocyclic ring.

7. A compound as claimed in claim 1, wherein L is a radical of Formula (A), (B) or (C) as defined in claim 1.

8. A compound as claimed in claim 7, wherein L is a radical of Formula (B) as defined in claim 1.

9. A compound as claimed in claim 1, wherein R$_3$ is independently s hydrogen or methyl.

10. A compound as claimed in claim 9, wherein R$_3$ is hydrogen.

11. A compound as claimed in claim 1, wherein:
R$_7$ and R$_8$ together form a heterocyclic ring; or
R$_7$ and R$_8$ are both methyl.

12. A compound as claimed in claim 11, wherein the heterocyclic ring is a pyrrolidinyl, piperidinyl, piperazinyl, N-alkylpiperazinyl or morpholinyl ring.

13. A compound as claimed in claim 1, which is a prodrug of a compound of Formula (I) as defined in claim 1.

14. A compound as claimed in claim 13, wherein R$_2$ is a radical of Formula (MMM):

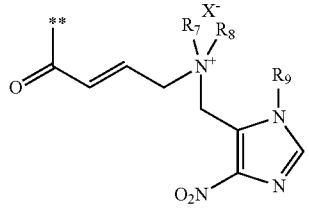

(MMM)

wherein R$_7$ and R$_8$ are as defined in claim 1, R$_9$ is hydrogen or C1-C6 alkyl, and X is a negatively charged counterion of a pharmaceutically acceptable salt.

15. A compound as claimed in claim 14, wherein X$^-$ is chloride, bromide, iodide, acetate, methanesulfonate or tosylate.

16. A compound as claimed in claim 1 which is selected from the group comprising:
(a) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (100);
(b) (S,E)-3-(2,6-dichloro-3,5-dimethoxyphenyl)-1-(1-(4-(dimethylamino)but-2-enoyl)piperidin-3-yl)-7-(methylamino)-3,4-dihydropyrimido[4,5-d]pyrimidin-2(1H)-one (101);
(c) (R,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (102);
(d) (S,E)-3-(2,6-dichloro-3,5-dimethoxyphenyl)-1-(1-(4-(dimethylamino)but-2-enoyl)pyrrolidin-3-yl)-7-(methylamino)-3,4-dihydropyrimido[4,5-d]pyrimidin-2(1H)-one (103);
(e) (S,E)-3-(2,6-dichloro-3,5-dimethoxyphenyl)-1-(1-(4-(dimethylamino)but-2-enoyl)pyrrolidin-3-yl)-7-(isopropylamino)-3,4-dihydropyrimido[4,5-d]pyrimidin-2(1H)-one (104);
(f) (S,E)-7-(cyclohexylamino)-3-(2,6-dichloro-3,5-dimethoxyphenyl)-1-(1-(4-(dimethylamino)but-2-enoyl)pyrrolidin-3-yl)-3,4-dihydropyrimido[4,5-d]pyrimidin-2(1H)-one (105);
(g) (S,E)-3-(2,6-dichloro-3,5-dimethoxyphenyl)-1-(1-(4-(dimethylamino)but-2-enoyl)pyrrolidin-3-yl)-7-(phenylamino)-3,4-dihydropyrimido[4,5-d]pyrimidin-2(1H)-one (106);
(h) (E)-3-(2,6-dichloro-3,5-dimethoxyphenyl)-1-(1-(4-(dimethylamino)but-2-enoyl)piperidin-4-yl)-7-(methylamino)-3,4-dihydropyrimido[4,5-d]pyrimidin-2(1H)-one (107);
(i) (E)-3-(2,6-dichloro-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (108);
(j) (E)-3-(2,6-dichloro-3,5-dimethoxyphenyl)-1-(1-(4-(dimethylamino)but-2-enoyl)piperidin-4-yl)-7-((tetrahydrofuran-3-yl)amino)-3,4-dihydropyrimido[4,5-d]pyrimidin-2(1H)-one (109);
(k) (E)-7-(cyclohexylamino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (110);
(l) (E)-3-(2,6-dichloro-3,5-dimethoxyphenyl)-1-(1-(4-(dimethylamino)but-2-enoyl)piperidin-4-yl)-7-((tetrahydro-2H-pyran-4-yl)amino)-3,4-dihydropyrimido[4,5-d]pyrimidin-2(1H)-one (111);
(m) (E)-3-(2,6-dichloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (112);
(n) (E)-3-(2,6-dichloro-3,5-dimethoxyphenyl)-1-(1-(4-(dimethylamino)but-2-enoyl)piperidin-4-yl)-7-((3-methoxyphenyl)amino)-3,4-dihydropyrimido[4,5-d]pyrimidin-2(1H)-one (113);
(o) (E)-3-(2,6-dichloro-3,5-dimethoxyphenyl)-1-(1-(4-(dimethylamino)but-2-enoyl)piperidin-4-yl)-7-(m-tolylamino)-3,4-dihydropyrimido[4,5-d]pyrimidin-2(1H)-one (114);
(p) (E)-3-(2,6-dichloro-3,5-dimethoxyphenyl)-1-(1-(4-(dimethylamino)but-2-enoyl)piperidin-4-yl)-7-((3-fluorophenyl)amino)-3,4-dihydropyrimido[4,5-d]pyrimidin-2(1H)-one (115);
(q) (E)-3-(2,6-dichloro-3,5-dimethoxyphenyl)-7-((3,5-difluorophenyl)amino)-1-(1-(4-(dimethylamino)but-2-enoyl)piperidin-4-yl)-3,4-dihydropyrimido[4,5-d]pyrimidin-2(1H)-one (116);
(r) (E)-3-(2,6-dichloro-3,5-dimethoxyphenyl)-7-((3,4-difluorophenyl)amino)-1-(1-(4-(dimethylamino)but-2-enoyl)piperidin-4-yl)-3,4-dihydropyrimido[4,5-d]pyrimidin-2(1H)-one (117);
(s) (E)-3-(2,6-dichloro-3,5-dimethoxyphenyl)-1-(1-(4-(dimethylamino)but-2-enoyl)piperidin-4-yl)-7-((4-fluoro-3-methoxyphenyl)amino)-3,4-dihydropyrimido[4,5-d] pyrimidin-2(1H)-one (118);
(t) (E)-7-((3-chloro-4-fluorophenyl)amino)-3-(2,6-dichloro-3,5-dimethoxyphenyl)-1-(1-(4-(dimethylamino)but-2-enoyl)piperidin-4-yl)-3,4-dihydropyrimido[4,5-d]pyrimidin-2(1H)-one (119);
(u) (E)-3-(2,6-dichloro-3,5-dimethoxyphenyl)-1-(1-(4-(dimethylamino)but-2-enoyl)piperidin-4-yl)-7-((4-fluorophenyl)amino)-3,4-dihydropyrimido[4,5-d]pyrimidin-2(1H)-one (120);
(v) (E)-3-(2,6-dichloro-3,5-dimethoxyphenyl)-1-(1-(4-(dimethylamino)but-2-enoyl)piperidin-4-yl)-7-((2-methoxyphenyl)amino)-3,4-dihydropyrimido[4,5-d]pyrimidin-2(1H)-one (121);
(w) (E)-3-(2,6-dichloro-3,5-dimethoxyphenyl)-1-(1-(4-(dimethylamino)but-2-enoyl)piperidin-4-yl)-7-((4-methoxyphenyl)amino)-3,4-dihydropyrimido[4,5-d]pyrimidin-2(1H)-one (122);
(x) (E)-3-(2,6-dichloro-3,5-dimethoxyphenyl)-7-(methylamino)-1-(1-(4-morpholinobut-2-enoyl)piperidin-4-yl)-3,4-dihydropyrimido[4,5-d]pyrimidin-2(1H)-one (123);
(y) (E)-3-(2,6-dichloro-3,5-dimethoxyphenyl)-7-(methylamino)-1-(1-(4-(piperidin-1-yl)but-2-enoyl)piperidin-4-yl)-3,4-dihydropyrimido[4,5-d]pyrimidin-2(1H)-one (124);
(z) (E)-N-(3-(3-(2,6-dichloro-3,5-dimethoxyphenyl)-7-(methylamino)-2-oxo-3,4-dihydropyrimido[4,5-d]pyrimidin-1(2H)-yl)propyl)-4-(dimethylamino)but-2-enamide (125);
(aa) (E)-N-(4-(3-(2,6-dichloro-3,5-dimethoxyphenyl)-7-(methylamino)-2-oxo-3,4-dihydropyrimido[4,5-d]pyrimidin-1(2H)-yl)cyclohexyl)-4-(dimethylamino)but-2-enamide (126);
(bb) (E)-3-(2-chloro-3,5-dimethoxyphenyl)-1-(1-(4-(dimethylamino)but-2-enoyl)piperidin-4-yl)-7-(phenylamino)-3,4-dihydropyrimido[4,5-d]pyrimidin-2(1H)-one (128);
(cc) (E)-3-(2,6-dichloro-3,5-dimethoxyphenyl)-1-(1-(4-(dimethylamino)but-2-enoyl)piperidin-4-yl)-7-((4-morpholinophenyl)amino)-3,4-dihydropyrimido[4,5-J]pyrimidin-2(1H)-one (129);
(dd) (E)-3-(2-chloro-3,5-dimethoxyphenyl)-1-(1-(4-(dimethylamino)but-2-enoyl) piperidin-4-yl)-7-((4-morpholinophenyl)amino)-3,4-dihydropyrimido[4,5-J]pyrimidin-2(1H)-one (130);
(ee) (E)-6-(2,6-dichloro-3,5-dimethoxyphenyl)-8-(1-(4-(dimethylamino)but-2-enoyl)piperidin-4-yl)-2-(methylamino)pyrido[2,3-d]pyrimidin-7(8H)-one (132);
(ff) (E)-6-(2,6-dichloro-3,5-dimethoxyphenyl)-8-(1-(4-(dimethylamino)but-2-enoyl)piperidin-4-yl)-2-(isopropylamino)pyrido[2,3-d]pyrimidin-7(8H)-one (133);
(gg) (E)-6-(2,6-dichloro-3,5-dimethoxyphenyl)-8-(1-(4-(dimethylamino)but-2-enoyl)piperidin-4-yl)-2-((tetrahydrofuran-3-yl)amino)pyrido[2,3-d]pyrimidin-7(8H)-one (134);
(hh) (E)-6-(2,6-dichloro-3,5-dimethoxyphenyl)-8-(1-(4-(dimethylamino)but-2-enoyl)piperidin-4-yl)-2-((tetrahydro-2H-pyran-4-yl)amino)pyrido[2,3-d]pyrimidin-7(8H)-one (135);
(ii) (E)-2-(cyclohexylamino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (136);
(jj) (E)-6-(2,6-dichloro-3,5-dimethoxyphenyl)-8-(1-(4-(dimethylamino)but-2-enoyl)piperidin-4-yl)-2-(((tetrahydro-2H-pyran-4-l)methyl)amino)pyrido[2,3-d]pyrimidin-7(8H)-one (137);
(kk) (E)-6-(2,6-dichloro-3,5-dimethoxyphenyl)-8-(1-(4-(dimethylamino)but-2-enoyl)piperidin-4-yl)-2-(phenylamino)pyrido[2,3-d]pyrimidin-7(8H)-one (138);
(ll) (E)-6-(2,6-dichloro-3,5-dimethoxyphenyl)-8-(1-(4-(dimethylamino)but-2-enoyl)piperidin-4-yl)-2-((4-fluorophenyl)amino)pyrido[2,3-d]pyrimidin-7(8H)-one (139);
(mm) (E)-6-(2,6-dichloro-3,5-dimethoxyphenyl)-8-(1-(4-(dimethylamino)but-2-enoyl)piperidin-4-yl)-2-((3-methoxyphenyl)amino)pyrido[2,3-d]pyrimidin-7(8H)-one (140);
(nn) (E)-6-(2,6-dichloro-3,5-dimethoxyphenyl)-8-(1-(4-(dimethylamino)but-2-enoyl)piperidin-4-yl)-2-((4-fluoro-3-methoxyphenyl)amino)pyrido[2,3-d]pyrimidin-7(8H)-one (141);
(oo) (E)-2-((3-chloro-4-fluorophenyl)amino)-6-(2,6-dichloro-3,5-dimethoxyphenyl)-8-(1-(4-(dimethylamino)but-2-enoyl)piperidin-4-yl)pyrido[2,3-d]pyrimidin-7(8H)-one (142);
(pp) (E)-3-(2,6-dichloro-3,5-dimethoxyphenyl)-1-(1-(4-(dimethylamino)but-2-enoyl)piperidin-4-yl)-7-(methylamino)-1,6-naphthyridin-2(1H)-one (148);
(qq) (E)-3-(2,6-dichloro-3,5-dimethoxyphenyl)-1-(1-(4-(dimethylamino)but-2-enoyl)piperidin-4-yl)-7-(isopropylamino)-1,6-naphthyridin-2(1H)-one (149);
(rr) (E)-3-(2,6-dibromo-3,5-dimethoxyphenyl)-1-(1-(4-(dimethylamino)but-2-enoyl)piperidin-4-yl)-7-(isopropylamino)-3,4-dihydropyrimido[4,5-d]pyrimidin-2(1H)-one (151);
(ss) (E)-6-(2,6-dibromo-3,5-dimethoxyphenyl)-8-(1-(4-(dimethylamino)but-2-enoyl)piperidin-4-yl)-2-(phenylamino)pyrido[2,3-d]pyrimidin-7(8H)-one (152);
(tt) (E)-6-(2,6-dibromo-3,5-dimethoxyphenyl)-8-(1-(4-(dimethylamino)but-2-enoyl)piperidin-4-yl)-2-(isopropylamino)pyrido[2,3-d]pyrimidin-7(8H)-one (153);
(uu) (E)-3-(2,6-dibromo-3,5-dimethoxyphenyl)-1-(1-(4-(dimethylamino)but-2-enoyl)piperidin-4-yl)-7-(isopropylamino)-1,6-naphthyridin-2(1H)-one (155);
(vv) (E)-3-(2,6-dichloro-3,5-dimethoxyphenyl)-1-(1-(4-(dimethylamino)but-2-enoyl)piperidin-4-yl)-7-(pyridin-2-ylamino)-3,4-dihydropyrimido[4,5-d]pyrimidin-2(1H)-one (157);
(ww) (E)-3-(2,6-dichloro-3,5-dimethoxyphenyl)-1-(1-(4-(dimethylamino)but-2-enoyl)piperidin-4-yl)-7-(pyridin-3-ylamino)-3,4-dihydropyrimido[4,5-d]pyrimidin-2(1H)-one (158);
(xx) (E)-3-(2,6-dichloro-3,5-dimethoxyphenyl)-1-(1-(4-(dimethylamino)but-2-enoyl)piperidin-4-yl)-7-(pyridin-4-ylamino)-3,4-dihydropyrimido[4,5-d]pyrimidin-2(1H)-one (159);
(yy) (E)-3-(2,6-dichloro-3,5-dimethoxyphenyl)-1-(1-(4-(dimethylamino)but-2-enoyl)piperidin-4-yl)-7-((1-methyl-1H-pyrazol-3-yl)amino)-3,4-dihydropyrimido[4,5-d]pyrimidin-2(1H)-one (160);
(zz) (E)-3-(2,6-dichloro-3,5-dimethoxyphenyl)-1-(1-(4-(dimethylamino)but-2-enoyl)piperidin-4-yl)-7-((5-morpholinopyridin-2-yl)amino)-3,4-dihydropyrimido[4,5-d]pyrimidin-2(1H)-one (161);
(aaa) (E)-3-(2,6-dichloro-3,5-dimethoxyphenyl)-1-(1-(4-(dimethylamino)but-2-enoyl)piperidin-4-yl)-7-(pyrimidin-4-ylamino)-3,4-dihydropyrimido[4,5-d]pyrimidin-2(1H)-one (162);
(bbb) (S,E)-4-(3-(3-(2,6-dichloro-3,5-dimethoxyphenyl)-7-(methylamino)-2-oxo-3,4-dihydropyrimido[4,5-d]pyrimidin-1(2H)-yl)pyrrolidin-1-yl)-N,N-dimethyl-N-((1-methyl-4-nitro-1H-imidazol-5-yl)methyl)-4-oxobut-2-en-1-aminium bromide (200);
(ccc) (S,E)-4-(3-(3-(2,6-dichloro-3,5-dimethoxyphenyl)-7-(isopropylamino)-2-oxo-3,4-dihydropyrimido[4,5-d]pyrimidin-1(2H)-yl)pyrrolidin-1-yl)-N,N-dimethyl-N-

((1-methyl-4-nitro-1H-imidazol-5-yl)methyl)-4-oxobut-2-en-1-aminium bromide (201);
(ddd) (E)-4-(4-(3-(2,6-dichloro-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (202);
(eee) (E)-4-(4-(3-(2,6-dichloro-3,5-dimethoxyphenyl)-2-oxo-7-((tetrahydro-2H-pyran-4-yl)amino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (203);
(fff) (E)-4-(4-(3-(2,6-dichloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (204);
(ggg) (E)-4-(4-(3-(2,6-dichloro-3,5-dimethoxyphenyl)-7-((4-fluorophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (205);
(hhh) (E)-4-(4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (206);
(iii) (E)-4-(4-(3-(2,6-dibromo-3,5-dimethoxyphenyl)-7-(isopropylamino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (207);
(jjj) (E)-4-(4-(6-(2,6-dichloro-3,5-dimethoxyphenyl)-2-(methylamino)-7-oxopyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (208);
(kkk) (E)-4-(4-(6-(2,6-dichloro-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (209);
(lll) (E)-4-(4-(6-(2,6-dibromo-3,5-dimethoxyphenyl)-2-(isopropylamino)-7-oxopyrido[2,3-d]pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (210);
(mmm) (E)-4-(4-(6-(2,6-dichloro-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (211);
(nnn) (E)-4-(4-(6-(2,6-dibromo-3,5-dimethoxyphenyl)-7-oxo-2-(phenylamino)pyrido[2,3-d] pyrimidin-8(7H)-yl)piperidin-1-yl)-N,N-dimethyl-N-((1-methyl-4-nitro-1H-imidazol-5-yl)methyl)-4-oxobut-2-en-1-aminium bromide (212);
(ooo) (E)-4-((4-(3-(2,6-dichloro-3,5-dimethoxyphenyl)-7-((4-methoxyphenyl)amino)-2-oxo-3,4-dihydropyrimido[4,5-d]pyrimidin-1(2H)-yl)cyclohexyl)amino)-N,N-dimethyl-N-((1-methyl-4-nitro-1H-imidazol-5-yl)methyl)-4-oxobut-2-en-1-aminium bromide (214);
(ppp) (E)-4-(4-(3-(2,6-dichloro-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (215);
(qqq) (E)-4-(4-(3-(2,6-dibromo-3,5-dimethoxyphenyl)-7-(isopropylamino)-2-oxo-1,6-naphthyridin-1(2H)-yl)piperidin-1-yl)-N,N-dimethyl-N-((1-methyl-4-nitro-1H-imidazol-5-yl)methyl)-4-oxobut-2-en-1-aminium bromide (216);
(rrr) (E)-4-(4-(3-(2-chloro-3,5-dimethoxyphenyl)-2-oxo-7-(phenylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (217);
(sss) (E)-4-(4-(3-(2,6-dichloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (218);
(ttt) (E)-4-(4-(3-(2-chloro-3,5-dimethoxyphenyl)-7-((4-morpholinophenyl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (219);
(uuu) (E)-4-(4-(3-(2,6-dichloro-3,5-dimethoxyphenyl)-2-oxo-7-(pyridin-2-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (221);
(vvv) (E)-4-(4-(3-(2,6-dichloro-3,5-dimethoxyphenyl)-2-oxo-7-(pyridin-3-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (222);
(www) (E)-4-(4-(3-(2,6-dichloro-3,5-dimethoxyphenyl)-2-oxo-7-(pyridin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium 2,2,2-trifluoroacetate (223);
(xxx) (E)-4-(4-(3-(2,6-dichloro-3,5-dimethoxyphenyl)-7-((1-methyl-1H-pyrazol-3-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (224);
(yyy) (E)-4-(4-(3-(2,6-dichloro-3,5-dimethoxyphenyl)-7-((5-morpholinopyridin-2-yl)amino)-2-oxo-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (225);
(zzz) (E)-4-(4-(3-(2,6-dichloro-3,5-dimethoxyphenyl)-2-oxo-7-(pyrimidin-4-ylamino)-3,4-dihydropyrimido[4,5-d]pyrimidin-1(2H)-yl)piperidin-1-yl)-N,N-dimethyl-N-((1-methyl-4-nitro-1H-imidazol-5-yl)methyl)-4-oxobut-2-en-1-aminium bromide (226); and
(aaaa) (E)-3-(2,6-dichloro-3,5-dimethoxyphenyl)-1-(1-(4-(dimethylamino)but-2-enoyl)piperidin-4-yl)-7-(phenylamino)-1,6-naphthyridin-2(1H)-one (232).

17. A pharmaceutical composition comprising a compound of claim 1, together with a pharmaceutically acceptable carrier.

18. A method of treating a hyper-proliferative disease associated with inhibition of a fibroblast growth factor receptor (FGFR) kinase comprising administering to a human or other animal a therapeutically effective amount of a compound as claimed in claim 1, wherein the hyper-proliferative disease is selected from the group consisting of squamous cell carcinoma, breast cancer, bladder cancer, liver cancer, multiple myeloma, urothelial cancer, gastric cancer, cholangiocarcinoma, melanoma, endometrial cancer, rhabdomyosarcoma, lung cancer, pancreatic cancer, glioma, kidney cancer, lymphoma, salivary gland cancer, and acute myeloid leukemia.

19. A method as claimed in claim 18, wherein the FGFR kinase is FGFR-1, FGFR-2, FGFR-3 or FGFR-4.

20. A method as claimed in claim 19, wherein the cancer is selected from the group consisting of lung cancer, breast cancer, endometrial cancer, urothelial cancer, bladder cancer, gastric cancer, multiple myeloma, acute myeloid leukemia, glioma, liver cancer, and melanoma.

21. A compound as claimed in claim 7, wherein L is a radical of Formula (A) as defined in claim 1.

22. A compound as claimed in claim 1, which is (E)-6-(2,6-dichloro-3,5-dimethoxyphenyl)-8-(1-(4-(dimethylamino)but-2-enoyl)piperidin-4-yl)-2-(methylamino)pyrido[2,3-d]pyrimidin-7(8H)-one (132) having the following chemical structure:

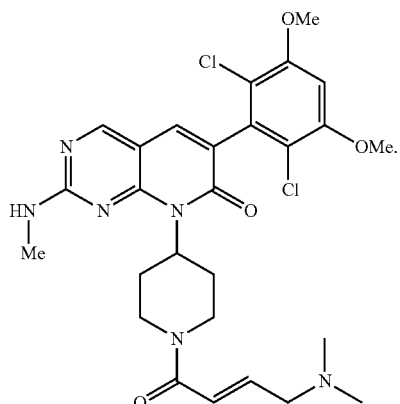

* * * * *

UNITED STATES PATENT AND TRADEMARK OFFICE
CERTIFICATE OF CORRECTION

| | | |
|---|---|---|
| PATENT NO. | : 11,192,890 B2 | Page 1 of 1 |
| APPLICATION NO. | : 16/490717 | |
| DATED | : December 7, 2021 | |
| INVENTOR(S) | : Patterson et al. | |

It is certified that error appears in the above-identified patent and that said Letters Patent is hereby corrected as shown below:

On the Title Page

In Column 2, item (57) under "Abstract", Line 5, delete "corral" and insert -- cornal --, therefor.

In the Claims

In Column 239, in Claim 1, Line 45, after "Y is" delete "N,".

In Column 239, in Claim 1, Line 66, after "radical" delete "of".

In Column 247, in Claim 9, Line 23, delete "independently s hydrogen" and insert -- hydrogen --, therefor.

In Column 247, in Claim 14, Line 49, delete "X" and insert -- X⁻ --, therefor.

In Column 249, in Claim 16, Line 38, delete "[4,5-J]" and insert -- [4,5-d] --, therefor.

In Column 249, in Claim 16, Line 42, delete "[4,5-J]" and insert -- [4,5-d] --, therefor.

Signed and Sealed this
Thirty-first Day of May, 2022

*Katherine Kelly Vidal*

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 978
<212> TYPE: DNA
<213> ORGANISM: Artificial Sequence
<220> FEATURE:
<223> OTHER INFORMATION: C584S FGFR1 kinase domain sequence

<400> SEQUENCE: 1

```
atgggccacc accaccacca ccactctgct gaaaacctgt acttccaggg tgctggtgtt      60
tctgaatacg aactgccgga gacccgcgt tgggaactgc cgcgtgaccg tctggttctg     120
ggtaaaccgc tgggtgaagg ttgcttcggt caggttgttc tggctgaagc tatcggtctg     180
gacaaagaca aaccgaaccg tgttaccaaa gttgctgtta aaatgctgaa atctgacgct     240
accgaaaaag acctgtctga cctgatctct gaaatggaaa tgatgaaaat gatcggtaaa     300
cacaaaaaca tcatcaacct gctgggtgct tgcacccagg acggtccgct gtacgttatc     360
gttgaatacg cttctaaagg taacctgcgt gaatacctgc aggctcgtcg tccgccgggt     420
ctggaatact cttacaaccc gtctcacaac ccggaagaac agctgtcttc taaagacctg     480
gtttcttgcg cttaccaggt tgctcgtggt atggaatacc tggcttctaa aaaatgcatc     540
caccgtgacc tggctgctcg taacgttctg gttaccgaag acaacgttat gaaaatcgct     600
gacttcggtc tggctcgtga catccaccac atcgactact acaaaaaaac caccaacggt     660
cgtctgccgg ttaaatggat ggctccggaa gctctgttcg accgtatcta cacccaccag     720
tctgacgttt ggtctttcgg tgttctgctg tgggaaatct tcaccctggg tggttctccg     780
tacccgggtg ttccggttga agaactgttc aaactgctga agaaggtca ccgtatggac     840 aaaccgtcta actgcaccaa cgaactgtac atgatgatgc gtgactgctg gcacgctgtt     900
ccgtctcagc gtccgacctt caaacagctg gttgaagacc tggaccgtat cgttgctctg     960
acctctaacc aggaataa                                                    978
```

<210> SEQ ID NO 2
<211> LENGTH: 325
<212> TYPE: PRT
<213> ORGANISM: Artificial Sequence
<220> FEATURE:
<223> OTHER INFORMATION: C584S FGFR1 kinase domain sequence

<400> SEQUENCE: 2

Met Gly His His His His His His Ser Ala Glu Asn Leu Tyr Phe Gln
1               5                   10                  15

Gly Ala Gly Val Ser Glu Tyr Glu Leu Pro Glu Asp Pro Arg Trp Glu
            20                  25                  30

Leu Pro Arg Asp Arg Leu Val Leu Gly Lys Pro Leu Gly Glu Gly Cys
        35                  40                  45

Phe Gly Gln Val Val Leu Ala Glu Ala Ile Gly Leu Asp Lys Asp Lys
    50                  55                  60

Pro Asn Arg Val Thr Lys Val Ala Val Lys Met Leu Lys Ser Asp Ala
65                  70                  75                  80

Thr Glu Lys Asp Leu Ser Asp Leu Ile Ser Glu Met Glu Met Lys
            85                  90                  95

Met Ile Gly Lys His Lys Asn Ile Ile Asn Leu Leu Gly Ala Cys Thr
            100                 105                 110

Gln Asp Gly Pro Leu Tyr Val Ile Val Glu Tyr Ala Ser Lys Gly Asn
        115                 120                 125

```
Leu Arg Glu Tyr Leu Gln Ala Arg Arg Pro Gly Leu Glu Tyr Ser
            130                 135                 140

Tyr Asn Pro Ser His Asn Pro Glu Glu Gln Leu Ser Ser Lys Asp Leu
145                 150                 155                 160

Val Ser Cys Ala Tyr Gln Val Ala Arg Gly Met Glu Tyr Leu Ala Ser
                165                 170                 175

Lys Lys Cys Ile His Arg Asp Leu Ala Ala Arg Asn Val Leu Val Thr
            180                 185                 190

Glu Asp Asn Val Met Lys Ile Ala Asp Phe Gly Leu Ala Arg Asp Ile
        195                 200                 205

His His Ile Asp Tyr Tyr Lys Lys Thr Thr Asn Gly Arg Leu Pro Val
    210                 215                 220

Lys Trp Met Ala Pro Glu Ala Leu Phe Asp Arg Ile Tyr Thr His Gln
225                 230                 235                 240

Ser Asp Val Trp Ser Phe Gly Val Leu Leu Trp Glu Ile Phe Thr Leu
                245                 250                 255

Gly Gly Ser Pro Tyr Pro Gly Val Pro Val Glu Glu Leu Phe Lys Leu
            260                 265                 270

Leu Lys Glu Gly His Arg Met Asp Lys Pro Ser Asn Cys Thr Asn Glu
        275                 280                 285

Leu Tyr Met Met Met Arg Asp Cys Trp His Ala Val Pro Ser Gln Arg
    290                 295                 300

Pro Thr Phe Lys Gln Leu Val Glu Asp Leu Asp Arg Ile Val Ala Leu
305                 310                 315                 320

Thr Ser Asn Gln Glu
            325

<210> SEQ ID NO 3
<211> LENGTH: 309
<212> TYPE: PRT
<213> ORGANISM: Artificial Sequence
<220> FEATURE:
<223> OTHER INFORMATION: C584S FGFR1 kinase domain sequence

<400> SEQUENCE: 3

Gly Ala Gly Val Ser Glu Tyr Glu Leu Pro Glu Asp Pro Arg Trp Glu
1               5                   10                  15

Leu Pro Arg Asp Arg Leu Val Leu Gly Lys Pro Leu Gly Glu Gly Cys
            20                  25                  30

Phe Gly Gln Val Val Leu Ala Glu Ala Ile Gly Leu Asp Lys Asp Lys
        35                  40                  45

Pro Asn Arg Val Thr Lys Val Ala Val Lys Met Leu Lys Ser Asp Ala
50                  55                  60

Thr Glu Lys Asp Leu Ser Asp Leu Ile Ser Glu Met Glu Met Met Lys
65                  70                  75                  80

Met Ile Gly Lys His Lys Asn Ile Ile Asn Leu Leu Gly Ala Cys Thr
                85                  90                  95

Gln Asp Gly Pro Leu Tyr Val Ile Val Glu Tyr Ala Ser Lys Gly Asn
            100                 105                 110

Leu Arg Glu Tyr Leu Gln Ala Arg Arg Pro Gly Leu Glu Tyr Ser
        115                 120                 125

Tyr Asn Pro Ser His Asn Pro Glu Glu Gln Leu Ser Ser Lys Asp Leu
    130                 135                 140

Val Ser Cys Ala Tyr Gln Val Ala Arg Gly Met Glu Tyr Leu Ala Ser
145                 150                 155                 160
```

```
Lys Lys Cys Ile His Arg Asp Leu Ala Ala Arg Asn Val Leu Val Thr
            165                 170                 175
Glu Asp Asn Val Met Lys Ile Ala Asp Phe Gly Leu Ala Arg Asp Ile
            180                 185                 190
His His Ile Asp Tyr Tyr Lys Lys Thr Thr Asn Gly Arg Leu Pro Val
            195                 200                 205
Lys Trp Met Ala Pro Glu Ala Leu Phe Asp Arg Ile Tyr Thr His Gln
    210                 215                 220
Ser Asp Val Trp Ser Phe Gly Val Leu Leu Trp Glu Ile Phe Thr Leu
225                 230                 235                 240
Gly Gly Ser Pro Tyr Pro Gly Val Pro Val Glu Glu Leu Phe Lys Leu
            245                 250                 255
Leu Lys Glu Gly His Arg Met Asp Lys Pro Ser Asn Cys Thr Asn Glu
            260                 265                 270
Leu Tyr Met Met Met Arg Asp Cys Trp His Ala Val Pro Ser Gln Arg
        275                 280                 285
Pro Thr Phe Lys Gln Leu Val Glu Asp Leu Asp Arg Ile Val Ala Leu
    290                 295                 300
Thr Ser Asn Gln Glu
305
```